(12) United States Patent
Panicker et al.

(10) Patent No.: US 12,145,999 B2
(45) Date of Patent: *Nov. 19, 2024

(54) PROTEIN S ANTIBODIES, METHODS OF MAKING AND USES THEREOF

(71) Applicant: Vega Therapeutics, Inc., South San Francisco, CA (US)

(72) Inventors: Sandip Panicker, South San Francisco, CA (US); Adam David Rosenthal, South San Francisco, CA (US); Tony Sang Young Byun, South San Francisco, CA (US)

(73) Assignee: Vega Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/506,872

(22) Filed: Nov. 10, 2023

(65) Prior Publication Data

US 2024/0084038 A1 Mar. 14, 2024

Related U.S. Application Data

(63) Continuation of application No. 17/923,503, filed as application No. PCT/US2021/030900 on May 5, 2021.

(60) Provisional application No. 63/169,755, filed on Apr. 1, 2021, provisional application No. 63/020,505, filed on May 5, 2020.

(51) Int. Cl.
*C07K 16/36* (2006.01)
*A61K 47/68* (2017.01)
*A61P 7/04* (2006.01)
*A61K 39/00* (2006.01)

(52) U.S. Cl.
CPC .......... *C07K 16/36* (2013.01); *A61K 47/6843* (2017.08); *A61P 7/04* (2018.01); *A61K 2039/505* (2013.01); *A61K 2039/54* (2013.01); *A61K 2039/545* (2013.01); *C07K 2317/21* (2013.01); *C07K 2317/24* (2013.01); *C07K 2317/32* (2013.01); *C07K 2317/34* (2013.01); *C07K 2317/52* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,147,638 A | 9/1992 | Esmon et al. |
| 5,187,067 A | 2/1993 | Koike et al. |
| 5,366,861 A | 11/1994 | Hosoda et al. |
| 6,180,370 B1 * | 1/2001 | Queen ................ C07K 16/089 435/69.6 |
| 6,423,313 B1 | 7/2002 | Esmon et al. |
| RE38,202 E | 7/2003 | Mertens et al. |
| 7,041,458 B2 | 5/2006 | Dahlbäck |
| 8,669,263 B2 | 3/2014 | Lemke et al. |
| 9,233,144 B2 | 1/2016 | Bernard-Pierrot et al. |
| 9,447,147 B2 | 9/2016 | Dockal et al. |
| 2003/0124118 A1 | 7/2003 | Rojkjaer |
| 2003/0143759 A1 | 7/2003 | Dahlback |
| 2003/0165485 A1 | 9/2003 | Bertilsson et al. |
| 2007/0077603 A1 | 4/2007 | Heeb et al. |
| 2008/0057059 A1 | 3/2008 | Rojkjaer |
| 2015/0246947 A1 | 9/2015 | Dockal et al. |
| 2016/0297892 A1 | 10/2016 | Heibroch Petersen et al. |
| 2023/0083243 A1 | 3/2023 | Panicker et al. |
| 2023/0174672 A1 | 6/2023 | Panicker et al. |

FOREIGN PATENT DOCUMENTS

| | | | |
|---|---|---|---|
| EP | 0944837 A1 | 9/1999 | |
| EP | 0944837 B1 | 12/2004 | |
| EP | 0972781 B1 | 1/2007 | |
| EP | 1780219 A2 | 5/2007 | |
| WO | WO-9301209 A1 * | 1/1993 | .......... C07K 14/745 |
| WO | WO-9823963 A1 | 6/1998 | |
| WO | WO-2007014749 A2 | 2/2007 | |
| WO | WO-2007018511 A1 | 2/2007 | |
| WO | WO-2021226243 A1 | 11/2021 | |
| WO | WO-2021226245 A1 | 11/2021 | |
| WO | WO-2022002880 A1 | 1/2022 | |
| WO | WO-2024124136 A1 | 6/2024 | |

OTHER PUBLICATIONS

Stryer, Biochemistry 4th, WH Freeman, New York. 1995 (Year: 1995).*
Colman, Research in Immunology 145.1 (1994): 33-36 (Year: 1994).*
Kipriyanov, Sergey M., and Fabrice Le Gall. "Generation and production of engineered antibodies." Molecular biotechnology 26.1 (2004): 39-60. (Year: 2004).*
Janeway, Charles A. "Immunobiology: The Immune System in Health and Disease." 2001 (Year: 2001).*
ClinicalTrials.gov, ID NCT05776069. Study of VGA039 in Healthy Volunteers and Patients With Von Willebrand Disease [online]. Version 1, dated Mar. 8, 2023 [retrieved on Nov. 30, 2023]. Retrieved from the Internet: https://clinicaltrials.gov/study/NCT05776069?term=NCT05776069&rank=1&tab=history&a=1; 7 printed pages.

(Continued)

*Primary Examiner* — Michael Szperka
*Assistant Examiner* — Lia E Taylor
(74) *Attorney, Agent, or Firm* — Cooley LLP

(57) ABSTRACT

Provided here are antibodies that bind Protein S, and methods of making and using such antibodies. In some embodiments, the Protein S antibodies provided herein are useful for treating a bleeding disorder or platelet disorder, or a condition characterized by reduced or impaired blood coagulation and/or clotting.

25 Claims, 53 Drawing Sheets

Specification includes a Sequence Listing.

(56) References Cited

OTHER PUBLICATIONS

ClinicalTrials.gov, ID NCT05776069. Study of VGA039 in Healthy Volunteers and Patients With Von Willebrand Disease [online]. Version 3, dated Apr. 4, 2023 [retrieved on Nov. 30, 2023]. Retrieved from the Internet: https://clinicaltrials.gov/study/NCT05776069?term=NCT05776069&rank=1&tab=history&a=3; 7 printed pages.

Hackeng, T.M., et al.; "Human protein S inhibits prothrombinase complex activity on endothelial cells and platelets via direct interactions with factors Va and Xa," J Biol Chem., (1994); 269(33):21051-21058.

Castoldi et al. (2009). "Hereditary and acquired protein S deficiencies are associated with low TFPI levels in plasma." Journal of Thrombosis and Haemostasis, 8:294-300.

Dahlbäck, B. (2022) "Calcium-dependent monoclonal antibody against Gla-domain of protein S efficiently inhibiting both protein C and TFPI anticoagulant pathways," International Society on Thrombosis and Haemostasis (ISTH) 2022 Congress, Jul. 9-13, London. 2022 Congress Abstracts [online], 2 pages. Retrieved from: https://abstracts.isth.org/abstract/calcium-dependent-monoclonal-antibody-against-gla-domain-of-protein-s-efficiently-inhibiting-both-protein-c-and-tfpi-anticoagulant-pathways/.

Dahlbäck, B. et al. (1990) "Characterization of Functionality Important Domains in Human Vitamin K-dependent Protein S Using Monoclonal Antibodies," J Biol Chem, 265(14):8127-8135.

Hackeng T. M., et al., "Protein S Stimulates Inhibition of the Tissue Factor Pathway by Tissue Factor Pathway Inhibitor," Proceedings of the National Academy of Sciences of the United States of America, Feb. 2006, vol. 103 (9), pp. 3106-3111.

International Preliminary Report on Patentability for International Application No. PCT/US2021/030900 dated Nov. 17, 2022, 8 pages.

International Preliminary Report on Patentability for International Application No. PCT/US2021/030902 dated Nov. 17, 2022, 8 pages.

International Search Report and Written Opinion for International Application No. PCT/US2021/030900, mailed Sep. 16, 2021, 12 pages.

International Search Report and Written Opinion for International Application No. PCT/US2021/030902, mailed Aug. 20, 2021, 16 pages.

Sakurai et al. (2018). "A microengineered vascularized bleeding model that integrates the principal components of hemostasis" Nature Communications. 9:509, pp. 1-9.

Baroni, M., et al.; "Membrane binding and anticoagulant properties of protein S natural variants," Thromb Res. (2010); 125(2):e33-e39.

Bologna, L., et al.; "Blocking Protein S Improves Hemostasis in Hemophilia a and B," Blood (2016); 128(22):79, 3 pages.

Borgel, D., et al.; "Implication of protein S thrombin-sensitive region with membrane binding via conformational changes in the gamma-carboxyglutamic acid-rich domain," Biochem J. (2001); 360(Pt 2):499-506.

Bos, M.H.A., et al.; "Does activated protein C-resistant factor V contribute to thrombin generation in hemophilic plasma?" J Thromb Haemost. (2005); 3(3):522-530.

Kaufman, R.J., et al.; "Molecular approaches for improved clotting factors for hemophilia," Blood (2013); 122(22):3568-3574.

Prince, R., et al.; "Targeting anticoagulant protein S to improve hemostasis in hemophilia," Blood (2018), 131(12):1360-1371.

Saller, F., et al.; "The protein S thrombin-sensitive region modulates phospholipid binding and the gamma-carboxyglutamic acid-rich (Gla) domain conformation in a non-specific manner," J Thromb Haemost (2006); 4(3):704-706.

Santa Cruz Biotechnology: Protein S Antibody (PS7): sc-52720, Product Sheet; [retrieved online May 30, 2024] URL: https://www.scbt.com/p/protein-s-antibody-ps7#citations, 3 pages.

Von Drygalski, A., et al.; "Superior in Vivo Hemostatic Properties of an Engineered Factor Va Variant for Hemophilia Mice," Blood (2012); 120(21):17, 2 pages.

\* cited by examiner

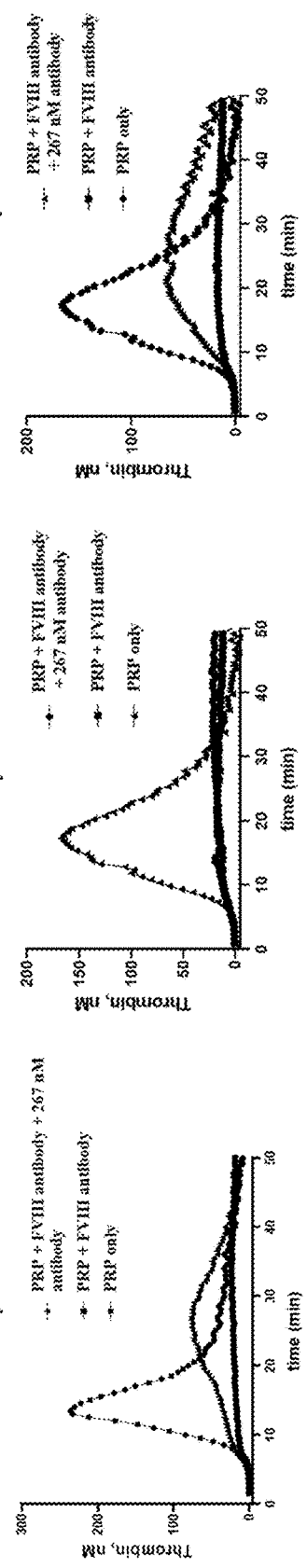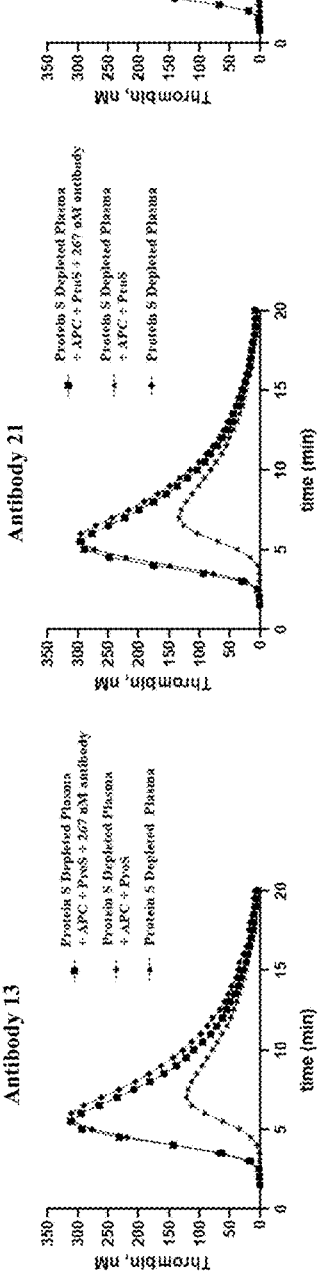
FIG. 5 — Dual Inhibitor, Antibody 13
FIG. 6 — Antibody 13
FIG. 7 — APC Specific Inhibitor, Antibody 21
FIG. 8 — Antibody 21
FIG. 9 — TFPI Specific Inhibitor, Antibody 23
FIG. 10 — Antibody 23

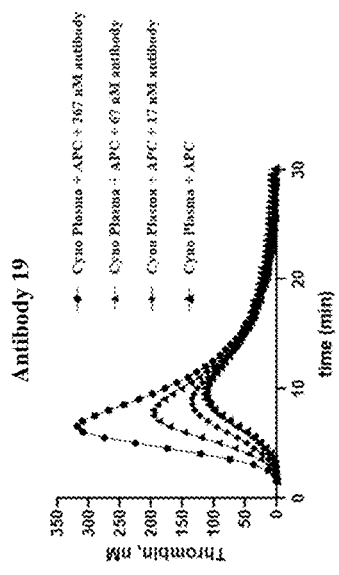
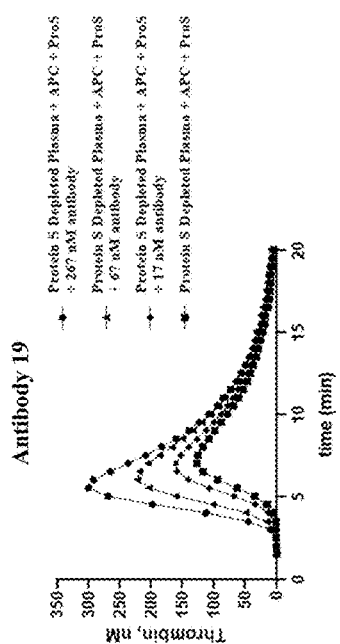
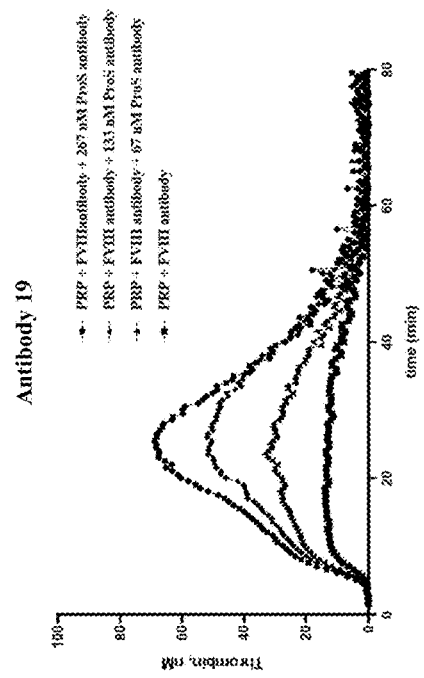
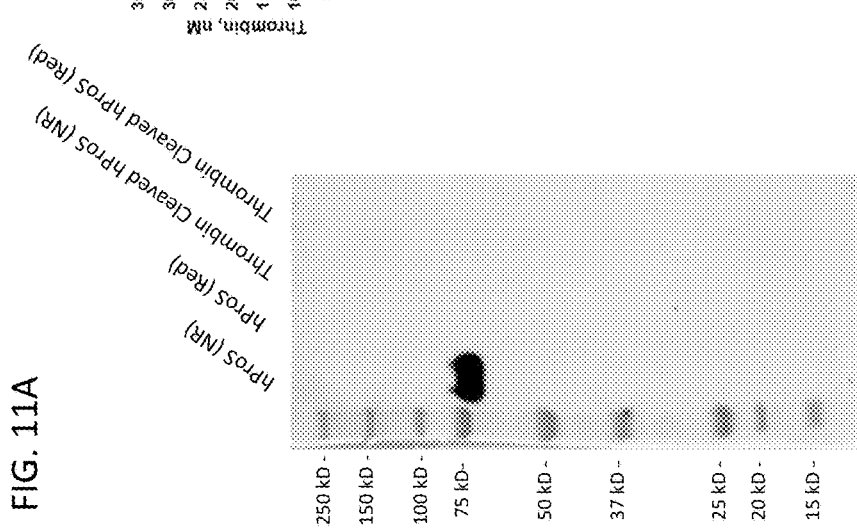
FIG. 11A
FIG. 11B
FIG. 11C
FIG. 11D

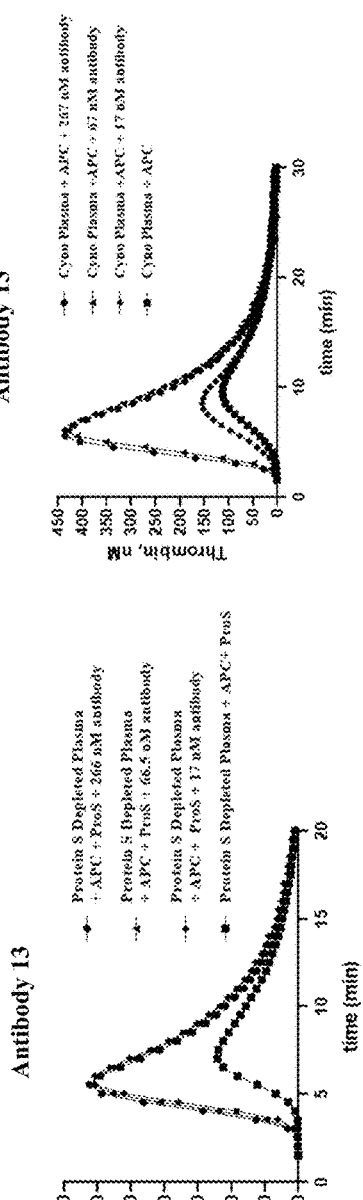
FIG. 12A
FIG. 12B
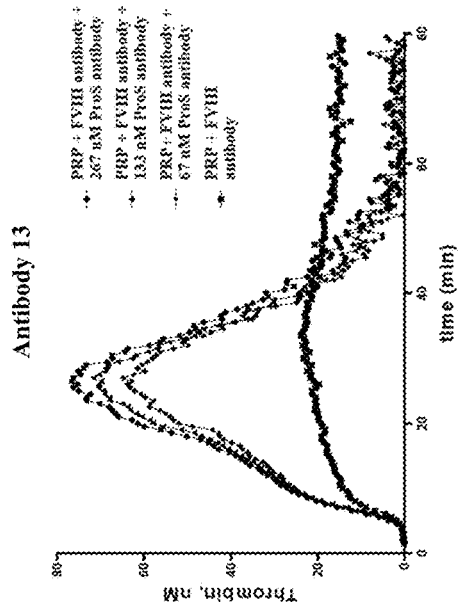
FIG. 12C
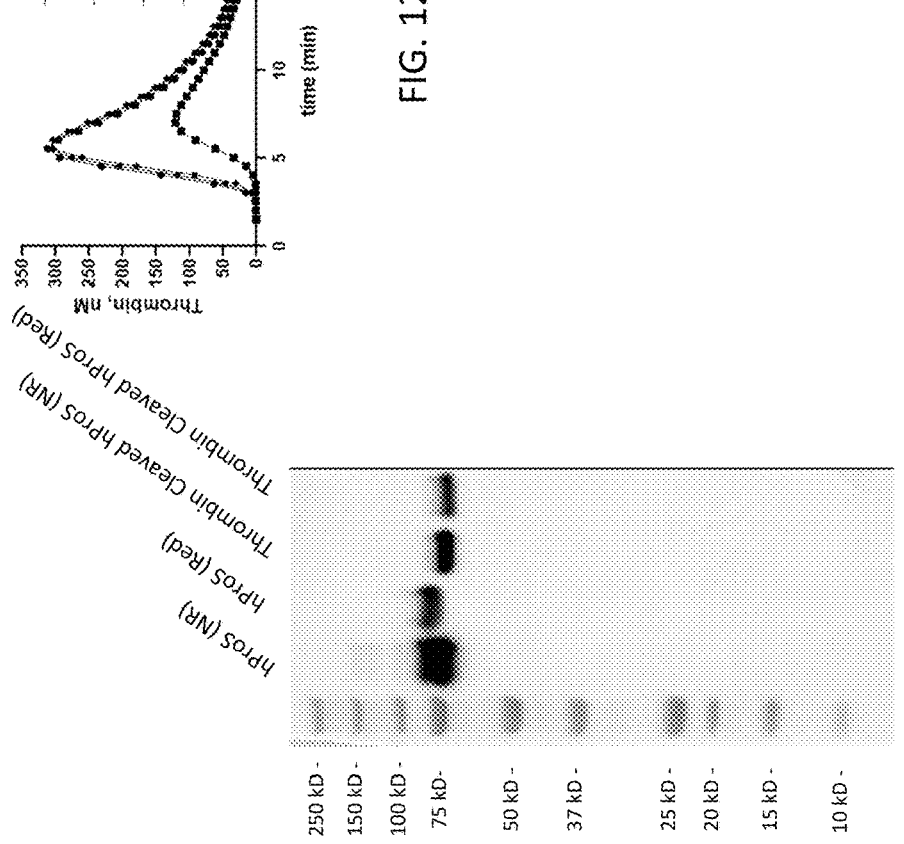
FIG. 12D

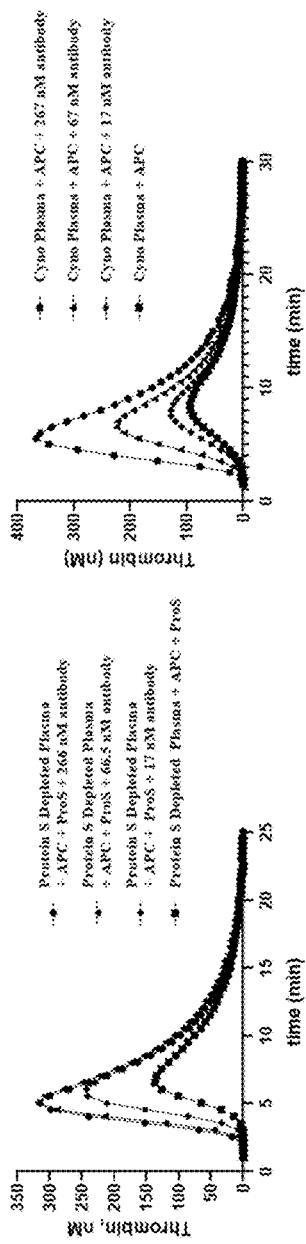
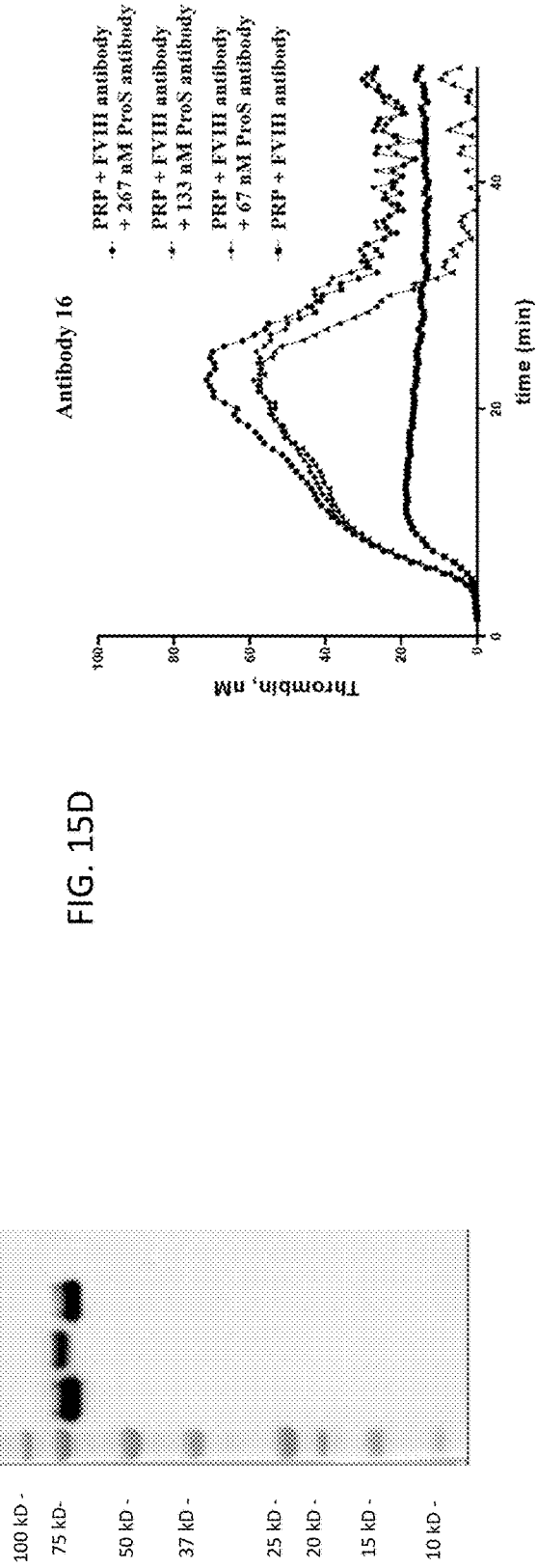
FIG. 15A
FIG. 15B
FIG. 15C
FIG. 15D

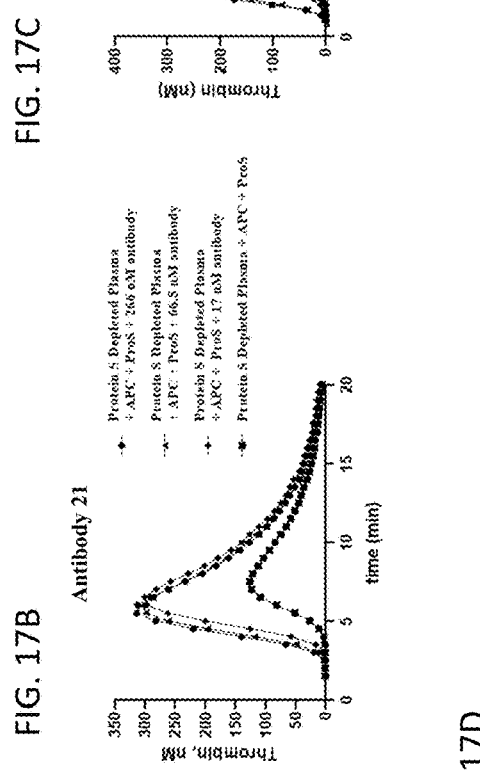
FIG. 17A
FIG. 17B
FIG. 17C
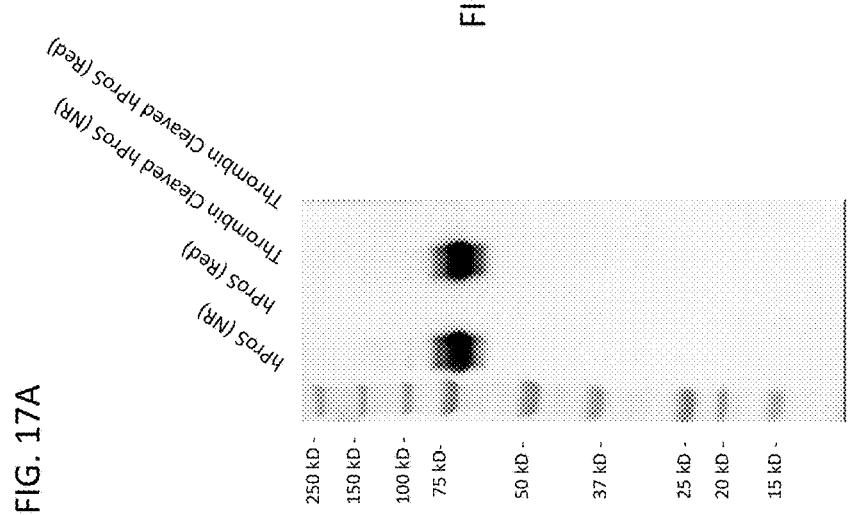
FIG. 17D

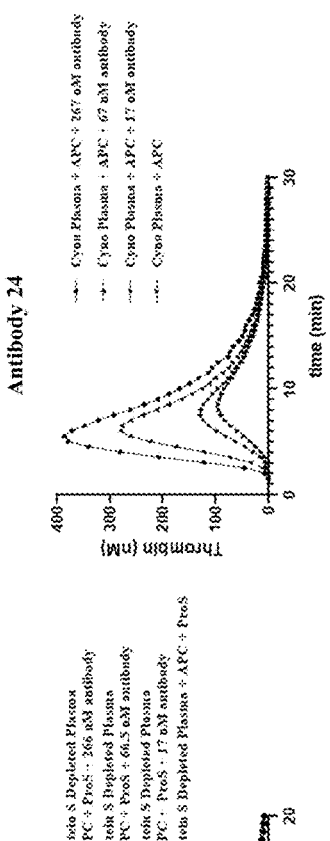
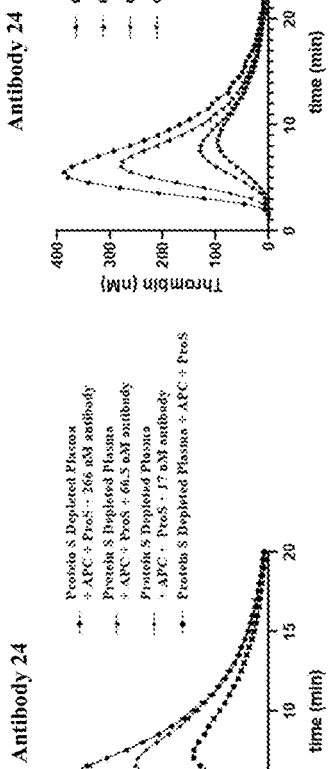
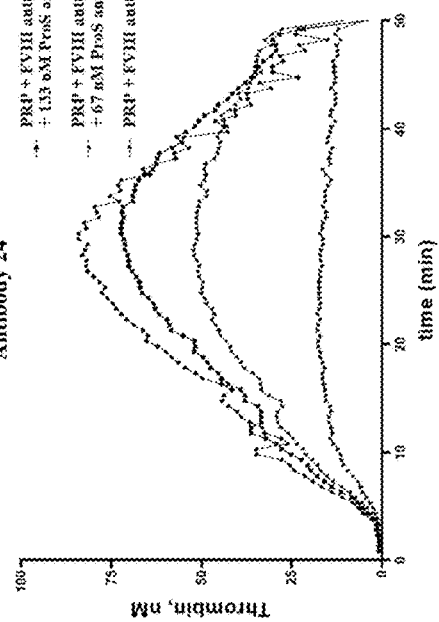
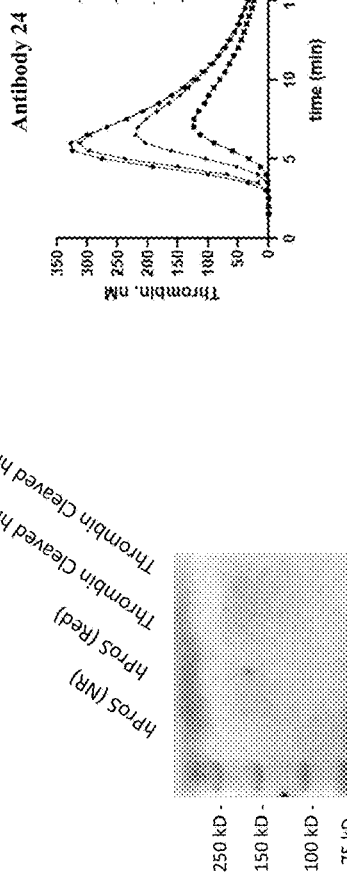
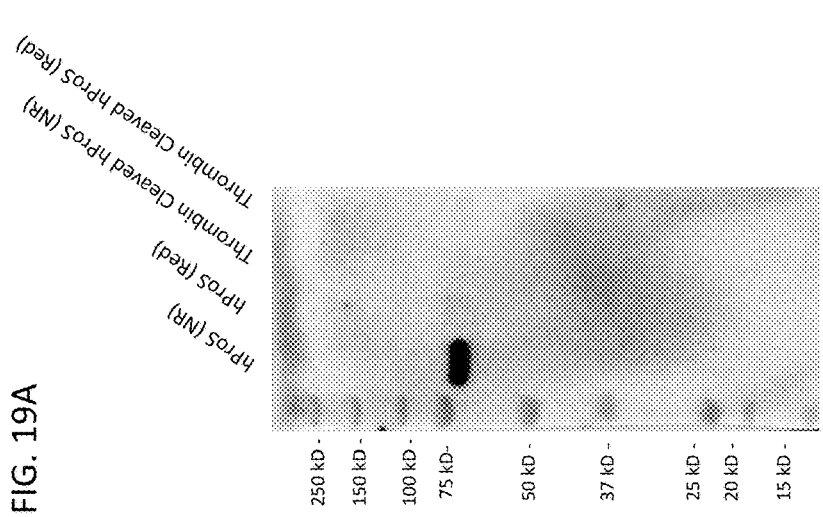
FIG. 19A
FIG. 19B
FIG. 19C
FIG. 19D

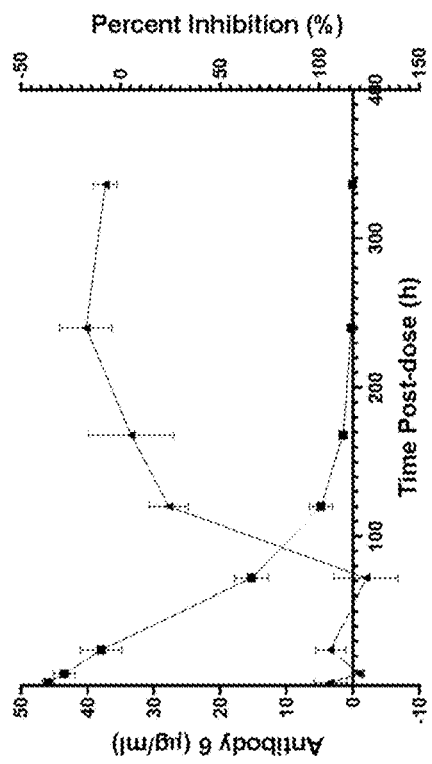
FIG. 28G
FIG. 28F
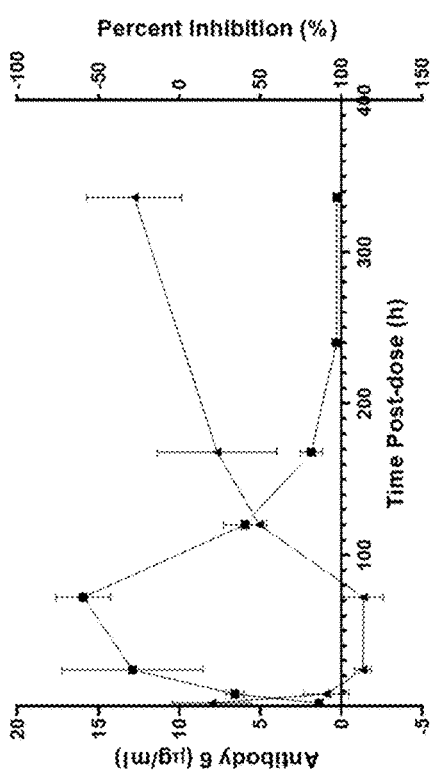
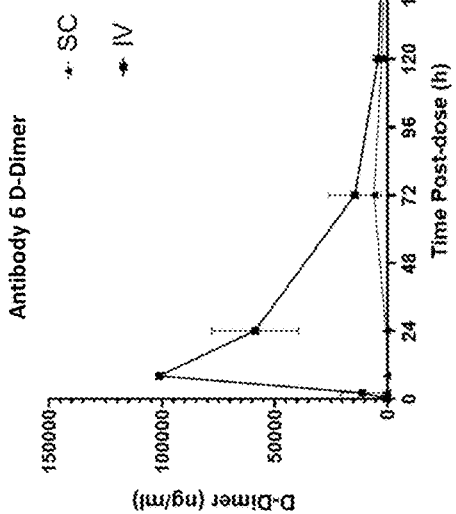
FIG. 28H

```
                           SEQUENCE LISTING

Sequence total quantity: 218
SEQ ID NO: 1           moltype = AA  length = 6
FEATURE                Location/Qualifiers
REGION                 1..6
                       note = Protein S antibody CDR-L1 sequence
source                 1..6
                       mol_type = protein
                       organism = synthetic construct
SEQUENCE: 1
KLGDKY                                                                    6

SEQ ID NO: 2           moltype = AA  length = 6
FEATURE                Location/Qualifiers
REGION                 1..6
                       note = Protein S antibody CDR-L1 sequence
source                 1..6
                       mol_type = protein
                       organism = synthetic construct
SEQUENCE: 2
SLRNYY                                                                    6

SEQ ID NO: 3           moltype = AA  length = 9
FEATURE                Location/Qualifiers
REGION                 1..9
                       note = Protein S antibody CDR-L1 sequence
source                 1..9
                       mol_type = protein
                       organism = synthetic construct
SEQUENCE: 3
SSDVGGYEF                                                                 9

SEQ ID NO: 4           moltype = AA  length = 6
FEATURE                Location/Qualifiers
REGION                 1..6
                       note = Protein S antibody CDR-L1 sequence
source                 1..6
                       mol_type = protein
```

```
SEQUENCE: 4
QSVSIY                                                                        6

SEQ ID NO: 5              moltype = AA   length = 6
FEATURE                   Location/Qualifiers
REGION                    1..6
                          note = Protein S antibody CDR-L1 sequence
source                    1..6
                          mol_type = protein
                          organism = synthetic construct
SEQUENCE: 5
QRINSN                                                                        6

SEQ ID NO: 6              moltype = AA   length = 11
FEATURE                   Location/Qualifiers
REGION                    1..11
                          note = Protein S antibody CDR-L1 sequence
source                    1..11
                          mol_type = protein
                          organism = synthetic construct
SEQUENCE: 6
QSLLHSNGYN Y                                                                 11

SEQ ID NO: 7              moltype =     length =
SEQUENCE: 7
000

SEQ ID NO: 8              moltype =     length =
SEQUENCE: 8
000

SEQ ID NO: 9              moltype = AA   length = 9
FEATURE                   Location/Qualifiers
REGION                    1..9
                          note = Protein S antibody CDR-L1 sequence
source                    1..9
                          mol_type = protein
                          organism = synthetic construct
SEQUENCE: 9
TGAVTASNY                                                                     9

SEQ ID NO: 10             moltype = AA   length = 6
FEATURE                   Location/Qualifiers
REGION                    1..6
                          note = Protein S antibody CDR-L1 sequence
source                    1..6
                          mol_type = protein
                          organism = synthetic construct
SEQUENCE: 10
QSVTSN                                                                        6

SEQ ID NO: 11             moltype = AA   length = 11
FEATURE                   Location/Qualifiers
REGION                    1..11
                          note = Protein S antibody CDR-L1 sequence
source                    1..11
                          mol_type = protein
                          organism = synthetic construct
SEQUENCE: 11
QSLVHSDGNT Y                                                                 11

SEQ ID NO: 12             moltype =     length =
SEQUENCE: 12
000

SEQ ID NO: 13             moltype =     length =
SEQUENCE: 13
000

SEQ ID NO: 14             moltype =     length =
SEQUENCE: 14
000

SEQ ID NO: 15             moltype =     length =
SEQUENCE: 15
000

SEQ ID NO: 16             moltype =     length =
```

```
SEQUENCE: 16
000

SEQ ID NO: 17            moltype =   length =
SEQUENCE: 17
000

SEQ ID NO: 18            moltype =   length =
SEQUENCE: 18
000

SEQ ID NO: 19            moltype =   length =
SEQUENCE: 19
000

SEQ ID NO: 20            moltype =   length =
SEQUENCE: 20
000

SEQ ID NO: 21            moltype = AA   length = 9
FEATURE                  Location/Qualifiers
REGION                   1..9
                         note = Protein S antibody CDR-L3 sequence
source                   1..9
                         mol_type = protein
                         organism = synthetic construct
SEQUENCE: 21
QAWDSNTVV                                                                  9

SEQ ID NO: 22            moltype = AA   length = 11
FEATURE                  Location/Qualifiers
REGION                   1..11
                         note = Protein S antibody CDR-L3 sequence
source                   1..11
                         mol_type = protein
                         organism = synthetic construct
SEQUENCE: 22
NSRDSSGNHV V                                                              11

SEQ ID NO: 23            moltype = AA   length = 10
FEATURE                  Location/Qualifiers
REGION                   1..10
                         note = Protein S antibody CDR-L3 sequence
source                   1..10
                         mol_type = protein
                         organism = synthetic construct
SEQUENCE: 23
SSYTRSSTVV                                                                10

SEQ ID NO: 24            moltype = AA   length = 9
FEATURE                  Location/Qualifiers
REGION                   1..9
                         note = Protein S antibody CDR-L3 sequence
source                   1..9
                         mol_type = protein
                         organism = synthetic construct
SEQUENCE: 24
QAWDSSTWV                                                                  9

SEQ ID NO: 25            moltype = AA   length = 9
FEATURE                  Location/Qualifiers
REGION                   1..9
                         note = Protein S antibody CDR-L3 sequence
source                   1..9
                         mol_type = protein
                         organism = synthetic construct
SEQUENCE: 25
QQRSNWPLT                                                                  9

SEQ ID NO: 26            moltype = AA   length = 9
FEATURE                  Location/Qualifiers
REGION                   1..9
                         note = Protein S antibody CDR-L3 sequence
source                   1..9
                         mol_type = protein
                         organism = synthetic construct
SEQUENCE: 26
QQYDNWPLT                                                                  9
```

```
SEQ ID NO: 27            moltype = AA   length = 8
FEATURE                  Location/Qualifiers
REGION                   1..8
                         note = Protein S antibody CDR-L3 sequence
source                   1..8
                         mol_type = protein
                         organism = synthetic construct
SEQUENCE: 27
MQALQTFT                                                                    8

SEQ ID NO: 28            moltype =     length =
SEQUENCE: 28
000

SEQ ID NO: 29            moltype =     length =
SEQUENCE: 29
000

SEQ ID NO: 30            moltype = AA   length = 9
FEATURE                  Location/Qualifiers
REGION                   1..9
                         note = Protein S antibody CDR-L3 sequence
source                   1..9
                         mol_type = protein
                         organism = synthetic construct
SEQUENCE: 30
ALWYSDHFV                                                                   9

SEQ ID NO: 31            moltype = AA   length = 8
FEATURE                  Location/Qualifiers
REGION                   1..8
                         note = Protein S antibody CDR-L3 sequence
source                   1..8
                         mol_type = protein
                         organism = synthetic construct
SEQUENCE: 31
QQYNNWPT                                                                    8

SEQ ID NO: 32            moltype = AA   length = 10
FEATURE                  Location/Qualifiers
REGION                   1..10
                         note = Protein S antibody CDR-L3 sequence
source                   1..10
                         mol_type = protein
                         organism = synthetic construct
SEQUENCE: 32
MQATQFPHLT                                                                 10

SEQ ID NO: 33            moltype = AA   length = 10
FEATURE                  Location/Qualifiers
REGION                   1..10
                         note = Protein S antibody CDR-H1 sequence
source                   1..10
                         mol_type = protein
                         organism = synthetic construct
SEQUENCE: 33
GGSISSSSYY                                                                 10

SEQ ID NO: 34            moltype = AA   length = 8
FEATURE                  Location/Qualifiers
REGION                   1..8
                         note = Protein S antibody CDR-H1 sequence
source                   1..8
                         mol_type = protein
                         organism = synthetic construct
SEQUENCE: 34
GGTFSSYS                                                                    8

SEQ ID NO: 35            moltype = AA   length = 10
FEATURE                  Location/Qualifiers
REGION                   1..10
                         note = Protein S antibody CDR-H1 sequence
source                   1..10
                         mol_type = protein
                         organism = synthetic construct
SEQUENCE: 35
GGSITSDGYH                                                                 10

SEQ ID NO: 36            moltype = AA   length = 8
```

-continued

```
FEATURE                 Location/Qualifiers
REGION                  1..8
                        note = Protein S antibody CDR-H1 sequence
source                  1..8
                        mol_type = protein
                        organism = synthetic construct
SEQUENCE: 36
GFTFDDYA                                                                  8

SEQ ID NO: 37           moltype = AA  length = 8
FEATURE                 Location/Qualifiers
REGION                  1..8
                        note = Protein S antibody CDR-H1 sequence
source                  1..8
                        mol_type = protein
                        organism = synthetic construct
SEQUENCE: 37
GFTFSTYG                                                                  8

SEQ ID NO: 38           moltype = AA  length = 9
FEATURE                 Location/Qualifiers
REGION                  1..9
                        note = Protein S antibody CDR-H1 sequence
source                  1..9
                        mol_type = protein
                        organism = synthetic construct
SEQUENCE: 38
GYSISSGYY                                                                 9

SEQ ID NO: 39           moltype = AA  length = 8
FEATURE                 Location/Qualifiers
REGION                  1..8
                        note = Protein S antibody CDR-H1 sequence
source                  1..8
                        mol_type = protein
                        organism = synthetic construct
SEQUENCE: 39
GDTFSNHA                                                                  8

SEQ ID NO: 40           moltype =     length =
SEQUENCE: 40
000

SEQ ID NO: 41           moltype =     length =
SEQUENCE: 41
000

SEQ ID NO: 42           moltype = AA  length = 8
FEATURE                 Location/Qualifiers
REGION                  1..8
                        note = Protein S antibody CDR-H1 sequence
source                  1..8
                        mol_type = protein
                        organism = synthetic construct
SEQUENCE: 42
GHTFTGYY                                                                  8

SEQ ID NO: 43           moltype = AA  length = 9
FEATURE                 Location/Qualifiers
REGION                  1..9
                        note = Protein S antibody CDR-H1 sequence
source                  1..9
                        mol_type = protein
                        organism = synthetic construct
SEQUENCE: 43
GGSISSTNW                                                                 9

SEQ ID NO: 44           moltype = AA  length = 8
FEATURE                 Location/Qualifiers
REGION                  1..8
                        note = Protein S antibody CDR-H1 sequence
source                  1..8
                        mol_type = protein
                        organism = synthetic construct
SEQUENCE: 44
GGSISNYY                                                                  8

SEQ ID NO: 45           moltype = AA  length = 7
FEATURE                 Location/Qualifiers
```

```
                        REGION              1..7
                                            note = Protein S antibody CDR-H2 sequence
                        source              1..7
                                            mol_type = protein
                                            organism = synthetic construct
SEQUENCE: 45
IYYSGNT                                                                                     7

SEQ ID NO: 46           moltype = AA  length = 8
FEATURE                 Location/Qualifiers
REGION                  1..8
                        note = Protein S antibody CDR-H2 sequence
source                  1..8
                        mol_type = protein
                        organism = synthetic construct
SEQUENCE: 46
IIPIFGTT                                                                                    8

SEQ ID NO: 47           moltype = AA  length = 7
FEATURE                 Location/Qualifiers
REGION                  1..7
                        note = Protein S antibody CDR-H2 sequence
source                  1..7
                        mol_type = protein
                        organism = synthetic construct
SEQUENCE: 47
IYYTGNT                                                                                     7

SEQ ID NO: 48           moltype = AA  length = 8
FEATURE                 Location/Qualifiers
REGION                  1..8
                        note = Protein S antibody CDR-H2 sequence
source                  1..8
                        mol_type = protein
                        organism = synthetic construct
SEQUENCE: 48
ITWNSGNI                                                                                    8

SEQ ID NO: 49           moltype = AA  length = 8
FEATURE                 Location/Qualifiers
REGION                  1..8
                        note = Protein S antibody CDR-H2 sequence
source                  1..8
                        mol_type = protein
                        organism = synthetic construct
SEQUENCE: 49
IYYDGINK                                                                                    8

SEQ ID NO: 50           moltype = AA  length = 7
FEATURE                 Location/Qualifiers
REGION                  1..7
                        note = Protein S antibody CDR-H2 sequence
source                  1..7
                        mol_type = protein
                        organism = synthetic construct
SEQUENCE: 50
IYYSGST                                                                                     7

SEQ ID NO: 51           moltype = AA  length = 8
FEATURE                 Location/Qualifiers
REGION                  1..8
                        note = Protein S antibody CDR-H2 sequence
source                  1..8
                        mol_type = protein
                        organism = synthetic construct
SEQUENCE: 51
YIPIFGTT                                                                                    8

SEQ ID NO: 52           moltype =    length =
SEQUENCE: 52
000

SEQ ID NO: 53           moltype =    length =
SEQUENCE: 53
000

SEQ ID NO: 54           moltype = AA  length = 8
FEATURE                 Location/Qualifiers
REGION                  1..8
```

```
                              note = Protein S antibody CDR-H2 sequence
source                        1..8
                              mol_type = protein
                              organism = synthetic construct
SEQUENCE: 54
INPNSGDT                                                                    8

SEQ ID NO: 55                 moltype = AA  length = 7
FEATURE                       Location/Qualifiers
REGION                        1..7
                              note = Protein S antibody CDR-H2 sequence
source                        1..7
                              mol_type = protein
                              organism = synthetic construct
SEQUENCE: 55
IYQTGST                                                                     7

SEQ ID NO: 56                 moltype = AA  length = 7
FEATURE                       Location/Qualifiers
REGION                        1..7
                              note = Protein S antibody CDR-H2 sequence
source                        1..7
                              mol_type = protein
                              organism = synthetic construct
SEQUENCE: 56
IYYIGIT                                                                     7

SEQ ID NO: 57                 moltype = AA  length = 17
FEATURE                       Location/Qualifiers
REGION                        1..17
                              note = Protein S antibody CDR-H3 sequence
source                        1..17
                              mol_type = protein
                              organism = synthetic construct
SEQUENCE: 57
ARCSGYGYSS GRSYFDY                                                         17

SEQ ID NO: 58                 moltype = AA  length = 11
FEATURE                       Location/Qualifiers
REGION                        1..11
                              note = Protein S antibody CDR-H3 sequence
source                        1..11
                              mol_type = protein
                              organism = synthetic construct
SEQUENCE: 58
EGGRVGADFD Y                                                               11

SEQ ID NO: 59                 moltype = AA  length = 12
FEATURE                       Location/Qualifiers
REGION                        1..12
                              note = Protein S antibody CDR-H3 sequence
source                        1..12
                              mol_type = protein
                              organism = synthetic construct
SEQUENCE: 59
ARRLSTGPYF DY                                                              12

SEQ ID NO: 60                 moltype = AA  length = 12
FEATURE                       Location/Qualifiers
REGION                        1..12
                              note = Protein S antibody CDR-H3 sequence
source                        1..12
                              mol_type = protein
                              organism = synthetic construct
SEQUENCE: 60
AKGRAVSDTF DI                                                              12

SEQ ID NO: 61                 moltype = AA  length = 7
FEATURE                       Location/Qualifiers
REGION                        1..7
                              note = Protein S antibody CDR-H3 sequence
source                        1..7
                              mol_type = protein
                              organism = synthetic construct
SEQUENCE: 61
AESDLDY                                                                     7

SEQ ID NO: 62                 moltype = AA  length = 18
FEATURE                       Location/Qualifiers
```

```
REGION                  1..18
                        note = Protein S antibody CDR-H3 sequence
source                  1..18
                        mol_type = protein
                        organism = synthetic construct
SEQUENCE: 62
ATTYSDIVTG YYNDAFDI                                                      18

SEQ ID NO: 63           moltype = AA  length = 20
FEATURE                 Location/Qualifiers
REGION                  1..20
                        note = Protein S antibody CDR-H3 sequence
source                  1..20
                        mol_type = protein
                        organism = synthetic construct
SEQUENCE: 63
ARGGLAGSHY KNYYYDGMDV                                                    20

SEQ ID NO: 64           moltype =   length =
SEQUENCE: 64
000

SEQ ID NO: 65           moltype =   length =
SEQUENCE: 65
000

SEQ ID NO: 66           moltype = AA  length = 14
FEATURE                 Location/Qualifiers
REGION                  1..14
                        note = Protein S antibody CDR-H3 sequence
source                  1..14
                        mol_type = protein
                        organism = synthetic construct
SEQUENCE: 66
ARDSQILWFG ELGY                                                          14

SEQ ID NO: 67           moltype = AA  length = 9
FEATURE                 Location/Qualifiers
REGION                  1..9
                        note = Protein S antibody CDR-H3 sequence
source                  1..9
                        mol_type = protein
                        organism = synthetic construct
SEQUENCE: 67
ARRFGELDY                                                                 9

SEQ ID NO: 68           moltype = AA  length = 11
FEATURE                 Location/Qualifiers
REGION                  1..11
                        note = Protein S antibody CDR-H3 sequence
source                  1..11
                        mol_type = protein
                        organism = synthetic construct
SEQUENCE: 68
AALSGDHAFD I                                                             11

SEQ ID NO: 69           moltype = AA  length = 106
FEATURE                 Location/Qualifiers
REGION                  1..106
                        note = Protein S monoclonal antibody variable light chain
                         sequence
source                  1..106
                        mol_type = protein
                        organism = synthetic construct
SEQUENCE: 69
SYELTQPPSV SVSPGQTASI TCSGDKLGDK YACWYQQKPG QSPVLVIYQD TKRPSGIPER         60
FSGSNSGNTA TLTISGTQAM DEADYYCQAW DSNTVVFGGG TKLTVL                       106

SEQ ID NO: 70           moltype = AA  length = 125
FEATURE                 Location/Qualifiers
REGION                  1..125
                        note = Protein S monoclonal antibody variable heavy chain
                         sequence
source                  1..125
                        mol_type = protein
                        organism = synthetic construct
SEQUENCE: 70
QLQLQESGPG LVKPSETLSL TCTVSGGSIS SSSYYWGWIR QPPGKGLEWI GNIYYSGNTY         60
YNPSLKSRVT ISVDTSKNQF SLKLSSMTAA DTAVYYCARC SGYGYSSGRS YFDYWGQETL        120
```

```
VTVSS                                                                   125

SEQ ID NO: 71           moltype = AA  length = 108
FEATURE                 Location/Qualifiers
REGION                  1..108
                        note = Protein S monoclonal antibody variable light chain
                          sequence
source                  1..108
                        mol_type = protein
                        organism = synthetic construct
SEQUENCE: 71
SSDLTQGPAV SVALGQTVRI TCQGDSLRNY YASWYQQKPG QAPVPVIYGK NDRPSGIPDR   60
FSGSISGNTA SLTITGAQAE DEAHYYCNSR DSSGNHVVFG GGTKLTVL               108

SEQ ID NO: 72           moltype = AA  length = 118
FEATURE                 Location/Qualifiers
REGION                  1..118
                        note = Protein S monoclonal antibody variable heavy chain
                          sequence
source                  1..118
                        mol_type = protein
                        organism = synthetic construct
SEQUENCE: 72
QVQLVQSGAE VKKPGSSVKV SCKVSGGTFS SYSISWVRQA PGQGLEWMGG IIPIFGTTNY   60
AQKFQGRVTI TADESTSTAY MDLSSLKSED TAMYYCEGGR VGADFDYWGQ GTLVTVSS   118

SEQ ID NO: 73           moltype = AA  length = 110
FEATURE                 Location/Qualifiers
REGION                  1..110
                        note = Protein S monoclonal antibody variable light chain
                          sequence
source                  1..110
                        mol_type = protein
                        organism = synthetic construct
SEQUENCE: 73
QSALTQPASV SGSPGQSITI SCTGTSSDVG GYEFVSWYQH HPGKAPKLMI YDVSSRPSGV   60
SNRFSGSKSG NTASLTISGL QAEDEADYYC SSYTRSSTVV FGGGARLTVL             110

SEQ ID NO: 74           moltype = AA  length = 120
FEATURE                 Location/Qualifiers
REGION                  1..120
                        note = Protein S monoclonal antibody variable heavy chain
                          sequence
source                  1..120
                        mol_type = protein
                        organism = synthetic construct
SEQUENCE: 74
QVQLQESGPG LVKPSQTLSL TCTVSGGSIT SDGYHWSWIR QYPGKGLDWI GYIYYTGNTY   60
YNPSLKSRVT ISVGTSQNQF SLKLISVTAA DTAVYYCARR LSTGPYFDYW GQGTLVTVSS 120

SEQ ID NO: 75           moltype = AA  length = 106
FEATURE                 Location/Qualifiers
REGION                  1..106
                        note = Protein S monoclonal antibody variable light chain
                          sequence
source                  1..106
                        mol_type = protein
                        organism = synthetic construct
SEQUENCE: 75
SYELNQPPSV SVSPGQTASI TCSGDKLGDK YASWYQQKPG QSPVVAIYQN SKRPSGIPER   60
FSASNSGNTA TLTISGTQAL DEADYYCQAW DSSTWVFGGG TKLTVL                 106

SEQ ID NO: 76           moltype = AA  length = 119
FEATURE                 Location/Qualifiers
REGION                  1..119
                        note = Protein S monoclonal antibody variable heavy chain
                          sequence
source                  1..119
                        mol_type = protein
                        organism = synthetic construct
SEQUENCE: 76
EVQLVESGGG LVQPGRSLRL SCAASGFTFD DYAMHWVRQA PGKGLEWVSG ITWNSGNIGY   60
ADSVKGRFTI SRDNAKNSLY LHMNSLRIED TAFYYCAKGR AVSDTFDIWG QGTMVTVSS  119

SEQ ID NO: 77           moltype = AA  length = 107
FEATURE                 Location/Qualifiers
REGION                  1..107
                        note = Protein S monoclonal antibody variable light chain
                          sequence
```

```
source                  1..107
                        mol_type = protein
                        organism = synthetic construct
SEQUENCE: 77
EIVLTQSPAT LSLSPGERAT LSCRASQSVS IYLAWYQQKP GQAPRLLIYD ASNRATGIPA    60
RFSGSGSGTD FTLTISSLEP EDFAVYYCQQ RSNWPLTFGP GTKVDIK                 107

SEQ ID NO: 78           moltype = AA  length = 114
FEATURE                 Location/Qualifiers
REGION                  1..114
                        note = Protein S monoclonal antibody variable heavy chain
                          sequence
source                  1..114
                        mol_type = protein
                        organism = synthetic construct
SEQUENCE: 78
QVQLVESGGG VVQPGRSLRL SCAASGFTFS TYGFHWVRQP PGKGLEWVAV IYYDGINKYY    60
ADSVKGRFTI SRDNSKNTLF LQMNSLRAED TAVYYCAESD LDYWGQGTLV TVSS         114

SEQ ID NO: 79           moltype = AA  length = 107
FEATURE                 Location/Qualifiers
REGION                  1..107
                        note = Protein S monoclonal antibody variable light chain
                          sequence
source                  1..107
                        mol_type = protein
                        organism = synthetic construct
SEQUENCE: 79
EIVMTQSPAT LSVSPGERAT LSCRASQRIN SNLAWYQQKP GQAPRLLIYG ASTRATGIPA    60
RFSGSGSGTE FTLTISSLQS EDFAAYYCQQ YDNWPLTFGG GTKVEIK                 107

SEQ ID NO: 80           moltype = AA  length = 125
FEATURE                 Location/Qualifiers
REGION                  1..125
                        note = Protein S monoclonal antibody variable heavy chain
                          sequence
source                  1..125
                        mol_type = protein
                        organism = synthetic construct
SEQUENCE: 80
QVQLQESGPG LVKPSETLSL TCAVSGYSIS SGYYWGWIRQ PPGKGLDWIG SIYYSGSTYY    60
NPSLKSRVTI SVDTSKNQIS LKLSSVTAAD TAVYYCATTY SDIVTGYYND AFDIWGQGTM   120
VTVSS                                                               125

SEQ ID NO: 81           moltype = AA  length = 111
FEATURE                 Location/Qualifiers
REGION                  1..111
                        note = Protein S monoclonal antibody variable light chain
                          sequence
source                  1..111
                        mol_type = protein
                        organism = synthetic construct
SEQUENCE: 81
DIVMTQSPLS LPVTPGEPAS ISCRSSQSLL HSNGYNYLDW YLQKPGQSPQ LLIYLGSNRA    60
SGVPDRFSGS GSGTDFTLKI SRVEAEDVGV YYCMQALQTF TFGPGTKVDI K            111

SEQ ID NO: 82           moltype = AA  length = 127
FEATURE                 Location/Qualifiers
REGION                  1..127
                        note = Protein S monoclonal antibody variable heavy chain
                          sequence
source                  1..127
                        mol_type = protein
                        organism = synthetic construct
SEQUENCE: 82
QVQLVQSGAE VKKPGSSVKV SCKASGDTFS NHAINWVRQA PGQGLEWMGG YIPIFGTTNS    60
AQKFRGRVTI TADKSTNTAY MALSSLRSED TAVYYCARGG LAGSHYKNYY YDGMDVWGQG   120
TTVTVSS                                                             127

SEQ ID NO: 83           moltype =    length =
SEQUENCE: 83
000

SEQ ID NO: 84           moltype =    length =
SEQUENCE: 84
000

SEQ ID NO: 85           moltype =    length =
SEQUENCE: 85
```

```
SEQ ID NO: 86          moltype =    length =
SEQUENCE: 86
000

SEQ ID NO: 87          moltype = AA   length = 109
FEATURE                Location/Qualifiers
REGION                 1..109
                       note = Protein S monoclonal antibody variable light chain
                         sequence
source                 1..109
                       mol_type = protein
                       organism = synthetic construct
SEQUENCE: 87
QAVVTQESAL TTSPGETVTL TCRSSTGAVT ASNYANWVQE KPDHLFTGLI GSTNNRAPGV    60
PARFSGSLIG DKAALTITGA QTEDEAIYFC ALWYSDHFVF GGGTKLTVL               109

SEQ ID NO: 88          moltype = AA   length = 121
FEATURE                Location/Qualifiers
REGION                 1..121
                       note = Protein S monoclonal antibody variable heavy chain
                         sequence
source                 1..121
                       mol_type = protein
                       organism = synthetic construct
SEQUENCE: 88
QVQLVQSGAE VKKPGASVKV SCKSSGHTFT GYYMHWVRQA PGQGLEWMGW INPNSGDTNY    60
AQKFQGRVTM TRDTSISTAY MEMSRLRSDD TAVYYCARDS QILWFGELGY WGQGTLVTVS   120
S                                                                  121

SEQ ID NO: 89          moltype = AA   length = 106
FEATURE                Location/Qualifiers
REGION                 1..106
                       note = Protein S monoclonal antibody variable light chain
                         sequence
source                 1..106
                       mol_type = protein
                       organism = synthetic construct
SEQUENCE: 89
EIVMTQSPAT LSVSPGERAT LSCRASQSVT SNLAWYQQKP GQAPRLLIYD ASTRATGIPA    60
RFSGSGSGTE FTLTISSLQS EDFAIYYCQQ YNNWPTFGQG TRLEIK                 106

SEQ ID NO: 90          moltype = AA   length = 116
FEATURE                Location/Qualifiers
REGION                 1..116
                       note = Protein S monoclonal antibody variable heavy chain
                         sequence
source                 1..116
                       mol_type = protein
                       organism = synthetic construct
SEQUENCE: 90
QVQLQESGPG LVKPSETLSL TCGVSGGSIS STNWWSWVRQ PPGKGLEWIG EIYQTGSTDY    60
DPSLKSRVTI SIDKSKNQFS LKLYSVTAAD TAVYYCARRF GELDYWGQGT LVTVSS      116

SEQ ID NO: 91          moltype = AA   length = 113
FEATURE                Location/Qualifiers
REGION                 1..113
                       note = Protein S monoclonal antibody variable light chain
                         sequence
source                 1..113
                       mol_type = protein
                       organism = synthetic construct
SEQUENCE: 91
DIVMTQTPLS SPVTLGQPAS ISCRSSQSLV HSDGNTYLSW LQQRPGQPPR LLIYKISNRF    60
SGVPDRFSGS GAGTDFTLKI SRVEAEDVGV YYCMQATQFP HLTFGGGTKV EIK         113

SEQ ID NO: 92          moltype = AA   length = 117
FEATURE                Location/Qualifiers
REGION                 1..117
                       note = Protein S monoclonal antibody variable heavy chain
                         sequence
source                 1..117
                       mol_type = protein
                       organism = synthetic construct
SEQUENCE: 92
QVQLQESGPG LVKPSETLSL TCTVSGGSIS NYYWNWIRQP PGKGLEWIGY IYYIGITDYN    60
PSLKSRVTIS VDTSKNQFSL KVTSVTAADT AVYYCAALSG DHAFDIWGQG TLVTVSS     117
```

```
SEQ ID NO: 93            moltype = DNA  length = 318
FEATURE                  Location/Qualifiers
misc_feature             1..318
                         note = Protein S monoclonal antibody variable light chain
                         sequence
source                   1..318
                         mol_type = other DNA
                         organism = synthetic construct
SEQUENCE: 93
tcctatgagc tgactcagcc accctcagtg tccgtgtccc caggacagac agccagcatc   60
acctgctctg gagatataaatt ggggataaa tatgcttgct ggtatcagca gaagccaggc  120
cagtcccctg tactggtcat ctatcaagat actaagcggc cctcaggat ccctgagcga   180
ttctctggct ccaactctgg gaacacagcc actctgacca tcagcgggac ccaggctatg   240
gatgaggctg actattactg tcaggcgtgg gacagcaaca ctgtggtctt cggcggaggg   300
accaagctga ccgtccta                                                 318

SEQ ID NO: 94            moltype = DNA  length = 375
FEATURE                  Location/Qualifiers
misc_feature             1..375
                         note = Protein S monoclonal antibody variable heavy chain
                         sequence
source                   1..375
                         mol_type = other DNA
                         organism = synthetic construct
SEQUENCE: 94
cagctgcagc tgcaggagtc gggcccagga ctggtgaagc cttcggagac cctgtccctc    60
acctgcactg tctctggtgg ctccatcagc agtagtagtt actactgggg ctggatccgc   120
cagcccccgg ggaagggact ggagtggatt gggaatatct attatagtgg gaacacctac   180
tacaacccgt ccctcaagag tcgagtcacc atatccgtag acacgtccaa gaaccagttc   240
tccctgaagc tgagctctat gaccgccgca gacacggctg tgtattactg tgcgagatgt   300
agtggctacg gtatagcag tggccggtcc tactttgact actggggcca ggaaaccctg    360
gtcaccgtct cctca                                                    375

SEQ ID NO: 95            moltype = DNA  length = 324
FEATURE                  Location/Qualifiers
misc_feature             1..324
                         note = Protein S monoclonal antibody variable light chain
                         sequence
source                   1..324
                         mol_type = other DNA
                         organism = synthetic construct
SEQUENCE: 95
tcctctgacc tgactcaggg ccctgctgtg tctgtggccc tgggacagac agtcaggatc    60
acatgccaag agacagcct cagaaactat tatgcaagct ggtaccagca gaagccagga   120
caggcccctg tacctgtcat ctatggtaaa aacgaccggc cctcaggat cccagaccga    180
ttctctggct ccatctcagg aaacacagct tccttgacca tcactggggc tcaggcgaa   240
gatgaggctc actattactg taactcccgg gacagcagtg taaccatgt ggtattcggc    300
ggagggacca agctgaccgt cctg                                          324

SEQ ID NO: 96            moltype = DNA  length = 354
FEATURE                  Location/Qualifiers
misc_feature             1..354
                         note = Protein S monoclonal antibody variable heavy chain
                         sequence
source                   1..354
                         mol_type = other DNA
                         organism = synthetic construct
SEQUENCE: 96
caggtgcagc tggtgcagtc tggggctgag gtgaagaagc ctgggtcctc ggtgaaggtc    60
tcctgcaagg tttctggagg caccttcagc agctattcta tcagctgggt gcgacaggcc   120
cctggacaag gcttgagtg gatgggaggg atcatcccta tatttggtac aacaaactac   180
gcacagaagt tccagggcag agtcacgatc accgcggacg aatccacgag cacagcctac   240
atggatctga gcagcctgaa atctgaggac acggccatgt attactgtga gggggtaga   300
gtgggagcgg actttgacta ctggggccag ggaaccctgg tcaccgtctc ctca          354

SEQ ID NO: 97            moltype = DNA  length = 330
FEATURE                  Location/Qualifiers
misc_feature             1..330
                         note = Protein S monoclonal antibody variable light chain
                         sequence
source                   1..330
                         mol_type = other DNA
                         organism = synthetic construct
SEQUENCE: 97
cagtctgccc tgactcagcc tgcctccgtg tctgggtctc ctggacagtc gatcaccatc    60
tcctgcactg gaaccagcag tgacgttggt ggttatgaat ttgtctcctg gtaccaacat   120
cacccaggca aagcccccaa actcatgatt tatgatgtca gtagtcggcc ctcagggtt   180
tctaatcgct tctctggctc caagtctggc aacacggcct ccctgaccat ctctgggctc   240
caggctgagg acgaggctga ttattactgc agctcatata cgcgcagcag cactgtggtg   300
```

```
ttcggcggcg gggccaggct gaccgtccta                               330
```

SEQ ID NO: 98          moltype = DNA   length = 360
FEATURE                Location/Qualifiers
misc_feature           1..360
                       note = Protein S monoclonal antibody variable heavy chain
                         sequence
source                 1..360
                       mol_type = other DNA
                       organism = synthetic construct
SEQUENCE: 98
```
caggtgcagc tgcaggagtc gggcccagga ctggtgaagc cttcacagac cctgtccctc  60
acctgcactg tctctggtgg ctccatcacc agtgatggtt accactggag ctggatccgc 120
cagtacccag ggaagggcct ggactggatt ggatacatct attacactgg gaacacctac 180
tacaacccgt ccctcaagag tcgagtgacc atatcagtag acacgtctca gaaccagttc 240
tccctgaagc tgatctctgt gactgccgcg gacacggccg tttattactg tgcgagaagg 300
ctgtcgactg ggccctactt tgactactgg ggccagggaa ccctggtcac cgtctcctcc 360
```

SEQ ID NO: 99          moltype = DNA   length = 318
FEATURE                Location/Qualifiers
misc_feature           1..318
                       note = Protein S monoclonal antibody variable light chain
                         sequence
source                 1..318
                       mol_type = other DNA
                       organism = synthetic construct
SEQUENCE: 99
```
tcctatgagc tgaatcagcc accctcagtg tccgtgtccc caggacagac agccagcatc  60
acctgctctg gagataaatt gggggataaa tatgcttcct ggtatcagca gaagccaggc 120
cagtcccctg tggtggccat ctatcaaaat agcaagcggc cctcagggat ccctgagcga 180
ttctctgcct ccaactctgg gaacacagcc actctgacca tcagcgggac ccaggctttg 240
gatgaggctg actattactg tcaggcgtgg gacagcagca cttgggtgtt cggcggaggg 300
accaagctga ccgtccta                                              318
```

SEQ ID NO: 100         moltype = DNA   length = 357
FEATURE                Location/Qualifiers
misc_feature           1..357
                       note = Protein S monoclonal antibody variable heavy chain
                         sequence
source                 1..357
                       mol_type = other DNA
                       organism = synthetic construct
SEQUENCE: 100
```
gaagtgcagc tggtggagtc tgggggaggc ttggtacagc ctggcaggtc cctgagactc  60
tcctgtgcag cctctggatt caccttttgat gattatgcca tgcactgggt ccggcaagct 120
ccagggaagg gcctggaatg ggtctcaggt attacttgga atagtggtaa cataggctat 180
gcggactctg tgaagggccg attcaccatc tccagagaca acgccaagaa ctccctgtat 240
ctgcacatga acagtctgag aattgaggac acggccttct attactgtgc aaaaggccga 300
gcagtgtctg atactttgat atctggggc caagggacaa tggtcaccgt ctcttca     357
```

SEQ ID NO: 101         moltype = DNA   length = 321
FEATURE                Location/Qualifiers
misc_feature           1..321
                       note = Protein S monoclonal antibody variable light chain
                         sequence
source                 1..321
                       mol_type = other DNA
                       organism = synthetic construct
SEQUENCE: 101
```
gaaattgtgt tgacacagtc tccagccacc ctgtctttgt ctccagggga aagagccacc  60
ctctcctgca gggccagtca gagtgttagt atctacttag cctggtacca acagaaacct 120
ggccaggctc ccaggctcct catctatgat gcatccaaca gggccactgg catcccagcc 180
aggttcagtg gcagtgggtc tgggacagac ttcactctca ccatcagcag cctagagcct 240
gaagattttg cagtttatta ctgtcagcag cgtagcaact ggcccctcac tttcggccct 300
gggaccaaag tggatatcaa a                                          321
```

SEQ ID NO: 102         moltype = DNA   length = 342
FEATURE                Location/Qualifiers
misc_feature           1..342
                       note = Protein S monoclonal antibody variable heavy chain
                         sequence
source                 1..342
                       mol_type = other DNA
                       organism = synthetic construct
SEQUENCE: 102
```
caggtgcagt tggtggaatc tgggggaggc gtggtccagc ctgggaggtc cctgagactc  60
tcctgtgcag cgtctggatt caccttcagt acctatggct tcactgggt ccgccagcct 120
ccaggcaagg gactggagtg ggtggcagtt atatattatg atggaattaa taatattat 180
gcagactccg tgaagggccg attcaccatc tccagagaca attccaagaa cacgctgttt 240
```

```
cttcaaatga acagcctgag agccgaggac acggctgtgt attactgtgc ggagtccgac    300
ttggactact ggggccaggg aaccctggtc accgtctcct ca                      342

SEQ ID NO: 103          moltype = DNA  length = 321
FEATURE                 Location/Qualifiers
misc_feature            1..321
                        note = Protein S monoclonal antibody variable light chain
                          sequence
source                  1..321
                        mol_type = other DNA
                        organism = synthetic construct
SEQUENCE: 103
gaaatagtga tgacgcagtc tccagccacc ctgtctgtgt ctccagggga aagagccacc    60
ctctcctgca gggccagtca gaggattaac agcaacttag cctggtacca gcagaaacct   120
ggccaggctc ccaggctcct catctatggt gcatccacca gggccactgg tatccccgcc   180
aggttcagtg gcagtgggtc tgggacagag ttcactctca ccatcagcag cctgcagtct   240
gaagattttg cagcttatta ctgtcagcag tatgataact ggccgctcac tttcggcgga   300
gggaccaagg tggagatcaa a                                             321

SEQ ID NO: 104          moltype = DNA  length = 375
FEATURE                 Location/Qualifiers
misc_feature            1..375
                        note = Protein S monoclonal antibody variable heavy chain
                          sequence
source                  1..375
                        mol_type = other DNA
                        organism = synthetic construct
SEQUENCE: 104
caggtgcagc tgcaggagtc gggcccagga ctggtgaagc cttcggagac cctgtccctc    60
acctgcgctg tctctggtta ttccatcagc agtggttact actggggctg gatccggcag   120
cccccaggga aggggctgga ctggattggg agtatctatt atagtgggag tacctactac   180
aacccgtccc tcaagagtcg agtcaccata tcagttgaca cgtccaagaa ccagatctcc   240
ctgaagctga gctctgtgac cgccgcagac acggccgtgt attactgtgc gaccacgtat   300
tccgatattg tgactggtta ttataatgat gcttttgata tctggggcca agggacaatg   360
gtcaccgtgt cttca                                                    375

SEQ ID NO: 105          moltype = DNA  length = 333
FEATURE                 Location/Qualifiers
misc_feature            1..333
                        note = Protein S monoclonal antibody variable light chain
                          sequence
source                  1..333
                        mol_type = other DNA
                        organism = synthetic construct
SEQUENCE: 105
gatattgtga tgactcagtc tccactctcc ctgcccgtca cccctggaga gccggcctcc    60
atctgctgca ggtctagtca gagcctcctg catagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattattgta tgcaagctct acaaactttc   300
actttcggcc ctgggaccaa agtggatatc aaa                                333

SEQ ID NO: 106          moltype = DNA  length = 381
FEATURE                 Location/Qualifiers
misc_feature            1..381
                        note = Protein S monoclonal antibody variable heavy chain
                          sequence
source                  1..381
                        mol_type = other DNA
                        organism = synthetic construct
SEQUENCE: 106
caggtgcagc tggtgcagtc tggggctgag gtgaagaagc ctgggtcctc ggtgaaggtc    60
tcctgtaagg cttctggaga caccttcagc aaccatgcta tcaactgggt gcgacaggcc   120
cctggacaag ggcttgagtg gatgggaggg tacatcccta tctttggtac aacaaactcc   180
gcacagaagt tccggggcag agtcacgatt accgcggaca atccacgaa cacagcctac   240
atggcgctga gcagcctgag atctgaggac acggccgttt attactgtgc gagagggggg   300
ctcgcgggga gtcattataa gaactactac tatgacggta tggacgtctg gggccagggg   360
accacggtca ccgtctcctc a                                             381

SEQ ID NO: 107          moltype =    length =
SEQUENCE: 107
000

SEQ ID NO: 108          moltype =    length =
SEQUENCE: 108
000

SEQ ID NO: 109          moltype =    length =
SEQUENCE: 109
```

```
SEQ ID NO: 110         moltype =    length =
SEQUENCE: 110
000

SEQ ID NO: 111         moltype = DNA   length = 327
FEATURE                Location/Qualifiers
misc_feature           1..327
                       note = Protein S monoclonal antibody variable light chain
                         sequence
source                 1..327
                       mol_type = other DNA
                       organism = synthetic construct
SEQUENCE: 111
caggctgttg tgactcagga atctgcactc accacatcac ctggtgaaac agtcacactc    60
acttgtcgct caagtactgg ggctgttaca gctagtaact atgccaactg ggtccaagaa   120
aaaccagatc atttgttcac tggtctaata ggtagtacca ataaccgagc tccaggtgtt   180
cctgccagat tctcaggctc cctgattgga gacaaggctg ccctcaccat cacaggggca   240
cagactgagg atgaggcaat atatttctgt gctctatggt acagcgacca tttcgtgttc   300
ggtggaggaa ccaaactgac tgtccta                                       327

SEQ ID NO: 112         moltype = DNA   length = 363
FEATURE                Location/Qualifiers
misc_feature           1..363
                       note = Protein S monoclonal antibody variable heavy chain
                         sequence
source                 1..363
                       mol_type = other DNA
                       organism = synthetic construct
SEQUENCE: 112
caggtgcaac tggtgcagtc tggggctgag gtgaagaagc ctggggcctc agtgaaggtc    60
tcctgcaagt cttctggcca caccttcacc ggctactata tgcactgggt gcgacaggcc   120
cctggacaag ggcttgagtg gatgggatgg atcaaccota acagtggtga cacaaactac   180
gcacagaagt ttcagggcag ggtcaccatg accaggdaca cgtccatcag cacagcctac   240
atggagatga gcaggctgag atctgacgac acggccgtgt attactgtgc gagagactcc   300
caaatactat ggttcgggga gttaggctac tggggccagg gaaccctggt caccgtctcc   360
tcc                                                                 363

SEQ ID NO: 113         moltype = DNA   length = 318
FEATURE                Location/Qualifiers
misc_feature           1..318
                       note = Protein S monoclonal antibody variable light chain
                         sequence
source                 1..318
                       mol_type = other DNA
                       organism = synthetic construct
SEQUENCE: 113
gaaatagtga tgacgcagtc tccagccacc ctgtctgtgt ctccagggga aagagccacc    60
ctctcctgca gggccagtca gagtgttacc agcaacttag cctggtacca gcagaaacct   120
ggccaggctc ccaggctcct catctatgat gcatccaaca gggcactggg tatcccaggc   180
aggttcagtg gcagtgggtc tgggacagag ttcactctca ccatcagcag cctgcagtct   240
gaagattttg caatttatta ctgtcagcag tataataact ggcccacctt cggccaaggg   300
acacgactgg agattaaa                                                 318

SEQ ID NO: 114         moltype = DNA   length = 348
FEATURE                Location/Qualifiers
misc_feature           1..348
                       note = Protein S monoclonal antibody variable heavy chain
                         sequence
source                 1..348
                       mol_type = other DNA
                       organism = synthetic construct
SEQUENCE: 114
caggtgcagc tgcaggagtc gggcccagga ctggtgaagc cttcggagac cctgtccctc    60
acctgcggtg tctctggtgg ctccatcagc agtactaact ggtggagttg ggtccgccag   120
cccccaggga aggggctgga gtggattggg gaaatctatc aaactgggag taccgactac   180
aacccgtccc tcaagagtcg agtcaccata tcaatagaca agtccaagaa ccagttctcc   240
ctgaagctgt actctgtgac cgccgcggac acggccgtgt attactgtgc gagaaggttc   300
ggggagttag actactgggg ccaggaacc ctggtcaccg tctcctca                 348

SEQ ID NO: 115         moltype = DNA   length = 339
FEATURE                Location/Qualifiers
misc_feature           1..339
                       note = Protein S monoclonal antibody variable light chain
                         sequence
source                 1..339
                       mol_type = other DNA
                       organism = synthetic construct
```

-continued

```
SEQUENCE: 115
gatattgtga tgacccagac tccactctcc tcacctgtca cccttggaca gccggcctcc    60
atctcctgca ggtctagtca aagcctcgta cacagtgatg gaaacaccta cttgagttgg   120
cttcagcaga ggccaggcca gcctccaaga ctcctaattt ataagatttc taaccggttc   180
tctgggtcc cagacagatt cagtggcagt ggggcaggga cagatttcac actgaaaatc    240
agcagggtgg aagctgagga tgtcggggtt tattactgca tgcaagctac acaatttccc   300
catctcactt tcggcggagg gaccaaggtg gagatcaaa                          339

SEQ ID NO: 116         moltype = DNA  length = 351
FEATURE                Location/Qualifiers
misc_feature           1..351
                       note = Protein S monoclonal antibody variable heavy chain
                        sequence
source                 1..351
                       mol_type = other DNA
                       organism = synthetic construct
SEQUENCE: 116
caggtgcagc tgcaggagtc gggcccagga ctggtgaagc cttcggagac cctgtccctc    60
acctgcactg tctctggtgg ctccatcagt aattactact ggaactggat ccggcagccc   120
ccagggaagg gactggagtg gattgggtat atctattaca ttgggatcac cgactacaac   180
ccctccctca gagtcgagt caccatatca gtagacacgt ccaagaacca gttctccctg    240
aaggtgacct ctgtgaccgc tgcggacacg gccgtgtatt actgtgcggc tctaagtggg   300
gatcatgctt ttgacatctg gggccaaggg acactggtca ccgtctcttc a            351

SEQ ID NO: 117         moltype = AA  length = 6
FEATURE                Location/Qualifiers
REGION                 1..6
                       note = Protein S antibody CDR-L1 sequence
source                 1..6
                       mol_type = protein
                       organism = synthetic construct
SEQUENCE: 117
QGINNY                                                                6

SEQ ID NO: 118         moltype =   length =
SEQUENCE: 118
000

SEQ ID NO: 119         moltype = AA  length = 9
FEATURE                Location/Qualifiers
REGION                 1..9
                       note = Protein S antibody CDR-L3 sequence
source                 1..9
                       mol_type = protein
                       organism = synthetic construct
SEQUENCE: 119
QQYNSYPRT                                                             9

SEQ ID NO: 120         moltype = AA  length = 10
FEATURE                Location/Qualifiers
REGION                 1..10
                       note = Protein S antibody CDR-H1 sequence
source                 1..10
                       mol_type = protein
                       organism = synthetic construct
SEQUENCE: 120
GGSITNSNYY                                                           10

SEQ ID NO: 121         moltype = AA  length = 7
FEATURE                Location/Qualifiers
REGION                 1..7
                       note = Protein S antibody CDR-H2 sequence
source                 1..7
                       mol_type = protein
                       organism = synthetic construct
SEQUENCE: 121
VYYSGTT                                                               7

SEQ ID NO: 122         moltype = AA  length = 14
FEATURE                Location/Qualifiers
REGION                 1..14
                       note = Protein S antibody CDR-H3 sequence
source                 1..14
                       mol_type = protein
                       organism = synthetic construct
SEQUENCE: 122
VRESESYYYY GSDV                                                      14

SEQ ID NO: 123         moltype = AA  length = 9
```

```
FEATURE                 Location/Qualifiers
REGION                  1..9
                        note = Protein S antibody CDR-L3 sequence
source                  1..9
                        mol_type = protein
                        organism = synthetic construct
SEQUENCE: 123
QQYNSYPIT                                                                     9

SEQ ID NO: 124          moltype = AA  length = 8
FEATURE                 Location/Qualifiers
REGION                  1..8
                        note = Protein S antibody CDR-H1 sequence
source                  1..8
                        mol_type = protein
                        organism = synthetic construct
SEQUENCE: 124
GFTFSSYN                                                                      8

SEQ ID NO: 125          moltype = AA  length = 8
FEATURE                 Location/Qualifiers
REGION                  1..8
                        note = Protein S antibody CDR-H2 sequence
source                  1..8
                        mol_type = protein
                        organism = synthetic construct
SEQUENCE: 125
ISSSSSYI                                                                      8

SEQ ID NO: 126          moltype = AA  length = 14
FEATURE                 Location/Qualifiers
REGION                  1..14
                        note = Protein S antibody CDR-H3 sequence
source                  1..14
                        mol_type = protein
                        organism = synthetic construct
SEQUENCE: 126
ARDEEWELLT GFDY                                                              14

SEQ ID NO: 127          moltype = AA  length = 6
FEATURE                 Location/Qualifiers
REGION                  1..6
                        note = Protein S antibody CDR-L1 sequence
source                  1..6
                        mol_type = protein
                        organism = synthetic construct
SEQUENCE: 127
QSISTF                                                                        6

SEQ ID NO: 128          moltype =     length =
SEQUENCE: 128
000

SEQ ID NO: 129          moltype = AA  length = 9
FEATURE                 Location/Qualifiers
REGION                  1..9
                        note = Protein S antibody CDR-L3 sequence
source                  1..9
                        mol_type = protein
                        organism = synthetic construct
SEQUENCE: 129
QQSYSTPRT                                                                     9

SEQ ID NO: 130          moltype = AA  length = 8
FEATURE                 Location/Qualifiers
REGION                  1..8
                        note = Protein S antibody CDR-H1 sequence
source                  1..8
                        mol_type = protein
                        organism = synthetic construct
SEQUENCE: 130
GGSISGNY                                                                      8

SEQ ID NO: 131          moltype = AA  length = 19
FEATURE                 Location/Qualifiers
REGION                  1..19
                        note = Protein S antibody CDR-H3 sequence
source                  1..19
                        mol_type = protein
```

```
                                                     -continued organism = synthetic construct
SEQUENCE: 131
ARDLDYFTWG AYSDWYFDL                                                            19

SEQ ID NO: 132              moltype =    length =
SEQUENCE: 132
000

SEQ ID NO: 133              moltype =    length =
SEQUENCE: 133
000

SEQ ID NO: 134              moltype =    length =
SEQUENCE: 134
000

SEQ ID NO: 135              moltype =    length =
SEQUENCE: 135
000

SEQ ID NO: 136              moltype = AA   length = 7
FEATURE                     Location/Qualifiers
REGION                      1..7
                            note = Protein S antibody CDR-L1 sequence
source                      1..7
                            mol_type = protein
                            organism = synthetic construct
SEQUENCE: 136
QSVGSSY                                                                          7

SEQ ID NO: 137              moltype = AA   length = 9
FEATURE                     Location/Qualifiers
REGION                      1..9
                            note = Protein S antibody CDR-L3 sequence
source                      1..9
                            mol_type = protein
                            organism = synthetic construct
SEQUENCE: 137
QQYGSSPYT                                                                        9

SEQ ID NO: 138              moltype = AA   length = 10
FEATURE                     Location/Qualifiers
REGION                      1..10
                            note = Protein S antibody CDR-H1 sequence
source                      1..10
                            mol_type = protein
                            organism = synthetic construct
SEQUENCE: 138
GDSVSNNNAA                                                                      10

SEQ ID NO: 139              moltype = AA   length = 9
FEATURE                     Location/Qualifiers
REGION                      1..9
                            note = Protein S antibody CDR-H2 sequence
source                      1..9
                            mol_type = protein
                            organism = synthetic construct
SEQUENCE: 139
TYYRSKWYN                                                                        9

SEQ ID NO: 140              moltype = AA   length = 12
FEATURE                     Location/Qualifiers
REGION                      1..12
                            note = Protein S antibody CDR-H3 sequence
source                      1..12
                            mol_type = protein
                            organism = synthetic construct
SEQUENCE: 140
ARGSSWYRFF DY                                                                   12

SEQ ID NO: 141              moltype = AA   length = 6
FEATURE                     Location/Qualifiers
REGION                      1..6
                            note = Protein S antibody CDR-L1 sequence
source                      1..6
                            mol_type = protein
                            organism = synthetic construct
SEQUENCE: 141
QNIHMW                                                                           6
```

```
SEQ ID NO: 142          moltype =    length =
SEQUENCE: 142
000

SEQ ID NO: 143          moltype = AA   length = 9
FEATURE                 Location/Qualifiers
REGION                  1..9
                        note = Protein S antibody CDR-L3 sequence
source                  1..9
                        mol_type = protein
                        organism = synthetic construct
SEQUENCE: 143
LQGQSYPFT                                                                  9

SEQ ID NO: 144          moltype = AA   length = 8
FEATURE                 Location/Qualifiers
REGION                  1..8
                        note = Protein S antibody CDR-H1 sequence
source                  1..8
                        mol_type = protein
                        organism = synthetic construct
SEQUENCE: 144
GYTFTNHW                                                                   8

SEQ ID NO: 145          moltype = AA   length = 8
FEATURE                 Location/Qualifiers
REGION                  1..8
                        note = Protein S antibody CDR-H2 sequence
source                  1..8
                        mol_type = protein
                        organism = synthetic construct
SEQUENCE: 145
IYPGGGYT                                                                   8

SEQ ID NO: 146          moltype = AA   length = 13
FEATURE                 Location/Qualifiers
REGION                  1..13
                        note = Protein S antibody CDR-H3 sequence
source                  1..13
                        mol_type = protein
                        organism = synthetic construct
SEQUENCE: 146
SRFGDQNWAW FAY                                                            13

SEQ ID NO: 147          moltype =    length =
SEQUENCE: 147
000

SEQ ID NO: 148          moltype = AA   length = 107
FEATURE                 Location/Qualifiers
REGION                  1..107
                        note = Protein S monoclonal antibody variable light chain
                         sequence
source                  1..107
                        mol_type = protein
                        organism = synthetic construct
SEQUENCE: 148
DIQMTQSPSS LSASVGDRVT ITCRASQGIN NYLAWFQQKP GKAPKSLIYA ASSLQSGVPS          60
KFSGSGSGTD FTLTISSLQP EDFATYYCQQ YNSYPRTFGQ GTKVEIK                      107

SEQ ID NO: 149          moltype = AA   length = 122
FEATURE                 Location/Qualifiers
REGION                  1..122
                        note = Protein S monoclonal antibody variable heavy chain
                         sequence
source                  1..122
                        mol_type = protein
                        organism = synthetic construct
SEQUENCE: 149
QLQLQESGPG LVKPSETLSL TCTVSGGSIT NSNYYWGWIR QPPGKGLEWI GSVYYSGTTY          60
YNPSLKSRVT ISVDPSKNQF SLKLSSVTAA DTAVYYCVRE SESYYYYGSD VWGQGTTVTV         120
SS                                                                       122

SEQ ID NO: 150          moltype = AA   length = 107
FEATURE                 Location/Qualifiers
REGION                  1..107
                        note = Protein S monoclonal antibody variable light chain
                         sequence
```

```
source                  1..107
                        mol_type = protein
                        organism = synthetic construct
SEQUENCE: 150
DIQMTQSPSS LSASVGDRVT ITCRASQGIN NYLAWFQQKP GKAPKSLIYA ASNLQSGVPL    60
KFSGSGSGTD FTLTISSLQP EDFATYYCQQ YNSYPITFGQ GTRLEIK                 107

SEQ ID NO: 151          moltype = AA   length = 121
FEATURE                 Location/Qualifiers
REGION                  1..121
                        note = Protein S monoclonal antibody variable heavy chain
                          sequence
source                  1..121
                        mol_type = protein
                        organism = synthetic construct
SEQUENCE: 151
EVQLVESGGG LVKPGGSLRL SCAASGFTFS SYNMNWVRQA PGRGLDWVSS ISSSSSYIYY    60
ADSVKGRFTI SRDNAKNSLY LQMNTLRAED TAVYYCARDE EWELLTGFDY WGQGTLVTVS   120
S                                                                   121

SEQ ID NO: 152          moltype = AA   length = 107
FEATURE                 Location/Qualifiers
REGION                  1..107
                        note = Protein S monoclonal antibody variable light chain
                          sequence
source                  1..107
                        mol_type = protein
                        organism = synthetic construct
SEQUENCE: 152
DIQMTQSPSS LSASVGDRVT ITCRASQSIS TFLNWYQQKP GKAPKLLIYA TSSLRSGVPS    60
RFSGSGSGTD FTLTISSLQP EDFAIYYCQQ SYSTPRTFGQ GTQVEIK                 107

SEQ ID NO: 153          moltype = AA   length = 125
FEATURE                 Location/Qualifiers
REGION                  1..125
                        note = Protein S monoclonal antibody variable heavy chain
                          sequence
source                  1..125
                        mol_type = protein
                        organism = synthetic construct
SEQUENCE: 153
QVQLQESGPG LVKPSETLSL TCTVSGGSIS GNYWSWIRQP PGKGLEWIGY IYYSGSTNYN    60
PSLKSRVTIS VDTSKNQFSL KLSSVTAADT AVYYCARDLD YFTWGAYSDW YFDLWGRGTL   120
VTVSS                                                               125

SEQ ID NO: 154          moltype =     length =
SEQUENCE: 154
000

SEQ ID NO: 155          moltype =     length =
SEQUENCE: 155
000

SEQ ID NO: 156          moltype = AA   length = 108
FEATURE                 Location/Qualifiers
REGION                  1..108
                        note = Protein S monoclonal antibody variable light chain
                          sequence
source                  1..108
                        mol_type = protein
                        organism = synthetic construct
SEQUENCE: 156
EIVLTQSPGT LSLSPGERAT LSCRASQSVG SSYLAWYQQK PGQAPRLLIS GASGRATGIP    60
DRFSGSGSGT DFTLTISRLE PEDFTVYYCQ QYGSSPYTFG QGTKLEIK                108

SEQ ID NO: 157          moltype = AA   length = 122
FEATURE                 Location/Qualifiers
REGION                  1..122
                        note = Protein S monoclonal antibody variable heavy chain
                          sequence
source                  1..122
                        mol_type = protein
                        organism = synthetic construct
SEQUENCE: 157
QVQLQQSGPG LVKPSQTLSL TCAISGDSVS NNNAAWNWIR QSPSRGLEWL GGTYYRSKWY    60
NDYAVSVKSR IIINPVTSKN QFSLQLNSVT PEDTAVYYCA RGSSWYRFFD YWGQGTLVTV   120
SS                                                                  122

SEQ ID NO: 158          moltype = AA   length = 107
```

```
FEATURE                 Location/Qualifiers
REGION                  1..107
                        note = Protein S monoclonal antibody variable light chain
                          sequence
source                  1..107
                        mol_type = protein
                        organism = synthetic construct
SEQUENCE: 158
DIQMNQSPSS LSASLGDTIT ITCRASQNIH MWLSWYQQKP GNIPKLLIFK TSNLHTGVPS      60
RFSGSGSGTD FTLTISSLQP EDIATYYCLQ GQSYPFTFGG GTKLEIK                  107

SEQ ID NO: 159          moltype = AA  length = 120
FEATURE                 Location/Qualifiers
REGION                  1..120
                        note = Protein S monoclonal antibody variable heavy chain
                          sequence
source                  1..120
                        mol_type = protein
                        organism = synthetic construct
SEQUENCE: 159
QVQLQQSGTE LVRPGTSVKM SCKAAGYTFT NHWIGWVKQR PGHGLEWIGD IYPGGGYTNY      60
NEKFKGKASL TADTSSTTAY MQLSSLTSED SAIYYCSRFG DQNWAWFAYW GQGTLVTVSA     120

SEQ ID NO: 160          moltype =   length =
SEQUENCE: 160
000

SEQ ID NO: 161          moltype =   length =
SEQUENCE: 161
000

SEQ ID NO: 162          moltype = DNA  length = 321
FEATURE                 Location/Qualifiers
misc_feature            1..321
                        note = Protein S monoclonal antibody variable light chain
                          sequence
source                  1..321
                        mol_type = other DNA
                        organism = synthetic construct
SEQUENCE: 162
gacatccaga tgacccagtc tccatcctca ctgtctgcat ctgtaggaga cagagtcacc      60
atcacttgtc gggcgagtca gggcattaac aattatttag cctggtttca gcagaaacca    120
gggaaagccc ctaagtccct gatctatgct gcatccagtt tgcaaagtgg ggtcccatca    180
aagttcagcg gcagtggatc tgggacagat ttcactctca ccatcagcag cctgcagcct    240
gaagattttg caacttatta ctgccaacag tataatagtt accctcggac gttcggccaa    300
gggaccaagg tggaaatcaa a                                              321

SEQ ID NO: 163          moltype = DNA  length = 366
FEATURE                 Location/Qualifiers
misc_feature            1..366
                        note = Protein S monoclonal antibody variable heavy chain
                          sequence
source                  1..366
                        mol_type = other DNA
                        organism = synthetic construct
SEQUENCE: 163
cagctgcagc tgcaggagtc gggcccagga ctggtgaagc cttcggagac cctgtccctc      60
acctgcactg tctctggtgg ctccatcacc aatagtaatt actactgggg ctggatccgc    120
cagccccag ggaagggact ggagtggatt gggagtgtct attatagtgg gaccacctac     180
tacaacccgt ccctcaagag tcgagtcacc atatccgtag acccgttcca gaaccagttc    240
tccctgaagc tgagctctgt gaccgccgca gacacggctg tgtattactg tgtgagagag    300
agtgagagct actactacta cggttcggac gtctggggcc aagggaccac ggtcaccgtc    360
tcctca                                                               366

SEQ ID NO: 164          moltype = DNA  length = 321
FEATURE                 Location/Qualifiers
misc_feature            1..321
                        note = Protein S monoclonal antibody variable light chain
                          sequence
source                  1..321
                        mol_type = other DNA
                        organism = synthetic construct
SEQUENCE: 164
gacatccaga tgacccagtc tccatcctca ctgtctgcat ctgtaggaga cagagtcacc      60
atcacttgtc gggcgagtca gggcattaac aattatttag cctggtttca gcagaaacca    120
gggaaagccc ctaagtccct gatctatgct gcatccaatt tgcaaagtgg ggtcccatta    180
aagttcagcg gcagtggatc tgggacagat ttcactctca ccatcagcag cctgcagcct    240
gaagattttg caacttatta ctgccaacag tataatagtt acccgatcac cttcggccaa    300
gggacacgac tggagattaa a                                              321
```

```
SEQ ID NO: 165          moltype = DNA  length = 363
FEATURE                 Location/Qualifiers
misc_feature            1..363
                        note = Protein S monoclonal antibody variable heavy chain
                          sequence
source                  1..363
                        mol_type = other DNA
                        organism = synthetic construct
SEQUENCE: 165
gaggtgcagc tggttgagtc tgggggaggc ctggtcaagc ctggggggtc cctgagactc   60
tcctgtgcag cctctggatt caccttcagt agctataaca tgaactgggt ccgccaggct  120
ccagggaggg ggctggactg ggtctcatcc attagtagta gtagtagtta catatactac  180
gcagactcag tgaagggccg attcaccatc tccagagaca acgccaagaa ctcactgtat  240
ctgcaaatga ataccctgag agccgaggac acggctgttt attactgtgc gagagatgag  300
gagtgggagc tactgacggg ctttgactac tggggccagg gaaccctggt caccgtctcc  360
tca                                                                363

SEQ ID NO: 166          moltype = DNA  length = 321
FEATURE                 Location/Qualifiers
misc_feature            1..321
                        note = Protein S monoclonal antibody variable light chain
                          sequence
source                  1..321
                        mol_type = other DNA
                        organism = synthetic construct
SEQUENCE: 166
gacatccaga tgacccagtc tccatcctcc ctgtctgcat ctgtaggaga cagagtcacc   60
atcacttgcc gggcaagtca gagcattagc accttttttaa attggtatca gcagaaacca  120
gggaaagccc ctaaactcct gatctatgct acatccagtt tgcgaagtgg ggtcccatca  180
aggttcagtg gcagtggatc tgggacagat ttcactctca ccatcagcag tctgcaacct  240
gaagattttg caatttatta ttgtcaacag agttacagta cccctcggac gttcggccaa  300
gggaccaggg tggaaatcaa a                                            321

SEQ ID NO: 167          moltype = DNA  length = 375
FEATURE                 Location/Qualifiers
misc_feature            1..375
                        note = Protein S monoclonal antibody variable heavy chain
                          sequence
source                  1..375
                        mol_type = other DNA
                        organism = synthetic construct
SEQUENCE: 167
caggtgcagc tgcaggagtc gggcccagga ctggtgaagc cttcggagac cctgtccctc   60
acctgcactg tctctggtgg ctccatcagt ggtaactact ggagctggat ccggcagccc  120
ccagggaagg gactggagtg gattgggtat atctattaca gtgggagcac caactacaat  180
ccctccctca agagtcgagt caccatatca gttgacacgt ccaagaacca gttctccctg  240
aagctgagct ctgtgaccgc tgcggatacg gccgtgtatt actgtgcgag agatcttgat  300
tactttactt ggggggctta ttctgactgg tacttcgatc tctgggccg tggcaccctg  360
gtcactgtct cctca                                                   375

SEQ ID NO: 168          moltype =    length =
SEQUENCE: 168
000

SEQ ID NO: 169          moltype =    length =
SEQUENCE: 169
000

SEQ ID NO: 170          moltype = DNA  length = 324
FEATURE                 Location/Qualifiers
misc_feature            1..324
                        note = Protein S monoclonal antibody variable light chain
                          sequence
source                  1..324
                        mol_type = other DNA
                        organism = synthetic construct
SEQUENCE: 170
gaaattgtgt tgacgcagtc tccaggcacc ctgtctttgt ctccagggga aagagccacc   60
ctctcctgca gggccagtca gagtgttggc agcagctact tagcctggta ccagcagaaa  120
cctggccagg ctcccaggct cctcatctct ggtgcatccg gcagggccac tggcatccca  180
gacaggttca gtggcagtgg gtctgggaca gacttcactc tcaccatcag cagactggag  240
cctgaagatt ttacagtgta ttactgtcag cagtatggta gctcaccgta cacttttggc  300
caggggacca agctggagat caaa                                         324

SEQ ID NO: 171          moltype = DNA  length = 366
FEATURE                 Location/Qualifiers
misc_feature            1..366
                        note = Protein S monoclonal antibody variable heavy chain
```

```
                        sequence
source                  1..366
                        mol_type = other DNA
                        organism = synthetic construct
SEQUENCE: 171
caggtacagc tgcagcagtc aggtccagga ctggtgaagc cctcgcagac cctctcactc   60
acctgtgcca tctccgggga cagtgtctct aacaacaatg ctgcttggaa ctggatcagg  120
cagtccccat cgagaggcct tgagtggctg ggagggacat actacaggtc caagtggtat  180
aatgattatg cagtatctgt gaaaagtcga ataatcatca acccagtcac atccaagaac  240
cagttctccc tacagctgaa ctctgtgact cccgaggaca cggctgtgta ttactgtgca  300
agaggcagca gctggtacag gttttttgac tactggggcc agggaaccct ggtcaccgtc  360
tcctca                                                             366

SEQ ID NO: 172          moltype = DNA  length = 321
FEATURE                 Location/Qualifiers
misc_feature            1..321
                        note = Protein S monoclonal antibody variable light chain
                        sequence
source                  1..321
                        mol_type = other DNA
                        organism = synthetic construct
SEQUENCE: 172
gacatccaga tgaaccagtc tccatccagt ctgtctgcat ccctcggaga cacaattacc   60
atcacttgcc gtgccagtca gaacattcat atgtggttaa gctggtacca gcagaaacca  120
ggaaatattc taaactattt gatctttaag acttccaatt tgcacacagg cgtcccatca  180
aggtttagtg gcagtggatc tggaacagat ttcacattaa ccatcagcag tctgcagcct  240
gaagacattg ccacttacta ctgtctacag ggtcaaagtt atccgttcac gttcggaggg  300
gggaccaagc tggaaataaa g                                            321

SEQ ID NO: 173          moltype = DNA  length = 360
FEATURE                 Location/Qualifiers
misc_feature            1..360
                        note = Protein S monoclonal antibody variable heavy chain
                        sequence
source                  1..360
                        mol_type = other DNA
                        organism = synthetic construct
SEQUENCE: 173
caggtccagc tgcagcagtc tggaactgag ctggtaaggc ctgggacttc agtgaagatg   60
tcctgtaagg ctgctggata caccttcact aaccactgga taggttgggt aaagcagagg  120
cctggacatg gccttgagtg gattggagat atttaccctg gaggtggtta tactaactac  180
aatgagaagt tcaagggcaa ggcctcactg actgcagaca catcctccac cacagcctac  240
atgcagctca gcagcctgac atctgaggac tctgccatct attactgttc aagattcggg  300
gatcaaaaact gggcctggtt tgcttactgg ggccaaggga ctctggtcac tgtctctgca  360

SEQ ID NO: 174          moltype = AA  length = 6
FEATURE                 Location/Qualifiers
REGION                  1..6
                        note = Hc-M1 VL CDR-1
source                  1..6
                        mol_type = protein
                        organism = synthetic construct
SEQUENCE: 174
QSISSY                                                               6

SEQ ID NO: 175          moltype =   length =
SEQUENCE: 175
000

SEQ ID NO: 176          moltype = AA  length = 8
FEATURE                 Location/Qualifiers
REGION                  1..8
                        note = Hc-M1 VL CDR-3
source                  1..8
                        mol_type = protein
                        organism = synthetic construct
SEQUENCE: 176
QQSYSSLT                                                             8

SEQ ID NO: 177          moltype = AA  length = 106
FEATURE                 Location/Qualifiers
REGION                  1..106
                        note = Hc-M1 VL V region
source                  1..106
                        mol_type = protein
                        organism = synthetic construct
SEQUENCE: 177
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ SYSSLTFGQG TRLEIK                 106
```

```
SEQ ID NO: 178          moltype = DNA  length = 318
FEATURE                 Location/Qualifiers
misc_feature            1..318
                        note = Hc-M1 VL
source                  1..318
                        mol_type = other DNA
                        organism = synthetic construct
SEQUENCE: 178
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagtt ccctcacctt cggccaaggg   300
acacgactgg agattaaa                                                 318

SEQ ID NO: 179          moltype = AA  length = 8
FEATURE                 Location/Qualifiers
REGION                  1..8
                        note = Hc-M1 VH CDR-1
source                  1..8
                        mol_type = protein
                        organism = synthetic construct
SEQUENCE: 179
GISFSNAW                                                              8

SEQ ID NO: 180          moltype = AA  length = 10
FEATURE                 Location/Qualifiers
REGION                  1..10
                        note = Hc-M1 VH CDR-2
source                  1..10
                        mol_type = protein
                        organism = synthetic construct
SEQUENCE: 180
IKANPDGGTT                                                           10

SEQ ID NO: 181          moltype = AA  length = 15
FEATURE                 Location/Qualifiers
REGION                  1..15
                        note = Hc-M1 VH CDR-3
source                  1..15
                        mol_type = protein
                        organism = synthetic construct
SEQUENCE: 181
TTELDILLWF TSFDY                                                     15

SEQ ID NO: 182          moltype = AA  length = 124
FEATURE                 Location/Qualifiers
REGION                  1..124
                        note = Hc-M1 VH V region
source                  1..124
                        mol_type = protein
                        organism = synthetic construct
SEQUENCE: 182
EVQLVESGGG LVKPGGSLRL SCAASGISFS NAWMSWVRQA PGKGLEWVGR IKANPDGGTT    60
DYAAPVKGRF TISRDDSKNT LYLQMNSLKT EDTAVYYCTT ELDILLWFTS FDYWGQGTLV   120
TVSS                                                                124

SEQ ID NO: 183          moltype = DNA  length = 372
FEATURE                 Location/Qualifiers
misc_feature            1..372
                        note = Hc-M1 VH
source                  1..372
                        mol_type = other DNA
                        organism = synthetic construct
SEQUENCE: 183
gaggtgcagc tggtggagtc tgggggaggc ttggtaaagc ctggggggtc ccttagactc    60
tcctgtgcag cctctggaat cagtttcagt aacgcctgga tgagctgggt ccgccaggct   120
ccagggaagg ggctggaatg ggttggccgt attaaagcca atcctgatgg tgggacaaca   180
gactacgctg cacccgtgaa aggcagattc accatctcaa gagatgattc aaaaaacacg   240
ctatatctgc aaatgaacag cctgaaaacc gaggacacag ccgtgtatta ctgtaccaca   300
gagttggaca ttttactatg gttcacctcc tttgactact ggggccaggg aaccctggtc   360
accgtctcct ca                                                       372

SEQ ID NO: 184          moltype = AA  length = 6
FEATURE                 Location/Qualifiers
REGION                  1..6
                        note = Od-M4 VL CDR-1
source                  1..6
```

```
                        mol_type = protein
                        organism = synthetic construct
SEQUENCE: 184
NIGGKS                                                                  6

SEQ ID NO: 185          moltype =   length =
SEQUENCE: 185
000

SEQ ID NO: 186          moltype = AA   length = 11
FEATURE                 Location/Qualifiers
REGION                  1..11
                        note = Od-M4 VL CDR-3
source                  1..11
                        mol_type = protein
                        organism = synthetic construct
SEQUENCE: 186
QVWEITSDHP A                                                           11

SEQ ID NO: 187          moltype = AA   length = 108
FEATURE                 Location/Qualifiers
REGION                  1..108
                        note = Od-M4 VL V region
source                  1..108
                        mol_type = protein
                        organism = synthetic construct
SEQUENCE: 187
SYVLTQPPSV SVAPGQTARI TCGGDNIGGK SVHWYQQKPG QAPVMVVYDD SDRPSGIPER       60
FAGSNSGNTA TLAISRVEAG DEADYYCQVW EITSDHPAFG GGTRLTVL                  108

SEQ ID NO: 188          moltype = DNA   length = 324
FEATURE                 Location/Qualifiers
misc_feature            1..324
                        note = Od-M4 VL
source                  1..324
                        mol_type = other DNA
                        organism = synthetic construct
SEQUENCE: 188
tcctatgtgc tgactcagcc accctcggtg tcagtggccc caggacagac ggccaggatt       60
acctgtgggg gagacaacat tggaggtaaa agtgtgcact ggtaccagca gaagccaggc     120
caggcccctg tgatggtcgt ctatgatgat agcgaccggc cctcaggat ccctgagcga     180
ttcgctggct ccaattctgg gaacacggcc accctggcca tcagcagggt cgaagccggg     240
gatgaggccg actattactg tcaggtgtgg gagataacta gtgatcatcc ggcattcggc     300
ggagggacca ggctgaccgt ccta                                            324

SEQ ID NO: 189          moltype = AA   length = 8
FEATURE                 Location/Qualifiers
REGION                  1..8
                        note = Od-M4 VH CDR-1
source                  1..8
                        mol_type = protein
                        organism = synthetic construct
SEQUENCE: 189
GFTFSSYS                                                                8

SEQ ID NO: 190          moltype = AA   length = 8
FEATURE                 Location/Qualifiers
REGION                  1..8
                        note = Od-M4 VH CDR-2
source                  1..8
                        mol_type = protein
                        organism = synthetic construct
SEQUENCE: 190
ISSSTRTI                                                                8

SEQ ID NO: 191          moltype = AA   length = 9
FEATURE                 Location/Qualifiers
REGION                  1..9
                        note = Od-M4 VH CDR-3
source                  1..9
                        mol_type = protein
                        organism = synthetic construct
SEQUENCE: 191
ARERSAFDY                                                               9

SEQ ID NO: 192          moltype = AA   length = 116
FEATURE                 Location/Qualifiers
REGION                  1..116
                        note = Od-M4 VH V region
```

```
source                    1..116
                          mol_type = protein
                          organism = synthetic construct
SEQUENCE: 192
EVQLVESGGG LVQPGGSLRL SCAASGFTFS SYSMNWVRQA PGKGLEWVAY ISSSTRTIFY    60
ADSVKGRFTI SRDNAKNSLY LQMNSLRDED TAFYYCARER SAFDYWGQGT LVTVSS       116

SEQ ID NO: 193            moltype = DNA   length = 348
FEATURE                   Location/Qualifiers
misc_feature              1..348
                          note = Od-M4 VH
source                    1..348
                          mol_type = other DNA
                          organism = synthetic construct
SEQUENCE: 193
gaggtgcagc tggtggagtc tgggggaggc ttggtacagc ctgggggttc cctgagactc    60
tcctgtgcag cctctggatt caccttcagt agctatagca tgaactgggt ccgccaggct   120
ccagggaagg ggctgagtg ggttgcatac attagtagta gtactcgtac catattctac    180
gcagactctg tgaagggccg attcaccatc tccagagaca atgccaagaa ctcactgtat   240
ctgcaaatga acagcctgag agacgaggac acggcttttt attattgtgc gagagaacgt   300
tcggcctttg actactgggg ccagggaacc ctggtcaccg tctcctca               348

SEQ ID NO: 194            moltype = AA   length = 6
FEATURE                   Location/Qualifiers
REGION                    1..6
                          note = Od-M7 VL CDR-1
source                    1..6
                          mol_type = protein
                          organism = synthetic construct
SEQUENCE: 194
KLGDKY                                                                6

SEQ ID NO: 195            moltype =   length =
SEQUENCE: 195
000

SEQ ID NO: 196            moltype = AA   length = 9
FEATURE                   Location/Qualifiers
REGION                    1..9
                          note = Od-M7 VL CDR-3
source                    1..9
                          mol_type = protein
                          organism = synthetic construct
SEQUENCE: 196
QAWDSSTVG                                                             9

SEQ ID NO: 197            moltype = AA   length = 106
FEATURE                   Location/Qualifiers
REGION                    1..106
                          note = Od-M7 VL V region
source                    1..106
                          mol_type = protein
                          organism = synthetic construct
SEQUENCE: 197
SYELTQPPSV SVSPGQTASI TCSGDKLGDK YVFWYQQKPG QSPVLVIYQD SKRPSGIPER    60
FSGSNSGNTA TLTISGTQTM DEADYYCQAW DSSTVGFGGG TKLAVL                  106

SEQ ID NO: 198            moltype = DNA   length = 318
FEATURE                   Location/Qualifiers
misc_feature              1..318
                          note = Od-M7 VL
source                    1..318
                          mol_type = other DNA
                          organism = synthetic construct
SEQUENCE: 198
tcctatgagc tgactcagcc accctcagtg tccgtgtccc caggacagac agccagcatc    60
acctgctctg gagataaatt gggggataaa tatgtttct ggtatcagca aaagccaggc    120
cagtcccctg tgttggtcat ctatcaagat agcaagcggc cctcagggat ccctgagcga   180
ttctctggct ccaactctgg gaacacagcc actctgacca tcagcgggac ccagactatg   240
gatgaggctg actattactg tcaggcgtgg gacagcagca ctgtgggatt cggcggaggg   300
accaagctgg ccgtcctg                                                  318

SEQ ID NO: 199            moltype = AA   length = 8
FEATURE                   Location/Qualifiers
REGION                    1..8
                          note = Od-M7 VH CDR-1
source                    1..8
                          mol_type = protein
                          organism = synthetic construct
```

```
SEQUENCE: 199
GYTFTNYY                                                                    8

SEQ ID NO: 200          moltype = AA  length = 8
FEATURE                 Location/Qualifiers
REGION                  1..8
                        note = Od-M7 VH CDR-2
source                  1..8
                        mol_type = protein
                        organism = synthetic construct
SEQUENCE: 200
ITPSGGTT                                                                    8

SEQ ID NO: 201          moltype = AA  length = 15
FEATURE                 Location/Qualifiers
REGION                  1..15
                        note = Od-M7 VH CDR-3
source                  1..15
                        mol_type = protein
                        organism = synthetic construct
SEQUENCE: 201
ARAGVQLDRR GWFDP                                                           15

SEQ ID NO: 202          moltype = AA  length = 122
FEATURE                 Location/Qualifiers
REGION                  1..122
                        note = Od-M7 VH V region
source                  1..122
                        mol_type = protein
                        organism = synthetic construct
SEQUENCE: 202
QVQLVQSGSE VKKPGASVKV SCKASGYTFT NYYIHWVRQA PGQGLEWMGI ITPSGGTTSY           60
AQKFQGRVTM TRDTSTNTVY MGLSSLRSED TAMYYCARAG VQLDRRGWFD PWGQGTLVTV          120
SS                                                                        122

SEQ ID NO: 203          moltype = DNA  length = 366
FEATURE                 Location/Qualifiers
misc_feature            1..366
                        note = Od-M7 VH
source                  1..366
                        mol_type = other DNA
                        organism = synthetic construct
SEQUENCE: 203
caggtgcagc tggtgcagtc tgggtctgag gtgaagaagc ctggggcctc agtgaaggtt          60
tcctgcaagg catctggata caccttcacc aactactata tacactgggt gcggcaggcc        120
cctgacaag ggcttgagtg gatgggaata atcacccta gtggtggtac cacaagctac          180
gcacagaagt tccagggcag agtcactatg accaggtgac cgtccacgaa cacagtctac        240
atgggctga gcagcctgag atctgaggac acggccatgt attactgtgc gagagccggg         300
gtacaactgg atcgacgagg gtggttcgac ccctggggcc agggaaccct ggtcaccgtc        360
tcctca                                                                   366

SEQ ID NO: 204          moltype = AA  length = 6
FEATURE                 Location/Qualifiers
REGION                  1..6
                        note = Od-M67 VL CDR-1
source                  1..6
                        mol_type = protein
                        organism = synthetic construct
SEQUENCE: 204
KLGDKY                                                                      6

SEQ ID NO: 205          moltype =     length =
SEQUENCE: 205
000

SEQ ID NO: 206          moltype = AA  length = 9
FEATURE                 Location/Qualifiers
REGION                  1..9
                        note = Od-M67 VL CDR-3
source                  1..9
                        mol_type = protein
                        organism = synthetic construct
SEQUENCE: 206
QAWDSSTAV                                                                   9

SEQ ID NO: 207          moltype = AA  length = 106
FEATURE                 Location/Qualifiers
REGION                  1..106
                        note = Od-M67 VL V region
```

```
source                  1..106
                        mol_type = protein
                        organism = synthetic construct
SEQUENCE: 207
SYELTQPPSV SVSPGQTASI TCSGDKLGDK YAFWYQQKPG QSPVLVIYQD NKRPSGIPER    60
FSGSNSGNTA TLTISGTQAV DEADYYCQAW DSSTAVFGGG TKLTVL                  106

SEQ ID NO: 208          moltype = DNA  length = 318
FEATURE                 Location/Qualifiers
misc_feature            1..318
                        note = Od-M67 VL
source                  1..318
                        mol_type = other DNA
                        organism = synthetic construct
SEQUENCE: 208
tcctatgagc tgactcagcc accctcagtg tccgtgtccc cgggacagac agccagcatc    60
acctgctctg gagataaatt gggggataaa tatgctttct ggtatcagca gaagccaggc   120
cagtcccctg tgctggtcat ctatcaagat aacaagccct cagggat ccctgagcga     180
ttctctggct ccaactctgg gaacacagcc actctaacca tcagcgggac ccaggctgtg   240
gatgaggctg actattactg tcaggcgtgg gacagcagca ctgcggtatt cggcggaggg   300
accaagctga ccgtccta                                                318

SEQ ID NO: 209          moltype = AA  length = 8
FEATURE                 Location/Qualifiers
REGION                  1..8
                        note = Od-M67 VH CDR-1
source                  1..8
                        mol_type = protein
                        organism = synthetic construct
SEQUENCE: 209
GYTFTSYY                                                             8

SEQ ID NO: 210          moltype = AA  length = 8
FEATURE                 Location/Qualifiers
REGION                  1..8
                        note = Od-M67 VH CDR-2
source                  1..8
                        mol_type = protein
                        organism = synthetic construct
SEQUENCE: 210
TSPSGRST                                                             8

SEQ ID NO: 211          moltype = AA  length = 17
FEATURE                 Location/Qualifiers
REGION                  1..17
                        note = Od-M67 VH CDR-3
source                  1..17
                        mol_type = protein
                        organism = synthetic construct
SEQUENCE: 211
ARGGVTIHLE RRGYFDY                                                  17

SEQ ID NO: 212          moltype = AA  length = 124
FEATURE                 Location/Qualifiers
REGION                  1..124
                        note = Od-M67 VH V region
source                  1..124
                        mol_type = protein
                        organism = synthetic construct
SEQUENCE: 212
QVQLVQSGAE VKKPGASVKV SCKASGYTFT SYYIHWVRQA PGQGLEWMGV TSPSGRSTSF    60
AQKFQGRVTM TRDTSTSAVY MDLDSLRSED TAVYYCARGG VTIHLERRGY FDYWGQGTLV   120
IVSS                                                                124

SEQ ID NO: 213          moltype = DNA  length = 372
FEATURE                 Location/Qualifiers
misc_feature            1..372
                        note = Od-M67 VH
source                  1..372
                        mol_type = other DNA
                        organism = synthetic construct
SEQUENCE: 213
caggtgcagc tggtgcagtc tggggctgag gtgaagaagc ctggggcctc agtgaaggtt    60
tcctgcaagg catctggata caccttcacc agctactgga tacactgggt gcgacaggcc   120
cctggacaag gccttgagtg gatgggagta accagcccta gtggtcgtag cacaagcttc   180
gcacagaagt tccagggcag agtcaccatg accaggggaca cgtccacgag cgcagtctat   240
atggacctgg acagcctgag atctgaggac acggccgtgt attactgtgc gagggggga   300
gtgacgatac acctggaacg acggggctac tttgactact ggggccaggg aaccctggtc   360
attgtctcct ca                                                      372
```

```
SEQ ID NO: 214          moltype = AA   length = 107
FEATURE                 Location/Qualifiers
REGION                  1..107
                        note = Kappa light chain
source                  1..107
                        mol_type = protein
                        organism = synthetic construct
SEQUENCE: 214
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 215          moltype = AA   length = 106
FEATURE                 Location/Qualifiers
REGION                  1..106
                        note = Lambda light chain
source                  1..106
                        mol_type = protein
                        organism = synthetic construct
SEQUENCE: 215
GQPKAAPSVT LFPPSSEELQ ANKATLVCLI SDFYPGAVTV AWKADSSPVK AGVETTTPSK    60
QSNNKYAASS YLSLTPEQWK SHRSYSCQVT HEGSTVEKTV APTECS                  106

SEQ ID NO: 216          moltype = AA   length = 676
FEATURE                 Location/Qualifiers
source                  1..676
                        mol_type = protein
                        organism = Homo sapiens
SEQUENCE: 216
MRVLGGRCGA LLACLLLVLP VSEANFLSKQ QASQVLVRKR RANSLLEETK QGNLERECIE    60
ELCNKEEARE VFENDPETDY FYPKYLVCLR SFQTGLFTAA RQSTNAYPDL RSCVNAIPDQ   120
CSPLPCNEDG YMSCKDGKAS FTCTCKPGWQ GEKCEFDINE CKDPSNINGG CSQICDNTPG   180
SYHCSCKNGF VMLSNKKDCK DVDECSLKPS ICGTAVCKNI PGDFECECPE GYRYNLKSKS   240
CEDIDECSEN MCAQLCVNYP GGYTCYCDGK KGFKLAQDQK SCEVVSVCLP LNLDTKYELL   300
YLAEQFAGVV LYLKFRLPEI SRFSAEFDFR TYDSEGVILY AESIDHSAWL LIALRGGKIE   360
VQLKNEHTSK ITTGGDVINN GLWNMVSVEE LEHSISIKIA KEAVMDINKP GPLFKPENGL   420
LETKVYFAGF PRKVESELIK PINPRLDGCI RSWNLMKQGA SGIKEIIQEK QNKHCLVTVE   480
KGSYYPGSGI AQFHIDYNNV SSAEGWHVNV TLNIRPSTGT GVMLALVSGN NTVPFAVSLV   540
DSTSEKSQDI LLSVENTVIY RIQALSLCSD QQSHLEFRVN RNNLELSTPL KIETISHEDL   600
QRQLAVLDKA MKAKVATYLG GLPDVPFSAT PVNAFYNGCM EVNINGVQLD LDEAISKHND   660
IRAHSCPSVW KKTKNS                                                   676

SEQ ID NO: 217          moltype = AA   length = 330
FEATURE                 Location/Qualifiers
source                  1..330
                        mol_type = protein
                        organism = Homo sapiens
SEQUENCE: 217
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 218          moltype = AA   length = 327
FEATURE                 Location/Qualifiers
source                  1..327
                        mol_type = protein
                        organism = Homo sapiens
SEQUENCE: 218
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                       327
```

PROTEIN S ANTIBODIES, METHODS OF MAKING AND USES THEREOF

CROSS REFERENCE TO RELATED APPLICATIONS

This application is continuation of U.S. patent application Ser. No. 17/923,503, filed on Nov. 4, 2022, which is a U.S. National Stage Application under 35 U.S.C. § 371 of International Application No. PCT/US2021/030900, filed on May 5, 2021, which claims priority to U.S. Provisional Patent Application No. 63/020,505, filed on May 5, 2020, and to U.S. Provisional Patent Application No. 63/169,755, filed on Apr. 1, 2021. The contents of each of the preceding applications are incorporated by reference herein in their entirety.

INCORPORATION OF SEQUENCE LISTING

The Sequence Listing associated with this application is provided electronically in XML file format and is hereby incorporated by reference into the specification. The name of the XML file containing the Sequence Listing is VEGA_001_03US_SeqList_ST26.xml. The XML file is 246,134 bytes and was created on Nov. 6, 2023.

BACKGROUND

Protein S (also known as ProS, ProS1) is a vitamin K-dependent plasma protein involved in the anti-coagulation cascade. The protein is multi-modular, comprising a γ-carboxy-glutamic acid domain (Gla domain), an epidermal growth factor-like domain (EGF domain), a thrombin-sensitive region (TSR), and a sex hormone binding globulin-like domain (SHBG-like domain). The protein is found in both a free form and as part of a complex with proteins such as C4 binding protein (C4BP) and tissue factor pathway inhibitor (TFPI). Among other functions, in its free form, Protein S is a cofactor in at least two pathways of the anti-coagulation cascade: (1) Protein S is a cofactor for plasma activated Protein C (APC), involved in the inactivation and degradation of coagulation factors Factor Va and Factor VIIIa; and (2) Protein S is also a cofactor for TFPI, also present in plasma, involved in the inactivation of coagulation factors Factor Xa and Factor VIIa.

Protein S is a potential therapeutic target for bleeding disorders, thus there is a need for agents that bind and modulate its activities within the coagulation pathway.

SUMMARY

Provided here are antibodies that bind Protein S, and methods of making and using such antibodies. In some embodiments, the Protein S antibodies provided herein are useful for treating a bleeding disorder, or a condition characterized by reduced or impaired blood coagulation and/or clotting.

Accordingly, in one aspect, provided herein are antibodies that bind Protein S, wherein the antibodies are inhibitors of the cofactor activity of Protein S for activated Protein C (APC), inhibitors of the cofactor activity of Protein S for tissue factor pathway inhibitor (TFPI), or inhibitors of the cofactor activity of Protein S for both APC and TFPI (dual inhibitor of cofactor activity), and wherein the antibody is human, humanized, or chimeric. In some preferred embodiments, the antibodies provided herein specifically bind Protein S.

In another aspect, provided herein are antibodies that bind Protein S, wherein the antibodies are capable of promoting coagulation and/or modulating a component in the coagulation cascade.

In another aspect, provided herein are exemplary Protein S antibodies comprising any one or more of the amino acid sequences of the complementarity determining region (CDR) sequences provided in Tables 1A, 1B, 1C, 2A, 2B, and 2C. In another aspect, the exemplary Protein S antibodies comprise any one of the CDR-L1 amino acid sequences of Table 1A; any one of the CDR-L2 amino acid sequences of Table 1B; any one of the CDR-L3 amino acid sequences of Table 1C; any one of the CDR-H1 amino acid sequences of Table 2A; any one of the CDR-H2 amino acid sequences of Table 2B; any one of the CDR-H3 amino acid sequences of Table 2B. In another aspect, provided herein are exemplary Protein S antibodies comprising the combinations of variable light chains and variable heavy chains presented in Table 4C. In another aspect, provided herein are the sequences of different antibodies as presented in Table 6. In another aspect, provided herein are nucleic acids encoding for any of the Protein S antibodies provided herein.

In another aspect, provided herein are pharmaceutical compositions comprising any one of the Protein S antibodies provided herein, and optionally a pharmaceutically acceptable excipient.

Provided herein are methods of using the exemplary Protein S antibodies described herein. Accordingly, in one aspect, provided herein is an in vitro method of promoting the coagulation of blood, comprising contacting any one of the Protein S antibodies provided herein with a blood sample.

In another aspect, provided herein is a method of promoting the coagulation of blood in a subject in need thereof, comprising administering to the subject any of the exemplary Protein S antibodies provided herein, or pharmaceutical compositions provided herein. In exemplary embodiments, the route of administration is subcutaneous.

In another aspect, provided herein is a method of promoting the generation of thrombin in a subject in need thereof, comprising administering to the subject any of the Protein S antibodies provided herein, or pharmaceutical compositions provided herein.

In another aspect, provided herein is a method of treating a condition in a subject in need thereof, comprising administering to the subject any of the Protein S antibodies provided herein, or pharmaceutical compositions provided herein, wherein the condition is selected from the group consisting of: bleeding disorders, platelet disorders, trauma, bleeding resulting from a surgery or a medical procedure, and combinations thereof.

In another aspect, provided herein is the use of any one of the Protein S antibodies or pharmaceutical compositions provided herein, for the treatment of a condition in a subject in need thereof. The condition may be selected from the group consisting of: bleeding disorders, platelet disorders, trauma, bleeding resulting from a surgery or a medical procedure, and combinations thereof.

In another aspect, any one of the Protein S antibodies or pharmaceutical compositions provided herein, may be used for the manufacture of a medicament for the treatment of a condition in a subject in need thereof. The condition may be selected from the group consisting of bleeding disorders, platelet disorders, trauma, bleeding resulting from a surgery or a medical procedure, and combinations thereof.

BRIEF DESCRIPTION OF THE DRAWINGS

FIGS. 5-10 depict the prototypic thrombin generation profiles of a dual inhibitor of APC and TFPI (Antibody 13; FIGS. 5, 6), an APC cofactor inhibitor (Antibody 21; FIGS. 7, 8), and a TFPI cofactor inhibitor (Antibody 23; FIGS. 9, 10) when using a TFPI cofactor assay and an APC cofactor assay.

FIGS. 11A-11H depict the characterization of Antibody 19 and Antibody 7, antibodies sharing the same human variable region, and are characterized as dual inhibitors.

FIGS. 12A-12H depict the characterization of Antibody 13 and Antibody 1, antibodies sharing the same human variable region, and are characterized as dual inhibitors.

FIGS. 15A-15H depict the characterization of Antibody 16 and Antibody 4, antibodies sharing the same human variable region, and are characterized as dual inhibitors.

FIGS. 17A-17H depict the characterization of Antibody 21 and Antibody 9, antibodies sharing the same human variable region, and are characterized as APC cofactor inhibitors.

FIGS. 19A-19H depict the characterization of Antibody 24 and Antibody 12, antibodies sharing the same human variable region, and are characterized as dual inhibitors.

Figure 1:
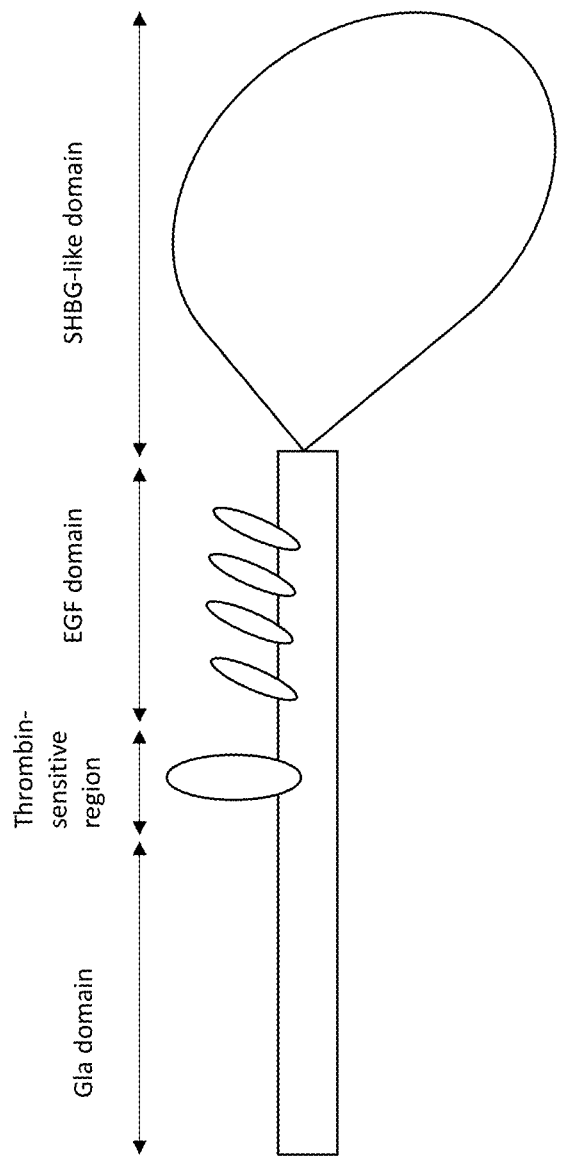
FIG. 1 depicts a schematic diagram of Protein S showing the modular domains of Protein S.

Also provided herein are antibody-drug conjugates, bispecific antibodies, and multispecific antibodies that exhibit specificity for and binding of Protein S.

The terms "polynucleotide" and "nucleic acid" are used interchangeably herein, and refer to a polymeric form of nucleotides of any length, which may be ribonucleotides or deoxyribonucleotides. The terms include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms encompass nucleic acids containing known analogues of natural nucleotides and having similar binding properties, and are metabolized in a manner similar to naturally-occurring nucleotides, unless specifically limited or stated otherwise.

When a nucleic acid or amino acid sequence is said to have a certain percent "sequence identity" or "identity" or is a certain percent "identical" to another nucleic acid or amino acid sequence, that percentage of bases or amino acids are the same, and in the same relative position, when the sequences are aligned, when comparing the two sequences.

The term "subject," as used herein refers to any subject for whom treatment or therapy is provided. The subject may be a mammalian subject. Mammalian subjects include, e. g., humans, non-human primates (e.g., cynomolgus monkey), rodents, (e.g., rats, mice), lagomorphs (e.g., rabbits), ungulates (e.g., cows, sheep, pigs, horses, goats, and the like), etc. In some embodiments, the subject is a human. In some embodiments, the subject is a non-human primate, e.g. a cynomolgus monkey. In some embodiments, the subject is a companion animal (e.g. cats, dogs).

All publications, patents, and patent applications mentioned in this specification are herein incorporated by reference to the same extent as if each individual publication, patent, or patent application was specifically and individually indicated to be incorporated by reference.

I. Antibodies that Bind and Modulate Protein S Activity

A. Protein S Antibodies

Provided here are antibodies that bind to Protein S, and in some embodiments are specific for Protein S. The Protein S can be of any species, e.g. any mammalian species. In some embodiments, the Protein S antibody binds to human Protein S. In some embodiments, the Protein S antibody binds to the Protein S of non-human primates. In some embodiments, the non-human primate is cynomolgus monkey.

The amino acid sequence of human Protein S, targeted by antibodies of the disclosure, is shown below as SEQ ID. NO: 216.

```
                                          (SEQ ID. NO: 216)
          10         20         30         40
    MRVLGGRCGA LLACLLLVLP VSEANFLSKQ QASQVLVRKR 50         60         70         80
    RANSLLEETK QGNLERECIE ELCNKEEARE VFENDPETDY 90        100        110        120
    FYPKYLVCLR SFQTGLFTAA RQSTNAYPDL RSCVNAIPDQ 130        140        150        160
    CSPLPCNEDG YMSCKDGKAS FTCTCKPGWQ GEKCEFDINE
```

-continued
```
         170        180        190        200
    CKDPSNINGG CSQICDNTPG SYHCSCKNGF VMLSNKKDCK 210        220        230        240
    DVDECSLKPS ICGTAVCKNI PGDFECECPE GYRYNLKSKS 250        260        270        280
    CEDIDECSEN MCAQLCVNYP GGYTCYCDGK KGFKLAQDQK 290        300        310        320
    SCEVVSVCLP LNLDTKYELL YLAEQFAGVV LYLKFRLPEI 330        340        350        360
    SRFSAEFDFR TYDSEGVILY AESIDHSAWL LIALRGGKIE 370        380        390        400
    VQLKNEHTSK ITTGGDVINN GLWNMVSVEE LEHSISIKIA 410        420        430        440
    KEAVMDINKP GPLFKPENGL LETKVYFAGF PRKVESELIK 450        460        470        480
    PINPRLDGCI RSWNLMKQGA SGIKEIIQEK QNKHCLVTVE 490        500        510        520
    KGSYYPGSGI AQFHIDYNNV SSAEGWHVNV TLNIRPSTGT 530        540        550        560
    GVMLALVSGN NTVPFAVSLV DSTSEKSQDI LLSVENTVIY 570        580        590        600
    RIQALSLCSD QQSHLEFRVN RNNLELSTPL KIETISHEDL 610        620        630        640
    QRQLAVLDKA MKAKVATYLG GLPDVPFSAT PVNAFYNGCM 650        660        670
    EVNINGVQLD LDEAISKHND IRAHSCPSVW KKTKNS
```

In some embodiments, provided herein are Protein S antibodies comprising a binding affinity (KD) to Protein S of about 0.0005 nM or lower, 0.001 nM or lower, 0.005 nM or lower, 0.01 nM or lower, 0.05 nM or lower, about 0.1 nM or lower, about 0.5 nM or lower, about 1 nM or lower, about 5 nM or lower, about 10 nM or lower, about 50 nM or lower, about 100 nM or lower, about 500 nM or lower, or about 1p M or lower.

The Protein S antibodies provided herein are capable of modulating one or more activities of Protein S, including, for example, modulating Protein S cofactor activity, as well as promoting coagulation and altering levels of markers associated with coagulation, and modulating a component in the coagulation cascade.

In some embodiments, the Protein S antibodies provided herein are capable of modulating the Protein S ability to act as a cofactor within pathways of the coagulation cascade.

Accordingly, in some embodiments, the Protein S antibodies provided herein are useful for reducing or inhibiting the cofactor activity of Protein S for activated Protein C ("APC").

In some embodiments, the Protein S antibodies provided herein are useful for reducing or inhibiting the cofactor activity of Protein S for tissue factor pathway inhibitor ("TFPI"). TFPI is an inhibitor of procoagulant activity and is produced as at least two alternatively spliced isoforms in humans, TFPIα, and TFPIβ, which differ in domain structure and mechanism for cell surface association. TFPIα, but not TFPIβ contains Kunitz domain 3, the domain which is believed to be involved in binding to Protein S. Without being held to any theory or mechanism, it is believed that the Protein S antibodies of the disclosure inhibit the cofactor activity of Protein S for at least TFPIα, as it contains Kunitz domain 3.

In some embodiments, the Protein S antibodies provided herein are useful for reducing or inhibiting the cofactor activity of Protein S for APC, but show negligible or no effect on cofactor activity of Protein S for TFPI (such antibodies are referred to interchangeably herein as "APC cofactor inhibitors", "APC cofactor specific inhibitors", or "APC pathway inhibitors").

In some embodiments, the Protein S antibodies provided herein are useful for reducing or inhibiting the cofactor activity of Protein S for TFPI, but show negligible or no effect on cofactor activity of Protein S for APC (such antibodies are referred to interchangeably herein as "TFPI cofactor inhibitors", "TFPI cofactor specific inhibitors", or "TFPI pathway inhibitors").

In some embodiments, the Protein S antibodies provided herein are useful for reducing or inhibiting the cofactor activity of Protein S for both APC and TFPI (such antibodies are referred to herein as "dual inhibitors"). The dual inhibitors of the disclosure may reduce the activities of APC and TFPI to different degrees.

In some embodiments, the Protein S antibodies provided herein are capable of causing a reduction in the activity of APC. For example, APC activity may be reduced by about 10%, about 20%, about 30%, about 40%, about 50%, about 60%, about 70%, about 80%, about 90%, or about 100% as compared to in the absence of the Protein S antibodies.

In some embodiments, the Protein S antibodies provided herein are capable of causing a reduction in the activity of TFPI. For example, TFPI activity may be reduced by about 10%, about 20%, about 30%, about 40%, about 50%, about 60%, about 70%, about 80%, about 90%, or about 100% as compared to in the absence of the Protein S antibodies.

In some embodiments, the Protein S antibodies provided herein are capable of causing a reduction in the activity of both APC and TFPI. For example, APC activity may be reduced by about 10%, about 20%, about 30%, about 40%, about 50%, about 60%, about 70%, about 80%, about 90%, or about 100%, and TFPI activity may also be reduced by about 10%, about 20%, about 30%, about 40%, about 50%, about 60%, about 70%, about 80%, about 90%, or about 100% as compared to in the absence of the Protein S antibodies. The reduction in APC activity and TFPI activity may be affected to different degrees by the same Protein S antibody.

In some embodiments, the Protein S antibodies provided herein are APC cofactor inhibitors, and the capability of the antibody for affecting the cofactor activity of Protein S for TFPI is negligible. In other embodiments, the Protein S antibodies provided herein are TFPI cofactor inhibitors, and the capability of the antibody for affecting the cofactor activity of Protein S for APC is negligible.

In some embodiments, the Protein S antibodies provided herein are capable of promoting coagulation and/or modulating a component in the coagulation cascade, e.g., in a subject in need thereof, or in a sample. In some embodiments, the Protein S antibodies provided herein are capable of promoting the clotting of blood. In some embodiments, the antibodies are capable of promoting clotting of blood by reducing the ability of Protein S to act as a cofactor for APC. For example, clotting of blood may be promoted by reducing APC activity by about 10%, about 20%, about 30%, about 40%, about 50%, about 60%, about 70%, about 80%, about 90%, or about 100%, as compared to in the absence of the Protein S antibodies.

In some embodiments, the antibodies are capable of promoting clotting of blood by reducing an ability of Protein S to act as a cofactor for TFPI. For example, clotting of blood may be promoted by reducing TFPI activity by about 10%, about 20%, about 30%, about 40%, about 50%, about 60%, about 70%, about 80%, about 90%, or about 100%, as compared to in the absence of the Protein S antibodies.

In some embodiments, the antibodies are capable of promoting clotting of blood by reducing an ability of Protein S to act as a cofactor for both APC and TFPI. For example, clotting of blood may be promoted by reducing both APC activity and TFPI activity by about 10%, about 20%, about 30%, about 40%, about 50%, about 60%, about 70%, about 80%, about 90%, or about 100%, as compared to in the absence of the Protein S antibodies.

In some embodiments, the Protein S antibodies provided herein are capable of promoting the generation of a marker associated with coagulation activity, and this can be exhibited in vitro (e.g. in a sample) and/or in vivo (e.g. upon administration to a subject). Such markers include, but are not limited to, thrombin, fibrin, D-dimer, clot formation, thrombin-antithrombin complex, fibrin degradation products, and prothrombin fragment F1.2.

In some embodiments, the Protein S antibodies provided herein are capable of promoting thrombin generation (e.g. includes restoring thrombin generation or restoring the levels of thrombin, e.g., in a subject in need thereof, or in a sample). In some embodiments, the antibodies are capable of promoting generation of thrombin in a subject in need thereof. In some embodiments, the generation of thrombin does not exceed a predetermined threshold level. In some embodiments, the generation of thrombin is partially restored. In some embodiments, the generation of thrombin does not exceed a predetermined percentage of a maximum thrombin generation. In some embodiments, the generation of thrombin does not exceed a predetermined percentage of an area under the curve of the maximum thrombin generation. In some embodiments, thrombin generation may be increased by about 5-fold to 50-fold, e.g. by about 5-fold, by about 10-fold, by about 15-fold, by about 20-fold, by about 25-fold, by about 30-fold, by about 35-fold, by about 40-fold, by about 45-fold, or even by about 50-fold, as compared to in the absence of the Protein S antibodies. Exemplary antibodies that promote thrombin generation are described in greater detail below, and include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, an amino acid sequence of GKN, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, an amino acid sequence of QNS, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, an amino acid sequence of QDT, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, an amino acid sequence of DAS, SEQ ID NO: 31, SEQ ID NO: 43, SEQ ID NO: 55, and SEQ ID NO: 67.

In some embodiments, the Protein S antibodies provided herein can restore or promote thrombin generation in a subject who is deficient in coagulation factors. In some exemplary embodiments, the coagulation factor deficiency is congenital. In some exemplary embodiments, the coagulation factor deficiency is acquired. In some embodiments, the Protein S antibodies provided herein can promote thrombin generation in a subject who is deficient in Factor VII, Factor VIII, Factor IX, Factor XI. For example, thrombin generation can be increased by about 5-fold to 50-fold, e.g. by about 5-fold, by about 10-fold, by about 15-fold, by about 20-fold, by about 25-fold, by about 30-fold, by about 35-fold, by about 40-fold, by about 45-fold, or even by about 50-fold, as compared to in the absence of the Protein S antibodies, when used to promote thrombin generation in a sample from a subject with a factor deficiency.

In some embodiments, the Protein S antibodies provided herein can promote thrombin generation in a subject who suffers from von Willebrand Disease (vWD) disease. In some embodiments, the vWD is a subtype selected from: vWD Type 1, vWD Type 2A, vWD Type 2B, vWD Type 2N, vWD Type 2M, vWD Type 3, and acquired vWD. In some exemplary embodiments, the vWD is a subtype selected from Type 1, Type 2, or Type 3. For example, thrombin generation can be increased by about 5-fold to 50-fold, e.g. by about 5-fold, by about 10-fold, by about 15-fold, by about 20-fold, by about 25-fold, by about 30-fold, by about 35-fold, by about 40-fold, by about 45-fold, or even by about 50-fold, as compared to in the absence of the Protein S antibodies, when used to promote thrombin generation in a sample from a subject with vWD disease.

Exemplary antibodies that may promote thrombin generation in a subject who is deficient in a coagulation factor (such as Factor VII, Factor VIII, Factor IX, Factor XI) or who has von Willebrand disease (such as Type 1, Type 2A, Type 2B, Type 2M, Type 2N or Type 3) include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, an amino acid sequence of GKN, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, an amino acid sequence of QNS, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, an amino acid sequence of QDT, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, an amino acid sequence of DAS, SEQ ID NO: 31, SEQ ID NO: 43, SEQ ID NO: 55, and SEQ ID NO: 67.

In some embodiments, the Protein S antibodies provided herein are capable of promoting fibrin generation, e.g., in a subject in need thereof, or in a sample. In some embodiments, the Protein S antibodies provided herein are capable of promoting fibrin deposition e.g., in a sample. In some embodiments, the Protein S antibodies provided herein are capable of promoting coagulation activity, wherein the coagulation activity is marked by a promotion of fibrin generation. For example, fibrin generation may be increased by about 5-fold to 50-fold, e.g. by about 5-fold, by about 10-fold, by about 15-fold, by about 20-fold, by about 25-fold, by about 30-fold, by about 35-fold, by about 40-fold, by about 45-fold, or even by about 50-fold, as compared to in the absence of the Protein S antibodies. as compared to in the absence of the Protein S antibodies. Exemplary antibodies that may promote fibrin generation include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, an amino acid sequence of GKN, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, an amino acid sequence of QNS, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, an amino acid sequence of QDT, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, an amino acid sequence of DAS, SEQ ID NO: 31, SEQ ID NO: 43, SEQ ID NO: 55, and SEQ ID NO: 67.

In some embodiments, the Protein S antibodies provided herein are capable of promoting increasing D-dimer levels, e.g., in a subject in need thereof, or in a sample. In some embodiments, the Protein S antibodies provided herein are capable of promoting coagulation activity, wherein the coagulation activity is marked by an increase in D-dimer levels. For example, D-dimer levels may be increased by about two-fold to about 10,000-fold. Exemplary antibodies that may promote an increase in D-dimer levels include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, an amino acid sequence of GKN, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, an amino acid sequence of QNS, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, an amino acid sequence of QDT, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, an amino acid sequence of DAS, SEQ ID NO: 31, SEQ ID NO: 43, SEQ ID NO: 55, and SEQ ID NO: 67.

In some embodiments, the Protein S antibodies provided herein are capable of promoting coagulation in a sample or in a subject. In some embodiments, the Protein S antibodies provided herein alter the levels of markers associated with coagulation activity in a sample or in a subject. For example, in some embodiments, the antibodies are capable of restoring or promoting thrombin generation in a sample, or in a subject. In some embodiments, the antibodies are capable of restoring fibrin deposition in a sample, or in a subject. In some embodiments, the antibodies provided herein are capable of promoting a restoration of fibrin deposition. In some embodiments, the antibodies provided herein are capable of increasing the levels of D-dimer in a sample, or in a subject. In some embodiments, the antibodies provided herein are capable of promoting an increase of D-dimer. In some embodiments, activity of the antibodies provided herein is dose-dependent. In some embodiments, activity of the antibodies provided herein is measured in vitro. In some embodiments, activity of the antibodies provided herein is measured in vivo.

In some embodiments, the Protein S antibodies provided herein are administered to a subject, wherein the antibody remains active in the subject for a period of time.

Figure 24B:
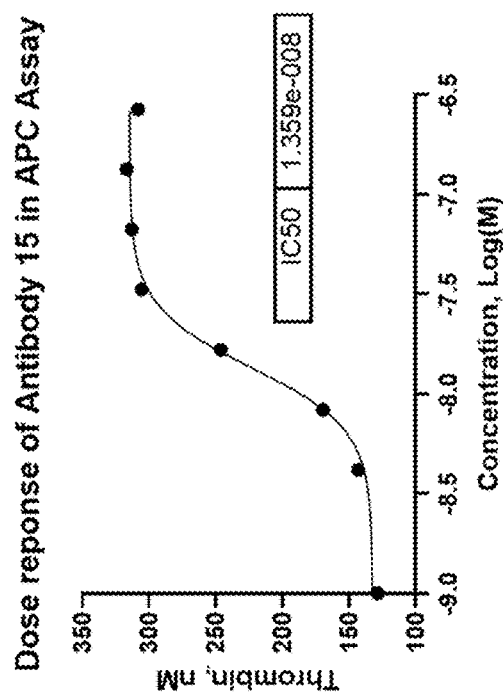
Figure 24A:
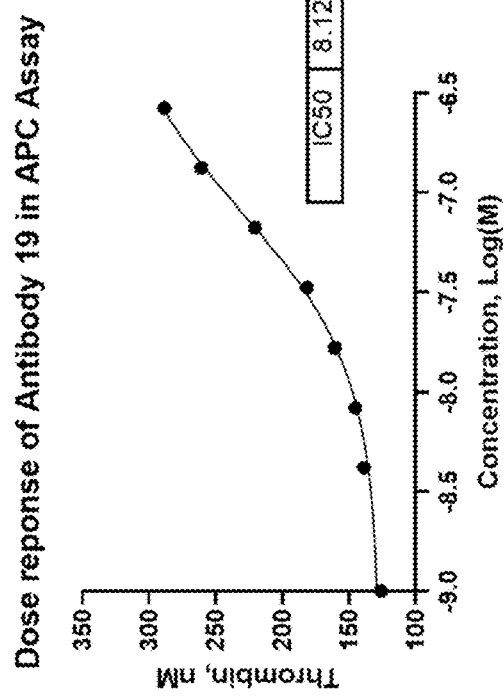

In some embodiments, the Protein S antibodies provided herein are administered to a subject, wherein the effect of the antibody is dose-dependent, such antibodies exhibit graded inhibition. FIG. 24A (Antibody 19) depicts an exemplary dose response curve of thrombin generation resulting from an antibody exhibiting graded inhibition. Antibodies exhibiting graded inhibition show concentration-dependent inhibition in vitro, where increasing concentrations of antibody result in incremental increases in thrombin generation over a wide concentration range. Exemplary antibodies that exhibit such graded inhibition include, but are not limited to, antibodies that comprise (a) the CDR amino acid sequences of SEQ ID NO: 1, an amino acid sequence of QDT, SEQ ID NO: 21, SEQ ID NO: 33, SEQ ID NO: 45, and SEQ ID NO: 57; or (b) the CDR amino acid sequences of SEQ ID NO: 10, an amino acid sequence of DAS, SEQ ID NO: 31, SEQ ID NO: 43, SEQ ID NO: 55, SEQ ID NO: 67.

In such embodiments, the graded inhibition can allow for increasing the dose of administration of the Protein S antibodies to a subject for added efficacy, or decreasing the dose to prevent excess thrombin generation, and/or potential thromboembolic complications, for example. Effectively, the dose can be adjusted to achieve the desired level of inhibition.

In some embodiments, the Protein S antibodies provided herein exhibit switch-like inhibition, wherein inhibition can be switched on or off. FIG. 24B (Antibody 15) depicts an exemplary dose response curve resulting from an antibody exhibiting switch-like inhibition. Antibodies exhibiting switch-like inhibition show abrupt concentration-dependent increases in thrombin generation in vitro, where upon reaching a concentration capable of promoting thrombin generation, achieves maximal thrombin generated within a narrow concentration range. Exemplary antibodies that exhibit such graded inhibition include, but are not limited to, antibodies that comprise (a) the CDR amino acid sequences of SEQ ID NO: 2, an amino acid sequence of GKN, SEQ ID NO: 22, SEQ ID NO: 34, SEQ ID NO: 46, and SEQ ID NO: 58; or (b) the CDR amino acid sequences of SEQ ID NO: 1, an amino acid sequence of QNS, SEQ ID NO: 24, SEQ ID NO: 36, SEQ ID NO: 48, and SEQ ID NO: 60.

In some embodiments, the Protein S antibodies provided herein are antibody fragments. In some embodiments, the antibody fragments are antigen-binding fragments (Fab), variable fragments (Fv) containing VH and VL, single chain variable fragments (scFv) containing VH and VL linked together in one chain, or other antibody variable region fragments, such as Fab', F(ab)2, F(ab')2, dsFv diabody, Fc, and Fd polypeptide fragments. The antibody fragments contain a Fc domain.

In some embodiments, the Protein S antibodies provided herein are monoclonal antibodies (mAbs). In some embodiments, the Protein S antibodies provided herein are human antibodies. In some embodiments, the Protein S antibodies provided herein are monoclonal human antibodies. In some embodiments, the Protein S antibodies provided herein are humanized antibodies. In some embodiments, the Protein S antibodies provided herein are monoclonal humanized antibodies. In some embodiments, the Protein S antibodies provided herein are chimeric antibodies. In some embodiments, the Protein S antibodies provided herein are monoclonal chimeric antibodies.

In some embodiments, the Protein S antibodies provided herein are full-length antibodies.

In some embodiments, the Protein S antibodies provided herein contain an Fc domain (either are full-length or for example, a single chain antibody linked to a Fc domain).

In some embodiments, the constant region (herein referred to also as a Fc domain, a Fc sequence or simply as a Fc) of a Protein S antibody is a human Fc domain. In some embodiments, the Fc domain of a full-length Protein S antibody is human IgG1, human IgG2, human IgG3, or human IgG4. In some embodiments, the Fc domain of a full-length Protein S antibody is that of a rat. In some embodiments, the Fc domain of a full-length Protein S antibody is rat IgG1 or rat IgG2b. In some embodiments, the Fc domain of a full-length Protein S antibody is that of a non-human primate, e.g. it is a cynomolgus monkey Fc domain.

In some embodiments, the Protein S antibodies provided herein are chimeric and comprise a variable region from one species, and a constant region from another species, e.g. comprise a human variable region and a rat constant region. In some embodiments, the rat constant region is rat IgG1 or IgG2b. In some embodiments, the antibodies comprise a human variable region and a human constant region. In exemplary embodiments, the human constant region is human IgG1, or human IgG4.

In some embodiments, the Protein S antibody contains an Fc domain, and the Fc domain of the antibody is a human IgG1 Fc. Exemplary, but non-limiting, human IgG1 Fc domain sequences are provided as SEQ ID NOS: 217.

```
                                            (SEQ ID NO: 217)
  1 ASTKGPSVFP LAPSSKSTSG GTAALGCLVK

DYFPEPVTVS WNSGALTSGV HTFPAVLQSS

61 GLYSLSSVVT VPSSSLGTQT YICNVNHKPS

NTKVDKKVEP KSCDKTHTCP PCPAPELLGG

121 PSVFLFPPKP KDTLMISRTP EVTCVVVDVS

HEDPEVKFNW YVDGVEVHNA KTKPREEQYN

181 STYRVVSVLT VLHQDWLNGK EYKCKVSNKA

LPAPIEKTIS KAKGQPREPQ VYTLPPSRDE
```

```
241 LTKNQVSLTC LVKGFYPSDI AVEWESNGQP

ENNYKTTPPV LDSDGSFFLY SKLTVDKSRW

301 QQGNVFSCSV MHEALHNHYT QKSLSLSPGK
```

In some embodiments, the Protein S antibody contains an Fc domain, and the Fc domain of the antibody is a human IgG4 Fc. An exemplary human IgG4 heavy chain Fc domain sequence is provided as SEQ ID NO: 218.

```
                                        (SEQ ID NO: 218)
ASTKGPSVFPLAPCSRSTSESTAALGCLVKDYFPEPVT

VSWNSGALTSGVHTFPAVLQSSGLYSLSSVVTVPSSSL

GTKTYTCNVDHKPSNTKVDKRVESKYGPPCPSCPAPEF

LGGPSVFLFPPKPKDTLMISRTPEVTCVVVDVSQEDPE

VQFNWYVDGVEVHNAKTKPREEQFNSTYRVVSVLTVLH

QDWLNGKEYKCKVSNKGLPSSIEKTISKAKGQPREPQV

YTLPPSQEEMTKNQVSLTCLVKGFYPSDIAVEWESNGQ

PENNYKTTPPVLDSDGSFFLYSRLTVDKSRWQEGNVFS

CSVMHEALHNHYTQKSLSLSLGK
```

The EU numbering scheme is one of many available antibody numbering schemes based on the residue numbers assigned to a canonical antibody sequence. Accordingly, a skilled artisan would understand that reference to a particular residue using the EU numbering scheme may or may not be exactly the residue in one of the antibodies of the disclosure. For example, if a Protein S antibody of the disclosure comprises a V215A substitution in the Fc, wherein the position number of the amino acid residue is of the EU numbering scheme, the residue may not be the actual residue 215 in that particular Protein S antibody. It may be actual residue number 213, or 214, or 215, or 216. Accordingly a skilled artisan will understand how to correspond the recited residue using the EU numbering scheme, to the actual residue in a Protein S antibody of the disclosure. The EU numbering system for antibodies is known in the art and is described, for example, at imgt.org/IMGTScientificChart/Numbering/Hu_IGHGnber.html.

In some embodiments, the Fc domain of a Protein S antibody is an IgG1 or IgG4 human Fc domain, and Fc variants comprise at least one amino acid substitution at a position selected from the group consisting of: 215, 221, 222, 228, 234, 235, 236, 239, 240, 241, 243, 244, 245, 247, 250, 252, 254, 256, 262, 263, 264, 265, 266, 267, 268, 269, 270, 292, 296, 297, 298, 299, 300, 305, 313, 324, 325, 326, 327, 328, 329, 330, 332, 333, 334, 345, 396, 428, 430, 433, 434, and 440, wherein the position numbers of the amino acid residues are of the EU numbering scheme.

In some embodiments, the Fc domain of a Protein S antibody is a human IgG1, and substitutions are introduced to reduce effector function, including N297A, N297Q, N297G, L235E, L234A, and L235A, wherein the position numbers of the amino acid residues are of the EU numbering scheme. In some embodiments, the Fc domain of a full-length Protein S antibody is human IgG4, and substitutions are introduced to reduce effector function, including L235E, and F234A/L235A, wherein the position numbers of the amino acid residues are of the EU numbering scheme. In some embodiments, the Fc domain of a full-length Protein S antibody is human IgG2, and substitutions are introduced to reduce effector function, including H268Q/V309L/A330S/P331S and V234A/G237A/P238S/H268A/V309L/A330S/P331S, wherein the position numbers of the amino acid residues are of the EU numbering scheme.

In some embodiments, the Fc domain of a Protein S antibody is a human IgG1, and substitutions are introduced to increase effector function, including G236A/S239D/I332E, K326W/E333S, S267E/H268F/S324T, and E345R/E430G/S440Y, wherein the position numbers of the amino acid residues are of the EU numbering scheme.

In some embodiments, the Fc domain of a Protein S antibody is an IgG4 human Fc domain, and the antibody is prone to the dynamic process of Fab-arm exchange. Accordingly, in some embodiments the IgG4 Fc domain comprises a S228P substitution, resulting in the reduction of this process, wherein the position number of the amino acid residues are of the EU numbering scheme.

In other embodiments, the Fc domain of a Protein S antibody is altered to increase its serum half-life. Such alterations include substitutions of a human IgG1 (e.g. SEQ ID NO: 217) such as T250Q/M428L, M252Y/S254T/T256E, M428L/N434S, S267E/L328F, N325S/L328F, and H433K/N434F, wherein the position number of the amino acid residues are of the EU numbering scheme.

In other embodiments, the Fc domain of a Protein S antibody is altered to increase its serum half-life. Such alterations include substitutions of a human IgG4 (e.g. SEQ ID NO: 218) such as T250Q/M428L, M252Y/S254T/T256E, M428L/N434S, S267E/L328F, N325S/L328F, and H433K/N434F, wherein the position number of the amino acid residues are of the EU numbering scheme.

In some embodiments, the Fc domain of a Protein S antibody is an IgG1 human Fc domain, and substitutions are introduced enhance effector function, including F243L/R292P/Y300L/V305I/P396L, S239D/I332E, S298A/E333A/K334A, L234Y/L235Q/G236W/S239M/H268D/D270E/S298A, D270E/K326D/A330M/K334E, wherein the position number of the amino acid residues are of the EU numbering scheme.

Exemplary Protein S Antibodies—CDR Sequences

Provided herein are exemplary CDR sequences of the Protein S antibodies disclosed herein.

Exemplary CDR sequences presented in Tables 1A-1C and 2A-2C below. As referred below, a light chain variable (VL) domain CDR1 region is referred to as CDR-L1; a VL CDR2 region is referred to as CDR-L2; a VL CDR3 region is referred to as CDR-L3; a heavy chain variable (VH) domain CDR1 region is referred to as CDR-H1; a VH CDR2 region is referred to as CDR-H2; and a VH CDR3 region is referred to as CDR-H3.

TABLE 1A

Exemplary Protein S Antibody CDR-L1 Sequences

KLGDKY (SEQ ID NO: 1)

SLRNYY (SEQ ID NO: 2)

SSDVGGYEF (SEQ ID NO: 3)

QSVSIY (SEQ ID NO: 4)

QRINSN (SEQ ID NO: 5)

QSLLHSNGYNY (SEQ ID NO: 6)

TGAVTASNY (SEQ ID NO: 9)

TABLE 1A-continued

Exemplary Protein S Antibody CDR-L1 Sequences

QSVTSN (SEQ ID NO: 10)

QSLVHSDGNTY (SEQ ID NO: 11)

QGINNY (SEQ ID NO: 117)

QSISTF (SEQ ID NO: 127)

QSVGSSY (SEQ ID NO: 136)

QNIHMW (SEQ ID NO: 141)

QSISSY (SEQ ID NO: 174)

NIGGKS (SEQ ID NO: 184)

KLGDKY (SEQ ID NO: 194)

KLGDKY (SEQ ID NO: 204)

TABLE 1B

Exemplary Protein S Antibody CDR-L2 Sequences

QDT (SEQ ID NO: 12)

GKN (SEQ ID NO: 13)

DVS (SEQ ID NO: 14)

QNS (SEQ ID NO: 15)

DAS (SEQ ID NO: 16)

GAS (SEQ ID NO: 17)

LGS (SEQ ID NO: 18)

STN (SEQ ID NO: 19)

KIS (SEQ ID NO: 20)

AAS (SEQ ID NO: 118)

ATS (SEQ ID NO: 128)

KTS (SEQ ID NO: 142)

AAS (SEQ ID NO: 175)

DDS (SEQ ID NO: 185)

QDS (SEQ ID NO: 195)

QDN (SEQ ID NO: 205)

TABLE 1C

Exemplary Protein S Antibody CDR-L3 Sequences

QAWDSNTVV (SEQ ID NO: 21)

NSRDSSGNHVV (SEQ ID NO: 22)

SSYTRSSTVV (SEQ ID NO: 23)

QAWDSSTWV (SEQ ID NO: 24)

QQRSNWPLT (SEQ ID NO: 25)

QQYDNWPLT (SEQ ID NO: 26)

TABLE 1C-continued

Exemplary Protein S Antibody CDR-L3 Sequences

MQALQTFT (SEQ ID NO: 27)

ALWYSDHFV (SEQ ID NO: 30)

QQYNNWPT (SEQ ID NO: 31)

MQATQFPHLT (SEQ ID NO: 32)

QQYNSYPRT (SEQ ID NO: 119)

QQYNSYPIT (SEQ ID NO: 123)

QQSYSTPRT (SEQ ID NO: 129)

QQYGSSPYT (SEQ ID NO: 137)

LQGQSYPFT (SEQ ID NO: 143)

QQSYSSLT (SEQ ID NO: 176)

QVWEITSDHPA (SEQ ID NO: 186)

QAWDSSTVG (SEQ ID NO: 196)

QAWDSSTAV (SEQ ID NO: 206)

TABLE 2A

Exemplary Protein S Antibody CDR-H1 Sequences

GGSISSSSYY (SEQ ID NO: 33)

GGTFSSYS (SEQ ID NO: 34)

GGSITSDGYH (SEQ ID NO: 35)

GFTFDDYA (SEQ ID NO: 36)

GFTFSTYG (SEQ ID NO: 37)

GYSISSGYY (SEQ ID NO: 38)

GDTFSNHA (SEQ ID NO: 39)

GHTFTGYY (SEQ ID NO: 42)

GGSISSTNW (SEQ ID NO: 43)

GGSISNYY (SEQ ID NO: 44)

GGSITNSNYY (SEQ ID NO: 120)

GFTFSSYN (SEQ ID NO: 124)

GGSISGNY (SEQ ID NO: 130)

GDSVSNNNAA (SEQ ID NO: 138)

GYTFTNHW (SEQ ID NO: 144)

GISFSNAW (SEQ ID NO: 179)

GFTFSSYS (SEQ ID NO: 189)

GYTFTNYY (SEQ ID NO: 199)

GYTFTSYY (SEQ ID NO: 209)

TABLE 2B

Exemplary Protein S Antibody CDR-H2 Sequences

IYYSGNT (SEQ ID NO: 45)

IIPIFGTT (SEQ ID NO: 46)

IYYTGNT (SEQ ID NO: 47)

ITWNSGNI (SEQ ID NO: 48)

IYYDGINK (SEQ ID NO: 49)

IYYSGST (SEQ ID NO: 50)

YIPIFGTT (SEQ ID NO: 51)

INPNSGDT (SEQ ID NO: 54)

IYQTGST (SEQ ID NO: 55)

IYYIGIT (SEQ ID NO: 56)

VYYSGTT (SEQ ID NO: 121)

ISSSSSYI (SEQ ID NO: 125)

TYYRSKWYN (SEQ ID NO: 139)

IYPGGGYT (SEQ ID NO: 145)

IKANPDGGTT (SEQ ID NO: 180)

ISSSTRTI (SEQ ID NO: 190)

ITPSGGTT (SEQ ID NO: 200)

TSPSGRST (SEQ ID NO: 210)

TABLE 2C

Exemplary Protein S Antibody CDR-H3 Sequences

ARCSGYGYSSGRSYFDY (SEQ ID NO: 57)

EGGRVGADFDY (SEQ ID NO: 58)

ARRLSTGPYFDY (SEQ ID NO: 59)

AKGRAVSDTFDI (SEQ ID NO: 60)

AESDLDY (SEQ ID NO: 61)

ATTYSDIVTGYYNDAFDI (SEQ ID NO: 62)

ARGGLAGSHYKNYYYDGMDV (SEQ ID NO: 63)

ARDSQILWFGELGY (SEQ ID NO: 66)

ARRFGELDY (SEQ ID NO: 67)

AALSGDHAFDI (SEQ ID NO: 68)

VRESESYYYYGSDV (SEQ ID NO: 122)

ARDEEWELLTGFDY (SEQ ID NO: 126)

ARDLDYFTWGAYSDWYFDL (SEQ ID NO: 131)

ARGSSWYRFFDY (SEQ ID NO: 140)

SRFGDQNWAWFAY (SEQ ID NO: 146)

TTELDILLWFTSFDY (SEQ ID NO: 181)

TABLE 2C-continued

Exemplary Protein S Antibody CDR-H3 Sequences

ARERSAFDY (SEQ ID NO: 191)

ARAGVQLDRRGWFDP (SEQ ID NO: 201)

ARGGVTIHLERRGYFDY (SEQ ID NO: 211)

In some embodiments, the Protein S antibodies provided herein include any one or more of the amino acid sequences of the CDR sequences provided in Tables 1A, 1B, 1C, 2A, 2B, and 2C.

In some embodiments, provided herein are Protein S antibodies, wherein the antibodies comprise:
(a) any one of the CDR-L1 amino acid sequences of Table 1A;
(b) any one of the CDR-L2 amino acid sequences of Table 1B;
(c) any one of the CDR-L3 amino acid sequences of Table 1C;
(d) any one of the CDR-H1 amino acid sequences of Table 2A;
(e) any one of the CDR-H2 amino acid sequences of Table 2B; and
(f) any one of the CDR-H3 amino acid sequences of Table 2C.

In some embodiments, provided herein are Protein S antibodies, wherein the light chain variable domain of the antibodies comprises:
(a) a CDR-L1 comprising the amino acid sequence of any one of SEQ ID NOs: 1-6, 9-11, 117, 127, 136, 141, 174, 184, 194, and 204;
a CDR-L2 comprising the amino acid sequence of any one of: QDT, GKN, DVS, QNS, DAS, GAS, LGS, STN, KIS, AAS, ATS, KTS, AAS, DDS, QDS, and QDN
; and
(b) a CDR-L3 comprising the amino acid sequence of any one of SEQ ID NOs: 21-27, 30-32, 119, 123, 129, 137, 143, 176, 186, 196, and 206.

In some embodiments, provided herein are Protein S antibodies, wherein the heavy chain variable domain of the antibodies comprises:
(a) a CDR-H1 comprising the amino acid sequence of any one of SEQ ID NOs: 33-39, 42-44, 120, 124, 130, 138, 144, 179, 189, 199, and 209;
(b) a CDR-H2 comprising the amino acid sequence of any one of SEQ ID NOs: 45-51, 54-56, 121, 125, 139, 145, 180, 190, 200, and 210;
(c) a CDR-H3 comprising the amino acid sequence of any one of SEQ ID NOs: 57-63, 66-68, 122, 126, 131, 140, 146, 181, 191, 201, and 211.

In some embodiments, provided herein are Protein S antibodies, wherein the light chain variable domain of the antibody comprises:
(a) a CDR-L1 comprising the amino acid sequence of SEQ ID NO: 1;
(b) a CDR-L2 comprising the amino acid sequence of QDT; and
(c) a CDR-L3 comprising the amino acid sequence of SEQ ID NO: 21.

In some embodiments, provided herein are Protein S antibodies, wherein the light chain variable domain of the antibody comprises:

(a) a CDR-L1 comprising the amino acid sequence of SEQ ID NO: 2;
(b) a CDR-L2 comprising the amino acid sequence of GKN; and
(c) a CDR-L3 comprising the amino acid sequence of SEQ ID NO: 22.

In some embodiments, provided herein are Protein S antibodies, wherein the light chain variable domain of the antibody comprises:
(a) a CDR-L1 comprising the amino acid sequence of SEQ ID NO: 3;
(b) a CDR-L2 comprising the amino acid sequence of DVS; and
(c) a CDR-L3 comprising the amino acid sequence of SEQ ID NO: 23.

In some embodiments, provided herein are Protein S antibodies, wherein the light chain variable domain of the antibody comprises:
(a) a CDR-L1 comprising the amino acid sequence of SEQ ID NO: 1;
(b) a CDR-L2 comprising the amino acid sequence of QNS; and
(c) a CDR-L3 comprising the amino acid sequence of SEQ ID NO: 24.

In some embodiments, provided herein are Protein S antibodies, wherein the light chain variable domain of the antibody comprises:
(a) a CDR-L1 comprising the amino acid sequence of SEQ ID NO: 4;
(b) a CDR-L2 comprising the amino acid sequence of DAS; and
(c) a CDR-L3 comprising the amino acid sequence of SEQ ID NO: 25.

In some embodiments, provided herein are Protein S antibodies, wherein the light chain variable domain of the antibody comprises:
(a) a CDR-L1 comprising the amino acid sequence of SEQ ID NO: 5;
(b) a CDR-L2 comprising the amino acid sequence of GAS; and
(c) a CDR-L3 comprising the amino acid sequence of SEQ ID NO: 26.

In some embodiments, provided herein are Protein S antibodies, wherein the light chain variable domain of the antibody comprises:
(a) a CDR-L1 comprising the amino acid sequence of SEQ ID NO: 6;
(b) a CDR-L2 comprising the amino acid sequence of LGS; and
(c) a CDR-L3 comprising the amino acid sequence of SEQ ID NO: 27.

In some embodiments, provided herein are Protein S antibodies, wherein the light chain variable domain of the antibody comprises:
(a) a CDR-L1 comprising the amino acid sequence of SEQ ID NO: 9;
(b) a CDR-L2 comprising the amino acid sequence of STN; and
(c) a CDR-L3 comprising the amino acid sequence of SEQ ID NO: 30.

In some embodiments, provided herein are Protein S antibodies, wherein the light chain variable domain of the antibody comprises:
(a) a CDR-L1 comprising the amino acid sequence of SEQ ID NO: 10;
(b) a CDR-L2 comprising the amino acid sequence of DAS; and
(c) a CDR-L3 comprising the amino acid sequence of SEQ ID NO: 31.

In some embodiments, provided herein are Protein S antibodies, wherein the light chain variable domain of the antibody comprises:
(a) a CDR-L1 comprising the amino acid sequence of SEQ ID NO: 11;
(b) a CDR-L2 comprising the amino acid sequence of KIS; and
(c) a CDR-L3 comprising the amino acid sequence of SEQ ID NO: 32.

In some embodiments, provided herein are Protein S antibodies, wherein the light chain variable domain of the antibody comprises:
(a) a CDR-L1 comprising the amino acid sequence of SEQ ID NO: 117;
(b) a CDR-L2 comprising the amino acid sequence of AAS; and
(c) a CDR-L3 comprising the amino acid sequence of SEQ ID NO: 119.

In some embodiments, provided herein are Protein S antibodies, wherein the light chain variable domain of the antibody comprises:
(a) a CDR-L1 comprising the amino acid sequence of SEQ ID NO: 117;
(b) a CDR-L2 comprising the amino acid sequence of AAS; and
(c) a CDR-L3 comprising the amino acid sequence of SEQ ID NO: 123.
(d)

In some embodiments, provided herein are Protein S antibodies, wherein the light chain variable domain of the antibody comprises:
(a) a CDR-L1 comprising the amino acid sequence of SEQ ID NO: 127;
(b) a CDR-L2 comprising the amino acid sequence of ATS; and
(c) a CDR-L3 comprising the amino acid sequence of SEQ ID NO: 129.

In some embodiments, provided herein are Protein S antibodies, wherein the light chain variable domain of the antibody comprises:
(a) a CDR-L1 comprising the amino acid sequence of SEQ ID NO: 136;
(b) a CDR-L2 comprising the amino acid sequence of GAS; and
(c) a CDR-L3 comprising the amino acid sequence of SEQ ID NO: 137.

In some embodiments, provided herein are Protein S antibodies, wherein the light chain variable domain of the antibody comprises:
(a) a CDR-L1 comprising the amino acid sequence of SEQ ID NO: 141;
(b) a CDR-L2 comprising the amino acid sequence of KTS; and
(c) a CDR-L3 comprising the amino acid sequence of SEQ ID NO: 143.

In some embodiments, provided herein are Protein S antibodies, wherein the light chain variable domain of the antibody comprises:
(a) a CDR-L1 comprising the amino acid sequence of SEQ ID NO: 174;
(b) a CDR-L2 comprising the amino acid sequence of AAS; and
(c) a CDR-L3 comprising the amino acid sequence of SEQ ID NO: 176.

In some embodiments, provided herein are Protein S antibodies, wherein the light chain variable domain of the antibody comprises:
(a) a CDR-L1 comprising the amino acid sequence of SEQ ID NO: 184;
(b) a CDR-L2 comprising the amino acid sequence of DDS; and
(c) a CDR-L3 comprising the amino acid sequence of SEQ ID NO: 186.

In some embodiments, provided herein are Protein S antibodies, wherein the light chain variable domain of the antibody comprises:
(a) a CDR-L1 comprising the amino acid sequence of SEQ ID NO: 194;
(b) a CDR-L2 comprising the amino acid sequence of QDS; and
(c) a CDR-L3 comprising the amino acid sequence of SEQ ID NO: 196.

In some embodiments, provided herein are Protein S antibodies, wherein the light chain variable domain of the antibody comprises:
(a) a CDR-L1 comprising the amino acid sequence of SEQ ID NO: 204;
(b) a CDR-L2 comprising the amino acid sequence of QDN; and
(c) a CDR-L3 comprising the amino acid sequence of SEQ ID NO: 206.

In some embodiments, provided herein are Protein S antibodies, wherein the heavy chain variable domain of the antibodies comprises:
(a) a CDR-H1 comprising the amino acid sequence of SEQ ID NO: 33;
(b) a CDR-H2 comprising the amino acid sequence of SEQ ID NO: 45; and
(c) a CDR-H3 comprising the amino acid sequence of SEQ ID NO: 57.

In some embodiments, provided herein are Protein S antibodies, wherein the heavy chain variable domain of the antibodies comprises:
(a) a CDR-H1 comprising the amino acid sequence of SEQ ID NO: 34;
(b) a CDR-H2 comprising the amino acid sequence of SEQ ID NO: 46; and
(c) a CDR-H3 comprising the amino acid sequence of SEQ ID NO: 58.

In some embodiments, provided herein are Protein S antibodies, wherein the heavy chain variable domain of the antibodies comprises:
(a) a CDR-H1 comprising the amino acid sequence of SEQ ID NO: 35;
(b) a CDR-H2 comprising the amino acid sequence of SEQ ID NO: 47; and
(c) a CDR-H3 comprising the amino acid sequence of SEQ ID NO: 59.

In some embodiments, provided herein are Protein S antibodies, wherein the heavy chain variable domain of the antibodies comprises:
(a) a CDR-H1 comprising the amino acid sequence of SEQ ID NO: 36;
(b) a CDR-H2 comprising the amino acid sequence of SEQ ID NO: 48; and
(c) a CDR-H3 comprising the amino acid sequence of SEQ ID NO: 60.

In some embodiments, provided herein are Protein S antibodies, wherein the heavy chain variable domain of the antibodies comprises:
(a) a CDR-H1 comprising the amino acid sequence of SEQ ID NO: 37;
(b) a CDR-H2 comprising the amino acid sequence of SEQ ID NO: 49; and
(c) a CDR-H3 comprising the amino acid sequence of SEQ ID NO: 61.

In some embodiments, provided herein are Protein S antibodies, wherein the heavy chain variable domain of the antibodies comprises:
(a) a CDR-H1 comprising the amino acid sequence of SEQ ID NO: 38;
(b) a CDR-H2 comprising the amino acid sequence of SEQ ID NO: 50; and
(c) a CDR-H3 comprising the amino acid sequence of SEQ ID NO: 62.

In some embodiments, provided herein are Protein S antibodies, wherein the heavy chain variable domain of the antibodies comprises:
(a) a CDR-H1 comprising the amino acid sequence of SEQ ID NO: 39;
(b) a CDR-H2 comprising the amino acid sequence of SEQ ID NO: 51; and
(c) a CDR-H3 comprising the amino acid sequence of SEQ ID NO: 63.

In some embodiments, provided herein are Protein S antibodies, wherein the heavy chain variable domain of the antibodies comprises:
(a) a CDR-H1 comprising the amino acid sequence of SEQ ID NO: 42;
(b) a CDR-H2 comprising the amino acid sequence of SEQ ID NO: 54; and
(c) a CDR-H3 comprising the amino acid sequence of SEQ ID NO: 66.

In some embodiments, provided herein are Protein S antibodies, wherein the heavy chain variable domain of the antibodies comprises:
(a) a CDR-H1 comprising the amino acid sequence of SEQ ID NO: 43;
(b) a CDR-H2 comprising the amino acid sequence of SEQ ID NO: 55; and
(c) a CDR-H3 comprising the amino acid sequence of SEQ ID NO: 67.

In some embodiments, provided herein are Protein S antibodies, wherein the heavy chain variable domain of the antibodies comprises:
(a) a CDR-H1 comprising the amino acid sequence of SEQ ID NO: 44;
(b) a CDR-H2 comprising the amino acid sequence of SEQ ID NO: 56; and
(c) a CDR-H3 comprising the amino acid sequence of SEQ ID NO: 68.

In some embodiments, provided herein are Protein S antibodies, wherein the heavy chain variable domain of the antibodies comprises:
(a) a CDR-H1 comprising the amino acid sequence of SEQ ID NO: 120;
(b) a CDR-H2 comprising the amino acid sequence of SEQ ID NO: 121; and
(c) a CDR-H3 comprising the amino acid sequence of SEQ ID NO: 122.

In some embodiments, provided herein are Protein S antibodies, wherein the heavy chain variable domain of the antibodies comprises:
(a) a CDR-H1 comprising the amino acid sequence of SEQ ID NO: 124;
(b) a CDR-H2 comprising the amino acid sequence of SEQ ID NO: 125; and (c) a CDR-H3 comprising the amino acid sequence of SEQ ID NO: 126.

In some embodiments, provided herein are Protein S antibodies, wherein the heavy chain variable domain of the antibodies comprises:
(a) a CDR-H1 comprising the amino acid sequence of SEQ ID NO: 130;
(b) a CDR-H2 comprising the amino acid sequence of SEQ ID NO: 50; and
(c) a CDR-H3 comprising the amino acid sequence of SEQ ID NO: 131.

In some embodiments, provided herein are Protein S antibodies, wherein the heavy chain variable domain of the antibodies comprises:
(a) a CDR-H1 comprising the amino acid sequence of SEQ ID NO: 138;
(b) a CDR-H2 comprising the amino acid sequence of SEQ ID NO: 139; and
(c) a CDR-H3 comprising the amino acid sequence of SEQ ID NO: 140.

In some embodiments, provided herein are Protein S antibodies, wherein the heavy chain variable domain of the antibodies comprises:
(a) a CDR-H1 comprising the amino acid sequence of SEQ ID NO: 144;
(b) a CDR-H2 comprising the amino acid sequence of SEQ ID NO: 145; and
(c) a CDR-H3 comprising the amino acid sequence of SEQ ID NO: 146.

In some embodiments, provided herein are Protein S antibodies, wherein the heavy chain variable domain of the antibodies comprises:
(a) a CDR-H1 comprising the amino acid sequence of SEQ ID NO: 179;
(b) a CDR-H2 comprising the amino acid sequence of SEQ ID NO: 180; and
(c) a CDR-H3 comprising the amino acid sequence of SEQ ID NO: 181.

In some embodiments, provided herein are Protein S antibodies, wherein the heavy chain variable domain of the antibodies comprises:
(a) a CDR-H1 comprising the amino acid sequence of SEQ ID NO: 189;
(b) a CDR-H2 comprising the amino acid sequence of SEQ ID NO: 190; and
(c) a CDR-H3 comprising the amino acid sequence of SEQ ID NO: 191.

In some embodiments, provided herein are Protein S antibodies, wherein the heavy chain variable domain of the antibodies comprises:
(a) a CDR-H1 comprising the amino acid sequence of SEQ ID NO: 199;
(b) a CDR-H2 comprising the amino acid sequence of SEQ ID NO: 200; and
(c) a CDR-H3 comprising the amino acid sequence of SEQ ID NO: 201.

In some embodiments, provided herein are Protein S antibodies, wherein the heavy chain variable domain of the antibodies comprises:
(a) a CDR-H1 comprising the amino acid sequence of SEQ ID NO: 209;
(b) a CDR-H2 comprising the amino acid sequence of SEQ ID NO: 210; and
(c) a CDR-H3 comprising the amino acid sequence of SEQ ID NO: 211.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 33;
(b) a CDR-H2 comprising the amino acid sequence of SEQ ID NO: 45; and
(c) a CDR-H3 comprising the amino acid sequence of SEQ ID NO: 57.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 34;
(b) a CDR-H2 comprising the amino acid sequence of SEQ ID NO: 46; and
(c) a CDR-H3 comprising the amino acid sequence of SEQ ID NO: 58.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 35;
(b) a CDR-H2 comprising the amino acid sequence of SEQ ID NO: 47; and
(c) a CDR-H3 comprising the amino acid sequence of SEQ ID NO: 59.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 36;
(b) a CDR-H2 comprising the amino acid sequence of SEQ ID NO: 48; and
(c) a CDR-H3 comprising the amino acid sequence of SEQ ID NO: 60.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 37;
(b) a CDR-H2 comprising the amino acid sequence of SEQ ID NO: 49; and
(c) a CDR-H3 comprising the amino acid sequence of SEQ ID NO: 61.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 38;

(b) a CDR-H2 comprising the amino acid sequence of SEQ ID NO: 50; and
(c) a CDR-H3 comprising the amino acid sequence of SEQ ID NO: 62.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 39;
(b) a CDR-H2 comprising the amino acid sequence of SEQ ID NO: 51; and
(c) a CDR-H3 comprising the amino acid sequence of SEQ ID NO: 63.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 42;
(b) a CDR-H2 comprising the amino acid sequence of SEQ ID NO: 54; and
(c) a CDR-H3 comprising the amino acid sequence of SEQ ID NO: 66.

In some embodiments, provided herein are Protein S antibodies, wherein the light chain variable domain of the antibodies comprises any one or more of the sequences provided in Tables TA, 1B, and 1C, and wherein the heavy chain variable domain of the antibodies comprises:
(a) a CDR-H1 comprising the amino acid sequence of SEQ ID NO: 43;
(b) a CDR-H2 comprising the amino acid sequence of SEQ ID NO: 55; and
(c) a CDR-H3 comprising the amino acid sequence of SEQ ID NO: 67.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 44;
(b) a CDR-H2 comprising the amino acid sequence of SEQ ID NO: 56; and
(c) a CDR-H3 comprising the amino acid sequence of SEQ ID NO: 68.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 120;
(b) a CDR-H2 comprising the amino acid sequence of SEQ ID NO: 121; and
(c) a CDR-H3 comprising the amino acid sequence of SEQ ID NO: 122.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 124;
(b) a CDR-H2 comprising the amino acid sequence of SEQ ID NO: 125; and
(c) a CDR-H3 comprising the amino acid sequence of SEQ ID NO: 126.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 130;
(b) a CDR-H2 comprising the amino acid sequence of SEQ ID NO: 50; and
(c) a CDR-H3 comprising the amino acid sequence of SEQ ID NO: 131.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 138;
(b) a CDR-H2 comprising the amino acid sequence of SEQ ID NO: 139; and
(c) a CDR-H3 comprising the amino acid sequence of SEQ ID NO: 140.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 144;
(b) a CDR-H2 comprising the amino acid sequence of SEQ ID NO: 145; and
(c) a CDR-H3 comprising the amino acid sequence of SEQ ID NO: 146.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(d) a CDR-H1 comprising the amino acid sequence of SEQ ID NO: 179;
(e) a CDR-H2 comprising the amino acid sequence of SEQ ID NO: 180; and
(f) a CDR-H3 comprising the amino acid sequence of SEQ ID NO: 181.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 189;
(b) a CDR-H2 comprising the amino acid sequence of SEQ ID NO: 190; and (c) a CDR-H3 comprising the amino acid sequence of SEQ ID NO: 191.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 199;
(b) a CDR-H2 comprising the amino acid sequence of SEQ ID NO: 200; and
(c) a CDR-H3 comprising the amino acid sequence of SEQ ID NO: 201.

In some embodiments, provided herein are Protein S antibodies, wherein the light chain variable domain of the antibodies comprises a CDR-L1 from Table 1A, a CDR-L2 from Table 1B, and a CDR-L3 from Table 1C, and wherein the heavy chain variable domain of the antibodies comprises:
(a) a CDR-H1 comprising the amino acid sequence of SEQ ID NO: 209;
(b) a CDR-H2 comprising the amino acid sequence of SEQ ID NO: 210; and
(c) a CDR-H3 comprising the amino acid sequence of SEQ ID NO: 211.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 1;
(b) a CDR-L2 comprising the amino acid sequence of QDT; and
(c) a CDR-L3 comprising the amino acid sequence of SEQ ID NO: 21.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 2;
(b) a CDR-L2 comprising the amino acid sequence of GKN; and
(c) a CDR-L3 comprising the amino acid sequence of SEQ ID NO: 22.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 3;
(b) a CDR-L2 comprising the amino acid sequence of DVS; and
(c) a CDR-L3 comprising the amino acid sequence of SEQ ID NO: 23.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 1;
(b) a CDR-L2 comprising the amino acid sequence of QNS; and
(c) a CDR-L3 comprising the amino acid sequence of SEQ ID NO: 24.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 4;
(b) a CDR-L2 comprising the amino acid sequence of DAS; and
(c) a CDR-L3 comprising the amino acid sequence of SEQ ID NO: 25.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 5;
(b) a CDR-L2 comprising the amino acid sequence of GAS; and
(c) a CDR-L3 comprising the amino acid sequence of SEQ ID NO: 26.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 6;
(b) a CDR-L2 comprising the amino acid sequence of LGS; and
(c) a CDR-L3 comprising the amino acid sequence of SEQ ID NO: 27.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comp comprises rise:
(a) a CDR-L1 comprising the amino acid sequence of SEQ ID NO: 9;
(b) a CDR-L2 comprising the amino acid sequence of STN; and
(c) a CDR-L3 comprising the amino acid sequence of SEQ ID NO: 30.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 10;
(b) a CDR-L2 comprising the amino acid sequence of DAS; and
(c) a CDR-L3 comprising the amino acid sequence of SEQ ID NO: 31.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:
(a) a CDR-L1 comprising the amino acid sequence of SEQ ID NO: 11;

(b) a CDR-L2 comprising the amino acid sequence of KIS; and (c) a CDR-L3 comprising the amino acid sequence of SEQ ID NO: 32.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 117;

(b) a CDR-L2 comprising the amino acid sequence of AAS; and (c) a CDR-L3 comprising the amino acid sequence of SEQ ID NO: 119.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 117;

(b) a CDR-L2 comprising the amino acid sequence of AAS; and (c) a CDR-L3 comprising the amino acid sequence of SEQ ID NO: 123.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 127;

(b) a CDR-L2 comprising the amino acid sequence of ATS; and (c) a CDR-L3 comprising the amino acid sequence of SEQ ID NO: 129.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 136;

(b) a CDR-L2 comprising the amino acid sequence of GAS; and (c) a CDR-L3 comprising the amino acid sequence of SEQ ID NO: 137.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 141;

(b) a CDR-L2 comprising the amino acid sequence of KTS; and (c) a CDR-L3 comprising the amino acid sequence of SEQ ID NO: 143.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 174;

(b) a CDR-L2 comprising the amino acid sequence of AAS; and (c) a CDR-L3 comprising the amino acid sequence of SEQ ID NO: 176.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 184;

(b) a CDR-L2 comprising the amino acid sequence of DDS; and (c) a CDR-L3 comprising the amino acid sequence of SEQ ID NO: 186.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 194;

(b) a CDR-L2 comprising the amino acid sequence of QDS; and (c) a CDR-L3 comprising the amino acid sequence of SEQ ID NO: 196.

In some embodiments, provided herein are Protein S antibodies, wherein the heavy chain variable domain of the antibodies comprises a CDR-H1 from Table 2A, a CDR-H2 from Table 2B, and a CDR-H3 from Table 2C, and wherein the light chain variable domain of the antibodies comprises:

(a) a CDR-L1 comprising the amino acid sequence of SEQ ID NO: 204;

(b) a CDR-L2 comprising the amino acid sequence of QDN; and (c) a CDR-L3 comprising the amino acid sequence of SEQ ID NO: 206.

In some embodiments, provided herein are Protein S antibodies, wherein the antibodies comprise the CDR amino acid sequences of SEQ ID NO: 1, QDT, SEQ ID NO: 21, SEQ ID NO: 33, SEQ ID NO: 45, and SEQ ID NO: 57.

In some embodiments, provided herein are Protein S antibodies, wherein the antibodies comprise the CDR amino acid sequences of SEQ ID NO: 2, GKN, SEQ ID NO: 22, SEQ ID NO: 34, SEQ ID NO: 46, and SEQ ID NO: 58.

In some embodiments, provided herein are Protein S antibodies, wherein the antibodies comprise the CDR amino acid sequences of SEQ ID NO: 3, DVS, SEQ ID NO: 23, SEQ ID NO: 35, SEQ ID NO: 47, and SEQ ID NO: 59.

In some embodiments, provided herein are Protein S antibodies, wherein the antibodies comprise the CDR amino acid sequences of SEQ ID NO: 1, QNS, SEQ ID NO: 24, SEQ ID NO: 36, SEQ ID NO: 48, and SEQ ID NO: 60.

In some embodiments, provided herein are Protein S antibodies, wherein the antibodies comprise the CDR amino acid sequences of SEQ ID NO: 4, DAS, SEQ ID NO: 25, SEQ ID NO: 37, SEQ ID NO: 49, and SEQ ID NO: 61.

In some embodiments, provided herein are Protein S antibodies, wherein the antibodies comprise the CDR amino acid sequences of SEQ ID NO: 5, GAS, SEQ ID NO: 26, SEQ ID NO: 38, SEQ ID NO: 50, and SEQ ID NO: 62.

In some embodiments, provided herein are Protein S antibodies, wherein the antibodies comprise the CDR amino acid sequences of SEQ ID NO: 6, LGS, SEQ ID NO: 27, SEQ ID NO: 39, SEQ ID NO: 51, and SEQ ID NO: 63.

In some embodiments, provided herein are Protein S antibodies, wherein the antibodies comprise the CDR amino acid sequences of SEQ ID NO: 9, STN, SEQ ID NO: 30, SEQ ID NO: 42, SEQ ID NO: 54, and SEQ ID NO: 66.

In some embodiments, provided herein are Protein S antibodies, wherein the antibodies comprise the CDR amino acid sequences of SEQ ID NO: 10, DAS, SEQ ID NO: 31, SEQ ID NO: 43, SEQ ID NO: 55, and SEQ ID NO: 67.

In some embodiments, provided herein are Protein S antibodies, wherein the antibodies comprise the CDR amino acid sequences of SEQ ID NO: 11, KIS, SEQ ID NO: 32, SEQ ID NO: 44, SEQ ID NO: 56, and SEQ ID NO: 68.

In some embodiments, provided herein are Protein S antibodies, wherein the antibodies comprise the CDR amino acid sequences of SEQ ID NO: 117, AAS, SEQ ID NO: 119, SEQ ID NO: 120, SEQ ID NO: 121, and SEQ ID NO: 122.

In some embodiments, provided herein are Protein S antibodies, wherein the antibodies comprise the CDR amino acid sequences of SEQ ID NO: 117, AAS, SEQ ID NO: 123, SEQ ID NO: 124, and SEQ ID NO: 125.

In some embodiments, provided herein are Protein S antibodies, wherein the antibodies comprise the CDR amino acid sequences of SEQ ID NO: 127, ATS, SEQ ID NO: 129, SEQ ID NO: 130, SEQ ID NO: 50, and SEQ ID NO: 131.

In some embodiments, provided herein are Protein S antibodies, wherein the antibodies comprise the CDR amino acid sequences of SEQ ID NO: 136, GAS, SEQ ID NO: 137, SEQ ID NO: 138, SEQ ID NO: 139, and SEQ ID NO: 140.

In some embodiments, provided herein are Protein S antibodies, wherein the antibodies comprise the CDR amino acid sequences of SEQ ID NO: 141, KTS, SEQ ID NO: 143, SEQ ID NO: 144, SEQ ID NO: 145, and SEQ ID NO: 146.

In some embodiments, provided herein are Protein S antibodies, wherein the antibodies comprise the CDR amino acid sequences of SEQ ID NO: 174, AAS, SEQ ID NO: 176, SEQ ID NO: 179, SEQ ID NO: 180, and SEQ ID NO: 181.

In some embodiments, provided herein are Protein S antibodies, wherein the antibodies comprise the CDR amino acid sequences of SEQ ID NO: 184, DDS, SEQ ID NO: 186, SEQ ID NO: 189, SEQ ID NO: 190, and SEQ ID NO: 191.

In some embodiments, provided herein are Protein S antibodies, wherein the antibodies comprise the CDR amino acid sequences of SEQ ID NO: 194, QDS, SEQ ID NO: 196, SEQ ID NO: 199, SEQ ID NO: 200, and SEQ ID NO: 201.

In some embodiments, provided herein are Protein S antibodies, wherein the antibodies comprise the CDR amino acid sequences of SEQ ID NO: 204, QDN, SEQ ID NO: 206, SEQ ID NO: 209, SEQ ID NO: 210, and SEQ ID NO: 211.

Exemplary Protein S Antibodies—Kappa and Lambda Light Chains

Provided herein are amino acid sequences for the kappa and lambda light chain constant regions of exemplary Protein S antibodies of the disclosure. Any of the Protein S antibodies provided herein (provided in the preceding section) may have a kappa light chain constant region or a lambda light chain constant region. The sequences of the kappa and lambda light chain constant regions are provided in Table 3.

TABLE 3

| | |
|---|---|
| Kappa light chain sequence | RTVAAPSVFIFPPSDEQLKSGTASV VCLLNNFYPREAKVQWKVDNALQS GNSQESVTEQDSKDSTYSLSSTLT LSKADYEKHKVYACEVTHQGLSSP VTKSFNRGEC (SEQ ID NO: 214) |

TABLE 3-continued

| | |
|---|---|
| Lambda light chain sequence | GQPKAAPSVTLFPPSSEELQANKAT LVCLISDFYPGAVTVAWKADSSPVK AGVETTTPSKQSNNKYAASSYLSLT PEQWKSHRSYSCQVTHEGSTVEKTV APTECS (SEQ ID NO: 215) |

In exemplary embodiments, the Protein S antibody having the light chain sequence of SEQ ID NO: 214 comprises CDRs having the amino acid sequences as set forth in SEQ ID NO: 2, GKN, SEQ ID NO: 22, SEQ ID NO: 34, SEQ ID NO: 46, and SEQ ID NO: 58.

In exemplary embodiments, the Protein S antibody having the light chain sequence of SEQ ID NO: 215 comprises CDRs having the amino acid sequences as set forth in SEQ ID NO: 2, GKN, SEQ ID NO: 22, SEQ ID NO: 34, SEQ ID NO: 46, and SEQ ID NO: 58.

In exemplary embodiments, the Protein S antibody having the light chain sequence of SEQ ID NO: 214 comprises CDRs having the amino acid sequences as set forth in SEQ ID NO: 10, DAS, SEQ ID NO: 31, SEQ ID NO: 43, SEQ ID NO: 55, and SEQ ID NO: 67.

In exemplary embodiments, the Protein S antibody having the light chain sequence of SEQ ID NO: 215 comprises CDRs having the amino acid sequences as set forth in SEQ ID NO: 10, DAS, SEQ ID NO: 31, SEQ ID NO: 43, SEQ ID NO: 55, and SEQ ID NO: 67.

In exemplary embodiments, the Protein S antibody having the light chain sequence of SEQ ID NO: 214 comprises CDRs having the amino acid sequences as set forth in SEQ ID NO: 174, AAS, SEQ ID NO: 176, SEQ ID NO: 179, SEQ ID NO: 180, and SEQ ID NO: 181.

In exemplary embodiments, the Protein S antibody having the light chain sequence of SEQ ID NO: 215 comprises CDRs having the amino acid sequences as set forth in SEQ ID NO: 174, AAS, SEQ ID NO: 176, SEQ ID NO: 179, SEQ ID NO: 180, and SEQ ID NO: 181.

In exemplary embodiments, the Protein S antibody having the light chain sequence of SEQ ID NO: 214 comprises the variable heavy and variable light chains having the amino acid sequences as set forth in SEQ ID NO: 71 and SEQ ID NO: 72.

In exemplary embodiments, the Protein S antibody having the light chain sequence of SEQ ID NO: 215 comprises the variable heavy and variable light chains having the amino acid sequences as set forth in SEQ ID NO: 71 and SEQ ID NO: 72.

In exemplary embodiments, the Protein S antibody having the light chain sequence of SEQ ID NO: 214 comprises the variable heavy and variable light chains having the amino acid sequences as set forth in SEQ ID NO: 89 and SEQ ID NO: 90.

In exemplary embodiments, the Protein S antibody having the light chain sequence of SEQ ID NO: 215 comprises the variable heavy and variable light chains having the amino acid sequences as set forth in SEQ ID NO: 89 and SEQ ID NO: 90.

In exemplary embodiments, the Protein S antibody having the light chain sequence of SEQ ID NO: 214 comprises the variable heavy and variable light chains having the amino acid sequences as set forth in SEQ ID NO: 177 and SEQ ID NO: 182.

In exemplary embodiments, the Protein S antibody having the light chain sequence of SEQ ID NO: 215 comprises the variable heavy and variable light chains having the amino acid sequences as set forth in SEQ ID NO: 177 and SEQ ID NO: 182.

Exemplary Protein S Antibodies—Variable Region Sequences

Provided herein are amino acid sequences for the variable domains of exemplary Protein S antibodies of the disclosure. The exemplary variable light chain amino acid sequences and exemplary variable heavy chain amino acid sequences are presented in Tables 4A and 4B below. Table 4C presents exemplary combinations of variable heavy and variable light chains.

Accordingly, in some embodiments, the Protein S antibodies of the disclosure comprise the variable chain amino acid sequence of any one of the combinations provided in Table 4C. In some embodiments, provided herein are Protein S antibodies, wherein the antibodies comprise a variable light chain comprising the amino acid sequence selected from SEQ ID NO: 69, 71, 73, 75, 77, 79, 81, 87, 89, 91, 148, 150, 152, 156 158, 177, 187, 197, and 207. In some embodiments, provided herein are Protein S antibodies, wherein the antibodies comprise a variable heavy chain comprising the amino acid sequence selected from SEQ ID NO: 70, 72, 74, 76, 78, 80, 82, 88, 90, 92, 149, 151, 153, 157 159, 182, 192, 202, and 212.

TABLE 4A

Exemplary Variable Light Chain Amino Acid Sequences of Protein S Monoclonal Antibodies SYELTQPPSVSVSPGQTASITCSGDKLGDKYACWY
QQKPGQSPVLVIYQDTKRPSGIPERFSGSNSGNTA
TLTISGTQAMDEADYYCQAWDSNTVVFGGGTKLTV
L
(SEQ ID NO: 69)

SSDLTQGPAVSVALGQTVRITCQGDSLRNYYASWY
QQKPGQAPVPVIYGKNDRPSGIPDRFSGSISGNTA
SLTITGAQAEDEAHYYCNSRDSSGNHVVFGGGTKL
TVL
(SEQ ID NO: 71)

QSALTQPASVSGSPGQSITISCTGTSSDVGGYEFV
SWYQHHPGKAPKLMIYDVSSRPSGVSNRFSGSKSG
NTASLTISGLQAEDEADYYCSSYTRSSTVVFGGGA
RLTVL
(SEQ ID NO: 73)

SYELNQPPSVSVSPGQTASITCSGDKLGDKYASWY
QQKPGQSPVVAIYQNSKRPSGIPERFSASNSGNTA
TLTISGTQALDEADYYCQAWDSSTWVFGGGTKLTV
L
(SEQ ID NO: 75)

EIVLTQSPATLSLSPGERATLSCRASQSVSIYLAW
YQQKPGQAPRLLIYDASNRATGIPARFSGSGSGTD
FTLTISSLEPEDFAVYYCQQRSNWPLTFGPGTKVD
IK
(SEQ ID NO: 77)

EIVMTQSPATLSVSPGERATLSCRASQRINSNLAW
YQQKPGQAPRLLIYGASTRATGIPARFSGSGSGTE
FTLTISSLQSEDFAAYYCQQYDNWPLTFGGGTKVE
IK
(SEQ ID NO: 79)

DIVMTQSPLSLPVTPGEPASISCRSSQSLLHSNGY
NYLDWYLQKPGQSPQLLIYLGSNRASGVPDRFSGS
GSGTDFTLKISRVEAEDVGVYYCMQALQTFTFGPG
TKVDIK
(SEQ ID NO: 81)

TABLE 4A-continued

Exemplary Variable Light Chain Amino Acid Sequences of Protein S Monoclonal Antibodies QAVVTQESALTTSPGETVTLTCRSSTGAVTASNYA
NWVQEKPDHLFTGLIGSTNNRAPGVPARFSGSLIG
DKAALTITGAQTEDEAIYFCALWYSDHFVFGGGTK
LTVL
(SEQ ID NO: 87)

EIVMTQSPATLSVSPGERATLSCRASQSVTSNLAW
YQQKPGQAPRLLIYDASTRATGIPARFSGSGSGTE
FTLTISSLQSEDFAIYYCQQYNNWPTFGQGTRLEI
K
(SEQ ID NO: 89)

DIVMTQTPLSSPVTLGQPASISCRSSQSLVHSDGN
TYLSWLQQRPGQPPRLLIYKISNRFSGVPDRFSGS
GAGTDFTLKISRVEAEDVGVYYCMQATQFPHLTFG
GGTKVEIK
(SEQ ID NO: 91)

DIQMTQSPSSLSASVGDRVTITCRASQGINNYLAW
FQQKPGKAPKSLIYAASSLQSGVPSKFSGSGSGTD
FTLTISSLQPEDFATYYCQQYNSYPRTFGQGTKVE
IK
(SEQ ID NO: 148)

DIQMTQSPSSLSASVGDRVTITCRASQGINNYLAW
FQQKPGKAPKSLIYAASNLQSGVPLKFSGSGSGTD
FTLTISSLQPEDFATYYCQQYNSYPITFGQGTRLE
IK
(SEQ ID NO: 150)

DIQMTQSPSSLSASVGDRVTITCRASQSISTFLNW
YQQKPGKAPKLLIYATSSLRSGVPSRFSGSGSGTD
FTLTISSLQPEDFAIYYCQQSYSTPRTFGQGTQVE
IK
(SEQ ID NO: 152)

EIVLTQSPGTLSLSPGERATLSCRASQSVGSSYLA
WYQQKPGQAPRLLISGASGRATGIPDRFSGSGSGT
DFTLTISRLEPEDFTVYYCQQYGSSPYTFGQGTKL
EIK
(SEQ ID NO: 156)

DIQMNQSPSSLSASLGDTITITCRASQNIHMWLSW
YQQKPGNIPKLLIFKTSNLHTGVPSRFSGSGSGTD
FTLTISSLQPEDIATYYCLQGQSYPFTFGGGTKLE
IK
(SEQ ID NO: 158)

DIQMTQSPSSLSASVGDRVTITCRASQSISSYLNW
YQQKPGKAPKLLIYAASSLQSGVPSRFSGSGSGTD
FTLTISSLQPEDFATYYCQQSYSSLTFGQGTRLEI
K
(SEQ ID NO: 177)

SYVLTQPPSVSVAPGQTARITCGGDNIGGKSVHWY
QQKPGQAPVMVVYDDSDRPSGIPERFAGSNSGNTA
TLAISRVEAGDEADYYCQVWEITSDHPAFGGGTR
LTVL
(SEQ ID NO: 187)

SYELTQPPSVSVSPGQTASITCSGDKLGDKYVFWY
QQKPGQSPVLVIYQDSKRPSGIPERFSGSNSGNTA
TLTISGTQTMDEADYYCQAWDSSTVGFGGGTKLAV
L
(SEQ ID NO: 197)

SYELTQPPSVSVSPGQTASITCSGDKLGDKYAFWY
QQKPGQSPVLVIYQDNKRPSGIPERFSGSNSGNTA
TLTISGTQAVDEADYYCQAWDSSTAVFGGGTKLTV
L
(SEQ ID NO: 207)

TABLE 4B

Exemplary Variable Heavy Chain Amino Acid Sequences of Protein S Monoclonal Antibodies QLQLQESGPGLVKPSETLSLTCTVSGGSISSSSYY
WGWIRQPPGKGLEWIGNIYYSGNTYYNPSLKSRVT
ISVDTSKNQFSLKLSSMTAADTAVYYCARCSGYGY
SSGRSYFDYWGQETLVTSS
(SEQ ID NO: 70)

QVQLVQSGAEVKKPGSSVKVSCKVSGGTFSSYSIS
WVRQAPGQGLEWMGGIIPIFGTTNYAQKFQGRVTI
TADESTSTAYMDLSSLKSEDTAMYYCEGGRVGADF
DYWGQGTLVTVSS
(SEQ ID NO: 72)

QVQLQESGPGLVKPSQTLSLTCTVSGGSITSDGYH
WSWIRQYPGKGLDWIGYIYYTGNTYYNPSLKSRVT
ISVGTSQNQFSLKLISVTAADTAVYYCARRLSTGP
YFDYWGQGTLVTVSS
(SEQ ID NO: 74)

EVQLVESGGGLVQPGRSLRLSCAASGFTFDDYAMH
WVRQAPGKGLEWVSGITWNSGNIGYADSVI<GRFT
ISRDNAI<NSLYLHMNSLRIEDTAFYYCAI<GRAV
SDTFDIWGQGTMVTVSS
(SEQ ID NO: 76)

QVQLVESGGGVVQPGRSLRLSCAASGFTFSTYGFH
WVRQPPGKGLEWVAVIYYDGINKYYADSVKGRFTI
SRDNSKNTLFLQMNSLRAEDTAVYYCAESDLDYWG
QGTLVTVSS
(SEQ ID NO: 78)

QVQLQESGPGLVKPSETLSLTCAVSGYSISSGYYW
GWIRQPPGKGLDWIGSIYYSGSTYYNPSLKSRVTI
SVDTSKNQISLKLSSVTAADTAVYYCATTYSDIVT
GYYNDAFDIWGQGTMVTVSS
(SEQ ID NO: 80)

QVQLVQSGAEVKKPGSSVKVSCKASGDTFSNHAIN
WVRQAPGQGLEWMGGYIPIFGTTNSAQKFRGRVTI
TADKSTNTAYMALSSLRSEDTAVYYCARGGLAGSH
YKNYYYDGMDVWGQGTTVTVSS
(SEQ ID NO: 82)

QVQLVQSGAEVKKPGASVKVSCKSSGHTFTGYYMH
WVRQAPGQGLEWMGWINPNSGDTNYAQKFQGRVTM
TRDTSISTAYMEMSRLRSDDTAVYYCARDSQILWF
GELGYWGQGTLVTVSS
(SEQ ID NO: 88)

QVQLQESGPGLVKPSETLSLTCGVSGGSISSTNWW
SWVRQPPGKGLEWIGEIYQTGSTDYDPSLKSRVTI
SIDKSKNQFSLKLYSVTAADTAVYYCARRFGELDY
WGQGTLVTVSS
(SEQ ID NO: 90)

QVQLQESGPGLVKPSETLSLTCTVSGGSISNYYWN
WIRQPPGKGLEWIGYIYYIGITDYNPSLKSRVTIS
VDTSKNQFSLKVTSVTAADTAVYYCAALSGDHAFD
IWGQGTLVTVSS
(SEQ ID NO: 92)

QLQLQESGPGLVKPSETLSLTCTVSGGSITNSNYY
WGWIRQPPGKGLEWIGSVYYSGTTYYNPSLKSRVT
ISVDPSKNQFSLKLSSVTAADTAVYYCVRESESYY
YYGSDVWGQGTTVTVSS
(SEQ ID NO: 149)

EVQLVESGGGLVKPGGSLRLSCAASGFTFSSYNMN
WVRQAPGRGLDWVSSISSSSSYIYYADSVKGRFTI
SRDNAKNSLYLQMNTLRAEDTAVYYCARDEEWELL
TGFDYWGQGTLVTVSS
(SEQ ID NO: 151)

TABLE 4B-continued

Exemplary Variable Heavy Chain Amino Acid Sequences of Protein S Monoclonal Antibodies QVQLQESGPGLVKPSETLSLTCTVSGGSISGNYWS
WIRQPPGKGLEWIGYIYYSGSTNYNPSLKSRVTIS
VDTSKNQFSLKLSSVTAADTAVYYCARDLDYFTWG
AYSDWYFDLWGRGTLVTVSS
(SEQ ID NO: 153)

QVQLQQSGPGLVKPSQTLSLTCAISGDSVSNNNAA
WNWIRQSPSRGLEWLGGTYYRSKWYNDYAVSVKSR
IIINPVTSKNQFSLQLNSVTPEDTAVYYCARGSSW
YRFFDYWGQGTLVTVSS
(SEQ ID NO: 157)

QVQLQQSGTELVRPGTSVKMSCKAAGYTFTNHWIG
WVKQRPGHGLEWIGDIYPGGGYTNYNEKFKGKASL
TADTSSTTAYMQLSSLTSEDSAIYYCSRFGDQNWA
WFAYWGQGTLVTVSA
(SEQ ID NO: 159)

EVQLVESGGGLVKPGGSLRLSCAASGISFSNAWMS
WVRQAPGKGLEWVGRIKANPDGGTTDYAAPVKGRF
TISRDDSKNTLYLQMNSLKTEDTAVYYCTTELDIL
LWFTSFDYWGQGTLVTVSS
(SEQ ID NO: 182)

EVQLVESGGGLVQPGGSLRLSCAASGFTFSSYSMN
WVRQAPGKGLEWVAYISSSTRTIFYADSVKGRFTI
SRDNAKNSLYLQMNSLRDEDTAFYYCARERSAFDY
WGQGTLVTVSS
(SEQ ID NO: 192)

QVQLVQSGSEVKKPGASVKVSCKASGYTFTNYYIH
WVRQAPGQGLEWMGIITPSGGTTSYAQKFQGRVTM
TRDTSTNTVYMGLSSLRSEDTAMYYCARAGVQLDR
RGWFDPWGQGTLVTVSS
(SEQ ID NO: 202)

QVQLVQSGAEVKKPGASVKVSCKASGYTFTSYYIH
WVRQAPGQGLEWMGVTSPSGRSTSFAQKFQGRVTM
TRDTSTSAVYMDLDSLRSEDTAVYYCARGGVTIHL
ERRGYFDYWGQGTLVIVSS
(SEQ ID NO: 212)

TABLE 4C

Exemplary Variable Light Chain and Variable Heavy Chain Amino Acid Sequence Combinations of Protein S Monoclonal Antibodies

| Combination Number | Variable Light Chain Amino Acid Sequence | Variable Heavy Chain Amino Acid Sequence |
|---|---|---|
| Combination 1 | SEQ ID NO: 69 | SEQ ID NO: 70 |
| Combination 2 | SEQ ID NO: 71 | SEQ ID NO: 72 |
| Combination 3 | SEQ ID NO: 73 | SEQ ID NO: 74 |
| Combination 4 | SEQ ID NO: 75 | SEQ ID NO: 76 |
| Combination 5 | SEQ ID NO: 77 | SEQ ID NO: 78 |
| Combination 6 | SEQ ID NO: 79 | SEQ ID NO: 80 |
| Combination 7 | SEQ ID NO: 81 | SEQ ID NO: 82 |
| Combination 10 | SEQ ID NO: 87 | SEQ ID NO: 88 |
| Combination 11 | SEQ ID NO: 89 | SEQ ID NO: 90 |
| Combination 12 | SEQ ID NO: 91 | SEQ ID NO: 92 |
| Combination 13 | SEQ ID NO: 148 | SEQ ID NO: 149 |
| Combination 14 | SEQ ID NO: 150 | SEQ ID NO: 151 |
| Combination 15 | SEQ ID NO: 152 | SEQ ID NO: 153 |
| Combination 17 | SEQ ID NO: 156 | SEQ ID NO: 157 |
| Combination 18 | SEQ ID NO: 158 | SEQ ID NO: 159 |
| Combination 19 | SEQ ID NO: 177 | SEQ ID NO: 182 |
| Combination 20 | SEQ ID NO: 187 | SEQ ID NO: 192 |
| Combination 21 | SEQ ID NO: 197 | SEQ ID NO: 202 |
| Combination 22 | SEQ ID NO: 207 | SEQ ID NO: 212 |

In some embodiments, the heavy and light chain variable domains of the Protein S antibodies provided herein include the amino acid sequence of any one of the numbered combinations presented in Table 4C.

In some embodiments, provided herein are Protein S antibodies, wherein the light chain variable domain of the antibodies comprise the amino acid sequence of SEQ ID NO: 69 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibodies comprise the amino acid sequence of SEQ ID NO: 70, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 69 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and wherein the heavy chain variable domain of the antibody comprises the amino acid sequence of SEQ ID NO: 70, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 1, an amino acid sequence of QDT, SEQ ID NO: 21, SEQ ID NO: 33, SEQ ID NO: 45, and SEQ ID NO: 57.

In some embodiments, provided herein are Protein S antibodies, wherein the light chain variable domain of the antibodies comprise the amino acid sequence of SEQ ID NO: 71 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 72, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 71 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 72, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 2, an amino acid sequence of GKN, SEQ ID NO: 22, SEQ ID NO: 34, SEQ ID NO: 46, and SEQ ID NO: 58.

In some embodiments, provided herein are Protein S antibodies, wherein the light chain variable domain of the antibodies comprise the amino acid sequence of SEQ ID NO: 73 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 74, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 73 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 74, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 3, an amino acid sequence of DVS, SEQ ID NO: 23, SEQ ID NO: 35, SEQ ID NO: 47, and SEQ ID NO: 59.

In some embodiments, provided herein are Protein S antibodies, wherein the light chain variable domain of the antibodies comprise the amino acid sequence of SEQ ID NO: 75 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 76, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 75 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 76, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 1, an amino acid sequence of QNS, SEQ ID NO: 24, SEQ ID NO: 36, SEQ ID NO: 48, and SEQ ID NO: 60.

In some embodiments, provided herein are Protein S antibodies, wherein the light chain variable domain of the antibodies comprise the amino acid sequence of SEQ ID NO: 77 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 78, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 77 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 78, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 4, an amino acid sequence of DAS, SEQ ID NO: 25, SEQ ID NO: 37, SEQ ID NO: 49, and SEQ ID NO: 61.

In some embodiments, provided herein are Protein S antibodies, wherein the light chain variable domain of the antibodies comprise the amino acid sequence of SEQ ID NO: 79 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 80, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 79 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 80, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 5, an amino acid sequence of GAS, SEQ ID NO: 26, SEQ ID NO: 38, SEQ ID NO: 50, and SEQ ID NO: 62.

In some embodiments, provided herein are Protein S antibodies, wherein the light chain variable domain of the antibodies comprise the amino acid sequence of SEQ ID NO: 81 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 82, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 81 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 82, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 6, an amino acid sequence of LGS, SEQ ID NO: 27, SEQ ID NO: 39, SEQ ID NO: 51, and SEQ ID NO: 63.

In some embodiments, provided herein are Protein S antibodies, wherein the light chain variable domain of the antibodies comprise the amino acid sequence of SEQ ID NO: 87 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 88, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 87 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 88, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 9, an amino acid sequence of STN, SEQ ID NO: 30, SEQ ID NO: 42, SEQ ID NO: 54, and SEQ ID NO: 66.

In some embodiments, provided herein are Protein S antibodies, wherein the light chain variable domain of the antibodies comprise the amino acid sequence of SEQ ID NO: 89 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 90, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 89 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 90, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 10, an amino acid sequence of DAS, SEQ ID NO: 31, SEQ ID NO: 43, SEQ ID NO: 55, and SEQ ID NO: 67.

In some embodiments, provided herein are Protein S antibodies, wherein the light chain variable domain of the antibodies comprise the amino acid sequence of SEQ ID NO: 91 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 92, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 91 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 92, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 11, an amino acid sequence of KIS, SEQ ID NO: 32, SEQ ID NO: 44, SEQ ID NO: 56, and SEQ ID NO: 68.

In some embodiments, provided herein are Protein S antibodies, wherein the light chain variable domain of the antibodies comprise the amino acid sequence of SEQ ID NO: 148 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 149, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 148 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 149, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 117, an amino acid sequence of AAS, SEQ ID NO: 119, SEQ ID NO: 120, SEQ ID NO: 121, and SEQ ID NO: 122.

In some embodiments, provided herein are Protein S antibodies, wherein the light chain variable domain of the antibodies comprise the amino acid sequence of SEQ ID NO: 150 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 151, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 150 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 151, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 117, an amino acid sequence of AAS, SEQ ID NO: 123, SEQ ID NO: 124, SEQ ID NO: 125, and SEQ ID NO: 126.

In some embodiments, provided herein are Protein S antibodies, wherein the light chain variable domain of the antibodies comprise the amino acid sequence of SEQ ID NO: 152 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 153, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 152 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 153, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 127, an amino acid sequence of ATS, SEQ ID NO: 129, SEQ ID NO: 130, SEQ ID NO: 50, and SEQ ID NO: 131.

In some embodiments, provided herein are Protein S antibodies, wherein the light chain variable domain of the antibodies comprise the amino acid sequence of SEQ ID NO: 156 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 157, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 156 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 157, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 136, an amino acid sequence of GAS, SEQ ID NO: 137, SEQ ID NO: 138, SEQ ID NO: 139, and SEQ ID NO: 140.

In some embodiments, provided herein are Protein S antibodies, wherein the light chain variable domain of the antibodies comprise the amino acid sequence of SEQ ID NO: 158 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 159, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 158 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 159, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 141, an amino acid sequence of KTS, SEQ ID NO: 143, SEQ ID NO: 144, SEQ ID NO: 145, and SEQ ID NO: 146.

In some embodiments, provided herein are Protein S antibodies, wherein the light chain variable domain of the antibodies comprise the amino acid sequence of SEQ ID NO: 177 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 182, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 177 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 182, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 174, an amino acid sequence of AAS, SEQ ID NO: 176, SEQ ID NO: 179, SEQ ID NO: 180, and SEQ ID NO: 181.

In some embodiments, provided herein are Protein S antibodies, wherein the light chain variable domain of the antibodies comprise the amino acid sequence of SEQ ID NO: 187 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 192, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 187 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 192, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 184, an amino acid sequence of DDS, SEQ ID NO: 186, SEQ ID NO: 189, SEQ ID NO: 190, and SEQ ID NO: 191.

In some embodiments, provided herein are Protein S antibodies, wherein the light chain variable domain of the antibodies comprise the amino acid sequence of SEQ ID NO: 197, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 202, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 197 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 202, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 194, an amino acid sequence of QDS, SEQ ID NO: 196, SEQ ID NO: 199, SEQ ID NO: 200, and SEQ ID NO: 201.

In some embodiments, provided herein are Protein S antibodies, wherein the light chain variable domain of the antibodies comprise the amino acid sequence of SEQ ID NO: 207, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the heavy chain variable domain of the antibody comprises the amino acid sequence of SEQ ID NO: 212, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, provided herein are Protein S antibodies, wherein the light chain variable domain of the antibodies comprise the amino acid sequence of SEQ ID NO: 207, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 212, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In such embodiments, the Protein S antibodies may comprise the CDR amino acid sequences of SEQ ID NO: 204, an amino acid sequence of QDN, SEQ ID NO: 206, SEQ ID NO: 209, SEQ ID NO: 210, and SEQ ID NO: 211.

As noted above, Protein S comprises four domains: the γ-carboxy-glutamic acid domain (Gla-domain), the thrombin-sensitive region (TSR), the epidermal growth factor-like domain (EGF domain), and the sex hormone binding globulin-like domain (SHBG domain). FIG. 1 depicts the schematic diagram of Protein S showing these modular domains of Protein S. The TSR is within the heavy chain of Protein S. The heavy chain of Protein S represents amino acids 42-296 of Protein S, the TSR represents amino acids 88-116, the signal peptide represents amino acids 1-24 and the propeptide represents amino acids 25-41.

In some embodiments, the Protein S antibodies provided herein bind to the Gla domain of Protein S. In some embodiments, the Protein S antibodies provided herein bind to the Gla domain and inhibit the cofactor activity of Protein S for both APC and TFPI. Exemplary antibodies that bind to the Gla domain and inhibit the cofactor activity of Protein S for both APC and TFPI may comprise the light chain variable domain comprising the amino acid sequence of SEQ ID NO: 77 and the heavy chain variable domain comprising the amino acid sequence of SEQ ID NO: 78; or such antibodies may comprise the light and heavy CDR amino acid sequences of SEQ ID NO: 4, an amino acid sequence of DAS, SEQ ID NO: 25, SEQ ID NO: 37, SEQ ID NO: 49, and SEQ ID NO: 61.

In some embodiments, the Protein S antibodies provided herein bind to EGF domain of Protein S. In some embodiments, the Protein S antibodies provided herein bind to the SHBG-like domain of Protein S. In some embodiments, the Protein S antibodies provided herein bind to the C-terminal region of Protein S. In some embodiments, the Protein S antibodies provided herein bind the C-terminal region of Protein S, and inhibit the cofactor activity of Protein S for TFPI.

In some embodiments, the Protein S antibodies provided herein bind to Protein S fragments. The Protein S fragments are referred to herein as the Protein S heavy chain when they are expressed recombinantly in a cell line, such as HEK293 cells, for example. The Protein S heavy chain comprises amino acids 42-296. In some embodiments, the Protein S antibodies provided herein bind the Protein S heavy chain. Exemplary antibodies that bind to the Protein S heavy chain may comprise the light chain variable domain comprising the amino acid sequence of SEQ ID NO: 69 and the heavy chain variable domain comprising the amino acid sequence of SEQ ID NO: 70, or may comprise the light and heavy CDR amino acid sequences of SEQ ID NO: 1, an amino acid sequence of QDT, SEQ ID NO: 21, SEQ ID NO: 33, SEQ ID NO: 45, and SEQ ID NO: 57. As another example, antibodies that bind to the Protein S heavy chain may comprise the light chain variable domain comprising the amino acid sequence of SEQ ID NO: 79 and the heavy chain variable domain comprising the amino acid sequence of SEQ ID NO: 80, or may comprise the light and heavy CDR amino acid sequences of SEQ ID NO: 5, an amino acid sequence of GAS, SEQ ID NO: 26, SEQ ID NO: 38, SEQ ID NO: 50, and SEQ ID NO: 62.

In some embodiments, the Protein S antibodies provided herein bind to the Protein S heavy chain comprising the TSR. In some embodiments, the Protein S antibodies provided herein bind to the Protein S heavy chain not comprising the TSR.

In some embodiments, the Protein S antibodies provided herein bind to the TSR of Protein S. In some embodiments, the Protein S antibodies provided herein do not bind to the TSR. In some embodiments, the Protein S antibodies provided herein bind to the heavy chain of Protein S, but do not bind the TSR region of the heavy chain. In some embodiments, the Protein S antibodies provided are dual inhibitors of APC and TFPI, and bind to the TSR of Protein S. In some embodiments, the Protein S antibodies provided are dual inhibitors of APC and TFPI, and do not bind to the TSR of Protein S. In some embodiments, the Protein S antibodies provided are inhibitors of APC, and do not bind to the TSR of Protein S. In some embodiments, the Protein S antibodies provided are inhibitors of TFPI, and do not bind to the TSR of Protein S.

Exemplary antibodies that bind to the TSR and are dual inhibitors of APC and TFPI may comprise the light chain variable domain comprising the amino acid sequence of SEQ ID NO: 89 and the heavy chain variable domain comprising the amino acid sequence of SEQ ID NO: 90, or may comprise the light and heavy CDR amino acid sequences of SEQ ID NO: 10, an amino acid sequence of DAS, SEQ ID NO: 31, SEQ ID NO: 43, SEQ ID NO: 55, and SEQ ID NO: 67. As another example, antibodies that bind to the TSR and are dual inhibitors of APC and TFPI may comprise the light chain variable domain comprising the amino acid sequence of SEQ ID NO: 75 and the heavy chain variable domain comprising the amino acid sequence of SEQ ID NO: 76, or may comprise the light and heavy CDR amino acid sequences of SEQ ID NO: 1, an amino acid sequence of QNS, SEQ ID NO: 24, SEQ ID NO: 36, SEQ ID NO: 48, and SEQ ID NO: 60.

In some embodiments, the Protein S antibodies provided herein do not bind to the TSR of Protein S, and cause a dual inhibition of the activity of APC and TFPI. In some embodiments, the Protein S antibodies provided herein do not bind to the TSR of Protein S, and cause an inhibition of the activity of APC. In some embodiments, the Protein S antibodies provided herein do not bind to the TSR of Protein S, and cause an inhibition of the activity of TFPI.

Exemplary antibodies that do not bind to the TSR and are dual inhibitors of APC and TFPI may comprise the light chain variable domain comprising the amino acid sequence of SEQ ID NO: 73 and the heavy chain variable domain comprising the amino acid sequence of SEQ ID NO: 74, or may comprise the light and heavy CDR amino acid sequences of SEQ ID NO: 3, an amino acid sequence of DVS, SEQ ID NO: 23, SEQ ID NO: 35, SEQ ID NO: 47, and SEQ ID NO: 59.

In some embodiments, the Protein S antibodies provided herein bind to a linear epitope of Protein S. Exemplary antibodies that bind to a linear epitope of Protein S may comprise the light chain variable domain comprising the amino acid sequence of SEQ ID NO: 77 and the heavy chain variable domain comprising the amino acid sequence of SEQ ID NO: 78, or may comprise the light and heavy CDR amino acid sequences of SEQ ID NO: 4, an amino acid sequence of DAS, SEQ ID NO: 25, SEQ ID NO: 37, SEQ ID NO: 49, and SEQ ID NO: 61.

In some embodiments, the Protein S antibodies provided herein bind to a conformational epitope, i.e., an epitope that is non-linear. Exemplary antibodies that bind to a non-linear epitope and inhibit the cofactor activity of Protein S for APC may comprise the light chain variable domain comprising the amino acid sequence of SEQ ID NO: 91 and the heavy chain variable domain comprising the amino acid sequence of SEQ ID NO: 92, or may comprise the light and heavy CDR amino acid sequences of SEQ ID NO: 11, an amino acid sequence of KIS, SEQ ID NO: 32, SEQ ID NO: 44, SEQ ID NO: 56, and SEQ ID NO: 68. Exemplary antibodies that bind to a non-linear epitope and inhibit the cofactor activity of Protein S for APC and TFPI may comprise the light chain variable domain comprising the amino acid sequence of SEQ ID NO: 89 and the heavy chain variable domain comprising the amino acid sequence of 90, or may comprise the light and heavy CDR amino acid sequences of SEQ ID NO: 10, an amino acid sequence of DAS, SEQ ID NO: 31, SEQ ID NO: 43, SEQ ID NO: 55, and SEQ ID NO: 67.

As discussed above, Protein S can be found in a free form, or in a complexed form. Protein S can form a complex with at least TFPI, or with C4b-binding protein (C4BP). In some embodiments, the Protein S antibodies provided herein are capable of binding to Protein S in a free form, but not when in complexed form. In some embodiments, the Protein S antibodies provided herein are capable of binding to Protein S when Protein S is complexed, but not in free form. In some embodiments, the Protein S antibodies provided herein are capable of binding to Protein S that is either in free or complexed form. In some embodiments, the Protein S antibodies provided herein bind to a complexed Protein S, wherein the Protein S is bound to TFPI. In some embodiments, the Protein S antibodies provided herein bind to a complexed Protein S, wherein the Protein S is bound to C4BP.

In some embodiments, the Protein S antibodies provided herein bind Protein S, and the binding affinity of the antibodies to Protein S is calcium-dependent. In some embodiments, the Protein S antibodies provided herein bind Protein S, and the binding affinity of the antibodies to Protein S is not calcium-dependent. In some embodiments, the Protein S antibodies provided herein are dual inhibitors of APC and TFPI, and the binding affinity of the antibodies to Protein S is calcium-dependent. In some embodiments, the Protein S antibodies provided herein are dual inhibitors of APC and TFPI, and the binding affinity of the antibodies to Protein S is calcium-independent. In some embodiments, the Protein S antibodies provided herein are inhibitors of APC, and the binding affinity of the antibodies to Protein S is calcium-dependent. In some embodiments, the Protein S antibodies provided herein are inhibitors of APC, and the binding affinity of the antibodies to Protein S is calcium-independent. In some embodiments, the Protein S antibodies provided herein are inhibitors of TFPI, and the binding affinity of the antibodies to Protein S is calcium-independent. In some embodiments, the Protein S antibodies provided herein are inhibitors of TFPI, and the binding affinity of the antibodies to Protein S is calcium-dependent.

Exemplary antibodies that are dual inhibitors of the Protein S cofactor activity of APC and TFPI, wherein the binding affinity of the antibodies to Protein S is calcium-independent, may comprise the light chain variable domain comprising the amino acid sequence of SEQ ID NO: 71 and the heavy chain variable domain comprising the amino acid sequence of 72, or may comprise the light and heavy CDR amino acid sequences of SEQ ID NO: 2, an amino acid sequence of GKN, SEQ ID NO: 22, SEQ ID NO: 34, SEQ ID NO: 46, and SEQ ID NO: 58.

Exemplary antibodies that are inhibitors of the Protein S cofactor activity of TFPI, wherein the wherein the binding affinity of the antibodies to Protein S is calcium-independent, may comprise the light chain variable domain comprising the amino acid sequence of SEQ ID NO: 87 and the heavy chain variable domain comprising the amino acid sequence of 88, or may comprise the light and heavy CDR amino acid sequences of SEQ ID NO: 9, an amino acid sequence of STN, SEQ ID NO: 30, SEQ ID NO: 42, SEQ ID NO: 54, and SEQ ID NO: 66.

Exemplary antibodies that are inhibitors of the Protein S cofactor activity of APC, wherein the wherein the binding affinity of the antibodies to Protein S is calcium-dependent, may comprise the light chain variable domain comprising the amino acid sequence of SEQ ID NO: 91 and the heavy chain variable domain comprising the amino acid sequence of 92, or may comprise the light and heavy CDR amino acid sequences of SEQ ID NO: 11, an amino acid sequence of KIS, SEQ ID NO: 32, SEQ ID NO: 44, SEQ ID NO: 56, and SEQ ID NO: 68.

Exemplary antibodies that are dual inhibitors of the Protein S cofactor activity of APC and TFPI, wherein the wherein the binding affinity of the antibodies to Protein S is calcium-dependent, may comprise the light chain variable domain comprising the amino acid sequence of SEQ ID NO: 89 and the heavy chain variable domain comprising the amino acid sequence of 90, or may comprise the light and heavy CDR amino acid sequences of SEQ ID NO: 10, an amino acid sequence of DAS, SEQ ID NO: 31, SEQ ID NO: 43, SEQ ID NO: 55, and SEQ ID NO: 67.

B. Generation of Protein S Antibodies

Production of the Protein S antibodies provided herein may be by use of any method known to those of ordinary skill in the art. In some embodiments, the antibodies are produced by hybridomas. In some embodiments, the antibodies are encoded by a nucleic acid and are expressed, purified, and isolated.

Accordingly, provided herein are nucleic acids encoding any of the antibodies disclosed herein, vectors comprising any of the nucleic acids encoding such antibodies, and host cells comprising such vectors. Also provided herein are exemplary nucleic acid sequences encoding for the variable heavy chains and variable light chains of the Protein S antibodies disclosed herein.

Tables 5A and 5B provide exemplary variable light chain nucleic acid sequences and exemplary variable heavy chain nucleic acid sequences. Exemplary combinations of nucleic acid sequences encoding for the variable heavy and light chain domains of the Protein S antibodies disclosed herein are presented in Table 5C. The exemplary amino acid sequences of Tables 4A-4C correspond to the nucleic acid sequences of Tables 5A-5C. The exemplary combinations of Table 5C correspond to the numbered combinations presented in Table 4C.

The person of ordinary skill in the art will appreciate that, because of redundancy in the triplet code, multiple nucleic acids may encode the same amino acid sequence. Thus, nucleic acid sequences that are not identical to those set forth in the tables below may still encode the Protein S antibodies of the disclosure.

TABLE 5A

Exemplary Variable Light Chain Nucleic Acid Sequences of Anti-Protein S Monoclonal Antibodies TCCTATGAGCTGACTCAGCCACCCTCAGTGTCCGT
GTCCCCAGGACAGACAGCCAGCATCACCTGCTCTG
GAGATAAATTGGGGGATAAATATGCTTGCTGGTAT
CAGCAGAAGCCAGGCCAGTCCCCTGTACTGGTCAT
CTATCAAGATACTAAGCGGCCCTCAGGGATCCCTG
AGCGATTCTCTGGCTCCAACTCTGGGAACACAGCC
ACTCTGACCATCAGCGGGACCCAGGCTATGGATGA
GGCTGACTATTACTGTCAGGCGTGGGACAGCAACA
CTGTGGTCTTCGGCGGAGGGACCAAGCTGACCGTC
CTA
(SEQ ID NO: 93)

TCCTCTGACCTGACTCAGGGCCCTGCTGTGTCTGT
GGCCCTGGGACAGACAGTCAGGATCACATGCCAAG
GAGACAGCCTCAGAAACTATTATGCAAGCTGGTAC
CAGCAGAAGCCAGGACAGGCCCCTGTACCTGTCAT
CTATGGTAAAAACGACCGGCCCTCAGGGATCCCAG
ACCGATTCTCTGGCTCCATCTCAGGAAACACAGCT
TCCTTGACCATCACTGGGGCTCAGGCGGAAGATGA
GGCTCACTATTACTGTAACTCCCGGGACAGCAGTG
GTAACCATGTGGTATTCGGCGGAGGGACCAAGCTG
ACCGTCCTG
(SEQ ID NO: 95)

CAGTCTGCCCTGACTCAGCCTGCCTCCGTGTCTGG
GTCTCCTGGACAGTCGATCACCATCTCCTGCACTG
GAACCAGCAGTGACGTTGGTGGTTATGAATTTGTC
TCCTGGTACCAACATCACCCAGGCAAAGCCCCCAA
ACTCATGATTTATGATGTCAGTAGTCGGCCCTCAG
GGGTTTCTAATCGCTTCTCTGGCTCCAAGTCTGGC
AACACGGCCTCCCTGACCATCTCTGGGCTCCAGGC
TGAGGACGAGGCTGATTATTACTGCAGCTCATATA
CGCGCAGCAGCACTGTGGTGTTCGGCGGCGGGGCC
AGGCTGACCGTCCTA
(SEQ ID NO: 97)

TCCTATGAGCTGAATCAGCCACCCTCAGTGTCCGT
GTCCCCAGGACAGACAGCCAGCATCACCTGCTCTG
GAGATAAATTGGGGGATAAATATGCTTCCTGGTAT
CAGCAGAAGCCAGGCCAGTCCCCTGTGGTGGCCAT
CTATCAAAATAGCAAGCGGCCCTCAGGGATCCCTG
AGCGATTCTCTGCCTCCAACTCTGGGAACACAGCC
ACTCTGACCATCAGCGGGACCCAGGCTTTGGATGA
GGCTGACTATTACTGTCAGGCGTGGGACAGCAGCA
CTTGGGTGTTCGGCGGAGGGACCAAGCTGACCGTC
CTA
(SEQ ID NO: 99)

GAAATTGTGTTGACACAGTCTCCAGCCACCCTGTC
TTTGTCTCCAGGGGAAAGAGCCACCCTCTCCTGCA
GGGCCAGTCAGAGTGTTAGTATCTACTTAGCCTGG

TABLE 5A-continued

Exemplary Variable Light Chain Nucleic Acid Sequences of Anti-Protein S Monoclonal Antibodies TACCAACAGAAACCTGGCCAGGCTCCCAGGCTCCT
CATCTATGATGCATCCAACAGGGCCACTGGCATCC
CAGCCAGGTTCAGTGGCAGTGGGTCTGGGACAGAC
TTCACTCTCACCATCAGCAGCCTAGAGCCTGAAGA
TTTTGCAGTTTATTACTGTCAGCAGCGTAGCAACT
GGCCCCTCACTTTCGGCCCTGGGACCAAAGTGGAT
ATCAAA
(SEQ ID NO: 101)

GAAATAGTGATGACGCAGTCTCCAGCCACCCTGTC
TGTGTCTCCAGGGGAAAGAGCCACCCTCTCCTGCA
GGGCCAGTCAGAGGATTAACAGCAACTTAGCCTGG
TACCAGCAGAAACCTGGCCAGGCTCCCAGGCTCCT
CATCTATGGTGCATCCACCAGGGCCACTGGTATCC
CCGCCAGGTTCAGTGGCAGTGGGTCTGGGACAGAG
TTCACTCTCACCATCAGCAGCCTGCAGTCTGAAGA
TTTTGCAGCTTATTACTGTCAGCAGTATGATAACT
GGCCGCTCACTTTCGGCGGAGGGACCAAGGTGGAG
ATCAAA
(SEQ ID NO: 103)

GATATTGTGATGACTCAGTCTCCACTCTCCCTGCC
CGTCACCCCTGGAGAGCCGGCCTCCATCTCCTGCA
GGTCTAGTCAGAGCCTCCTGCATAGTAATGGATAC
AACTATTTGGATTGGTACCTGCAGAAGCCAGGGCA
GTCTCCACAGCTCCTGATCTATTTGGGTTCTAATC
GGGCCTCCGGGGTCCCTGACAGGTTCAGTGGCAGT
GGATCAGGCACAGATTTTACACTGAAAATCAGCAG
AGTGGAGGCTGAGGATGTTGGGGTTTATTATTGTA
TGCAAGCTCTACAAACTTTCACTTTCGGCCCTGGG
ACCAAAGTGGATATCAAA
(SEQ ID NO: 105)

CAGGCTGTTGTGACTCAGGAATCTGCACTCACCAC
ATCACCTGGTGAAACAGTCACACTCACTTGTCGCT
CAAGTACTGGGGCTGTTACAGCTAGTAACTATGCC
AACTGGGTCCAAGAAAAACCAGATCATTTGTTCAC
TGGTCTAATAGGTAGTACCAATAACCGAGCTCCAG
GTGTTCCTGCCAGATTCTCAGGCTCCCTGATTGGA
GACAAGGCTGCCCTCACCATCACAGGGGCACAGAC
TGAGGATGAGGCAATATATTTCTGTGCTCTATGGT
ACAGCGACCATTTCGTGTTCGGTGGAGGAACCAAA
CTGACTGTCCTA
(SEQ ID NO: 111)

GAAATAGTGATGACGCAGTCTCCAGCCACCCTGTC
TGTGTCTCCAGGGGAAAGAGCCACCCTCTCCTGCA
GGGCCAGTCAGAGTGTTACCAGCAACTTAGCCTGG
TACCAGCAGAAACCTGGCCAGGCTCCCAGGCTCCT
CATCTATGATGCATCCACCAGGGCCACTGGTATCC
CAGCCAGGTTCAGTGGCAGTGGGTCTGGGACAGAG
TTCACTCTCACCATCAGCAGCCTGCAGTCTGAAGA
TTTTGCAATTTATTACTGTCAGCAGTATAATAACT
GGCCCACCTTCGGCCAAGGGACACGACTGGAGATT
AAA
(SEQ ID NO: 113)

GATATTGTGATGACCCAGACTCCACTCTCCTCACC
TGTCACCCTTGGACAGCCGGCCTCCATCTCCTGCA
GGTCTAGTCAAAGCCTCGTACACAGTGATGGAAAC
ACCTACTTGAGTTGGCTTCAGCAGAGGCCAGGCCA
GCCTCCAAGACTCCTAATTTATAAGATTTCTAACC
GGTTCTCTGGGGTCCCAGACAGATTCAGTGGCAGT
GGGGCAGGGACAGATTTCACACTGAAAATCAGCAG
GGTGGAAGCTGAGGATGTCGGGGTTTATTACTGCA
TGCAAGCTACACAATTTCCCCATCTCACTTTCGGC
GGAGGGACCAAGGTGGAGATCAAA
(SEQ ID NO: 115)

GACATCCAGATGACCCAGTCTCCATCCTCACTGTC
TGCATCTGTAGGAGACAGAGTCACCATCACTTGTC
GGGCGAGTCAGGGCATTAACAATTATTTAGCCTGG
TTTCAGCAGAAACCAGGGAAAGCCCCTAAGTCCCT
GATCTATGCTGCATCCAGTTTGCAAAGTGGGGTCC
CATCAAAGTTCAGCGGCAGTGGATCTGGGACAGAT
TTCACTCTCACCATCAGCAGCCTGCAGCCTGAAGA

TABLE 5A-continued

Exemplary Variable Light Chain Nucleic
Acid Sequences of Anti-
Protein S Monoclonal Antibodies TTTTGCAACTTATTACTGCCAACAGTATAATAGTT
ACCCTCGGACGTTCGGCCAAGGGACCAAGGTGGAA
ATCAAA
(SEQ ID NO: 162)

GACATCCAGATGACCCAGTCTCCATCCTCACTGTC
TGCATCTGTAGGAGACGAGTCACCATCACTTGTC
GGGCGAGTCAGGGCATTAACAATTATTTAGCCTGG
TTTCAGCAGAAACCAGGGAAAGCCCCTAAGTCCCT
GATCTATGCTGCATCCAATTTGCAAAGTGGGGTCC
CATTAAAGTTCAGCGGCAGTGGATCTGGGACAGAT
TTCACTCTCACCATCAGCAGCCTGCAGCCTGAAGA
TTTTGCAACTTATTACTGCCAACAGTATAATAGTT
ACCCGATCACCTTCGGCCAAGGGACACGACTGGAG
ATTAAA
(SEQ ID NO: 164)

GACATCCAGATGACCCAGTCTCCATCCTCCCTGTC
TGCATCTGTAGGAGACGAGTCACCATCACTTGCC
GGGCAAGTCAGAGCATTAGCACCTTTTTAAATTGG
TATCAGCAGAAACCAGGGAAAGCCCCTAAACTCCT
GATCTATGCTACATCCAGTTTGCAAGTGGGGTCC
CATCAAGGTTCAGTGGCAGTGGATCTGGGACAGAT
TTCACTCTCACCATCAGCAGTCTGCAACCTGAAGA
TTTTGCAATTTATTATTGTCAACAGAGTTACAGTA
CCCCTCGGACGTTCGGCCAAGGGACCCAGGTGGAA
ATCAAA
(SEQ ID NO: 166)

GAAATTGTGTTGACGCAGTCTCCAGGCACCCTGTC
TTTGTCTCCAGGGGAAAGAGCCACCCTCTCCTGCA
GGGCCAGTCAGAGTGTTGGCAGCAGCTACTTAGCC
TGGTACCAGCAGAAACCTGGCCAGGCTCCCAGGCT
CCTCATCTCTGGTGCATCCGGCAGGGCCACTGGCA
TCCCAGACAGGTTCAGTGGCAGTGGGTCTGGGACA
GACTTCACTCTCACCATCAGCAGACTGGAGCCTGA
AGATTTTACAGTGTATTACTGTCAGCAGTATGGTA
GCTCACCGTACACTTTTGGCCAGGGGACCAAGCTG
GAGATCAAA
(SEQ ID NO: 170)

GACATCCAGATGAACCAGTCTCCATCCAGTCTGTC
TGCATCCCTCGGAGACACAATTACCATCACTTGCC
GTGCCAGTCAGAACATTCATATGTGGTTAAGCTGG
TACCAGCAGAAACCAGGAAATATTCCTAAACTATT
GATCTTTAAGACTTCCACACAGGCGCC
CATCAAGGTTTAGTGGCAGTGGATCTGGAACAGAT
TTCACATTAACCATCAGCAGTCTGCAGCCTGAAGA
CATTGCCACTTACTACTGTCTACAGGGTCAAAGTT
ATCCGTTCACGTTCGGAGGGGGGACCAAGCTGGAA
ATAAAG
(SEQ ID NO: 172)

GACATCCAGATGACCCAGTCTCCATCCTCCCTGTC
TGCATCTGTAGGAGACAGAGTCACCATCACTTGCC
GGGCAAGTCAGAGCATTAGCAGCTATTTAAATTGG
TATCAGCAGAAACCAGGGAAAGCCCCTAAGCTCCT
GATCTATGCTGCATCCAGTTTGCAAAGTGGGGTCC
CATCAAGGTTCAGTGGCAGTGGATCTGGGACAGAT
TTCACTCTCACCATCAGCAGTCTGCAACCTGAAGA
TTTTGCAACTTACTACTGTCAACAGAGTTACAGTT
CCCTCACCTTCGGCCAAGGGACACGACTGGAGATT
AAA
(SEQ ID NO: 178)

TCCTATGTGCTGACTCAGCCACCCTCGGTGTCAGT
GGCCCCAGGACAGACGGCCAGGATTACCTGTGGGG
GAGACAACATTGGAGGTAAAAGTGTGCACTGGTAC
CAGCAGAAGCCAGGCCAGGCCCCTGTGATGGTCGT
CTATGATGATAGCGACCGGCCCTCAGGGATCCCTG
AGCGATTCGCTGGCTCCAATTCTGGGAACACGGCC
ACCCTGGCCATCAGCAGGGTCGAAGCCGGGGATGA
GGCCGACTATTACTGTCAGGTGTGGGAGATAACTA
GTGATCATCCGGCATTCGGCGGAGGGACCAGGCTG
ACCGTCCTA
(SEQ ID NO: 188)

TABLE 5A-continued

Exemplary Variable Light Chain Nucleic
Acid Sequences of Anti-
Protein S Monoclonal Antibodies TCCTATGAGCTGACTCAGCCACCCTCAGTGTCCGT
GTCCCCAGGACAGACAGCCAGCATCACCTGCTCTG
GAGATAAATTGGGGGATAAATATGTTTTCTGGTAT
CAGCAGAAGCCAGGCCAGTCCCCTGTGTTGGTCAT
CTATCAAGATAGCAAGCGGCCCTCAGGGATCCCTG
AGCGATTCTCTGGCTCCAACTCTGGGAACACAGCC
ACTCTGACCATCAGCGGGACCCAGACTATGGATGA
GGCTGACTATTACTGTCAGGCGTGGGACAGCAGCA
CTGTGGGATTCGGCGGAGGGACCAAGCTGGCCGTC
CTG
(SEQ ID NO: 198)

TCCTATGAGCTGACTCAGCCACCCTCAGTGTCCGT
GTCCCCGGGACAGACAGCCAGCATCACCTGCTCTG
GAGATAAATTGGGGGATAAATATGCTTTCTGGTAT
CAGCAGAAGCCAGGCCAGTCCCCTGTGCTGGTCAT
CTATCAAGATAACAAGCGGCCCTCAGGGATCCCTG
AGCGATTCTCTGGCTCCAACTCTGGGAACACAGCC
ACTCTAACCATCAGCGGGACCCAGGCTGTGGATGA
GGCTGACTATTACTGTCAGGCGTGGGACAGCAGCA
CTGCGGTATTCGGCGGAGGGACCAAGCTGACCGTC
CTA
(SEQ ID NO: 208)

TABLE 5B

Exemplary Variable Heavy Chain Nucleic
Acid Sequences of Anti-
Protein S Monoclonal Antibodies CAGCTGCAGCTGCAGGAGTCGGGCCCAGGACTGGT
GAAGCCTTCGGAGACCCTGTCCCTCACCTGCACTG
TCTCTGGTGGCTCCATCAGCAGTAGTAGTTACTAC
TGGGGCTGGATCCGCCAGCCCCCGGGGAAGGGACT
GGAGTGGATTGGGAATATCTATTATAGTGGGAACA
CCTACTACAACCCGTCCCTCAAGAGTCGAGTCACC
ATATCCGTAGACACGTCCAAGAACCAGTTCTCCCT
GAAGCTGAGCTCTATGACCGCCGCAGACACGGCTG
TGTATTACTGTGCGAGATGTAGTGGCTACGGGTAT
AGCAGTGGCCGGTCCTACTTTGACTACTGGGGCCA
GGGAACCCTGGTCACCGTCTCCTCA
(SEQ ID NO: 94)

CAGGTGCAGCTGGTGCAGTCTGGGGCTGAGGTGAA
GAAGCCTGGGTCCTCGGTGAAGGTCTCCTGCAAGG
TTTCTGGAGGCACCTTCAGCAGCTATTCTATCAGC
TGGGTGCGACAGGCCCCTGGACAAGGGCTTGAGTG
GATGGGAGGGATCATCCCTATATTTGGTACAACAA
ACTACGCACAGAAGTTCCAGGGCAGAGTCACGATC
ACCGCGGACGAATCCACGAGCACAGCCTACATGGA
TCTGAGCAGCCTGAAATCTGAGGACACGGCCATGT
ATTACTGTGAGGGGGTAGAGTGGGAGCGGACTTT
GACTACTGGGGCCAGGGAACCCTGGTCACCGTCTC
CTCA
(SEQ ID NO: 96)

CAGGTGCAGCTGCAGGAGTCGGGCCCAGGACTGGT
GAAGCCTTCACAGACCCTGTCCCTCACCTGCACTG
TCTCTGGTGGCTCCATCACCAGTGATGGTTACCAC
TGGAGCTGGATCCGCCAGTACCCAGGGAAGGGCCT
GGACTGGATTGGATACATCTATTACACTGGGAACA
CCTACTACAACCCGTCCCTCAAGAGTCGAGTGACC
ATATCAGTAGGCACGTCTCCGAACCAGTTCTCCCT
GAAGCTGATCTCTGTGACTGCCGCGGACACGGCCG
TTTATTACTGTGCGAGAAGGCTGTCGACTGGGCCC
TACTTTGACTACTGGGGCCAGGGAACCCTGGTCAC
CGTCTCCTCC
(SEQ ID NO: 98)

GAAGTGCAGCTGGTGGAGTCTGGGGGAGGCTTGGT
ACAGCCTGGCAGGTCCCTGAGACTCTCCTGTGCAG
CCTCTGGATTCACCTTTGATGATTATGCCATGCAC

TABLE 5B-continued

Exemplary Variable Heavy Chain Nucleic Acid Sequences of Anti- Protein S Monoclonal Antibodies TGGGTCCGGCAAGCTCCAGGGAAGGGCCTGGAATG
GGTCTCAGGTATTACTTGGAATAGTGGTAACATAG
GCTATGCGGACTCTGTGAAGGGCCGATTCACCATC
TCCAGAGACAACGCCAAGAACTCCCTGTATCTGCA
CATGAACAGTCTGAGAATTGAGGACACGGCCTTCT
ATTACTGTGCAAAAGGCCGAGCAGTGTCTGATACT
TTTGATATCTGGGGCCAAGGGACAATGGTCACCGT
CTCTTCA
(SEQ ID NO: 100)

CAGGTGCAGTTGGTGGAATCTGGGGGAGGCGTGGT
CCAGCCTGGGAGGTCCCTGAGACTCTCCTGTGCAG
CGTCTGGATTCACCTTCAGTACCTATGGCTTTCAC
TGGGTCCGCCAGCCTCCAGGCAAGGGACTGGAGTG
GGTGGCAGTTATATATTATGATGGAATTAATAAAT
ATTATGCAGACTCCGTGAAGGGCCGATTCACCATC
TCCAGAGACAATTCCAAGAACACGCTGTTTCTTCA
AATGAACAGCCTGAGAGCCGAGGACACGGCTGTGT
ATTACTGTGCGGAGTCCGACTTGGACTACTGGGGC
CAGGGAACCCTGGTCACCGTCTCCTCA
(SEQ ID NO:
102)

CAGGTGCAGCTGCAGGAGTCGGGCCCAGGACTGGT
GAAGCCTTCGGAGACCCTGTCCCTCACCTGCGCTG
TCTCTGGTTATTCCATCAGCAGTGGTTACTACTGG
GGCTGGATCCGGCAGCCCCCAGGGAAGGGGCTGGA
CTGGATTGGGAGTATCTATTATAGTGGGAGTACCT
ACTACAACCCGTCCCTCAAGAGTCGAGTCACCATA
TCAGTTGACACGTCCAAGAACCAGATCTCCCTGAA
GCTGAGCTCTGTGACCGCCGCAGACACGGCCGTGT
ATTACTGTGCGACCACGTATTCCGATATTGTGACT
GGTTATTATAATGATGCTTTTGATATCTGGGGCCA
AGGGACAATGGTCACCGTCTCTTCA
(SEQ ID NO: 104)

CAGGTGCAGCTGGTGCAGTCTGGGGCTGAGGTGAA
GAAGCCTGGGTCCTCGGTGAAGGTCTCCTGTAAGG
CTTCTGGAGACACCTTCAGCAACCATGCTATCAAC
TGGGTGCGACAGGCCCCTGGACAAGGGCTTGAGTG
GATGGGAGGGTACATCCCTATCTTTGGTACAACAA
ACTCCGCACAGAAGTTCCGGGGCAGAGTCACGATT
ACCGCGGACAAATCCACGAACACAGCCTACATGGC
GCTGAGCAGCCTGAGATCTGAGGACACGGCCGTTT
ATTACTGTGCGAGAGGGGGCTCGCGGGGAGTCAT
TATAAGAACTACTACTATGACGGTATGGACGTCTG
GGGCCAGGGGACCACGGTCACCGTCTCCTCA
(SEQ ID NO: 106)

CAGGTGCAACTGGTGCAGTCTGGGGCTGAGGTGAA
GAAGCCTGGGGCCTCAGTGAAGGTCTCCTGCAAGT
CTTCTGGCCACACCTTCACCGGCTACTATATGCAC
TGGGTGCGACAGGCCCCTGGACAAGGGCTTGAGTG
GATGGGATGGATCAACCCTAACAGTGGTGACACAA
ACTACGCACAGAAGTTTCAGGGCAGGGTCACCATG
ACCAGGGACACGTCCATCAGCACAGCCTACATGGA
GATGAGCAGGCTGAGATCTGACGACACGGCCGTGT
ATTACTGTGCGAGAGACTCCCAAATACTATGGTTC
GGGGAGTTAGGCTACTGGGGCCAGGGAACCCTGGT
CACCGTCTCCTCC
(SEQ ID NO: 112)

CAGGTGCAGCTGCAGGAGTCGGGCCCAGGACTGGT
GAAGCCTTCGGAGACCCTGTCCCTCACCTGCGGTG
TCTCTGGTGGCTCCATCAGCAGTACTAACTGGTGG
AGTTGGGTCCGCCAGCCCCCAGGGAAGGGGCTGGA
GTGGATTGGGAAATCTATCAAACTGGGAGTACCG
ACTACGACCCGTCCCTCAAGAGTCGAGTCACCATA
TCAATAGACAAGTCCAAGAACCAGTTCTCCCTGAA
GCTGTACTCTGTGACCGCCGCGGACACGGCCGTGT
ATTACTGTGCGAGAAGGTTCGGGGAGTTAGACTAC
TGGGGCCAGGGAACCCTGGTCACCGTCTCCTCA
(SEQ
ID NO: 114)

CAGGTGCAGCTGCAGGAGTCGGGCCCAGGACTGGT
GAAGCCTTCGGAGACCCTGTCCCTCACCTGCACTG
TCTCTGGTGGCTCCATCGTAATTACTACTGGAAC
TGGATCCGGCAGCCCCCAGGGAAGGGACTGGAGTG
GATTGGGTATATCTATTACATTGGGATCACCGACT
ACAACCCCTCCCTCAAGAGTCGAGTCACCATATCA
GTAGACACGTCCAAGAACCAGTTCTCCCTGAAGGT
GACCTCTGTGACCGCTGCGGACACGGCCGTGTATT
ACTGTGCGGCTCTAAGTGGGGATCATGCTTTTGAC
ATCTGGGGCCAAGGGACACTGGTCACCGTCTCTTC
A
(SEQ ID NO: 116)

CAGCTGCAGCTGCAGGAGTCGGGCCCAGGACTGGT
GAAGCCTTCGGAGACCCTGTCCCTCACCTGCACTG
TCTCTGGTGGCTCCATCACCAATAGTAATTACTAC
TGGGGCTGGATCCGCCAGCCCCCAGGGAAGGGACT
GGAGTGGATTGGGAGTGTCTATTATAGTGGGACCA
CCTACTACAACCCGTCCCTCAAGAGTGAGTCACC
ATATCCGTAGACCCGTCCAAGAACCAGTTCTCCCT
GAAGCTGAGCTCTGTGACCGCCGCAGACACGGCTG
TGTATTACTGTGTGAGAGAGAGTGAGAGCTACTAC
TACTACGGTTCGGACGTCTGGGGCCAAGGGACCAC
GGTCACCGTCTCCTCA
(SEQ ID NO: 163)

GAGGTGCAGCTGGTTGAGTCTGGGGGAGGCCTGGT
CAAGCCTGGGGGGTCCCTGAGACTCTCCTGTGCAG
CCTCTGGATTCACCTTCAGTAGCTATAACATGAAC
TGGGTCCGCCAGGCTCCAGGGAGGGGCTGGACTG
GGTCTCATCCATTAGTAGTAGTAGTTACATAT
ACTACGCAGACTCAGTGAAGGGCCGATTCACCATC
TCCAGAGACAACGCCAAGAACTCACTGTATCTGCA
AATGAATACCCTGAGAGCCGAGGACACGGCTGTTT
ATTACTGTGCGAGAGATGAGGAGTGGGAGCTACTG
ACGGGCTTTGACTACTGGGGCCAGGGAACCCTGGT
CACCGTCTCCTCA
(SEQ ID NO: 165)

CAGGTGCAGCTGCAGGAGTCGGGCCCAGGACTGGT
GAAGCCTTCGGAGACCCTGTCCCTCACCTGCACTG
TCTCTGGTGGCTCCATCAGTGGTAACTACTGGAGC
TGGATCCGGCAGCCCCCAGGGAAGGGACTGGAGTG
GATTGGGTATATCTATTACAGTGGGAGCACCAACT
ACAATCCCTCCCTCAAGAGTCGAGTCACCATATCA
GTTGACACGTCCAAGAACCAGTTCTCCCTGAAGCT
GAGCTCTGTGACCGCTGCGGATACGGCCGTGTATT
ACTGTGCGAGAGATCTTGATTACTTTACTTGGGGG
GCTTATTCTGACTGGTACTTCGATCTCTGGGGCCG
TGGCACCCTGGTCACTGTCTCCTCA
(SEQ ID NO: 167)

CAGGTACAGCTGCAGCAGTCAGGTCCAGGACTGGT
GAAGCCCTCGCAGACCCTCTCACTCACCTGTGCCA
TCTCCGGGGACAGTGTCTCTAACAACAATGCTGCT
TGGAACTGGATCAGGCAGTCCCCATCGAGAGGCCT
TGAGTGGCTGGGAGGGACATACACAGGTCCAAGT
GGTATAATGATTATGCAGTATCTGTGAAAAGTCGA
ATAATCATCAACCCAGTCACATCCAAGAACCAGTT
CTCCCTACAGCTGAACTCTGTGACTCCCGAGGACA
CGGCTGTGTATTACTGTGCAAGAGGCAGCAGCTGG
TACAGGTTTTTTGACTACTGGGGCCAGGGAACCCT
GGTCACCGTCTCCTCA
(SEQ ID NO: 171)

CAGGTCCAGCTGCAGCAGTCTGGAACTGAGCTGGT
AAGGCCTGGGACTTCAGTGAAGATGTCCTGTAAGG
CTGCTGGATACACCTTCACTAACCACTGGATAGGT
TGGGTAAAGCAGAGGCCTGGACATGGCCTTGAGTG
GATTGGAGATATTTACCCTGGAGGTGGTTATACTA
ACTACAATGAGAAGTTCAAGGGCAAGGCCTCACTG

TABLE 5B-continued

Exemplary Variable Heavy Chain Nucleic Acid Sequences of Anti-Protein S Monoclonal Antibodies ACTGCAGACACATCCTCCACCACAGCCTACATGCA
GCTCAGCAGCCTGACATCTGAGGACTCTGCCATCT
ATTACTGTTCAAGATTCGGGGATCAAAACTGGGCC
TGGTTTGCTTACTGGGGCCAAGGGACTCTGGTCAC
TGTCTCTGCA
(SEQ ID NO: 173)

GAGGTGCAGCTGGTGGAGTCTGGGGGAGGCTTGGT
AAAGCCTGGGGGGTCCCTTAGACTCTCCTGTGCAG
CCTCTGGAATCAGTTTCAGTAACGCCTGGATGAGC
TGGGTCCGCCAGGCTCCAGGGAAGGGGCTGGAATG
GGTTGGCCGTATTAAAGCCAATCCTGATGGTGGGA
CAACAGACTACGCTGCACCCGTGAAAGGCAGATTC
ACCATCTCAAGAGATGATTCAAAAAACACGCTATA
TCTGCAAATGAACAGCCTGAAAACCGAGGACACAG
CCGTGTATTACTGTACCACAGAGTTGGACATTTTA
CTATGGTTCACCTCCTTTGACTACTGGGGCCAGGG
AACCCTGGTCACCGTCTCCTCA
(SEQ ID NO: 183)

GAGGTGCAGCTGGTGGAGTCTGGGGGAGGCTTGGT
ACAGCCTGGGGGGTCCCTGAGACTCTCCTGTGCAG
CCTCTGGATTCACCTTCAGTAGCTATAGCATGAAC
TGGGTCCGCCAGGCTCCAGGGAAGGGGCTGGAGTG
GGTTGCATACATTAGTAGTAGTACTCGTACCATAT
TCTACGCAGACTCTGTGAAGGGCCGATTCACCATC
TCCAGAGACAATGCCAAGAACTCACTGTATCTGCA
AATGAACAGCCTGAGAGACGAGGACACGGCTTTTT
ATTATTGTGCGAGAGAACGTTCGGCCTTTGACTAC
TGGGGCCAGGGAACCCTGGTCACCGTCTCCTCA
(SEQ ID NO: 193)

CAGGTGCAGCTGGTGCAGTCTGGGTCTGAGGTGAA
GAAGCCTGGGGCCTCAGTGAAGGTTTCCTGCAAGG
CATCTGGATACACCTTCACCAACTACTATATACAC
TGGGTGCGGCAGGCCCCTGGACAAGGGCTTGAGTG
GATGGGAATAATCACCCCTAGTGGTGGTACCACAA
GCTACGCACAGAAGTTCCAGGGCAGAGTCACTATG
ACCAGGGACACGTCCACGAACACAGTCTACATGGG
GCTGAGCAGCCTGAGATCTGAGGACACGGCCATGT
ATTACTGTGCGAGAGCCGGGGTACAACTGGATCGA
CGAGGGTGGTTCGACCCCTGGGGCCAGGGAACCCT
GGTCACCGTCTCCTCA
(SEQ ID NO: 203)

CAGGTGCAGCTGGTGCAGTCTGGGGCTGAGGTGAA
GAAGCCTGGGGCCTCAGTGAAGGTTTCCTGCAAGG
CATCTGGATACACCTTCACCAGCTACTATATACAC
TGGGTACGACAGGCCCCTGGACAAGGGCTTGAGTG
GATGGGAGTAACCAGCCCTAGTGGTCGTAGCACAA
GCTTCGCACAGAAGTTCCAGGGCAGAGTCACCATG
ACCAGGGACACGTCCACGAGCGCAGTCTATATGGA
CCTGGACAGCCTGAGATCTGAGGACACGGCCGTGT
ATTACTGTGCGAGAGGGGGAGTGACGATACACCTG
GAACGACGGGCTACTTTGACTACTGGGGCCAGGG
AACCCTGGTCATTGTCTCCTCA
(SEQ ID NO: 213)

TABLE 5C

Exemplary Variable Light Chain and Variable Heavy Chain Nucleic Acid Sequences of Anti-Protein S Monoclonal Antibodies

| Combination Number | Variable Light Chain Nucleic Acid Sequence | Variable Heavy Chain Nucleic Acid Sequence |
|---|---|---|
| Combination 1 | SEQ ID NO: 93 | SEQ ID NO: 94 |
| Combination 2 | SEQ ID NO: 95 | SEQ ID NO: 96 |
| Combination 3 | SEQ ID NO: 97 | SEQ ID NO: 98 |
| Combination 4 | SEQ ID NO: 99 | SEQ ID NO: 100 |
| Combination 5 | SEQ ID NO: 101 | SEQ ID NO: 102 |
| Combination 6 | SEQ ID NO: 103 | SEQ ID NO: 104 |
| Combination 7 | SEQ ID NO: 105 | SEQ ID NO: 106 |
| Combination 10 | SEQ ID NO: 111 | SEQ ID NO: 112 |
| Combination 11 | SEQ ID NO: 113 | SEQ ID NO: 114 |
| Combination 12 | SEQ ID NO: 115 | SEQ ID NO: 116 |
| Combination 13 | SEQ ID NO: 162 | SEQ ID NO: 163 |
| Combination 14 | SEQ ID NO: 164 | SEQ ID NO: 165 |
| Combination 15 | SEQ ID NO: 166 | SEQ ID NO: 167 |
| Combination 17 | SEQ ID NO: 170 | SEQ ID NO: 171 |
| Combination 18 | SEQ ID NO: 172 | SEQ ID NO: 173 |
| Combination 19 | SEQ ID NO: 178 | SEQ ID NO: 183 |
| Combination 20 | SEQ ID NO: 188 | SEQ ID NO: 193 |
| Combination 21 | SEQ ID NO: 198 | SEQ ID NO: 203 |
| Combination 22 | SEQ ID NO: 208 | SEQ ID NO: 213 |

In some embodiments, provided herein are nucleic acids encoding any of the Protein S antibodies disclosed herein. In some embodiments, provided herein are nucleic acids comprising any one or more of the nucleic acid sequences of Tables 5A-5B. In some embodiments, the heavy chain and light chain variable domains of the Protein S antibodies disclosed herein are encoded by a nucleic acid comprising any one or more of the nucleic acid sequences of Tables 5A-5B.

In some embodiments, the variable domain of the Protein S antibodies of the disclosure are encoded by a nucleic acid, wherein the light chain variable domain of the antibody is encoded by the nucleic acid sequence of SEQ ID NO: 93 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 94, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 93 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 94, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 95 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 96, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 95 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 96, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 97 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 98, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 97 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 98, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 99 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 100, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 99 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 100, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 101 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 102, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 101 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 102, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 103 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 104, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 103 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 104, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 105 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 106, or a nucleic acid sequence with at least 80%, 81%, 82%, 83%, 84%, 85%, 86%, 87%, 88%, 89%, 90%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 105 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 106, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 111 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 112, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 111 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 112, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 113 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 114, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 113 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 114, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 115 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 116, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 115 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 116, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 162 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 163, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 162 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 163, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 164 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 165, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 164 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 165, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 166 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 167, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 166 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 167, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 170 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 171, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 170 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 171, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 172 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 173, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 172 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 173, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 178 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 183, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 178 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 183, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 188 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 193, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 188 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 193, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 198 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 203, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 198 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 203, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 208 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the heavy chain variable domain of the antibody is encoded by the nucleic acid sequence of SEQ ID NO: 213, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

In some embodiments, the variable domain of the Protein S antibodies of the disclosure are encoded by a nucleic acid, wherein the light chain variable domain of the antibody is encoded by the nucleic acid sequence of SEQ ID NO: 208 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 213, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

The disclosure also provides vectors comprising any nucleic acid of the disclosure. In some embodiments, the nucleic acid of the vector comprises any one or more of the nucleic acid sequences provided in Tables 5A-5B. In some embodiments, the vector is an expression vector or an expression construct. In some embodiments, the vector is a mammalian vector. In some embodiments, the vector is a viral vector.

In some embodiments, the Protein S antibodies provided herein are produced by culturing a cell under suitable conditions for leading to the expression of the Protein S antibody, wherein the cell comprises a vector.

II. Uses of Protein S Antibodies

A. Therapeutic Protein S Antibodies

Provided herein are antibodies that recognize and selectively and/or specifically bind to Protein S, including Protein S fragments. The antibodies disclosed herein may be used for therapeutics in a subject. In some embodiments, the subject is a mammalian subject. In some embodiments, the mammalian subject is a human subject. In some embodiments, the mammalian subject is a non-human primate, e.g. a cynomolgus monkey.

In some embodiments, the Protein S antibodies provided herein are useful for treating a condition in a subject, wherein the condition is associated with the coagulation cascade. In some embodiments, the Protein S antibodies provided herein are useful for reducing an ability of Protein S to act as a cofactor within the coagulation cascade for the treatment of a condition in a subject.

In some embodiments, the Protein S antibodies provided herein are useful for reducing an ability of Protein S to act as a cofactor for APC, TFPI, or APC and TFPI for the treatment of a bleeding disorder or other diseases, e.g., a platelet disorder.

In some embodiments, provided herein is a method of promoting the coagulation of blood, the method comprising contacting any one of the Protein S antibodies disclosed herein with Protein S. In some embodiments, the contacting takes place in plasma. In some embodiments, the method is in vitro. In some embodiments, the method is in vivo. In some embodiments, the method is in vivo, and the method further comprises administering any one of the Protein S antibodies disclosed herein to a subject in need thereof.

In some embodiments, provided herein is a method of promoting the coagulation of blood, the method comprising contacting any one of the Protein S antibodies disclosed herein with a blood sample. Exemplary antibodies that may be used in a method for promoting the coagulation of blood include, but are not limited to, antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, an amino acid sequence of GKN, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, an amino acid sequence of QNS, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, an amino acid sequence of QDT, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, an amino acid sequence of DAS, SEQ ID NO: 31, SEQ ID NO: 43, SEQ ID NO: 55, and SEQ ID NO: 67.

In some embodiments, the coagulation of blood is marked by an increase in thrombin generation. Exemplary antibodies wherein use of the antibodies in the method for promoting the coagulation of blood, and wherein the coagulation of blood is marked by an increase in thrombin generation, include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, an amino acid sequence of GKN, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, an amino acid sequence of QNS, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, an amino acid sequence of QDT, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, an amino acid sequence of DAS, SEQ ID NO: 31, SEQ ID NO: 43, SEQ ID NO: 55, and SEQ ID NO: 67.

In some embodiments, the coagulation of blood is marked by an increase in fibrin generation. Exemplary antibodies wherein use of the antibodies in the method of promoting the coagulation of blood, and wherein the coagulation of blood is marked by an increase in fibrin generation include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, an amino acid sequence of GKN, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, an amino acid sequence of QNS, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, an amino acid sequence of QDT, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, an amino acid sequence of DAS, SEQ ID NO: 31, SEQ ID NO: 43, SEQ ID NO: 55, and SEQ ID NO: 67.

In some embodiments, the coagulation of blood is marked by an increase in D-dimer.

In some embodiments, the blood sample is obtained from a subject having a coagulation factor deficiency or von Willebrand disease (vWD), or a platelet disorder. In some embodiments, the vWD is a subtype selected from: vWD Type 1, vWD Type 2A, vWD Type 2B, vWD Type 2N, vWD Type 2M, vWD Type 3, and acquired vWD. Exemplary antibodies wherein use of the antibodies for a method for promoting coagulation of blood, and wherein the blood is a blood sample obtained from a subject having a coagulation factor deficiency (e.g. such as Factor VII deficiency, Factor VIII deficiency, Factor IX deficiency, Factor XI deficiency) or von Willebrand disease may comprise the light chain variable domain comprising the amino acid sequence of SEQ ID NO: 75 and the heavy chain variable domain comprising the amino acid sequence of SEQ ID NO: 76, or may comprise the light and heavy CDR amino acid sequences of SEQ ID NO: 1, an amino acid sequence of QNS, SEQ ID NO: 24, SEQ ID NO: 36, SEQ ID NO: 48, and SEQ ID NO: 60.

In some embodiments, provided herein is a method of promoting the coagulation of blood in a subject in need thereof, the method comprising administering to the subject any one of the Protein S antibodies disclosed herein, or any one of the pharmaceutical compositions disclosed herein. In some embodiments, the antibody remains active in the subject for a period of time, wherein the period of time is antibody dose-dependent. In some embodiments, the period of time is about 50 hours to about 170 hours. Exemplary antibodies wherein use of the antibodies for a method of promoting the coagulation of blood in a subject in need thereof, wherein the activity of the antibody is dose-dependent, may comprise the light chain variable domain comprising the amino acid sequence of SEQ ID NO: 71 and the heavy chain variable domain comprising the amino acid sequence of SEQ ID NO: 72, or may comprise the light and heavy CDR amino acid sequences of SEQ ID NO: 2, an amino acid sequence of GKN, SEQ ID NO: 22, SEQ ID NO: 34, SEQ ID NO: 46, and SEQ ID NO: 58.

In some embodiments, provided herein is a method of promoting generation of thrombin in a subject in need thereof, the method comprising administering to the subject any one of the Protein S antibodies disclosed herein, or any one of the pharmaceutical compositions disclosed herein. In some embodiments, the subject suffers from a disease or condition selected from the group consisting of bleeding disorders, and platelet disorders. In some embodiments, the subject suffers from trauma and/or bleeding resulting from a surgery or a medical procedure. For example, the medical procedure may be a procedure in which bleeding may occur, but not necessarily so. In some embodiments, the medical procedure is a dental procedure. Exemplary antibodies that may be used in a method of promoting generation of thrombin in a subject in need thereof may comprise the light and heavy CDR amino acid sequences of SEQ ID NO: 2, an amino acid sequence of GKN, SEQ ID NO: 22, SEQ ID NO: 34, SEQ ID NO: 46, and SEQ ID NO: 58, or may comprise the amino acid sequence of SEQ ID NO: 75 and the heavy chain variable domain comprising the amino acid sequence of SEQ ID NO: 76, or may comprise the light and heavy CDR amino acid sequences of SEQ ID NO: 1, an amino acid sequence of QNS, SEQ ID NO: 24, SEQ ID NO: 36, SEQ ID NO: 48, and SEQ ID NO: 60, or may comprise the amino acid sequence of SEQ ID NO: 69 and the heavy chain variable domain comprising the amino acid sequence of SEQ ID NO: 70, and may comprise the light and heavy CDR amino acid sequences of SEQ ID NO: 1, an amino acid sequence of QDT, SEQ ID NO: 21, SEQ ID NO: 33, SEQ ID NO: 45, and SEQ ID NO: 57.

In some embodiments, provided herein is a method of treating a condition in a subject in need thereof, wherein the disease is selected from the group consisting of bleeding disorders, and platelet disorders, and the method comprises administering to the subject any one of the Protein S antibodies disclosed herein, or any one of the pharmaceutical compositions disclosed herein. In some embodiments, the condition is a bleeding disorder. In some embodiments, the bleeding disorder is selected from the group consisting of hemophilia A, hemophilia B, von Willebrand disease (vWD, which may be a subtype selected from: vWD Type 1, vWD Type 2A, vWD Type 2B, vWD Type 2N, vWD Type 2M, vWD Type 3, and acquired vWD), menorrhagia including menorrhagia due to a congenital or acquired factor deficiency, Factor I deficiency, Factor II deficiency, Factor V deficiency, Factor VII deficiency, Factor X deficiency, Factor XI deficiency (hemophilia C), Factor VIII deficiency (hemophilia A), Factor IX deficiency (hemophilia B), trauma, and hereditary hemorrhagic telangiectasia. In some embodiments, the bleeding is associated with surgery, e.g. in a subject with a type of hemophilia. In some embodiments, the bleeding is associated with a medical procedure, e.g., a dental procedure. In some embodiments, the bleeding disorder is vWD, and the subject also suffers from menorrhagia. In some embodiments, the bleeding disorder is vWD, and the subject is undergoing a prophylactic treatment. In some embodiments, the subject suffers from menorrhagia associated with any one or more bleeding disorders and/or platelet disorders. In some embodiments, the subject is a hemophilia carrier. In some embodiments, the subject is a hemophilia carrier, and suffers from menorrhagia. In some embodiments, the condition is a platelet disorder. In some embodiments, the platelet disorder includes but is not limited to Bernard-Soulier syndrome, Glanzmann's thrombasthenia, and platelet storage pool deficiencies. In some embodiments, the platelet disorder is a platelet storage pool deficiency. In some embodiments, the platelet storage pool deficiency includes but is not limited to: Gray platelet syndrome, Quebec platelet disorder, and MYH9-related thrombocytopenia (MYH9RD). In some embodiments, the subject has a bleeding disorder, and has inhibitors. In some embodiments, the bleeding disorder is hemophilia A or hemophilia B, wherein the subject has inhibitors. In some embodiments, the bleeding disorder is vWD. For example, the inhibitors may be developed in the subject as a response to factor replacement therapy. Exemplary antibodies that may be used for a method of treating a condition in a subject in need thereof, wherein the disease is selected from the group consisting of bleeding disorders, and platelet disorders, include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, an amino acid sequence of GKN, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, an amino acid sequence of QNS, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, an amino acid sequence of QDT, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, an amino acid sequence of DAS, SEQ ID NO: 31, SEQ ID NO: 43, SEQ ID NO: 55, and SEQ ID NO: 67.

In some embodiments, a subject in need thereof may be treated with any of the Protein S antibodies provided herein, wherein the treatment is a routine prophylaxis to prevent or reduce the frequency of bleeding episodes. In some embodiments, a subject in need thereof may be treated with any of the Protein S antibodies provided herein, wherein the treatment is an on-demand treatment used for the control of bleeding episodes. In some embodiments, a subject in need thereof may be treated with any of the Protein S antibodies provided herein, wherein the treatment is a perioperative management of bleeding. For example, a perioperative management treatment may be used for treating a subject prior to, during, and/or after surgery or other medical procedure, or prior to, during, and/or after trauma.

In some embodiments, the treatment with any of the Protein S antibodies provided herein is provided as a chronic therapy, with dosing occurring continuously over time. In some embodiments, the treatment with any of the Protein S antibodies provided herein is provided as an intermittent therapy, with dosing occurring at irregular intervals. As an example, such an intermittent therapy can be used for a subject having menorrhagia. In some embodiments, the treatment with any of the Protein S antibodies provided herein is provided as an acute therapy, with dosing occurring for a short finite period of time. For example, the acute therapy may be administered for spontaneous bleeding episodes, or in conjunction with a surgery or other medical procedure, or after experiencing a trauma.

In some embodiments, the method of treatment of a subject may be a combination one of the above, e.g., the method of treatment may be prophylactic, and on-demand. In some embodiments, a prophylactic method of treatment may be a chronic therapy. In some embodiments, a prophylactic method of treatment may be an acute therapy. In some embodiments, a prophylactic method of treatment may be an intermittent therapy. In some embodiments, an on-demand treatment may be an acute therapy. In some embodiments, an on-demand treatment may be an intermittent treatment.

In some embodiments, treatment of a subject in need thereof comprises administering to the subject any of the Protein S antibodies provided herein, wherein the Protein S antibodies provided herein are Fab fragments. Without being bound to any theory, in some embodiments a shorter half-life of a Fab fragment, in relation to a full-length antibody with the same VH/VL may be beneficial for an acute treatment or on-demand. In some embodiments, the Fab fragment Protein S antibodies are administered to a subject in need thereof to reduce risk of bleeding.

B. Combination Therapies

The administration of any one of the therapeutic Protein S antibodies provided herein may be a monotherapy, or may be in combination with any other known drugs or treatments for diseases or conditions. In some embodiments, the other known drugs or treatments are useful for treating disorders, diseases, or conditions associated with reduced or impaired clotting. In some embodiments, the disorder, condition is a bleeding disorder. In some embodiments, the disorder, disease, or condition is a bleeding disorder or a platelet disorder.

In some embodiments, the administration of any of the therapeutic Protein S antibodies provided herein may be with a factor replacement therapy. In some embodiments, the administration of any of the therapeutic Protein S antibodies provided herein may be with the administration of a recombinant Factor VII.

C. Administration of Therapeutic Protein S Antibodies

The in vivo administration of the therapeutic Protein S antibodies described herein may be carried out intravenously, intramuscularly, subcutaneously, topically, orally, transdermally, intraperitoneally, intraorbitally, intrathecally, intraventricularly, intranasally, transmucosally, through implantation, or through inhalation. Administration of the therapeutic Protein S antibodies may be performed with any suitable excipients, carriers, or other agents to provide suitable or improved tolerance, transfer, delivery, and the like.

In some embodiments, the in vivo administration of any of the therapeutic Protein S antibodies provided herein may be an intravenous administration. In some embodiments, the intravenous administration may be provided as a prophylactic treatment. In some embodiments, the prophylactic treatment may be a routine prophylaxis. In some embodiments, the routine prophylaxis may have a regular dosing schedule. In some exemplary embodiments, the regular dosing schedule may be once weekly, twice weekly, once monthly, twice monthly, or three times monthly. In some embodiments, the intravenous administration may be provided as an on-demand treatment. In some embodiments, the intravenous administration may be provided as a chronic therapy. In some embodiments, the intravenous administration may be provided as an intermittent therapy. In some embodiments, the intravenous administration may be provided as an acute therapy. In some embodiments, an intermittent therapy may have a regular dosing schedule for the duration of the intermittent therapy. In some embodiments, an acute therapy may have a regular dosing schedule for the duration of the acute therapy. For example, administration of any of the therapeutic Protein S antibodies provided herein for an acute therapy by intravenous administration may occur on a regular dosing schedule for a predetermined duration of days, e.g., 7 days, 14 days, or more. Exemplary antibodies that may be used for an in vivo intravenous administration include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, an amino acid sequence of GKN, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, an amino acid sequence of QNS, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, an amino acid sequence of QDT, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, an amino acid sequence of DAS, SEQ ID NO: 31, SEQ ID NO: 43, SEQ ID NO: 55, and SEQ ID NO: 67.

In some embodiments, the in vivo administration of any of the therapeutic Protein S antibodies provided herein may be a subcutaneous administration. In some embodiments, the subcutaneous administration may be provided as a prophylactic treatment. In some embodiments, the prophylactic treatment may be a routine prophylaxis. In some embodiments, the routine prophylaxis may have a regular dosing schedule. In some exemplary embodiments, the regular dosing schedule may be once weekly, twice weekly, once monthly, twice monthly, or three times monthly. In some embodiments, the subcutaneous administration may be provided as an on-demand treatment. In some embodiments, the subcutaneous administration may be provided as a chronic therapy. In some embodiments, the subcutaneous administration may be provided as an intermittent therapy. In some embodiments, the subcutaneous administration may be provided as an acute therapy. In some embodiments, an intermittent therapy may have a regular dosing schedule for the duration of the intermittent therapy. In some embodiments, an acute therapy may have a regular dosing schedule for the duration of the acute therapy. For example, administration of any of the therapeutic Protein S antibodies provided herein for an acute therapy by subcutaneous administration may occur on a regular dosing schedule for a predetermined duration of days, e.g., 7 days, 14 days, or more. Exemplary antibodies that may be used for an in vivo subcutaneous administration include, but are not limited to antibodies that (a) comprise the light chain variable domain comprising the amino acid sequence of SEQ ID NO: 71 and the heavy chain variable domain comprising the amino acid sequence of SEQ ID NO: 72, (b) comprise the light and heavy CDR amino acid sequences of SEQ ID NO: 2, an amino acid sequence of GKN, SEQ ID NO: 22, SEQ ID NO: 34, SEQ ID NO: 46, and SEQ ID NO: 58, (c) comprise the amino acid sequence of SEQ ID NO: 75 and the heavy chain variable domain comprising the amino acid sequence of SEQ ID NO: 76, (d) comprise the light and heavy CDR amino acid sequences of SEQ ID NO: 1, an amino acid sequence of QNS, SEQ ID NO: 24, SEQ ID NO: 36, SEQ ID NO: 48, and SEQ ID NO: 60, (e) comprise the amino acid sequence of SEQ ID NO: 69 and the heavy chain variable domain comprising the amino acid sequence of SEQ ID NO: 70, (f) comprise the light and heavy CDR amino acid sequences of SEQ ID NO: 1, an amino acid sequence of QDT, SEQ ID NO: 21, SEQ ID NO: 33, SEQ ID NO: 45, and SEQ ID NO: 57, (g) comprise the amino acid sequence of SEQ ID NO: 89 and the heavy chain variable domain comprising the amino acid sequence of SEQ ID NO: 90, and (h) comprise the light and heavy CDR amino acid sequences of SEQ ID NO: 10, an amino acid sequence of DAS, SEQ ID NO: 31, SEQ ID NO: 43, SEQ ID NO: 55, and SEQ ID NO: 67.

In some embodiments, the Protein S antibodies provided herein may be provided in a small volume amenable for injection, such as for subcutaneous administration. In some embodiments, the Protein S antibodies provided herein may be provided in a small volume amenable for injection by use of a pen-like auto-injector device. In some embodiments, the device is a syringe, for example a pre-filled syringe.

In some embodiments provided herein are single-dose vials useful for either subcutaneous or intravenous administration.

Accordingly, a therapeutically effective amount of the Protein S antibodies provided herein may be provided in a small volume for subcutaneous administration to a subject in need thereof. In some embodiments, the Protein S antibodies provided herein may be provided in a large volume amenable for administration by a subcutaneous infusion device, for subcutaneous infusion to a subject in need thereof.

D. Pharmaceutical Compositions

The disclosure also provides pharmaceutical compositions comprising any one of the Protein S antibodies disclosed herein, and optionally a pharmaceutical acceptable excipient or carrier. In some embodiments, the pharmaceutical composition is sterile. The pharmaceutical compositions may be formulated to be compatible with their intended routes of administration. In some embodiments, the pharmaceutical compositions of the disclosure are suitable for administration to a human subject.

E. Diagnostic Antibodies

The antibodies provided herein may also be used for diagnostic purposes. For example, diagnostic antibodies could be used for detecting protein S deficiencies, or for detecting protein S levels in plasma prior to dosing (e.g. as a companion diagnostic).

Accordingly, in some embodiments, a Protein S antibody of the disclosure is conjugated to a label, for example a detectable label, a spin label, a colorimetric label, a radioactive label, an enzymatic label, a fluorescent label, or a magnetic label. The label may be detectable by spectroscopic, photochemical, biochemical, immunochemical, fluorescent, electrical, optical or chemical methods. Useful labels include, but are not limited to, magnetic beads (e.g. DYNABEADS®), fluorescent dyes (e.g., fluorescein isothiocyanate, red, rhodamine, and the like), radiolabels (e.g., 3H, 125I, 35S, 14C, or 32P), enzymes (e.g., LacZ, CAT, horseradish peroxidase, alkaline phosphatase and others, commonly used as detectable enzymes, either as marker gene products or in an ELISA), biotin, avidin, or streptavidin and colorimetric labels such as colloidal gold colored glass or plastic (e.g. polystyrene, polypropylene, latex, etc.) beads, and nanoparticles. In some embodiments, provided herein are substrates to which one or more Protein S antibodies of the disclosure is attached.

Detection may be carried out on any biological sample obtained from a subject. Biological samples include, but are not limited to whole blood, plasma, serum, saliva, urine, feces, synovial fluid, cerebrospinal fluid, bronchial lavage, ascites fluid, bone marrow aspirate, pleural effusion, tissue, cells, a biopsy, interstitial fluid, lymphatic fluid, or fractions thereof derived from a subject. In some embodiments, the biological sample comprises cells and the cells are in culture, in a suspension, on a slide, in intact tissue, or in preparation ready for a FACs analysis.

III. Kits and Articles of Manufacture

The disclosure also provides a kit or article of manufacture comprising any one of the antibodies disclosed herein, or any pharmaceutical composition disclosed herein. In some embodiments, the kits may further include instructional materials for carrying out any of the methods disclosed herein. In some embodiments, the kits may further include sterile containers or vials for holding the antibodies and/or pharmaceutical compositions disclosed herein. In some embodiments, the kits may further include sterile delivery devices for administering the antibodies and/or pharmaceutical compositions disclosed herein. In some embodiments, an article of manufacture comprises any pharmaceutical composition of the disclosure.

IV. Exemplary Enumerated Embodiments

Exemplary enumerated embodiments of the disclosure are as follows.

1. An antibody that binds Protein S, wherein the antibody is an inhibitor of the cofactor activity of Protein S for activated Protein C (APC), an inhibitor of the cofactor activity of Protein S for tissue factor pathway inhibitor (TFPI), or an inhibitor of the cofactor activity of Protein S for both APC and TFPI, and wherein the antibody is human, humanized, or chimeric.

2. An antibody that binds Protein S, wherein the antibody is capable of promoting coagulation and/or modulating a component in the coagulation cascade.

3. The antibody of any one of Enumerated Embodiments 1-2, wherein the antibody is an inhibitor for the cofactor activity of Protein S for APC.

4. The antibody of any one of Enumerated Embodiments 1-2, wherein the antibody is an inhibitor for the cofactor activity of Protein S for TFPI.

5. The antibody of any one of Enumerated Embodiments 1-2, wherein the antibody is an inhibitor for the cofactor activity of Protein S for both APC and TFPI.

6. The antibody of Enumerated Embodiment 3, wherein the capability of the antibody for inhibiting the cofactor activity of Protein S for TFPI is negligible.

7. The antibody of Enumerated Embodiment 4, wherein the capability of the antibody for inhibiting the cofactor activity of Protein S for APC is negligible.

8. The antibody of any one of Enumerated Embodiments 1-7, wherein the antibody binds to the C-terminus of Protein S.

9. The antibody of any one of Enumerated Embodiments 1-7, wherein the antibody binds to the N-terminus of Protein S.

10. The antibody of any one of Enumerated Embodiments 1-9, wherein the antibody binds to a thrombin-sensitive region of the Protein S.

11. The antibody of any one of Enumerated Embodiments 1-9, wherein the antibody binds to an EGF region of the Protein S.

12. The antibody of any one of Enumerated Embodiments 1-9, wherein the antibody binds to an SHBG region of Protein S.

13. The antibody of any one of Enumerated Embodiments 1-12, wherein the antibody is capable of promoting generation of a marker associated with coagulation activity.

14. The antibody of any one of Enumerated Embodiments 1-13, wherein the antibody is capable of promoting thrombin generation.

15. The antibody of any one of Enumerated Embodiments 1-14, wherein the antibody is capable of promoting D-dimer levels.

16. The antibody of any one of Enumerated Embodiments 1-15, wherein the antibody is capable of promoting fibrin generation.

17. The antibody of any one of Enumerated Embodiments 1-16, wherein activity of the antibody is dose-dependent.

18. The antibody of any one of Enumerated Embodiments 1-17, wherein activity of the antibody is measured in vitro.

19. The antibody of any one of Enumerated Embodiments 1-17, wherein activity of the antibody is measured in vivo.

20. The antibody of any one of Enumerated Embodiments 1-19, wherein the binding affinity of the antibody to Protein S is calcium-dependent.

21. The antibody of any one of Enumerated Embodiments 1-19, wherein the binding affinity of the antibody to Protein S is calcium-independent.

22. The antibody of any one of Enumerated Embodiments 1-21, wherein the antibody binds to free Protein S.

23. The antibody of any one of Enumerated Embodiments 1-21, wherein the antibody binds to complexed Protein S.

24. The antibody of Enumerated Embodiment 23, wherein the Protein S is complexed with C4BP.

25. The antibody of Enumerated Embodiment 23, wherein the Protein S is complexed with TFPI.

26. The antibody of any one of Enumerated Embodiments 1-25, wherein the antibody is a monoclonal antibody.

27. The antibody of any one of Enumerated Embodiments 1-26, wherein the antibody is a full-length antibody.

28. The antibody of any one of Enumerated Embodiments 1-26, wherein the antibody is an antibody fragment.

29. The antibody of any one of Enumerated Embodiments 1-28, wherein the antibody is a humanized antibody.

30. The antibody of any of Enumerated Embodiments 1-29, wherein the antibody comprises a Fc domain.

31. The antibody of Enumerated Embodiment 30, wherein the Fc domain is human.

32. The antibody of Enumerated Embodiment 31, wherein the human Fc domain is IgG1, IgG2, IgG3, or IgG4.

33. The antibody of Enumerated Embodiment 32, wherein the Fc domain of the antibody is human IgG4, optionally SEQ ID NO: 218, and comprises at least one amino acid substitution at a position selected from the group consisting of: 215, 221, 222, 228, 234, 235, 236, 239, 240, 241, 243, 244, 245, 247, 250, 252, 254, 256, 262, 263, 264, 265, 266, 267, 268, 269, 270, 292, 296, 297, 298, 299, 300, 305, 313, 324, 325, 326, 327, 328, 329, 330, 332, 333, 334, 345, 396, 428, 430, 433, 434, and 440, or comprises one or more of the substitutions selected from the group consisting of T250Q/M428L, M252Y/S254T/T256E, M428L/N434S, S267E/L328F, N325S/L328F, and H433K/N434F, wherein the position numbers of the amino acid residues are of the EU numbering scheme.

34. The antibody of Enumerated Embodiment 27, wherein the antibody is a human antibody.

35. The antibody of Enumerated Embodiment 27, wherein the antibody is a chimeric antibody.

36. The antibody of any one of Enumerated Embodiments 1-35, wherein the antibody is conjugated.

37. The antibody of Enumerated Embodiment 36, wherein the antibody is conjugated to a label.

38. The antibody of any one of Enumerated Embodiments 1-37, wherein the antibody comprises any one or more of the amino acid sequences of the CDR sequences provided in Tables 1A, 1B, 1C, 2A, 2B, and 2C.

39. The Protein S antibody of any one of Enumerated Embodiments 1-38, wherein the antibody comprises:
(a) any one of the CDR-L1 amino acid sequences of Table 1A;
(b) any one of the CDR-L2 amino acid sequences of Table 1B;
(c) any one of the CDR-L3 amino acid sequences of Table 1C;
(d) any one of the CDR-H1 amino acid sequences of Table 2A;
(e) any one of the CDR-H2 amino acid sequences of Table 2B; and
(f) any one of the CDR-H3 amino acid sequences of Table 2C.

40. The Protein S antibody of any one of Enumerated Embodiments 1-39, wherein the light chain variable domain of the antibody comprises:
(a) a CDR-L1 comprising the amino acid sequence of any one of SEQ ID NOs: 1-6, 9-11, 117, 127, 136, 141, 174, 184, 194, and 204;
(b) a CDR-L2 comprising the amino acid sequence of any one of the following: QDT, GKN, DVS, QNS, DAS, GAS, LGS, STN, KIS, AAS, ATS, KTS, AAS, DDS, QDS, or QDN
; and
(c) a CDR-L3 comprising the amino acid sequence of any one of SEQ ID NOs: 21-27, 30-32, 119, 123, 129, 137, 143, 176, 186, 196, and 206.

41. The Protein S antibody of any one of Enumerated Embodiments 1-40, wherein the heavy chain variable domain of antibody comprises:
   (a) a CDR-H1 comprising the amino acid sequence of any one of SEQ ID NOs: 33-39, 42-44, 120, 124, 130, 138, 144, 179, 189, 199, and 209;
   (b) a CDR-H2 comprising the amino acid sequence of any one of SEQ ID NOs: 45-51, 54-56, 121, 125, 139, 145, 180, 190, 200, and 210; and
   (c) a CDR-H3 comprising the amino acid sequence of any one of SEQ ID NOs: 57-63, 66-68, 122, 126, 131, 140, 146, 181, 191, 201, and 211.

42. The Protein S antibody of any one of Enumerated Embodiments 1-41, wherein the light chain variable domain of the antibody comprises:
   (a) a CDR-L1 comprising the amino acid sequence of SEQ ID NO: 1;
   (b) a CDR-L2 comprising the amino acid sequence of an amino acid sequence of QDT; and
   (c) a CDR-L3 comprising the amino acid sequence of SEQ ID NO: 21.

43. The Protein S antibody of any one of Enumerated Embodiments 1-41, wherein the light chain variable domain of the antibody comprises:
   (a) a CDR-L1 comprising the amino acid sequence of SEQ ID NO: 2;
   (b) a CDR-L2 comprising the amino acid sequence of an amino acid sequence of GKN; and
   (c) a CDR-L3 comprising the amino acid sequence of SEQ ID NO: 22.

44. The Protein S antibody of any one of Enumerated Embodiments 1-41, wherein the light chain variable domain of the antibody comprises:
   (a) a CDR-L1 comprising the amino acid sequence of SEQ ID NO: 3;
   (b) a CDR-L2 comprising the amino acid sequence of an amino acid sequence of DVS; and
   (c) a CDR-L3 comprising the amino acid sequence of SEQ ID NO: 23.

45. The Protein S antibody of any one of Enumerated Embodiments 1-41, wherein the light chain variable domain of the antibody comprises:
   (a) a CDR-L1 comprising the amino acid sequence of SEQ ID NO: 1;
   (b) a CDR-L2 comprising the amino acid sequence of an amino acid sequence of QNS; and
   (c) a CDR-L3 comprising the amino acid sequence of SEQ ID NO: 24.

46. The Protein S antibody of any one of Enumerated Embodiments 1-41, wherein the light chain variable domain of the antibody comprises:
   (a) a CDR-L1 comprising the amino acid sequence of SEQ ID NO: 4;
   (b) a CDR-L2 comprising the amino acid sequence of an amino acid sequence of DAS; and
   (c) a CDR-L3 comprising the amino acid sequence of SEQ ID NO: 25.

47. The Protein S antibody of any one of Enumerated Embodiments 1-41, wherein the light chain variable domain of the antibody comprises:
   (a) a CDR-L1 comprising the amino acid sequence of SEQ ID NO: 5;
   (b) a CDR-L2 comprising the amino acid sequence of an amino acid sequence of GAS; and
   (c) a CDR-L3 comprising the amino acid sequence of SEQ ID NO: 26.

48. The Protein S antibody of any one of Enumerated Embodiments 1-41, wherein the light chain variable domain of the antibody comprises:
   (a) a CDR-L1 comprising the amino acid sequence of SEQ ID NO: 6;
   (b) a CDR-L2 comprising the amino acid sequence of an amino acid sequence of LGS; and
   (c) a CDR-L3 comprising the amino acid sequence of SEQ ID NO: 27.

49. The Protein S antibody of any one of Enumerated Embodiments 1-41, wherein the light chain variable domain of the antibody comprises:
   (a) a CDR-L1 comprising the amino acid sequence of SEQ ID NO: 9;
   (b) a CDR-L2 comprising the amino acid sequence of an amino acid sequence of STN; and
   (c) a CDR-L3 comprising the amino acid sequence of SEQ ID NO: 30.

50. The Protein S antibody of any one of Enumerated Embodiments 1-41, wherein the light chain variable domain of the antibody comprises:
   (a) a CDR-L1 comprising the amino acid sequence of SEQ ID NO: 10;
   (b) a CDR-L2 comprising the amino acid sequence of an amino acid sequence of DAS; and
   (c) a CDR-L3 comprising the amino acid sequence of SEQ ID NO: 31.

51. The Protein S antibody of any one of Enumerated Embodiments 1-41, wherein the light chain variable domain of the antibody comprises:
   (a) a CDR-L1 comprising the amino acid sequence of SEQ ID NO: 11;
   (b) a CDR-L2 comprising the amino acid sequence of an amino acid sequence of KIS; and
   (c) a CDR-L3 comprising the amino acid sequence of SEQ ID NO: 32.

52. The Protein S antibody of any one of Enumerated Embodiments 1-41, wherein the light chain variable domain of the antibody comprises:
   (a) a CDR-L1 comprising the amino acid sequence of SEQ ID NO: 117;
   (b) a CDR-L2 comprising the amino acid sequence of an amino acid sequence of AAS; and
   (c) a CDR-L3 comprising the amino acid sequence of SEQ ID NO: 119.

53. The Protein S antibody of any one of Enumerated Embodiments 1-41, wherein the light chain variable domain of the antibody comprises:
   (a) a CDR-L1 comprising the amino acid sequence of SEQ ID NO: 117;
   (b) a CDR-L2 comprising the amino acid sequence of an amino acid sequence of AAS; and
   (c) a CDR-L3 comprising the amino acid sequence of SEQ ID NO: 123.

54. The Protein S antibody of any one of Enumerated Embodiments 1-41, wherein the light chain variable domain of the antibody comprises:
   (a) a CDR-L1 comprising the amino acid sequence of SEQ ID NO: 127;
   (b) a CDR-L2 comprising the amino acid sequence of an amino acid sequence of ATS; and
   (c) a CDR-L3 comprising the amino acid sequence of SEQ ID NO: 129.

55. The Protein S antibody of any one of Enumerated Embodiments 1-41, wherein the light chain variable domain of the antibody comprises:
   (a) a CDR-L1 comprising the amino acid sequence of SEQ ID NO: 136;
   (b) a CDR-L2 comprising the amino acid sequence of an amino acid sequence of GAS; and
   (c) a CDR-L3 comprising the amino acid sequence of SEQ ID NO: 137.

56. The Protein S antibody of any one of Enumerated Embodiments 1-41, wherein the light chain variable domain of the antibody comprises:
   (a) a CDR-L1 comprising the amino acid sequence of SEQ ID NO: 141;
   (b) a CDR-L2 comprising the amino acid sequence of an amino acid sequence of KTS; and
   (c) a CDR-L3 comprising the amino acid sequence of SEQ ID NO: 143.

57. The Protein S antibody of any one of Enumerated Embodiments 1-41, wherein the light chain variable domain of the antibody comprises:
   (a) a CDR-L1 comprising the amino acid sequence of SEQ ID NO: 174;
   (b) a CDR-L2 comprising the amino acid sequence of an amino acid sequence of AAS; and
   (c) a CDR-L3 comprising the amino acid sequence of SEQ ID NO: 176.

58. The Protein S antibody of any one of Enumerated Embodiments 1-41, wherein the light chain variable domain of the antibody comprises:
   (a) a CDR-L1 comprising the amino acid sequence of SEQ ID NO: 184;
   (b) a CDR-L2 comprising the amino acid sequence of an amino acid sequence of DDS; and
   (c) a CDR-L3 comprising the amino acid sequence of SEQ ID NO: 186.

59. The Protein S antibody of any one of Enumerated Embodiments 1-41, wherein the light chain variable domain of the antibody comprises:
   (a) a CDR-L1 comprising the amino acid sequence of SEQ ID NO: 194;
   (b) a CDR-L2 comprising the amino acid sequence of an amino acid sequence of QDS; and
   (c) a CDR-L3 comprising the amino acid sequence of SEQ ID NO: 196.

60. The Protein S antibody of any one of Enumerated Embodiments 1-41, wherein the light chain variable domain of the antibody comprises:
   (a) a CDR-L1 comprising the amino acid sequence of SEQ ID NO: 204;
   (b) a CDR-L2 comprising the amino acid sequence of an amino acid sequence of QDN; and
   (c) a CDR-L3 comprising the amino acid sequence of SEQ ID NO: 206.

61. The Protein S antibody of any one of Enumerated Embodiments 1-60, wherein the heavy chain variable domain of the antibody comprises:
   (a) a CDR-H1 comprising the amino acid sequence of SEQ ID NO: 33;
   (b) a CDR-H2 comprising the amino acid sequence of SEQ ID NO: 45; and
   (c) a CDR-H3 comprising the amino acid sequence of SEQ ID NO: 57.

62. The Protein S antibody of any one of Enumerated Embodiments 1-60, wherein the heavy chain variable domain of the antibody comprises:
   (a) a CDR-H1 comprising the amino acid sequence of SEQ ID NO: 34;
   (b) a CDR-H2 comprising the amino acid sequence of SEQ ID NO: 46; and
   (c) a CDR-H3 comprising the amino acid sequence of SEQ ID NO: 58.

63. The Protein S antibody of any one of Enumerated Embodiments 1-60, wherein the heavy chain variable domain of the antibody comprises:
   (a) a CDR-H1 comprising the amino acid sequence of SEQ ID NO: 35;
   (b) a CDR-H2 comprising the amino acid sequence of SEQ ID NO: 47; and
   (c) a CDR-H3 comprising the amino acid sequence of SEQ ID NO: 59.

64. The Protein S antibody of any one of Enumerated Embodiments 1-60, wherein the heavy chain variable domain of the antibody comprises:
   (a) a CDR-H1 comprising the amino acid sequence of SEQ ID NO: 36;
   (b) a CDR-H2 comprising the amino acid sequence of SEQ ID NO: 48; and
   (c) a CDR-H3 comprising the amino acid sequence of SEQ ID NO: 60.

65. The Protein S antibody of any one of Enumerated Embodiments 1-60, wherein the heavy chain variable domain of the antibody comprises:
   (a) a CDR-H1 comprising the amino acid sequence of SEQ ID NO: 37;
   (b) a CDR-H2 comprising the amino acid sequence of SEQ ID NO: 49; and
   (c) a CDR-H3 comprising the amino acid sequence of SEQ ID NO: 61.

66. The Protein S antibody of any one of Enumerated Embodiments 1-60, wherein the heavy chain variable domain of the antibody comprises:
   (a) a CDR-H1 comprising the amino acid sequence of SEQ ID NO: 38;
   (b) a CDR-H2 comprising the amino acid sequence of SEQ ID NO: 50; and
   (c) a CDR-H3 comprising the amino acid sequence of SEQ ID NO: 62.

67. The Protein S antibody of any one of Enumerated Embodiments 1-60, wherein the heavy chain variable domain of the antibody comprises:
   (a) a CDR-H1 comprising the amino acid sequence of SEQ ID NO: 39;
   (b) a CDR-H2 comprising the amino acid sequence of SEQ ID NO: 51; and
   (c) a CDR-H3 comprising the amino acid sequence of SEQ ID NO: 63.

68. The Protein S antibody of any one of Enumerated Embodiments 1-60, wherein the heavy chain variable domain of the antibody comprises:
   (a) a CDR-H1 comprising the amino acid sequence of SEQ ID NO: 42;
   (b) a CDR-H2 comprising the amino acid sequence of SEQ ID NO: 54; and
   (c) a CDR-H3 comprising the amino acid sequence of SEQ ID NO: 66.

69. The Protein S antibody of any one of Enumerated Embodiments 1-60, wherein the heavy chain variable domain of the antibody comprises:
   (a) a CDR-H1 comprising the amino acid sequence of SEQ ID NO: 43;
   (b) a CDR-H2 comprising the amino acid sequence of SEQ ID NO: 55; and (c) a CDR-H3 comprising the amino acid sequence of SEQ ID NO: 67.

70. The Protein S antibody of any one of Enumerated Embodiments 1-60, wherein the heavy chain variable domain of the antibody comprises:
(a) a CDR-H1 comprising the amino acid sequence of SEQ ID NO: 44;
(b) a CDR-H2 comprising the amino acid sequence of SEQ ID NO: 56; and
(c) a CDR-H3 comprising the amino acid sequence of SEQ ID NO: 68.

71. The Protein S antibody of any one of Enumerated Embodiments 1-60, wherein the heavy chain variable domain of the antibody comprises:
(a) a CDR-H1 comprising the amino acid sequence of SEQ ID NO: 120;
(b) a CDR-H2 comprising the amino acid sequence of SEQ ID NO: 121; and
(c) a CDR-H3 comprising the amino acid sequence of SEQ ID NO: 122.

72. The Protein S antibody of any one of Enumerated Embodiments 1-60, wherein the heavy chain variable domain of the antibody comprises:
(a) a CDR-H1 comprising the amino acid sequence of SEQ ID NO: 124;
(b) a CDR-H2 comprising the amino acid sequence of SEQ ID NO: 125; and
(c) a CDR-H3 comprising the amino acid sequence of SEQ ID NO: 126.

73. The Protein S antibody of any one of Enumerated Embodiments 1-60, wherein the heavy chain variable domain of the antibody comprises:
(a) a CDR-H1 comprising the amino acid sequence of SEQ ID NO: 130;
(b) a CDR-H2 comprising the amino acid sequence of SEQ ID NO: 50; and
(c) a CDR-H3 comprising the amino acid sequence of SEQ ID NO: 131.

74. The Protein S antibody of any one of Enumerated Embodiments 1-60, wherein the heavy chain variable domain of the antibody comprises:
(a) a CDR-H1 comprising the amino acid sequence of SEQ ID NO: 138;
(b) a CDR-H2 comprising the amino acid sequence of SEQ ID NO: 139; and
(c) a CDR-H3 comprising the amino acid sequence of SEQ ID NO: 140.

75. The Protein S antibody of any one of Enumerated Embodiments 1-60, wherein the heavy chain variable domain of the antibody comprises:
(a) a CDR-H1 comprising the amino acid sequence of SEQ ID NO: 144;
(b) a CDR-H2 comprising the amino acid sequence of SEQ ID NO: 145; and
(c) a CDR-H3 comprising the amino acid sequence of SEQ ID NO: 146.

76. The Protein S antibody of any one of Enumerated Embodiments 1-60, wherein the heavy chain variable domain of the antibody comprises:
(a) a CDR-H1 comprising the amino acid sequence of SEQ ID NO: 179;
(b) a CDR-H2 comprising the amino acid sequence of SEQ ID NO: 180; and
(c) a CDR-H3 comprising the amino acid sequence of SEQ ID NO: 181.

77. The Protein S antibody of any one of Enumerated Embodiments 1-60, wherein the heavy chain variable domain of the antibody comprises:
(a) a CDR-H1 comprising the amino acid sequence of SEQ ID NO: 189;
(b) a CDR-H2 comprising the amino acid sequence of SEQ ID NO: 190; and
(c) a CDR-H3 comprising the amino acid sequence of SEQ ID NO: 191.

78. The Protein S antibody of any one of Enumerated Embodiments 1-60, wherein the heavy chain variable domain of the antibody comprises:
(a) a CDR-H1 comprising the amino acid sequence of SEQ ID NO: 199;
(b) a CDR-H2 comprising the amino acid sequence of SEQ ID NO: 200; and
(c) a CDR-H3 comprising the amino acid sequence of SEQ ID NO: 201.

79. The Protein S antibody of any one of Enumerated Embodiments 1-60, wherein the heavy chain variable domain of the antibody comprises:
(a) a CDR-H1 comprising the amino acid sequence of SEQ ID NO: 209;
(b) a CDR-H2 comprising the amino acid sequence of SEQ ID NO: 210; and
(c) a CDR-H3 comprising the amino acid sequence of SEQ ID NO: 211.

80. The Protein S antibody of any one of Enumerated Embodiments 1-41, wherein the antibody comprises the light and heavy CDR amino acid sequences of SEQ ID NO: 1, an amino acid sequence of QDT, SEQ ID NO: 21, SEQ ID NO: 33, SEQ ID NO: 45, and SEQ ID NO: 57.

81. The Protein S antibody of any one of Enumerated Embodiments 1-41, wherein the antibody comprises the light and heavy CDR amino acid sequences of SEQ ID NO: 2, an amino acid sequence of GKN, SEQ ID NO: 22, SEQ ID NO: 34, SEQ ID NO: 46, and SEQ ID NO: 58.

82. The Protein S antibody of any one of Enumerated Embodiments 1-41, wherein the antibody comprises the light and heavy CDR amino acid sequences of SEQ ID NO: 3, an amino acid sequence of DVS, SEQ ID NO: 23, SEQ ID NO: 35, SEQ ID NO: 47, and SEQ ID NO: 59.

83. The Protein S antibody of any one of Enumerated Embodiments 1-41, wherein the antibody comprises the light and heavy CDR amino acid sequences of SEQ ID NO: 1, an amino acid sequence of QNS, SEQ ID NO: 24, SEQ ID NO: 36, SEQ ID NO: 48, and SEQ ID NO: 60.

84. The Protein S antibody of any one of Enumerated Embodiments 1-41, wherein the antibody comprises the light and heavy amino acid sequences of SEQ ID NO: 4, an amino acid sequence of DAS, SEQ ID NO: 25, SEQ ID NO: 37, SEQ ID NO: 49, and SEQ ID NO: 61.

85. The Protein S antibody of any one of Enumerated Embodiments 1-41, wherein the antibody comprises the light and heavy CDR amino acid sequences of SEQ ID NO: 5, an amino acid sequence of GAS, SEQ ID NO: 26, SEQ ID NO: 38, SEQ ID NO: 50, and SEQ ID NO: 62.

86. The Protein S antibody of any one of Enumerated Embodiments 1-41, wherein the antibody comprises the light and heavy CDR amino acid sequences of SEQ ID NO: 6, an amino acid sequence of LGS, SEQ ID NO: 27, SEQ ID NO: 39, SEQ ID NO: 51, and SEQ ID NO: 63.

87. The Protein S antibody of any one of Enumerated Embodiments 1-41, wherein the antibody comprises the light and heavy CDR amino acid sequences of SEQ ID NO: 9, an amino acid sequence of STN, SEQ ID NO: 30, SEQ ID NO: 42, SEQ ID NO: 54, and SEQ ID NO: 66.

88. The Protein S antibody of any one of Enumerated Embodiments 1-41, wherein the antibody comprises the light and heavy CDR amino acid sequences of SEQ ID NO: 10, an amino acid sequence of DAS, SEQ ID NO: 31, SEQ ID NO: 43, SEQ ID NO: 55, and SEQ ID NO: 67.

89. The Protein S antibody of any one of Enumerated Embodiments 1-41, wherein the antibody comprises the light and heavy CDR amino acid sequences of SEQ ID NO: 11, an amino acid sequence of KIS, SEQ ID NO: 32, SEQ ID NO: 44, SEQ ID NO: 56, and SEQ ID NO: 68.

90. The Protein S antibody of any one of Enumerated Embodiments 1-41, wherein the antibody comprises the light and heavy CDR amino acid sequences of SEQ ID NO: 117, an amino acid sequence of AAS, SEQ ID NO: 119, SEQ ID NO: 120, SEQ ID NO: 121, and SEQ ID NO: 122.

91. The Protein S antibody of any one of Enumerated Embodiments 1-41, wherein the antibody comprises the light and heavy CDR amino acid sequences of SEQ ID NO: 117, an amino acid sequence of AAS, SEQ ID NO: 123, SEQ ID NO: 124, SEQ ID NO: 125, and SEQ ID NO: 126.

92. The Protein S antibody of any one of Enumerated Embodiments 1-41, wherein the antibody comprises the light and heavy CDR amino acid sequences of SEQ ID NO: 127, an amino acid sequence of ATS, SEQ ID NO: 129, SEQ ID NO: 130, SEQ ID NO: 50, and SEQ ID NO: 131.

93. The Protein S antibody of any one of Enumerated Embodiments 1-41, wherein the antibody comprises the light and heavy CDR amino acid sequences of SEQ ID NO: 136, an amino acid sequence of GAS, SEQ ID NO: 137, SEQ ID NO: 138, SEQ ID NO: 139, and SEQ ID NO: 140.

94. The Protein S antibody of any one of Enumerated Embodiments 1-41, wherein the antibody comprises the light and heavy CDR amino acid sequences of SEQ ID NO: 141, an amino acid sequence of KTS, SEQ ID NO: 143, SEQ ID NO: 144, SEQ ID NO: 145, and SEQ ID NO: 146.

95. The Protein S antibody of any one of Enumerated Embodiments 1-41, wherein the antibody comprises the light and heavy CDR amino acid sequences of SEQ ID NO: 174, an amino acid sequence of AAS, SEQ ID NO: 176, SEQ ID NO: 179, SEQ ID NO: 180, and SEQ ID NO: 181.

96. The Protein S antibody of any one of Enumerated Embodiments 1-41, wherein the antibody comprises the light and heavy CDR amino acid sequences of SEQ ID NO: 184, an amino acid sequence of DDS, SEQ ID NO: 186, SEQ ID NO: 189, SEQ ID NO: 190, and SEQ ID NO: 191.

97. The Protein S antibody of any one of Enumerated Embodiments 1-41, wherein the antibody comprises the light and heavy CDR amino acid sequences of SEQ ID NO: 194, an amino acid sequence of QDS, SEQ ID NO: 196, SEQ ID NO: 199, SEQ ID NO: 200, and SEQ ID NO: 201.

98. The Protein S antibody of any one of Enumerated Embodiments 1-41, wherein the antibody comprises the light and heavy CDR amino acid sequences of SEQ ID NO: 204, an amino acid sequence of QDN, SEQ ID NO: 206, SEQ ID NO: 209, SEQ ID NO: 210, and SEQ ID NO: 211.

99. The Protein S antibody of any one of Enumerated Embodiments 1-98, wherein the antibody comprises the variable chain amino acid sequence of any one of the amino acid sequences provided in Table 4A, and/or the variable chain amino acid sequence of any one of the amino acid sequences provided in Table 4B.

100. The Protein S antibody of any one of Enumerated Embodiments 1-99, wherein the antibody comprises the light and heavy variable chain amino acid sequence of any one of the amino acid sequence combinations provided in Table 4C.

101. The Protein S antibody of any one of Enumerated Embodiments 1-100, wherein the light chain variable domain of the antibody comprises the amino acid sequence of SEQ ID NO: 69 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and wherein the heavy chain variable domain of the antibody comprises the amino acid sequence of SEQ ID NO: 70, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

102. The Protein S antibody of one of Enumerated Embodiments 1-100, wherein the light chain variable domain of the antibody comprises the amino acid sequence of SEQ ID NO: 71 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 72, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

103. The Protein S antibody of any one of Enumerated Embodiments 1-100, wherein the light chain variable domain of the antibody comprises the amino acid sequence of SEQ ID NO: 73 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 74, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

104. The Protein S antibody of any one of Enumerated Embodiments 1-100, wherein the light chain variable domain of the antibody comprises the amino acid sequence of SEQ ID NO: 75 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 76, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

105. The Protein S antibody of any one of Enumerated Embodiments 1-100, wherein the light chain variable domain of the antibody comprises the amino acid sequence of SEQ ID NO: 77 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 78, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

106. The Protein S antibody of any one of Enumerated Embodiments 1-100, wherein the light chain variable domain of the antibody comprises the amino acid sequence of SEQ ID NO: 79 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 80, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

107. The Protein S antibody of any one of Enumerated Embodiments 1-100, wherein the light chain variable domain of the antibody comprises the amino acid sequence of SEQ ID NO: 81 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 82, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

108. The Protein S antibody of any one of Enumerated Embodiments 1-100, wherein the light chain variable domain of the antibody comprises the amino acid sequence of SEQ ID NO: 87 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 88, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

109. The Protein S antibody of any one of Enumerated Embodiments 1-100, wherein the light chain variable domain of the antibody comprises In some embodiments, provided herein are Protein S antibodies, wherein the light chain variable domain of the antibodies comprise the amino acid sequence of SEQ ID NO: 89 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 90, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

110. The Protein S antibody of any one of Enumerated Embodiments 1-100, wherein the light chain variable domain of the antibody comprises the amino acid sequence of SEQ ID NO: 91 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 92, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

111. The Protein S antibody of any one of Enumerated Embodiments 1-100, wherein the light chain variable domain of the antibody comprises the amino acid sequence of SEQ ID NO: 148 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 149, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

112. The Protein S antibody of any one of Enumerated Embodiments 1-100, wherein the light chain variable domain of the antibody comprises the amino acid sequence of SEQ ID NO: 150 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 151, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

113. The Protein S antibody of any one of Enumerated Embodiments 1-100, wherein the light chain variable domain of the antibody comprises the amino acid sequence of SEQ ID NO: 152 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 153, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

114. The Protein S antibody of any one of Enumerated Embodiments 1-100, wherein the light chain variable domain of the antibody comprises the amino acid sequence of SEQ ID NO: 156 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 157, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

115. The Protein S antibody of any one of Enumerated Embodiments 1-100, wherein the light chain variable domain of the antibody comprises the amino acid sequence of SEQ ID NO: 158 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 159, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

116. The Protein S antibody of any one of Enumerated Embodiments 1-100, wherein the light chain variable domain of the antibody comprises the amino acid sequence of SEQ ID NO: 177 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 182, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

117. The Protein S antibody of any one of Enumerated Embodiments 1-100, wherein the light chain variable domain of the antibody comprises the amino acid sequence of SEQ ID NO: 187 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 192, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

118. The Protein S antibody of any one of Enumerated Embodiments 1-41, wherein the light chain variable domain of the antibody comprises the amino acid sequence of SEQ ID NO: 197 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 202, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

119. The Protein S antibody of any one of Enumerated Embodiments 1-100, wherein the light chain variable domain of the antibody comprises the amino acid sequence of SEQ ID NO: 207 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody comprises the amino acid sequence of SEQ ID NO: 212, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

120. The Protein S antibody of any one of Enumerated Embodiments 1-119, wherein the light chain comprises the amino acid sequence of SEQ ID NO: 214.

121. The Protein S antibody of any one of Enumerated Embodiments 1-119, wherein the light chain comprises the amino acid sequence of SEQ ID NO: 215.

122. A pharmaceutical composition comprising any one of the antibodies of Enumerated Embodiments 1-121, and optionally a pharmaceutically acceptable excipient.

123. A complex comprising Protein S and the antibody of any one of Enumerated Embodiments 1-119, wherein the antibody is bound to the Protein S, and the Protein S is free.

124. A complex comprising Protein S and the antibody of any one of Enumerated Embodiments 1-119, wherein the antibody is bound to the Protein S, and the Protein S is complexed.

125. The complex of Enumerated Embodiment 124, wherein the Protein S is bound to C4BP.

126. The complex of Enumerated Embodiment 124, wherein the Protein S is bound to TFPI.

127. A nucleic acid encoding for any one of the antibodies of Enumerated Embodiments 1-121.

128. The nucleic acid of Enumerated Embodiment 127, comprising any one of the nucleic acid sequences selected from Table 5A.

129. The nucleic acid of any one of Enumerated Embodiments 127-128, comprising any one of the nucleic acid sequences selected from Table 5B.

130. The nucleic acid of any one of Enumerated Embodiments 127-129, wherein the nucleic acid comprises the nucleic acid sequence of any one of the nucleic acid sequence combinations provided in Table 5C.

131. The nucleic acid of any one of Enumerated Embodiments 127-130, wherein the light chain variable domain of the Protein S antibody is encoded by the nucleic acid sequence of SEQ ID NO: 93 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 94, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

132. The nucleic acid of any one of Enumerated Embodiments 127-130, wherein the light chain variable domain of the Protein S antibody is encoded by the nucleic acid sequence of SEQ ID NO: 95 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 96, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

133. The nucleic acid of any one of Enumerated Embodiments 127-130, wherein the light chain variable domain of the Protein S antibody is encoded by the nucleic acid sequence of SEQ ID NO: 97 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 98, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

134. The nucleic acid of any one of Enumerated Embodiments 127-130, wherein the light chain variable domain of the Protein S antibody is encoded by the nucleic acid sequence of SEQ ID NO: 99 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 100, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

135. The nucleic acid of any one of Enumerated Embodiments 127-130, wherein the light chain variable domain of the Protein S antibody is encoded by the nucleic acid sequence of SEQ ID NO: 101 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 102, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

136. The nucleic acid of any one of Enumerated Embodiments 127-130, wherein the light chain variable domain of the Protein S antibody is encoded by the nucleic acid sequence of SEQ ID NO: 103 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 104, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

137. The nucleic acid of any one of Enumerated Embodiments 127-130, wherein the light chain variable domain of the Protein S antibody is encoded by the nucleic acid sequence of SEQ ID NO: 105 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 106, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

138. The nucleic acid of any one of Enumerated Embodiments 127-130, wherein the light chain variable domain of the Protein S antibody is encoded by the nucleic acid sequence of SEQ ID NO: 111 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 112, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

139. The nucleic acid of any one of Enumerated Embodiments 127-130, wherein the light chain variable domain of the Protein S antibody is encoded by the nucleic acid sequence of SEQ ID NO: 113 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 114, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

140. The nucleic acid of any one of Enumerated Embodiments 127-130, wherein the light chain variable domain of the Protein S antibody is encoded by the nucleic acid sequence of SEQ ID NO: 115 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 116, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

141. The nucleic acid of any one of Enumerated Embodiments 127-130, wherein the light chain variable domain of the Protein S antibody is encoded by the nucleic acid sequence of SEQ ID NO: 162 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 163, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

142. The nucleic acid of any one of Enumerated Embodiments 127-130, wherein the light chain variable domain of the Protein S antibody is encoded by the nucleic acid sequence of SEQ ID NO: 164 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 165, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

143. The nucleic acid of any one of Enumerated Embodiments 127-130, wherein the light chain variable domain of the Protein S antibody is encoded by the nucleic acid sequence of SEQ ID NO: 166 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 167, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

144. The nucleic acid of any one of Enumerated Embodiments 127-130, wherein the light chain variable domain of the Protein S antibody is encoded by the nucleic acid sequence of SEQ ID NO: 170 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 171, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

145. The nucleic acid of any one of Enumerated Embodiments 127-130, wherein the light chain variable domain of the Protein S antibody is encoded by the nucleic acid sequence of SEQ ID NO: 172 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 173, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

146. The nucleic acid of any one of Enumerated Embodiments 127-130, wherein the light chain variable domain of the Protein S antibody is encoded by the nucleic acid sequence of SEQ ID NO: 178 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 183, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

147. The nucleic acid of any one of Enumerated Embodiments 127-130, wherein the light chain variable domain of the Protein S antibody is encoded by the nucleic acid sequence of SEQ ID NO: 188 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 193, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

148. The nucleic acid of any one of Enumerated Embodiments 127-130, wherein the light chain variable domain of the Protein S antibody is encoded by the nucleic acid sequence of SEQ ID NO: 198 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 203, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

149. The nucleic acid of any one of Enumerated Embodiments 127-130, wherein the light chain variable domain of the Protein S antibody is encoded by the nucleic acid sequence of SEQ ID NO: 208 or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the heavy chain variable domain of the antibody is encoded by the nucleic acid sequence of SEQ ID NO: 213, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto.

150. A vector comprising the nucleic acid of any one of Enumerated Embodiments 127-149.

151. An in vitro method of promoting the coagulation of blood, comprising contacting the antibody of any one of Enumerated Embodiments 1-121 with a blood sample.

152. The method of Enumerated Embodiment 151, wherein the blood sample comprises plasma.

153. The method of any one of Enumerated Embodiments 151-152, wherein a marker associated with coagulation activity is increased.

154. The method of any one of Enumerated Embodiments 151-153, wherein thrombin generation is promoted.

155. The method of any one of Enumerated Embodiments 151-154, wherein fibrin generation is promoted.

156. The method of any one of Enumerated Embodiments 151-155, wherein D-dimer levels are promoted.

157. The method of any one of Enumerated Embodiments 151-156, wherein the blood sample is obtained from a subject having a coagulation factor deficiency, von Willebrand disease, or a platelet disorder.

158. A method of promoting the coagulation of blood in a subject in need thereof, comprising administering to the subject the antibody of any one of Enumerated Embodiments 1-121 or the pharmaceutical composition of Enumerated Embodiment 122.

159. The method of Enumerated Embodiment 158, wherein a marker associated with coagulation activity is increased.

160. The method of any of Enumerated Embodiments 158-159, wherein thrombin generation is promoted in the subject.

161. The method of any of Enumerated Embodiments 158-160, wherein fibrin generation is promoted in the subject.

162. The method of any of Enumerated Embodiments 153-161, wherein D-dimer levels are increased in the subject.

163. The method of any of Enumerated Embodiments 153-162, wherein the antibody remains active in the subject for a period of time.

164. method of any of Enumerated Embodiments 151-163, wherein activity of the antibody is dose-dependent.

165. A method of promoting the generation of thrombin in a subject in need thereof, comprising administering to the subject the antibody of any one of Enumerated Embodiments 1-121 or the pharmaceutical composition of Enumerated Embodiment 122.

166. The method of Enumerated Embodiment 165, wherein the subject has a coagulation factor deficiency, von Willebrand disease, or a platelet disorder, and the antibody restores or promotes the generation of thrombin.

167. A method of treating a condition in a subject in need thereof, comprising administering to the subject the antibody of Enumerated Embodiments 1-121 or the pharmaceutical composition of Enumerated Embodiment 122, wherein the condition is selected from the group consisting of: bleeding disorders, platelet disorders, trauma, and bleeding resulting from a surgery or a medical procedure.

168. The method of Enumerated Embodiment 167, wherein the method of treating is prophylactic.

169. The method of Enumerated Embodiment 167, wherein the method of treating is on-demand.

170. The method of any one of Enumerated Embodiments 167-169, wherein the method is prophylactic and on-demand.

171. The method of any one of Enumerated Embodiments 168 or 170, wherein the prophylactic method of treating is a routine prophylaxis.

172. The method of any one of Enumerated Embodiments 167-171, wherein the administration of the antibody of any one of Enumerated Embodiments 1-119 is a subcutaneous administration.

173. The method of any one of Enumerated Embodiments 158-172, wherein the method of treating is acute.

174. The method of any one of Enumerated Embodiments 158-172, wherein the method of treating is chronic.

175. The method of any one of Enumerated Embodiments 158-172, wherein the method of treating is perioperative.

176. The method of any one of Enumerated Embodiments 158-172, wherein the method of treating is intermittent.

177. The method of any one of Enumerated Embodiments 158-176, wherein the antibody exhibits graded inhibition.

178. The method of any one of Enumerated Embodiments 158-176, wherein the antibody exhibits switch-like inhibition.

179. The method of any one of Enumerated Embodiments 167-178, wherein the subject suffers from two or more conditions selected from the group consisting of: bleeding disorders, platelet disorders, trauma, and bleeding resulting from a surgery or a medical procedure.

180. The method of any one of Enumerated Embodiments 165-179, wherein the subject suffers from a bleeding disorder selected from the group consisting of: hemophilia A, hemophilia B, von Willebrand disease (vWD) disease, menorrhagia, Factor I deficiency, Factor II deficiency, Factor V deficiency, Factor VII deficiency, Factor X deficiency, Factor XI deficiency, Factor VIII deficiency (hemophilia A), Factor IX deficiency (hemophilia B), trauma, and hereditary hemorrhagic telangiectasia.

181. The method of any one of Enumerated Embodiments 158-180, wherein the subject is a hemophilia carrier.

182. The method of any one of Enumerated Embodiments 165-181, wherein the subject suffers from menorrhagia.

183. The method of any one of Enumerated Embodiments 158-182, wherein the subject suffers from menorrhagia associated with one or more of the bleeding disorders or the platelet disorders.

184. The method of Enumerated Embodiment 180, wherein the bleeding disorder is vWD, and wherein the subject is undergoing a prophylactic treatment.

185. The method of Enumerated Embodiment 180, wherein the bleeding disorder is vWD, and the vWD is a subtype selected from: vWD Type 1, vWD Type 2A, vWD Type 2B, vWD Type 2N, vWD Type 2M, vWD Type 3, and acquired vWD.

186. The method of any one of Enumerated Embodiments 167-185, wherein the condition is a platelet disorder selected from the group consisting of: Bernard-Soulier syndrome, Glanzmann's thrombasthenia, and platelet storage pool deficiency.

187. The method of Enumerated Embodiment 186, wherein the platelet disorder is a platelet storage pool deficiency selected from the group consisting of: Gray platelet syndrome, Quebec platelet disorder, and MYH9-related thrombocytopenia (MYH9RD).

188. The method of Enumerated Embodiment 180, wherein the bleeding disorder is selected from Factor I deficiency, Factor II deficiency, Factor V deficiency, Factor VII deficiency, Factor X deficiency, Factor XI deficiency, Factor VIII deficiency (hemophilia A), Factor IX deficiency (hemophilia B), and vWD disease, and wherein the subject has inhibitors.

189. The method of any one of Enumerated Embodiments 167-188, wherein the antibody or the pharmaceutical composition is capable of promoting thrombin generation in the subject.

190. The method of any one of Enumerated Embodiments 165-166, wherein the thrombin generation does not exceed a predetermined threshold level.

191. The method of any one of Enumerated Embodiments 165-166 and 190, wherein the thrombin generation is antibody concentration-dependent.

193. A kit or article of manufacture comprising an antibody of any one of Enumerated Embodiments 1-121 or the pharmaceutical composition of Enumerated Embodiment 122.

193. Use of the antibody of any one of Enumerated Embodiments 1-121 or the pharmaceutical composition of Enumerated Embodiment 122 for the treatment of a condition in a subject in need thereof.

194. Use of the antibody of any one of Enumerated Embodiments 1-121 or the pharmaceutical composition of Enumerated Embodiment 122 for the manufacture of a medicament for the treatment of a condition in a subject in need thereof.

The present invention is not limited in scope by the specific embodiments described herein, which are intended as illustrations of individual aspects or embodiments of the invention. Functionally equivalent methods and components are within the scope of the invention. Various modifications of the invention, in addition to those described here, are apparent to those skilled in the art from the foregoing description and accompanying drawings. Such modifications fall within the scope of the invention.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the antibodies of the present invention and practice the claimed methods. The following examples therefore, specifically point out the preferred embodiments of the present invention, and are not to be construed as limiting in any way the remainder of the disclosure.

EXAMPLES

Example 1: Generation of Protein S Antibodies

The Protein S antibodies of the disclosure were generated as follows. Animals (e.g., mice, rats) were immunized with a full-length purified human plasma Protein S. Three immunization campaigns were carried out and standard techniques were used to generate hybridoma libraries from the animals. Flow cytometry and single cell sorting was used to generate single cell clones. Supernatants from these single clones were then screened for binding to both human and cynomolgus monkey Protein S. Clones that exhibited binding to both human and cynomolgus monkey Protein S were selected for expanded growth. The expanded cultures were then purified over Protein G or Protein A Sepharose using standard techniques. These purified antibody preparations were used in subsequent functional assays. The selected Protein S antibodies had a human or mouse variable region and a rat Fc domain, or a mouse Fc domain.

Antibodies having a human variable region and a rat or mouse Fc domain were made into fully human antibodies maintaining the human variable domain as the parent antibody, but with a human IgG4 Fc domain. Table 6 below lists the Antibody number used to designate the human antibodies in the first column and the corresponding parental rodent antibodies (with the human variable region) in the second column. The second column also includes a single antibody with a mouse variable domain and a mouse Fc domain. The subsequent columns provide the variable light chain/variable heavy chain amino acid sequences and nucleic acid sequences, and the last column provides the amino acid sequences of the set of six CDRs that map to each Antibody.

TABLE 6

| Human Antibody: Protein S Antibody with Human Fc | Rat Antibody: Protein S Antibody with Rat Fc | Variable Light Chain, Variable Heavy Chain (Amino Acid Sequences) | Variable Light Chain, Variable Heavy Chain (Nucleic Acid Sequences) | CDR Combination (Amino Acid Sequences) |
|---|---|---|---|---|
| Antibody 1 | Antibody 13 | SEQ ID NO: 71, SEQ ID NO: 72 | SEQ ID NO: 95, SEQ ID NO: 96 | SEQ ID NO: 2, SEQ ID NO: 13, SEQ ID NO: 22, SEQ ID NO: 34, SEQ ID NO: 46, SEQ ID NO: 58 |
| Antibody 2 | Antibody 14 | SEQ ID NO: 73, SEQ ID NO: 74 | SEQ ID NO: 97, SEQ ID NO: 98 | SEQ ID NO: 3, SEQ ID NO: 14, SEQ ID NO: 23, |

TABLE 6-continued

| Human Antibody: Protein S Antibody with Human Fc | Rat Antibody: Protein S Antibody with Rat Fc | Variable Light Chain, Variable Heavy Chain (Amino Acid Sequences) | Variable Light Chain, Variable Heavy Chain (Nucleic Acid Sequences) | CDR Combination (Amino Acid Sequences) |
|---|---|---|---|---|
| | | | | SEQ ID NO: 35, SEQ ID NO: 47, SEQ ID NO: 59 |
| Antibody 3 | Antibody 15 | SEQ ID NO: 75, SEQ ID NO: 76 | SEQ ID NO: 99, SEQ ID NO: 100 | SEQ ID NO: 1, SEQ ID NO: 15, SEQ ID NO: 24, SEQ ID NO: 36, SEQ ID NO: 48, SEQ ID NO: 60 |
| Antibody 4 | Antibody 16 | SEQ ID NO: 77, SEQ ID NO: 78 | SEQ ID NO: 101, SEQ ID NO: 102 | SEQ ID NO: 4, SEQ ID NO: 16, SEQ ID NO: 25, SEQ ID NO: 37, SEQ ID NO: 49, SEQ ID NO: 61 |
| Antibody 6 | Antibody 18 | SEQ ID NO: 91, SEQ ID NO: 92 | SEQ ID NO: 115, SEQ ID NO: 116 | SEQ ID NO: 11, SEQ ID NO: 20, SEQ ID NO: 32, SEQ ID NO: 44, SEQ ID NO: 56, SEQ ID NO: 68 |
| Antibody 7 | Antibody 19 | SEQ ID NO: 69, SEQ ID NO: 70 | SEQ ID NO: 93, SEQ ID NO: 94 | SEQ ID NO: 1, SEQ ID NO: 12, SEQ ID NO: 21, SEQ ID NO: 33, SEQ ID NO: 45, SEQ ID NO: 57 |
| Antibody 8 | Antibody 20 | SEQ ID NO: 79, SEQ ID NO: 80 | SEQ ID NO: 103, SEQ ID NO: 104 | SEQ ID NO: 5, SEQ ID NO: 17, SEQ ID NO: 26, SEQ ID NO: 38, SEQ ID NO: 50, SEQ ID NO: 62 |
| Antibody 9 | Antibody 21 | SEQ ID NO: 81, SEQ ID NO: 82 | SEQ ID NO: 105, SEQ ID NO; 106 | SEQ ID NO: 6, SEQ ID NO: 18, SEQ ID NO: 27, SEQ ID NO: 39, SEQ ID NO: 51, SEQ ID NO: 63 |
| Antibody 11 | Antibody 23 | SEQ ID NO: 87, SEQ ID NO: 88 | SEQ ID NO: 111, SEQ ID NO: 112 | SEQ ID NO: 9, SEQ ID NO: 19, SEQ ID NO: 30, SEQ ID NO: 42, SEQ ID NO: 54, SEQ ID NO: 66 |
| Antibody 12 | Antibody 24 | SEQ ID NO: 89, SEQ ID NO: 90 | SEQ ID NO: 113, SEQ ID NO: 114 | SEQ ID NO: 10, SEQ ID NO: 16, SEQ ID NO: 31, SEQ ID NO: 43, SEQ ID NO: 55, SEQ ID NO: 67 |
| Antibody 29 | Antibody 35 | SEQ ID NO: 148, SEQ ID NO: 149 | SEQ ID NO: 162, SEQ ID NO: 163 | SEQ ID NO: 117, SEQ ID NO: 118, SEQ ID NO: 119, SEQ ID NO: 120, SEQ ID NO: 121, SEQ ID NO: 122 |
| Antibody 30 | Antibody 36 | SEQ ID NO: 150, SEQ ID NO: 151 | SEQ ID NO: 164, SEQ ID NO: 165 | SEQ ID NO: 117, SEQ ID NO: 118, SEQ ID NO: 123, SEQ ID NO: 124, SEQ ID NO: 125, SEQ ID NO: 126 |
| Antibody 25 | Antibody 31 | SEQ ID NO: 152, SEQ ID NO: 153 | SEQ ID NO: 166, SEQ ID NO: 167 | SEQ ID NO: 127, SEQ ID NO: 128, SEQ ID NO: 129, SEQ ID NO: 130, SEQ ID NO: 50, SEQ ID NO: 131 |

TABLE 6-continued

| Human Antibody: Protein S Antibody with Human Fc | Rat Antibody: Protein S Antibody with Rat Fc | Variable Light Chain, Variable Heavy Chain (Amino Acid Sequences) | Variable Light Chain, Variable Heavy Chain (Nucleic Acid Sequences) | CDR Combination (Amino Acid Sequences) |
|---|---|---|---|---|
| Antibody 27 | Antibody 33 | SEQ ID NO: 156, SEQ ID NO: 157 | SEQ ID NO: 170, SEQ ID NO: 171 | SEQ ID NO: 136, SEQ ID NO: 17, SEQ ID NO: 137, SEQ ID NO: 138, SEQ ID NO: 139, SEQ ID NO: 140 |
| Antibody 28 | Antibody 34* (*mouse variable region/mouse Fc) | SEQ ID NO: 158, SEQ ID NO: 159 | SEQ ID NO: 172, SEQ ID NO: 173 | SEQ ID NO: 141, SEQ ID NO: 142, SEQ ID NO: 143, SEQ ID NO: 144, SEQ ID NO: 145, SEQ ID NO: 146 |
| Antibody 37 | Antibody 38 | SEQ ID NO: 177, SEQ ID NO: 182 | SEQ ID NO: 178, SEQ ID NO: 183 | SEQ ID NO: 174, SEQ ID NO: 175, SEQ ID NO: 176, SEQ ID NO: 179, SEQ ID NO: 180, SEQ ID NO: 181 |
| Antibody 39 | Antibody 40 | SEQ ID NO: 187, SEQ ID NO: 192 | SEQ ID NO: 188, SEQ ID NO: 193 | SEQ ID NO: 184, SEQ ID NO: 185, SEQ ID NO: 186, SEQ ID NO: 189, SEQ ID NO: 190, SEQ ID NO: 191 |
| Antibody 41 | Antibody 42 | SEQ ID NO: 197, SEQ ID NO: 202 | SEQ ID NO: 198, SEQ ID NO: 203 | SEQ ID NO: 194, SEQ ID NO: 195, SEQ ID NO: 196, SEQ ID NO: 199, SEQ ID NO: 200, SEQ ID NO: 201 |
| Antibody 43 | Antibody 44 | SEQ ID NO: 207, SEQ ID NO: 212 | SEQ ID NO: 208, SEQ ID NO: 213 | SEQ ID NO: 204, SEQ ID NO: 205, SEQ ID NO: 206, SEQ ID NO: 209, SEQ ID NO: 210, SEQ ID NO: 211 |

Example 2: Assessing Thrombin Generation in APC and TFPI Cofactor Activity Screening Assays Assessing APC and TFPI Cofactor Activity with Screening Assays FIGS. 2A-2B depict exemplary assays performed to assess APC and TFPI cofactor activity, respectively and demonstrate how a APC cofactor inhibitor and a TFPI cofactor inhibitor would behave in the assay.

Figure 2B:
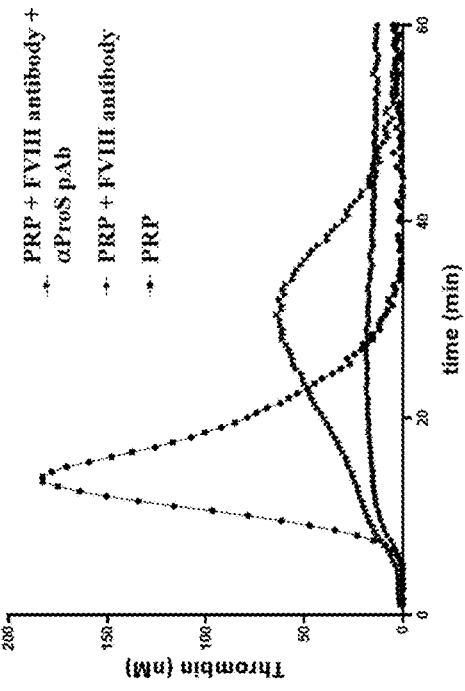
FIGS. 2A-2B depict the results of screening assays performed to assess APC and TFPI cofactor activity, respectively, using control Protein S antibodies. In this and subsequent figures, ProS=Protein S; mAb=monoclonal antibody; pAb=polyclonal antibody; PRP=platelet rich plasma.
Figure 2A:
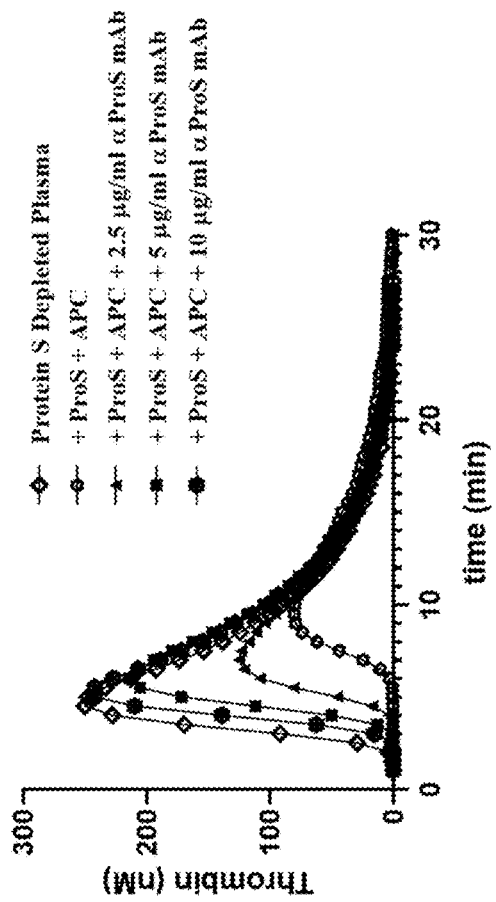

FIGS. 2A-2B depict assays performed to assess APC and TFPI cofactor activity, respectively. For the APC cofactor activity screening assay depicted in FIG. 2A, the following were tested: Protein S depleted platelet poor plasma, Protein S depleted plasma reconstituted with a Protein S and APC mixture, and Protein S depleted plasma reconstituted with a Protein S and APC mixture in the presence of varying concentrations of an anti-Protein S monoclonal antibody (mAb). The Protein S and APC mixture was made by pre-mixing Protein S and APC and adding to the Protein S depleted plasma to create a Protein S-dependent assay, due to APC not showing inhibition of thrombin generation in the absence of Protein S. As shown, the addition of the pre-mixed Protein S and APC mixture to Protein S depleted plasma shows significantly less tissue factor-induced thrombin generation than the Protein S depleted plasma alone. Addition of anti-Protein S mAbs to the Protein S depleted plasma+Protein S and APC mixture restored tissue factor-induced thrombin generation in a concentration-dependent manner.

For the TFPI cofactor activity screening assay depicted in FIG. 2B, the following were tested: platelet rich plasma with no treatment (also referred to herein as platelet-rich plasma, or PRP), a commercial Factor VIII (FVIII) neutralizing antibody, and a FVIII antibody and Protein S polyclonal antibody (pAB) mixture. The FVIII antibody acts as a neutralizing antibody and inhibits tissue factor induced thrombin generation. Addition of the neutralizing Protein S antibodies enhanced thrombin generation in the presence of the FVIII antibody. Neutralizing Protein C antibodies did not show an effect on thrombin generation in the TFPI cofactor activity assay, suggesting that endogenous Protein C or activated Protein C does not inhibit thrombin generation in this assay.

Figure 3:
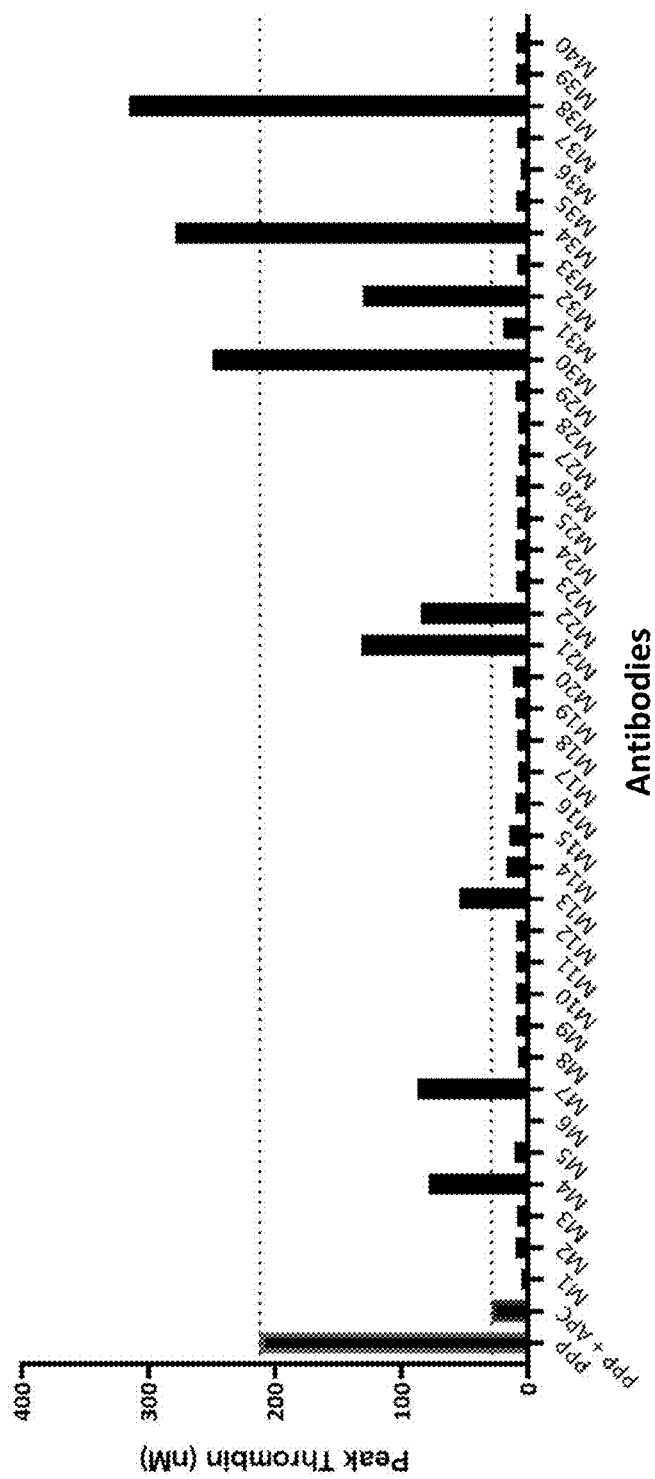
FIGS. 3-4 depict peak thrombin levels generated by Protein S monoclonal antibodies, identified from hybridoma libraries, in the APC cofactor and TFPI cofactor screening assays, respectively.
Figure 4:
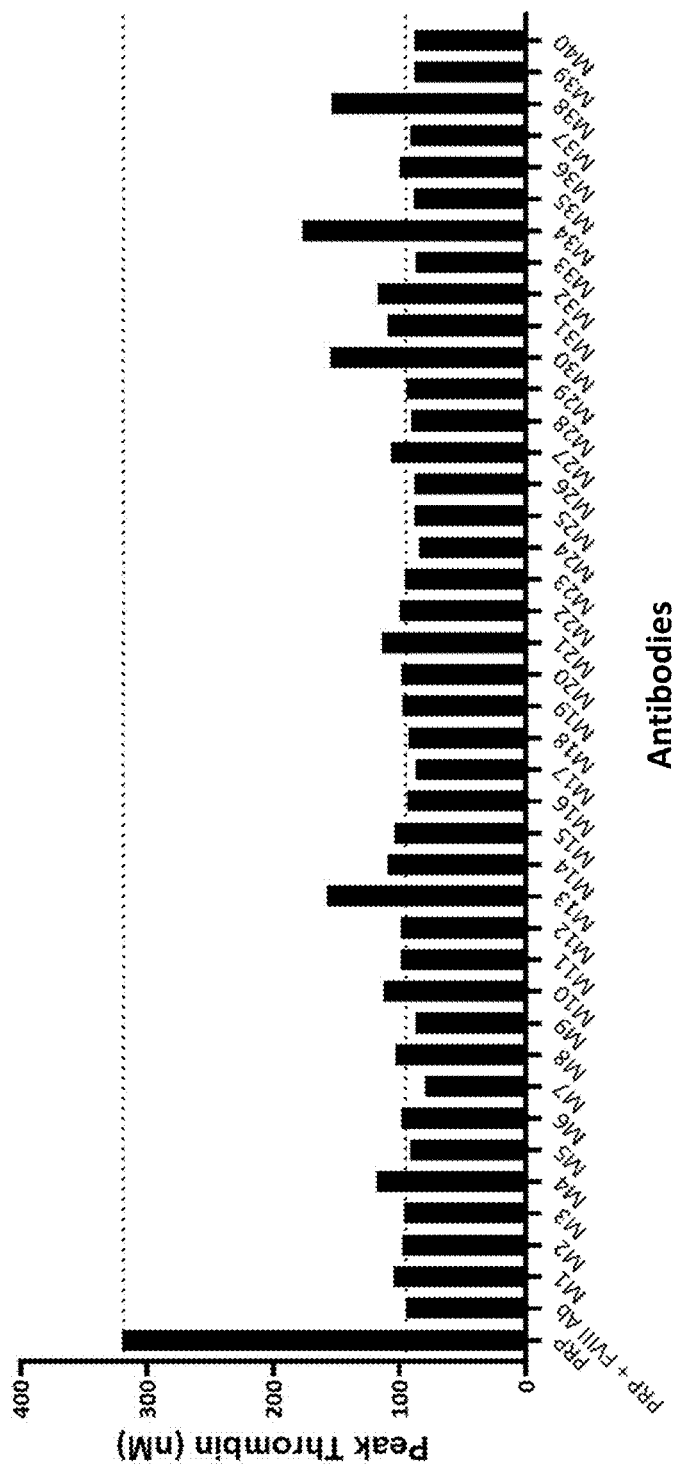

Clones M1-M40 were generated from a rat hybridoma library described in Example 1. The cofactor activity assays performed as described when referring to FIGS. 2A-2B were used to measure the amount of thrombin generation in the presence of clones M1-M40 generated from a rat hybridoma library. FIGS. 3-4 depict the peak thrombin levels generated from an APC cofactor screening assay (APC assay) and a TFPI cofactor screening assay, respectively, of the clones M1-M40. Controls used for the APC assay depicted in FIG. 3 were platelet-poor plasma ("PPP") alone and PPP with APC. Controls used for the TFPI assay depicted in FIG. 4 were platelet-rich plasma ("PRP") alone and PRP with a commercial neutralizing FVIII antibody.

Example 3: Characterization of Selected Protein S Antibodies

Characterization of Inhibitor Type by Cofactor Activity Assays

As a general matter, Protein S antibodies can be identified as either a dual inhibitor of Protein S cofactor activity for both APC and TFPI, for APC only (APC cofactor inhibitor), or for TFPI (TFPI cofactor inhibitor) only. The antibodies can be categorized by assessment of the thrombin generation profiles shown when assaying each antibody using the cofactor activity assays described in FIGS. 2A-2B.

FIGS. 5-6 depict thrombin generation in the presence of Antibody 13 in the TFPI cofactor assay (FIG. 5) and the APC cofactor assay (FIG. 6). As shown in the TFPI cofactor activity assay using PRP, robust thrombin generation occurred in the absence of FVIII antibody and was reduced by addition of the FVIII antibody. Addition of 267 nM Antibody 13 promoted thrombin generation in the presence of the FVIII antibody. As shown in the APC cofactor activity assay, thrombin generation was reduced by addition of both APC and Protein S to Protein S depleted plasma. Addition of 267 nM Antibody 13 to Protein S depleted plasma containing APC and Protein S rescued thrombin generation. Since Antibody 13 induced thrombin generation in both the TFPI and APC cofactor assays, Antibody 13 was characterized as a dual inhibitor.

FIGS. 7-8 depict the thrombin generation of Antibody 21 when using a TFPI cofactor assay (FIG. 7) and an APC cofactor assay (FIG. 8). As shown in the TFPI cofactor activity assay depicted in FIG. 7, in PRP, robust thrombin generation occurred in the absence of FVIII antibody. Thrombin generation was reduced by addition of the FVIII antibody only. Addition of 267 nM Antibody 21 showed no rescue of the thrombin generation. As shown in the APC cofactor activity assay depicted in FIG. 8, thrombin generation was reduced by addition of a mixture of APC and Protein S, which was rescued by the addition of 267 nM Antibody 21. Because Antibody 21 did not induce thrombin generation in the TFPI cofactor assay but did rescue thrombin generation in the APC cofactor assay, Antibody 21 was characterized as an APC cofactor inhibitor.

FIGS. 9-10 depict the thrombin generation of Antibody 23 when using a TFPI cofactor assay (FIG. 9) and an APC cofactor assay (FIG. 10). As shown in the TFPI cofactor activity assay depicted in FIG. 9, in PRP, robust thrombin generation occurred in the absence of FVIII antibody. Thrombin generation was reduced by addition of the FVIII antibody only. Addition of 267 nM Antibody 23 promoted thrombin generation. As shown in the APC cofactor activity assay depicted in FIG. 10, in Protein S depleted plasma, thrombin generation was reduced by addition of a mixture of APC and Protein S. Addition of 267 nM Antibody 23 to Protein S depleted plasma with APC+Protein S showed limited rescue of the thrombin generation. Since Antibody 23 induced thrombin generation in the TFPI cofactor assay but not in the APC cofactor assay, Antibody 23 was characterized as a TFPI cofactor inhibitor.

Characterization of Protein S Antibodies

The assay results depicted in FIGS. 11A-20H were used to characterize the exemplary Protein S antibodies provided herein. The antibodies were characterized as an inhibitor of APC cofactor activity (APC cofactor inhibitor), an inhibitor of TFPI cofactor activity (TFPI cofactor inhibitor), or a dual inhibitor. Binding regions and calcium dependence were also determined. The results of the characterization assays are summarized in Tables 7 and 8 below and described in further detail in the below sections.

TABLE 7

| Protein S Antibody | Fc | Pathway Inhibitor (APC, TFPI, or Dual) | IC50 APC (nM) | Hill Coefficient | IC50 TFPI (nM) | Hill Coefficient |
|---|---|---|---|---|---|---|
| Antibody 13 | Rat | Dual | 5.30E−09 | 2.56 | 5.11E−08 | 5.62 |
| Antibody 14 | Rat | Dual | 8.76E−09 | 2.26 | 7.33E−08 | 2.46 |
| Antibody 15 | Rat | Dual | 1.35E−08 | 2.80 | 7.73E−08 | 3.79 |
| Antibody 16 | Rat | Dual | 1.40E−08 | 2.69 | 4.63E−08 | 3.9 |
| Antibody 18 | Rat | APC | 1.28E−08 | 2.7 | N/A | N/A |
| Antibody 19 | Rat | Dual | 8.12E−08 | 1.06 | 1.05E−07 | 1.39 |
| Antibody 20 | Rat | Dual | 1.28E−08 | 2.70 | N/A | N/A |
| Antibody 21 | Rat | APC only | 6.23E−09 | 2.10 | N/A | N/A |
| Antibody 23 | Rat | TFPI only | N/A | N/A | <4.4E−09 | N/A |
| Antibody 24 | Rat | Dual | 1.79E−08 | 1.6 | 7.36E−08 | 1.59 |
| Antibody 31 | Rat | APC only | 9.90E−08 | 1.12 | N/A | N/A |
| Antibody 33 | Rat | Dual | 5.81E−08 | 2.48 | 3.4E−08 | 2.21 |
| Antibody 34 | Mouse | APC only | 9.58E−08 | 2.28 | N/A | N/A |
| Antibody 35 | Rat | APC only | 3.71E−07 | 0.68 | N/A | N/A |
| Antibody 36 | Rat | Dual | 1.53E−08 | 1.55 | 6.05E−09 | 3.53 |
| Antibody 38 | Rat | APC only | 8.40E−08 | 0.70 | N/A | N/A |
| Antibody 40 | Rat | APC only | 1.19E−08 | 2.82 | N/A | N/A |
| Antibody 42 | Rat | APC only | 2.15E−07 | 1.37 | N/A | N/A |
| Antibody 44 | Rat | APC only | 4.92E−07 | 0.87 | N/A | N/A |

TABLE 8

| Protein S Antibody with Rat Fc | Pathway Inhibitor | Binds Heavy Chain | Calcium-Dependent Binding | Binds Thrombin-Sensitive Region of Protein S |
|---|---|---|---|---|
| Antibody 13 | Dual | Yes | No | No |
| Antibody 14 | Dual | Yes | No | No |
| Antibody 15 | Dual | Yes | Yes | Yes |
| Antibody 16 | Dual | Yes | Yes | No |
| Antibody 19 | Dual | Yes | Yes | Yes |
| Antibody 20 | Dual | Yes | Yes | No |
| Antibody 24 | Dual | Yes | Yes | Yes |
| Antibody 18 | APC | Yes | Yes | No |
| Antibody 21 | APC | Yes | No | No |
| Antibody 23 | TFPI | No | No | No |
| Antibody 31 | APC | No | No | No |
| Antibody 33 | Dual | No | Yes | No |

TABLE 8-continued

| Protein S Antibody with Rat Fc | Pathway Inhibitor | Binds Heavy Chain | Calcium-Dependent Binding | Binds Thrombin-Sensitive Region of Protein S |
|---|---|---|---|---|
| Antibody 34 | APC | No | Yes | No |
| Antibody 35 | APC | No | Yes | No |
| Antibody 36 | Dual | No | Yes | No |
| Antibody 38 | APC | No | Yes | No |
| Antibody 40 | APC | No | Yes | No |
| Antibody 42 | APC | No | No | No |
| Antibody 44 | APC | Yes | No | No |

Binding characteristics of the Protein S antibodies were also determined. Binding interaction analysis was obtained by Surface Plasmon Resonance in a Biacore X100 instrument. The human anti-IgG (Fc) antibody was immobilized to the carboxymethylated dextran membrane on the sensor chip surface (CM5) via the free amine method for a contact time of 420 seconds. Human anti-IgG antibody at 25 µg/mL in 0.15 M NaCl was immobilized to 9,785 RU in 10 mM sodium acetate pH 5.0. Each tested monoclonal antibody (Antibody 1-12) was captured at a fixed concentration (0.25 µg/mL) with immobilized human anti-IgG antibody. Experimentally, the capture ligand level for the antibodies tested was determined to be 66-99 RL, corresponding to a $R_{max}$ of 61-91 RU. No signs of mass transport limitation were observed.

The following experimental conditions were used: purified Protein S was injected at concentrations: 2-128 nM, 1:2-fold dilution. Dilution and running buffer were as follows: Hbs-EP+5 mM $CaCl_2$). Regeneration was obtained by 3 M $MgCl_2$. Binding constants (ka, kd, and KD) were determined using the Biacore X100 evaluation software, assuming a 1:1 interaction of Protein S and the tested monoclonal antibody under investigation. The resulting data are presented in Table 9 below.

TABLE 9

| | Ka (1/MS) | Kd (1/S) | KD nM |
|---|---|---|---|
| Antibody 1 | 2.90E+05 | 3.90E−04 | 1.33 |
| Antibody 2 | 3.46E+05 | 5.60E−04 | 1.63 |
| Antibody 3 | 2.53E+05 | 5.69E−04 | 2.24 |

TABLE 9-continued

| | Ka (1/MS) | Kd (1/S) | KD nM |
|---|---|---|---|
| Antibody 4 | 3.99E+05 | 1.65E−03 | 4.13 |
| Antibody 6 | 2.80E+05 | 1.60E−03 | 5.79 |
| Antibody 7 | 2.52E+05 | 5.00E−03 | 20.00 |
| Antibody 8 | 1.32E+05 | 8.23E−04 | 6.25 |
| Antibody 9 | 2.12E+05 | 3.36E−03 | 15.90 |
| Antibody 11 | 1.16E+05 | 1.13E−03 | 9.60 |
| Antibody 12 | 6.57E+05 | 9.47E−03 | 14.40 |

Binding characteristics of the Protein S antibodies were also further characterized using Octet. Using the Octet System (Sartorius), the binding of each antibody to both human and cynomolgus monkey ("cyno" in Table 10) Protein S was determined. The human Fc antibodies were immobilized onto anti-human Fc capture probes by placing the probes into 10 µg/ml antibody solution in 10 mg/ml bovine serum albumin, 20 mM Tris pH 7.0, 150 mM NaCl, and 4 mM calcium chloride. Next, the bound antibodies were placed into solutions containing 500 nM, 250 nM, 125 nM 62.5 nM, 31.25 nM, 15.625 nM and 7.81 nM Protein S and the association rates were measured. Next, the probes were placed into buffer and the dissociation rates were measured. A summary of the resulting data is provided in Table 10 below.

TABLE 10

| Antibody | $k_{on}$ (l/Ms) | kdis (1/s) | KD (human) (M) | $k_{on}$ (1/Ms) | kdis (1/s) | KD (cyno) (M) |
|---|---|---|---|---|---|---|
| Antibody 1 | 1.69E+05 | <1.0E−07 | <1.0E−12 | 1.39E+05 | <1.0E−07 | <1.0E−12 |
| Antibody 2 | 2.07E+05 | <1.0E−07 | <1.0E−12 | 1.54E+05 | <1.0E−07 | <1.0E−12 |
| Antibody 3 | 1.64E+05 | 8.86E−06 | 5.42E−11 | 1.27E+05 | <1.0E−07 | <1.0E−12 |
| Antibody 4 | 2.71E+05 | 7.08E−04 | 2.62E−09 | 2.01E+05 | 3.08E−03 | 1.53E−08 |
| Antibody 6 | 2.26E+05 | 3.32E−04 | 1.47E−09 | 1.40E+05 | 3.94E−04 | 2.81E−09 |
| Antibody 7 | 1.72E+05 | 1.41E−03 | 8.18E−09 | 1.37E+05 | 2.32E−03 | 1.69E−08 |
| Antibody 8 | 1.31E+05 | 6.70E−05 | 5.14E−10 | 8.58E+04 | 1.33E−04 | 1.55E−09 |
| Antibody 9 | 3.04E+05 | 1.62E−04 | 5.33E−10 | 1.66E+05 | 4.42E−05 | 2.66E−10 |
| Antibody 11 | 8.52E+04 | 3.40E−05 | 3.99E−10 | 8.21E+04 | <1.0E−07 | <1.0E−12 |
| Antibody 12 | 3.09E+05 | 2.32E−03 | 7.49E−09 | 2.58E+05 | 2.91E−03 | 1.13E−08 |
| Antibody 25 | 1.43E+05 | <1.0E−07 | <1.0E−12 | 1.24E+05 | <1.0E−07 | <1.0E−12 |
| Antibody 27 | 2.77E+05 | 1.59E−04 | 5.74E−10 | 6.79E+04 | 2.33E−03 | 3.43E−08 |
| Antibody 28 | 1.56E+05 | 1.06E−03 | 6.78E−09 | 1.09E+05 | 1.06E−03 | 9.81E−09 |
| Antibody 29 | 8.19E+04 | 1.73E−03 | 2.11E−08 | 8.82E+04 | 1.77E−03 | 2.00E−08 |
| Antibody 30 | 2.42E+04 | 2.79E−04 | 1.15E−08 | 3.50E+04 | 7.30E−04 | 2.09E−08 |
| Antibody 37 | 2.18E+05 | 8.32E−05 | 3.82E−10 | 1.77E+05 | 1.19E−04 | 6.72E−10 |
| Antibody 39 | 2.34E+05 | 5.84E−05 | 2.50E−10 | 1.91E+05 | 8.02E−05 | 4.19E−10 |
| Antibody 41 | 8.00E+04 | 1.10E−03 | 1.38E−08 | 9.64E+04 | 1.88E−03 | 1.95E−08 |
| Antibody 43 | 3.20E+05 | 6.36E−04 | 1.99E−09 | 2.68E+05 | 1.04E−03 | 3.88E−09 |

Antibody 19 and Antibody 7

FIGS. 11A-11H depict the characterization of Antibody 19 and Antibody 7. Antibody 19 and Antibody 7 both comprise the same human variable regions, while Antibody 19 comprises a rat Fc domain and Antibody 7 comprises a human IgG4 Fc domain.

FIG. 11A depicts a Western blot showing that Antibody 19 binds Protein S in the Thrombin Sensitive Region (TSR) of Protein S. A full-length human Protein S protein (Reduced (Red) and Non-reduced (NR)) and a thrombin-cleaved Protein S fragment (cleaved in the Thrombin Sensitive Region (TSR), NR and Red) were used. By Western blot, Antibody 19 bound the full Protein S, but not the thrombin-cleaved Protein S, indicating that Antibody 19 binds at the TSR. Because no signal was observed with the reduced Protein S, the epitope for this antibody is not a linear epitope.

Binding to the heavy chain of Protein S was determined using an ELISA based method. Briefly, high binding ELISA plates were coated with recombinant heavy chain Protein S expressed and purified from HEK293 cells. The "heavy chain" of Protein S represents a fragment of Protein S spanning amino acids 42-296. The coated plate was blocked with 1% casein solution. Then, buffer containing 1 µg/ml of antibody was applied to the well with buffer containing 1 mM calcium chloride. For antibodies that bound this fragment of Protein S, it was concluded that the epitope on Protein S for that antibody is between amino acids 42-296 of Protein S. Table 11 below summarizes the results of the heavy chain binding assay for all Antibodies. (antibodies that do bind this region have ODs greater than about 0.48 OD).

TABLE 11

| Antibody | Binding to heavy chain (OD) |
| --- | --- |
| Antibody 13 | 1.63 |
| Antibody 14 | 2.03 |
| Antibody 15 | 1.78 |
| Antibody 16 | 1.67 |
| Antibody 18 | 0.60 |
| Antibody 19 | 0.61 |
| Antibody 20 | 1.54 |
| Antibody 21 | 1.58 |
| Antibody 23 | 0.10 |
| Antibody 24 | 0.71 |
| Antibody 31 | 0.13 |
| Antibody 33 | 0.11 |
| Antibody 34 | 0.16 |
| Antibody 35 | 0.08 |
| Antibody 36 | 0.08 |
| Antibody 38 | 0.10 |
| Antibody 40 | 0.11 |
| Antibody 42 | 0.11 |
| Antibody 44 | 0.48 |

Calcium dependence of binding was determined using an ELISA based method. Briefly, high binding ELISA plates were coated with human Protein S. Then, buffer containing 1 µg/ml of antibody was applied to the well with either buffer containing 1 mM EDTA or 1 mM calcium chloride. If the level of binding of Protein S was reduced dramatically (greater than 85% of the absorbance observed in the presence of calcium) when EDTA was added, it was concluded that the binding was calcium-dependent. Table 12 summarizes the results of the calcium dependence assay for all Antibodies.

TABLE 12

| | Binding to Protein S in EDTA (OD) | Binding to Protein S in CaCl2 (OD) |
| --- | --- | --- |
| Antibody 13 | 0.48 | 1.77 |
| Antibody 14 | 0.75 | 2.03 |
| Antibody 15 | 0.07 | 1.86 |
| Antibody 16 | 0.17 | 1.95 |
| Antibody 18 | 0.10 | 1.96 |
| Antibody 19 | 0.06 | 1.68 |
| Antibody 20 | 0.26 | 1.93 |
| Antibody 21 | 1.40 | 1.92 |
| Antibody 23 | 0.26 | 0.57 |
| Antibody 24 | 0.06 | 1.72 |
| Antibody 31 | 0.63 | 1.03 |
| Antibody 33 | 0.20 | 1.23 |
| Antibody 34 | 0.06 | 0.51 |
| Antibody 35 | 0.11 | 0.96 |
| Antibody 36 | 0.03 | 0.60 |
| Antibody 38 | 0.09 | 1.38 |
| Antibody 40 | 0.11 | 0.51 |
| Antibody 42 | 0.53 | 0.67 |
| Antibody 44 | 0.89 | 1.17 |

FIGS. 11B-11D depict the results of an APC cofactor assay for Antibody 19 using Protein S deficient human PPP, cynomolgus monkey PPP, and a TFPI cofactor assay using human PRP, respectively.

Figure 11F:
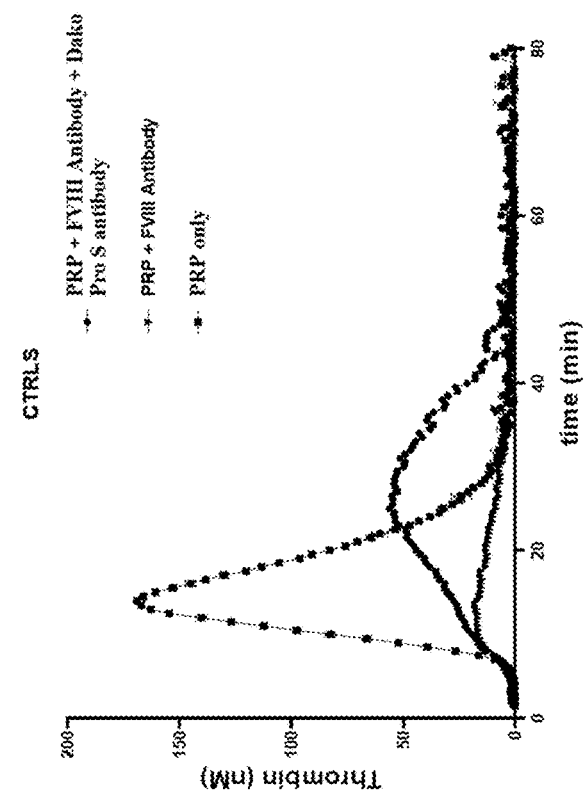
Figure 11E:
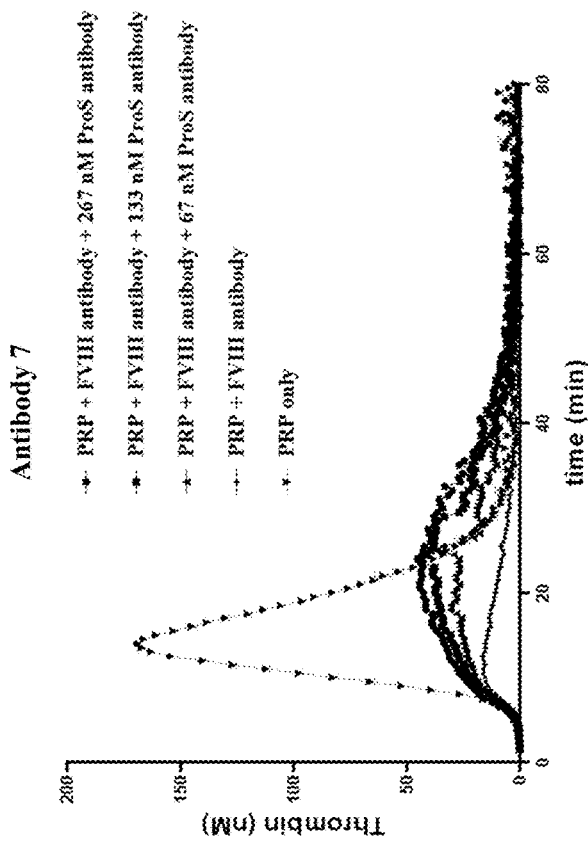

FIGS. 11E and 11F depict the results of a TFPI cofactor assay in human PRP using Antibody 7 and controls, respectively. A rabbit polyclonal human Protein S antibody labeled Dako was used as a positive control.

Figure 11H:
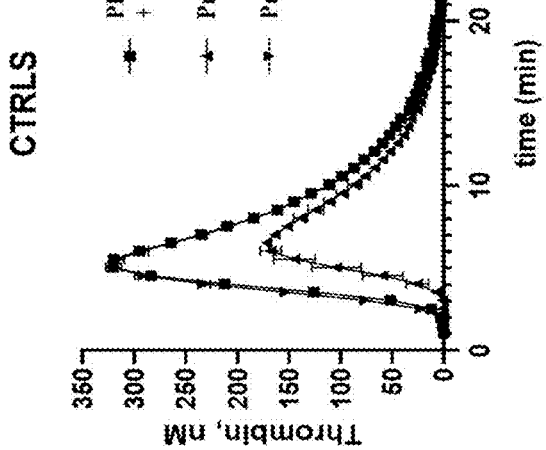
Figure 11G:
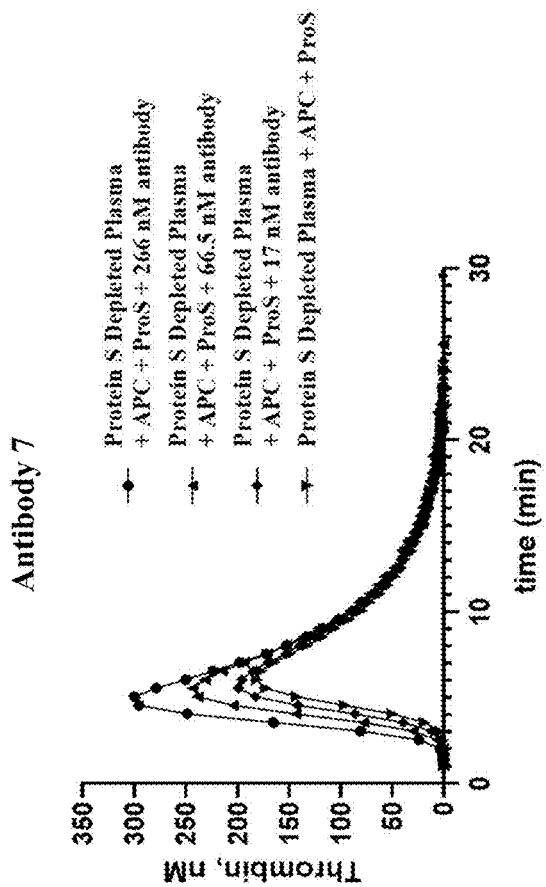

FIGS. 11G-11H depict the results of a PPP with APC assay performed with Antibody 7, and controls, respectively.

These results indicate that Antibody 19 and Antibody 7 are dual inhibitors.

Antibody 13 and Antibody 1

FIGS. 12A-12H depict the characterization of Antibody 13 and Antibody 1, antibodies sharing the same human variable region, and are characterized as dual inhibitors.

FIG. 12A depicts a Western blot showing that Antibody 13 does not bind to Protein S in the TSR of Protein S. The Western blot was carried out as described for FIG. 11A. By Western blot, Antibody 13 bound the full Protein S, the thrombin-cleaved Protein S, the reduced Protein S, and the reduced thrombin-cleaved Protein S, indicating that Antibody 13 does not bind Protein S at the TSR. Binding to reduced Protein S showed that the epitope for Antibody 13 is a linear epitope.

Binding to the heavy chain of Protein S was determined using an ELISA based method, as described herein. Antibody 13 was determined to bind to the heavy chain of Protein S. Calcium dependence was determined, also as described above, and Antibody 13 showed calcium-independent binding.

FIGS. 12B-12D depict the results of an APC cofactor assay for Antibody 13 using Protein S deficient human PPP, cynomolgus monkey PPP, and a TFPI cofactor assay using human PRP, respectively.

Figure 12F:
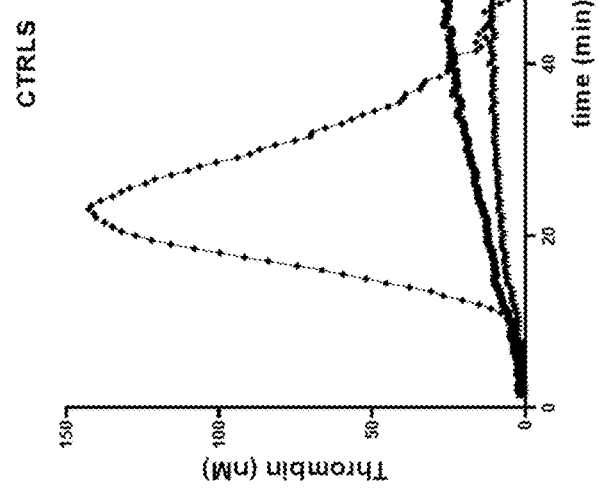
Figure 12E:
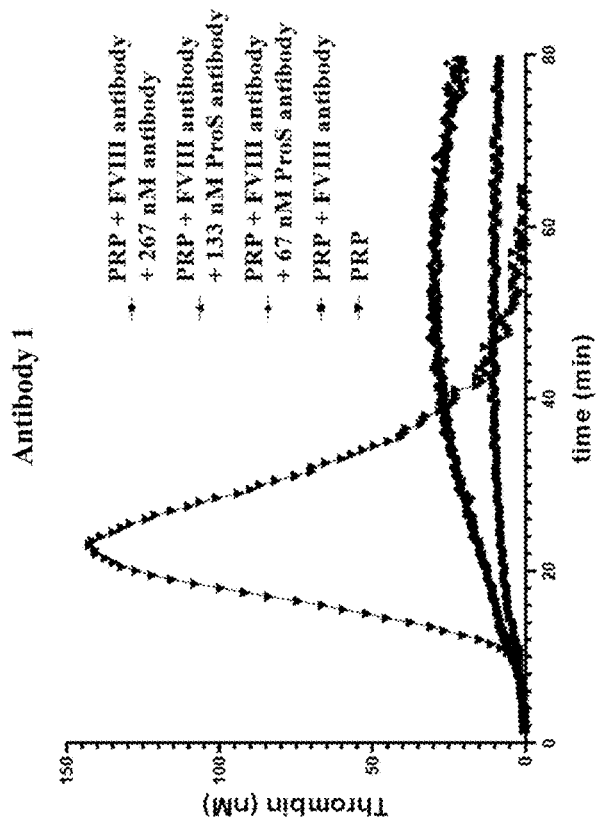

FIGS. 12E and 12F depict the results of a TFPI cofactor assay in human PRP using Antibody 1 and controls, respectively. A rabbit polyclonal human Protein S antibody labeled Dako was used as a positive control.

Figure 12H:
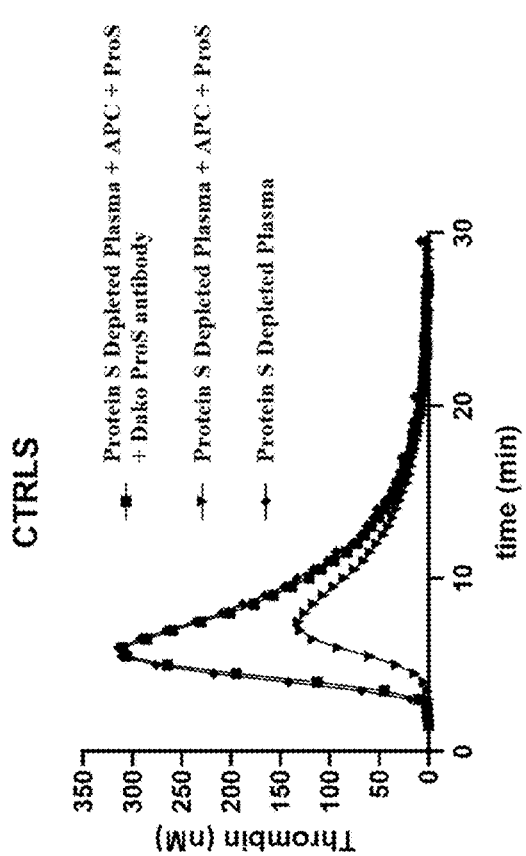
Figure 12G:
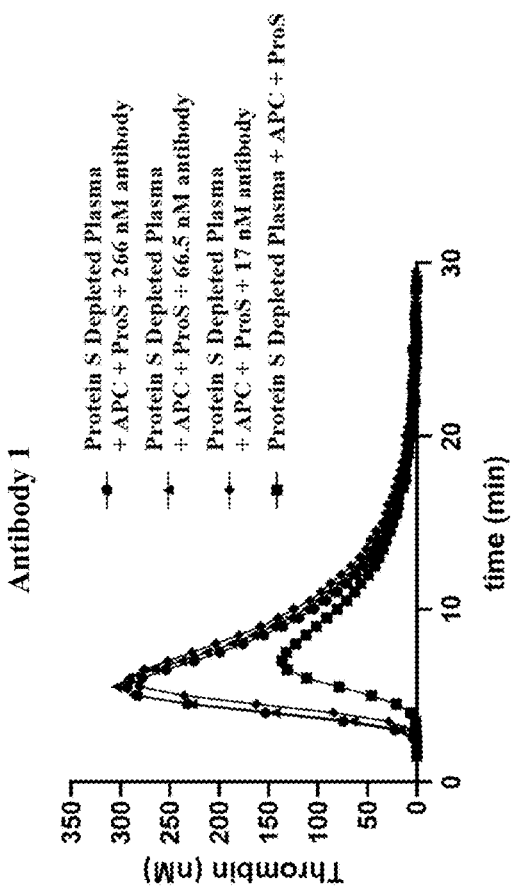

FIGS. 12G-12H depict the results of the APC cofactor assay performed with Antibody 1, and controls, respectively.

These results indicate that Antibody 13 and Antibody 1 are dual inhibitors.

Antibody 14 and Antibody 2

FIGS. 13A-13H depict the characterization of Antibody 14 and Antibody 2, antibodies sharing the same human variable region, and are characterized as dual inhibitors.

Figure 13A:
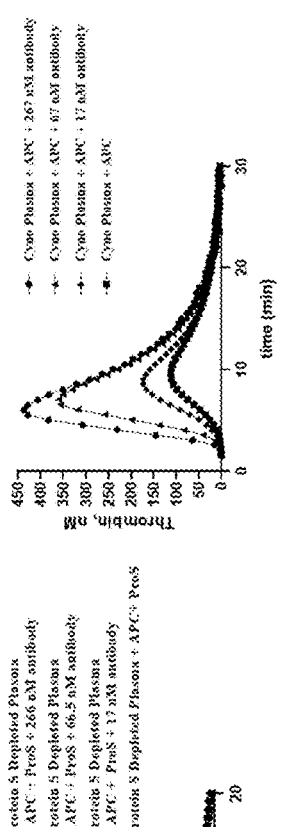
FIGS. 13A-13H depict the characterization of Antibody 14 and Antibody 2, antibodies sharing the same human variable region, and are characterized as dual inhibitors.

FIG. 13A depicts a Western blot showing that Antibody 14 does not bind Protein S in the TSR of Protein S. The Western blot was carried out as described for FIG. 11A. By Western blot, Antibody 14 bound the full Protein S and the thrombin-cleaved Protein S, but did not bind the reduced Protein S, and the reduced thrombin-cleaved Protein S. These results indicate that Antibody 14 does not bind Protein S at the TSR, and the lack of signal observed with the reduced Protein S showed that the epitope for this antibody is not a linear epitope.

Binding to the heavy chain of Protein S was determined using an ELISA based method, as described herein. Antibody 14 was determined to bind to the heavy chain of Protein S. Calcium dependence was determined, also as described above, and Antibody 14 showed binding that was calcium-independent.

Figure 13B:
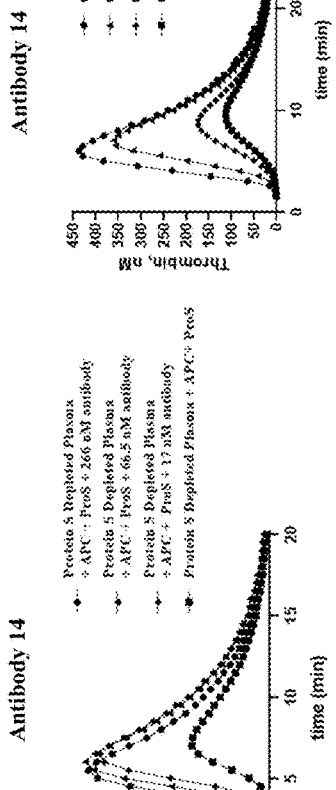
Figure 13C:
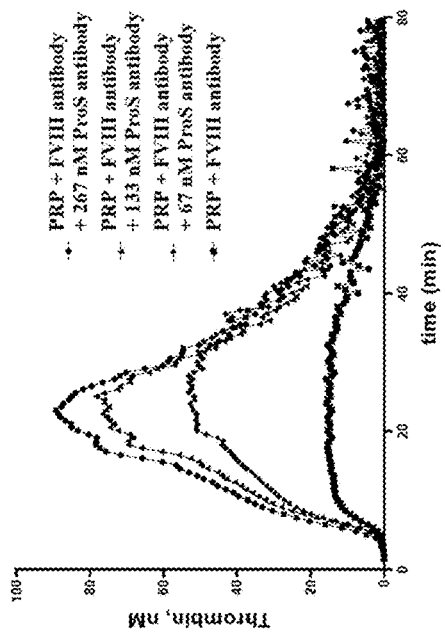
Figure 13D:
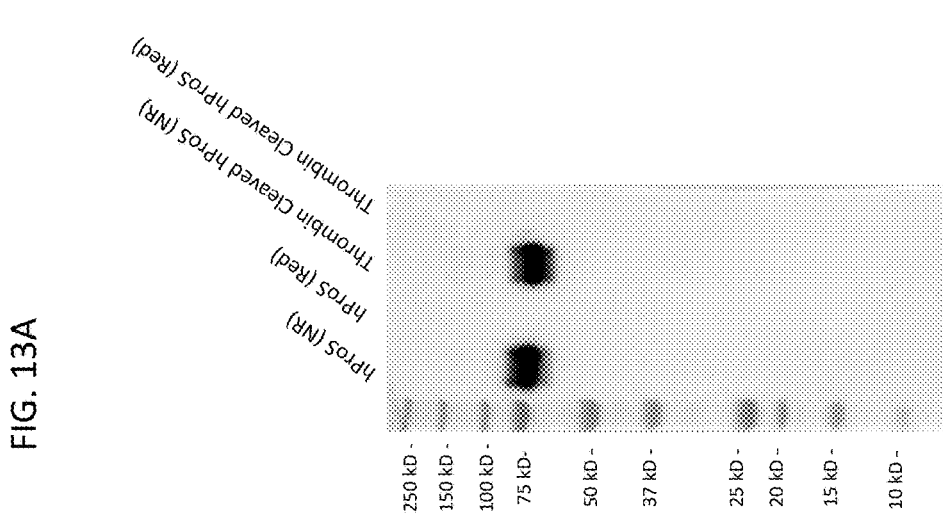

FIGS. 13B-13D depict the results of an APC cofactor assay for Antibody 14 using Protein S deficient human PPP, cynomolgus monkey PPP, and a TFPI cofactor assay using human PRP, respectively.

Figure 13E:
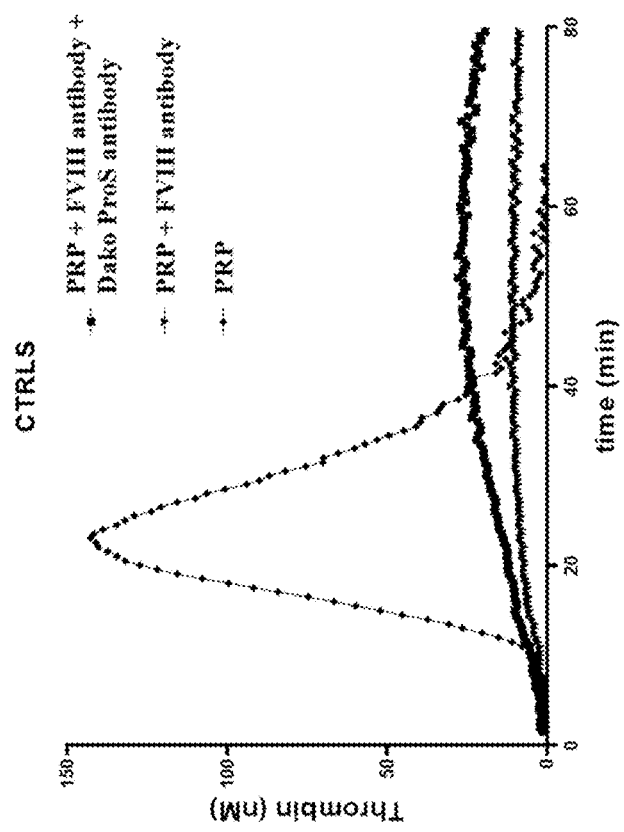
Figure 13F:
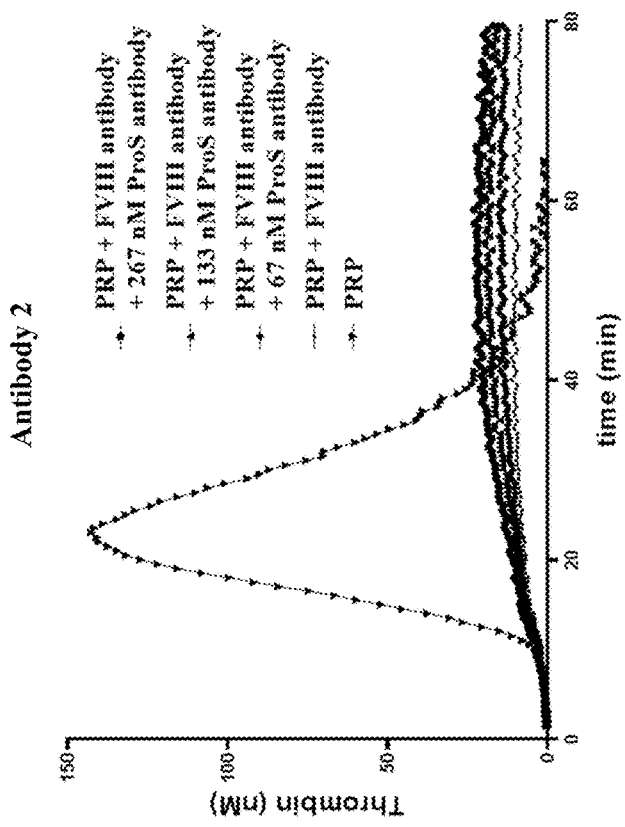

FIGS. 13E and 13F depict the results of a TFPI cofactor assay in human PRP using Antibody 2 and controls, respectively. A rabbit polyclonal human Protein S antibody labeled Dako was used as a positive control.

Figure 13H:
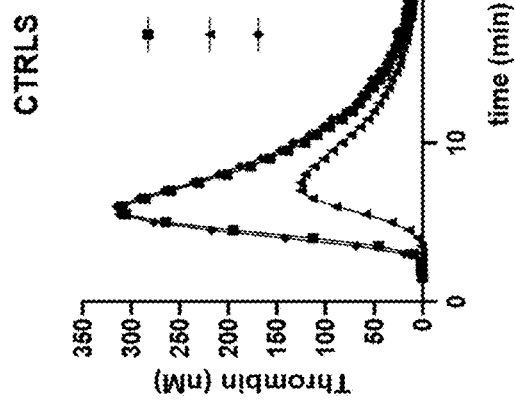
Figure 13G:
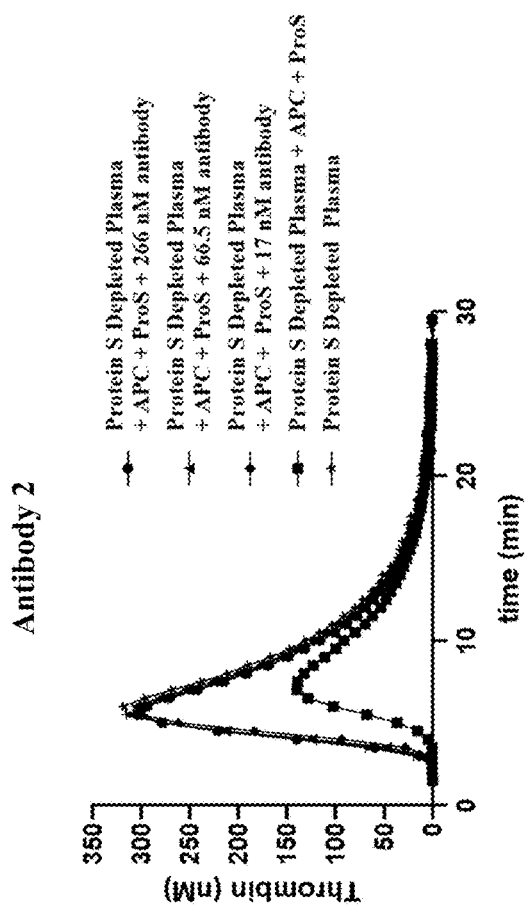

FIGS. 13G-13H depict the results of the APC cofactor assay performed with Antibody 2 and controls, respectively.

These results indicate that Antibody 14 and Antibody 2 are dual inhibitors.

Antibody 15 and Antibody 3

FIGS. 14A-14H depict the characterization of Antibody 15 and Antibody 3, antibodies sharing the same human variable region, and are characterized as dual inhibitors.

Figure 14B:
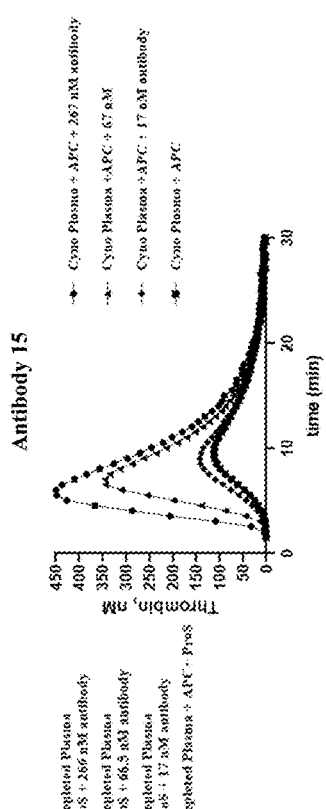
FIGS. 14A-14H depict the characterization of Antibody 15 and Antibody 3, antibodies sharing the same human variable region, and are characterized as dual inhibitors.
Figure 14C:
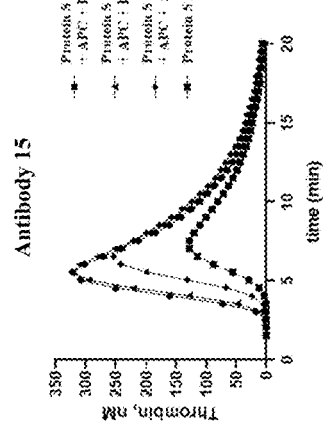
Figure 14D:
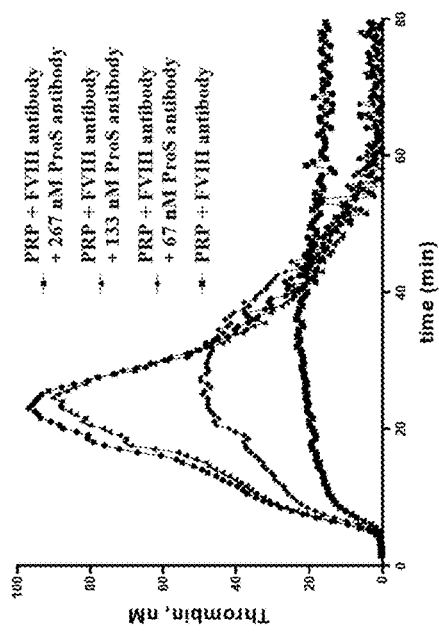
Figure 14A:
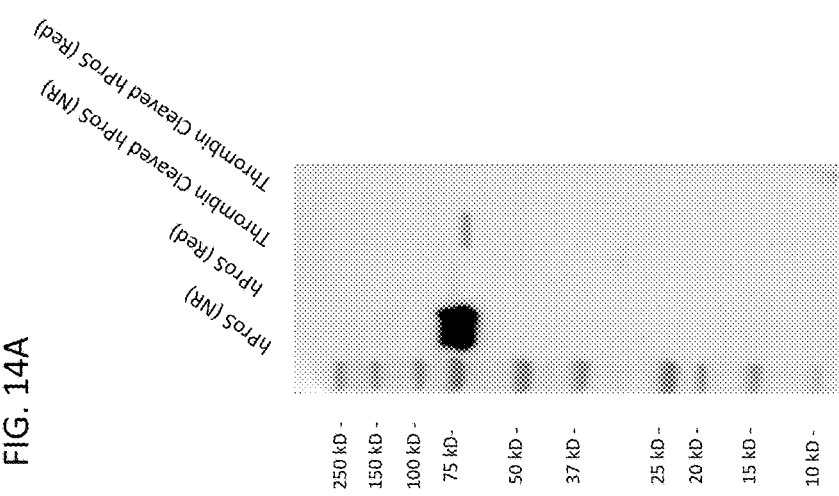

FIG. 14A depicts a Western blot showing that Antibody 15 binds Protein S in the TSR region of Protein S. The Western blot was carried out as described for FIG. 11A. By Western blot, Antibody 15 bound the full Protein S and showed a small band for the thrombin-cleaved Protein S, but did not bind the reduced Protein S, and the reduced thrombin-cleaved Protein S. These results indicate that Antibody 15 binds Protein S at the TSR, and the lack of signal observed with the reduced Protein S showed that the epitope for this antibody is not a linear epitope.

Binding to the heavy chain of Protein S was determined using an ELISA based method, as described above. Antibody 15 was determined to bind to the heavy chain of Protein S. Calcium dependence was determined, also as described above, and Antibody 15 showed binding that was calcium-dependent.

FIGS. 14B-14D depict the results of an APC cofactor assay for Antibody 15 using Protein S deficient human PPP, cynomolgus monkey PPP, and a TFPI cofactor assay using human PRP, respectively.

Figure 14F:
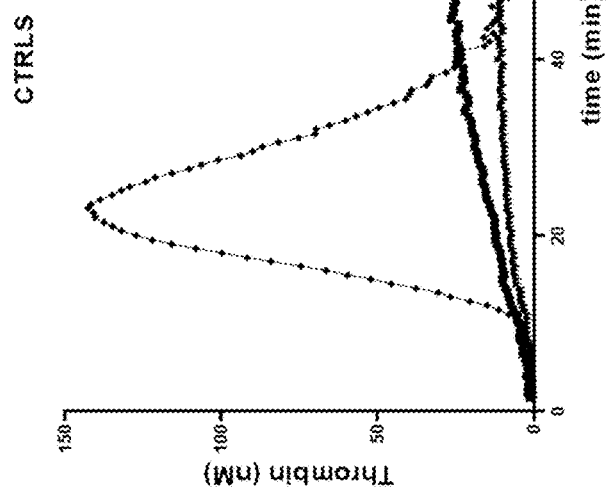
Figure 14E:
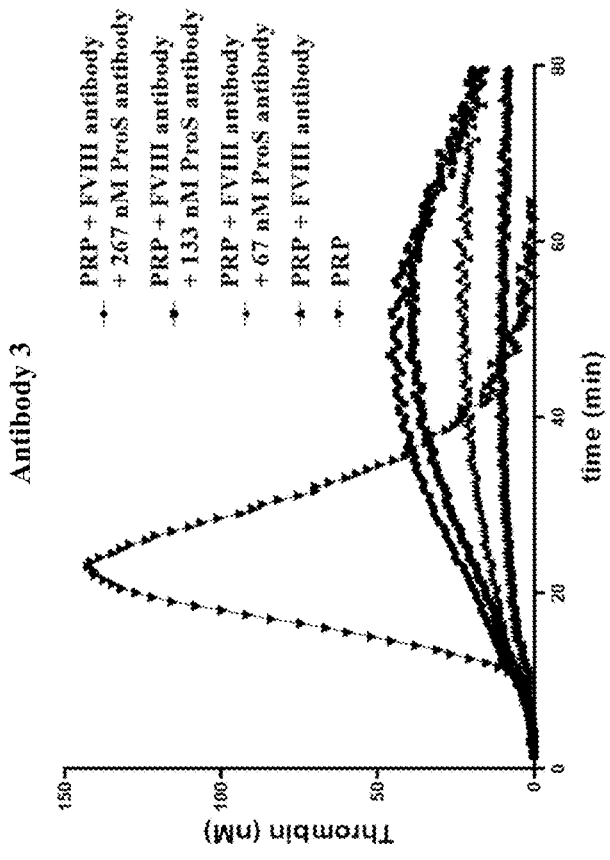

FIGS. 14E and 14F depict the results of a TFPI cofactor assay in human PRP using Antibody 3 and controls, respectively. A rabbit polyclonal human Protein S antibody labeled Dako was used as a positive control.

Figure 14G:
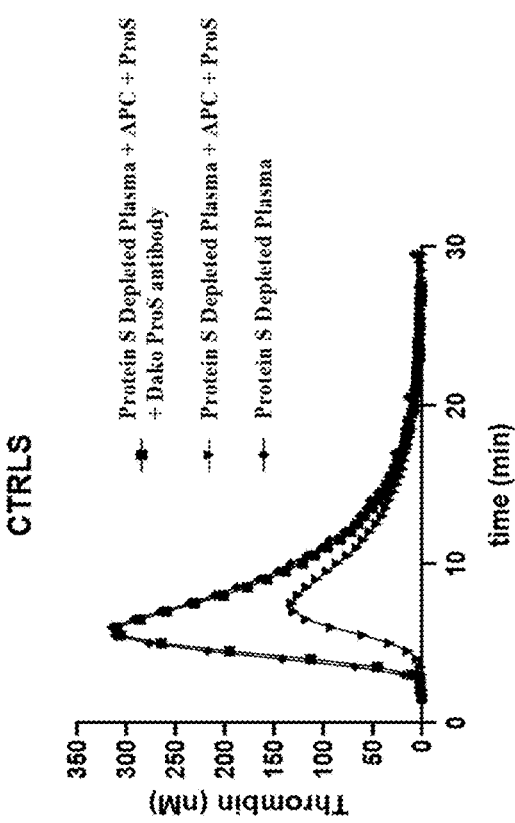
Figure 14H:
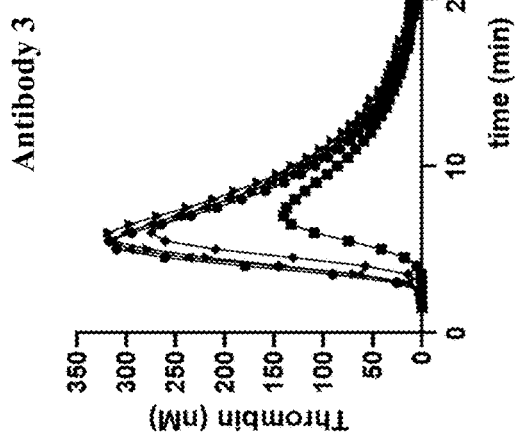

FIGS. 14G-14H depict the results of the APC cofactor assay performed with Antibody 3 and controls, respectively.

These results indicate that Antibody 15 and Antibody 3 are dual inhibitors.

Antibody 16 and Antibody 4

FIGS. 15A-15H depict the characterization of Antibody 16 and Antibody 4, antibodies sharing the same human variable region, and are characterized as dual inhibitors.

FIG. 15A depicts a Western blot showing that Antibody 16 binds Protein S in the Gla-domain of Protein S. The Western blot was carried out as described for FIG. 11A. By Western blot, Antibody 16 bound the full Protein S, the thrombin-cleaved Protein S, the reduced Protein S, but did not bind the reduced thrombin-cleaved Protein S. These results indicate that Antibody 16 binds Protein S at the Gla-domain, and the signal observed with the reduced Protein S showed that the epitope for this antibody is a linear epitope.

Binding to the heavy chain of Protein S was determined using an ELISA based method, as described herein. Antibody 16 was determined to bind to the heavy chain of Protein S. Calcium dependence was determined, also as described herein, and Antibody 16 showed binding that was calcium-dependent.

FIGS. 15B-15D depict the results of an APC cofactor assay for Antibody 16 using Protein S deficient human PPP, cynomolgus monkey PPP, and a TFPI cofactor assay using human PRP, respectively.

Figure 15F:
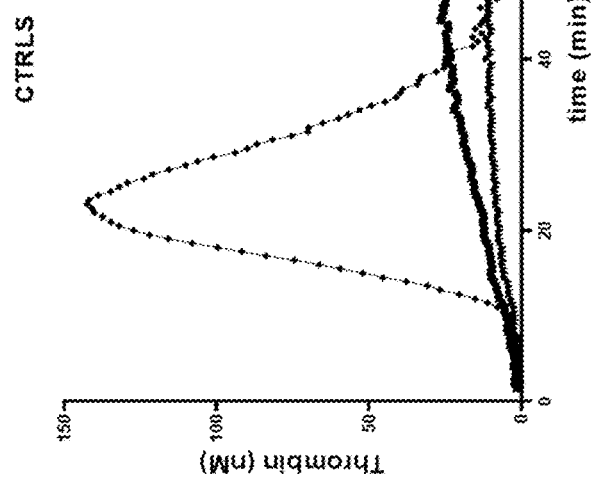
Figure 15E:
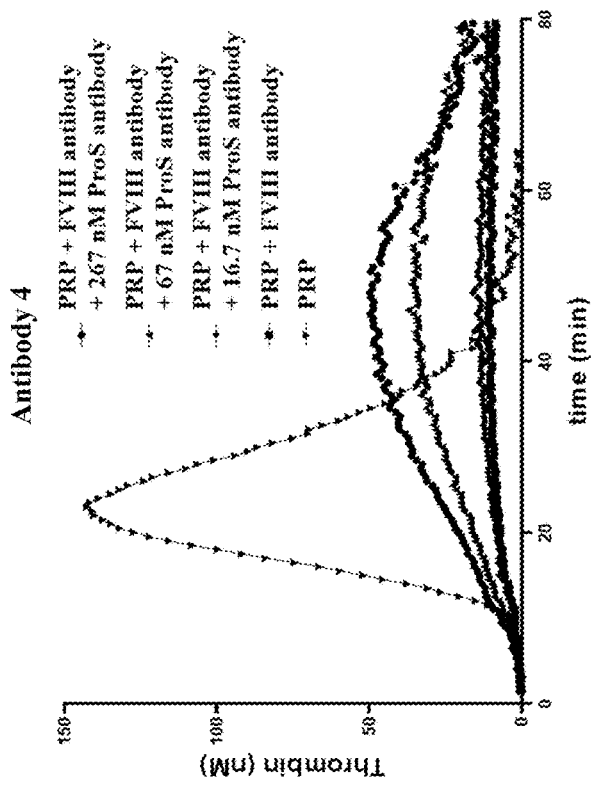

FIGS. 15E and 15F depict the results of a TFPI cofactor assay in human PRP using Antibody 4 and controls, respectively. A rabbit polyclonal human Protein S antibody labeled Dako was used as a positive control.

Figure 15H:
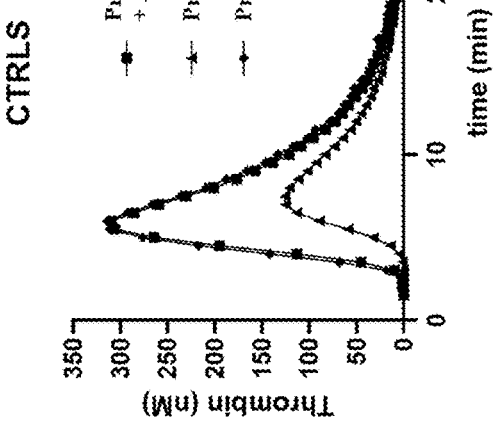
Figure 15G:
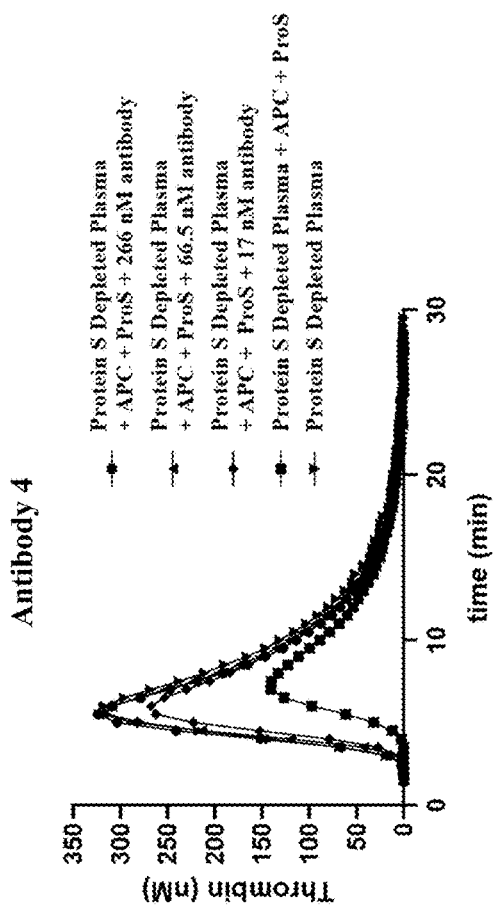

FIGS. 15G-15H depict the results of the APC cofactor assay performed with Antibody 4, and controls, respectively.

These results indicate that Antibody 16 and Antibody 4 are dual inhibitors.

Antibody 20 and Antibody 8

FIGS. 16A-16H depict the characterization of Antibody 20 and Antibody 8, antibodies sharing the same human variable region, and are characterized as dual inhibitors.

Figure 16A:
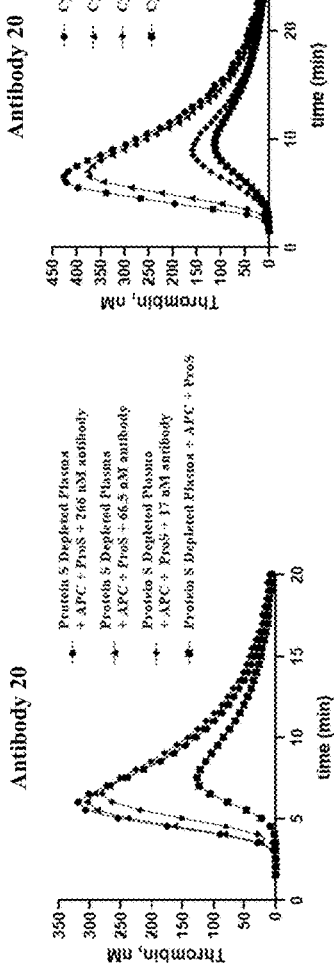
FIGS. 16A-16H depict the characterization of Antibody 20 and Antibody 8, antibodies sharing the same human variable region, and are characterized as dual inhibitors.

FIG. 16A depicts a Western blot showing that Antibody 20 does not bind Protein S in the TSR of Protein S. The Western blot was carried out as described for FIG. 11A. By Western blot, Antibody 20 bound the full Protein S and the thrombin-cleaved Protein S, but did not bind the reduced Protein S or the reduced thrombin-cleaved Protein S. These results indicate that Antibody 20 does not bind Protein S at the TSR, and the lack of signal observed with the reduced Protein S showed that the epitope for this antibody is not a linear epitope.

Binding to the heavy chain of Protein S was determined using an ELISA based method, as described herein. Antibody 20 was determined to bind to the heavy chain of Protein S. Calcium dependence was determined, also as described herein, and Antibody 20 showed binding that was calcium-dependent.

Figure 16B:
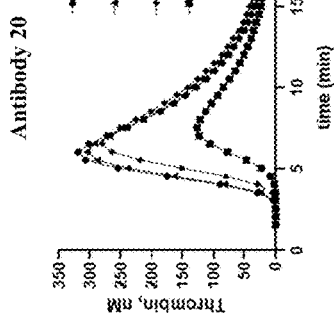
Figure 16C:
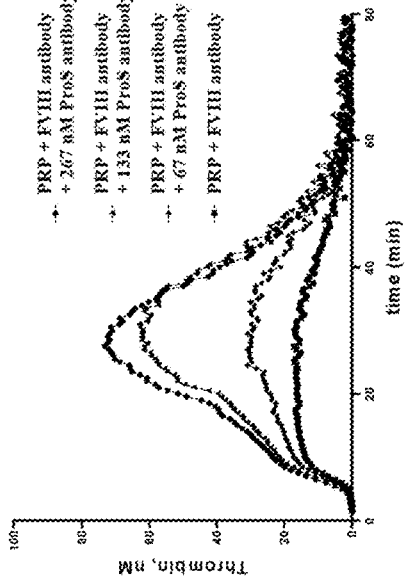
Figure 16D:
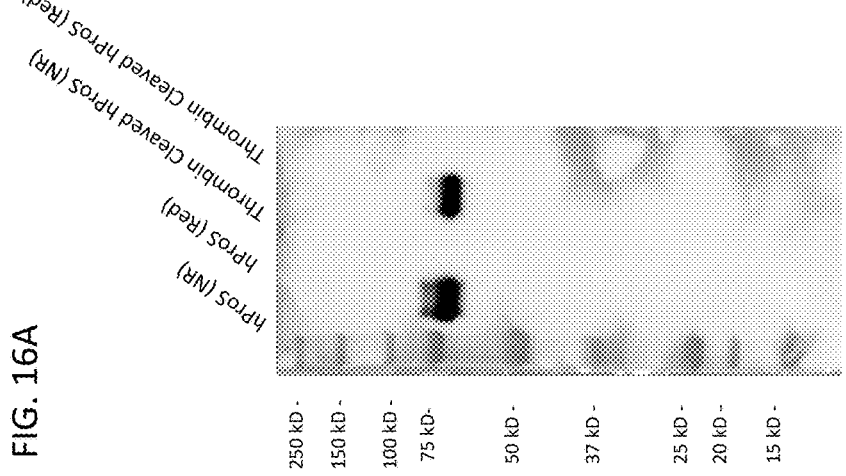

FIGS. 16B-16D depict the results of an APC cofactor assay for Antibody 20 using Protein S deficient human PPP, cynomolgus monkey PPP, and a TFPI cofactor assay using human PRP, respectively.

Figure 16F:
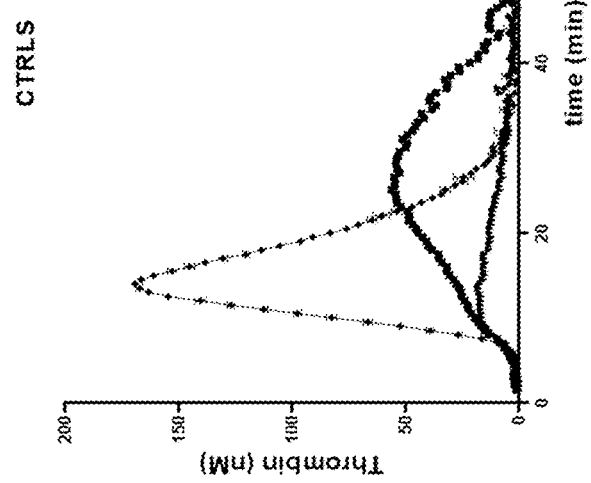
Figure 16E:
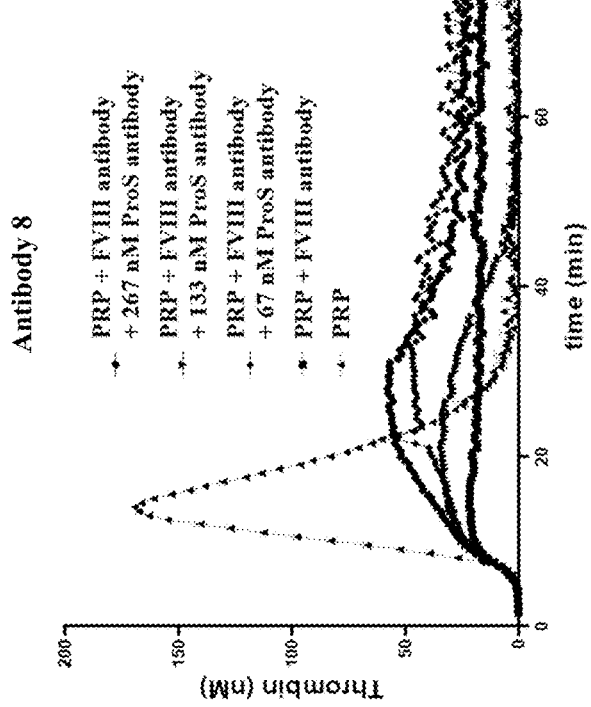

FIGS. 16E and 16F depict the results of a TFPI cofactor assay in human PRP using Antibody 8 and controls, respectively. A rabbit polyclonal human Protein S antibody labeled Dako was used as a positive control.

Figure 16H:
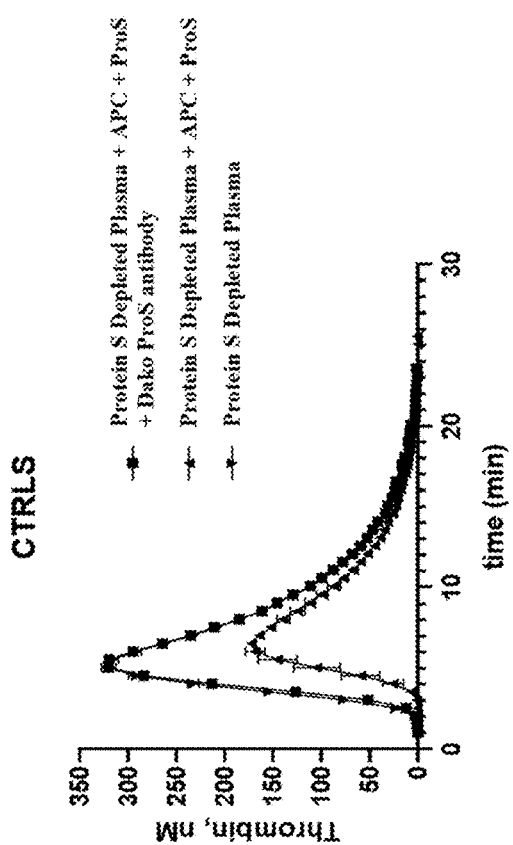
Figure 16G:
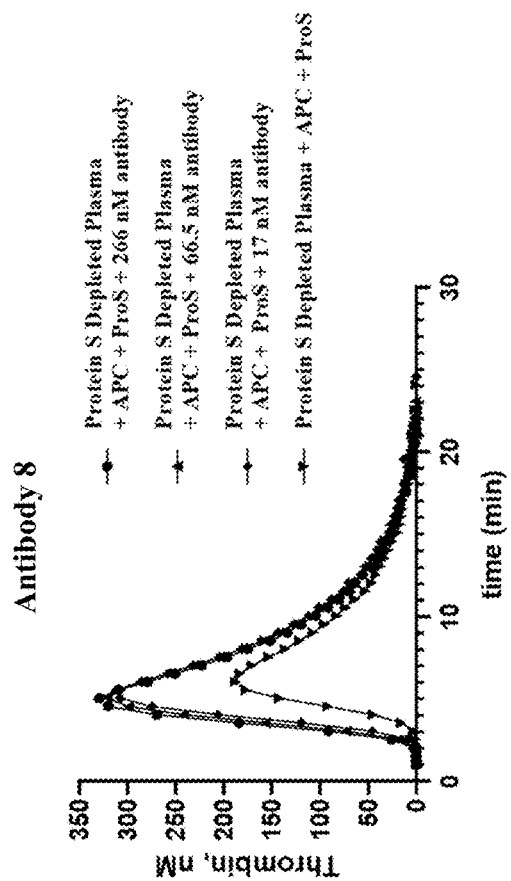

FIGS. 16G-16H depict the results of the APC cofactor assay performed with Antibody 8 and controls, respectively.

These results indicate that Antibody 20 and Antibody 8 are dual inhibitors.

Antibody 21 and Antibody 9

FIGS. 17A-17H depict the characterization of Antibody 21 and Antibody 9, antibodies sharing the same human variable region, and are characterized as APC cofactor inhibitors.

FIG. 17A depicts a Western blot showing that Antibody 21 does not bind Protein S in the TSR of Protein S. The Western blot was carried out as described for FIG. 11A. By Western blot, Antibody 21 bound the full Protein S and the thrombin-cleaved Protein S, but did not bind the reduced Protein S or the reduced thrombin-cleaved Protein S. These results indicate that Antibody 21 does not bind Protein S at the TSR, and the lack of signal observed with the reduced Protein S showed that the epitope for this antibody is not a linear epitope.

Binding to the heavy chain of Protein S was determined using an ELISA based method, as described herein. Antibody 21 was determined to bind to the heavy chain of Protein S. Calcium dependence was determined, also as described herein, and Antibody 21 showed binding that was calcium-independent.

FIGS. 17B-17D depict the results of an APC cofactor assay for Antibody 21 using Protein S deficient human PPP, cynomolgus monkey PPP, and a TFPI cofactor assay using human PRP, respectively.

Figure 17F:
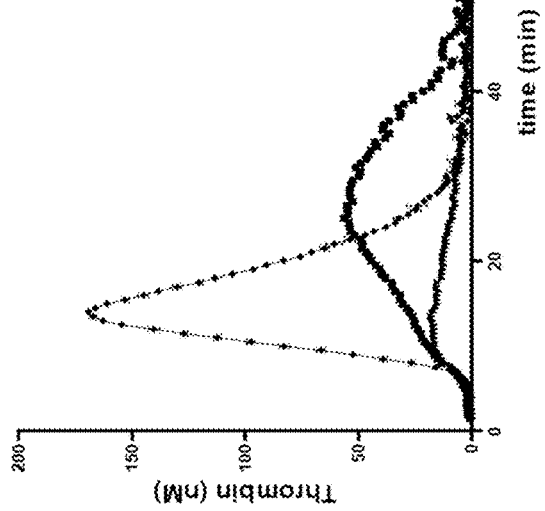
Figure 17E:
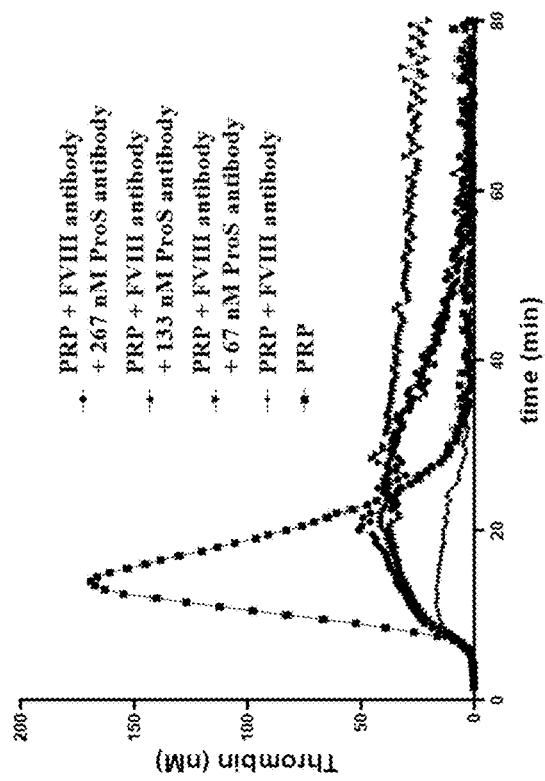

FIGS. 17E and 17F depict the results of a TFPI cofactor assay in human PRP using Antibody 9 and controls, respectively. A rabbit polyclonal human Protein S antibody labeled Dako was used as a positive control.

Figure 17H:
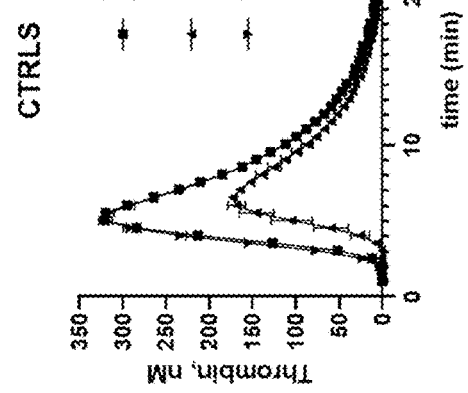
Figure 17G:
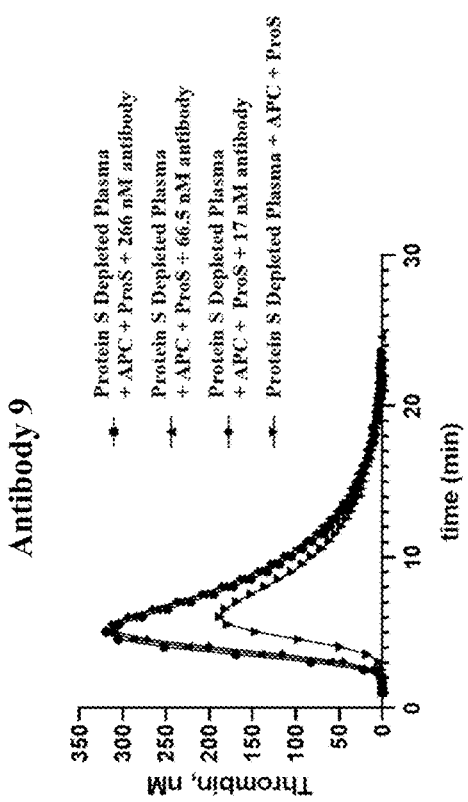

FIGS. 17G-17H depict the results of the APC cofactor assay performed with Antibody 9 and controls, respectively.

These results indicate that Antibody 21 and Antibody 9 are APC cofactor inhibitors.

Antibody 23 and Antibody 11

FIGS. 18A-18G depict the characterization of Antibody 23 and Antibody 11, antibodies sharing the same human variable region, and are characterized as TFPI cofactor inhibitors.

Binding to the heavy chain of Protein S was determined using an ELISA based method, as described herein. Antibody 23 was determined to not bind to the heavy chain of Protein S. Calcium dependence was determined, also as described herein, and Antibody 23 showed binding that was calcium-independent.

Figure 18A:
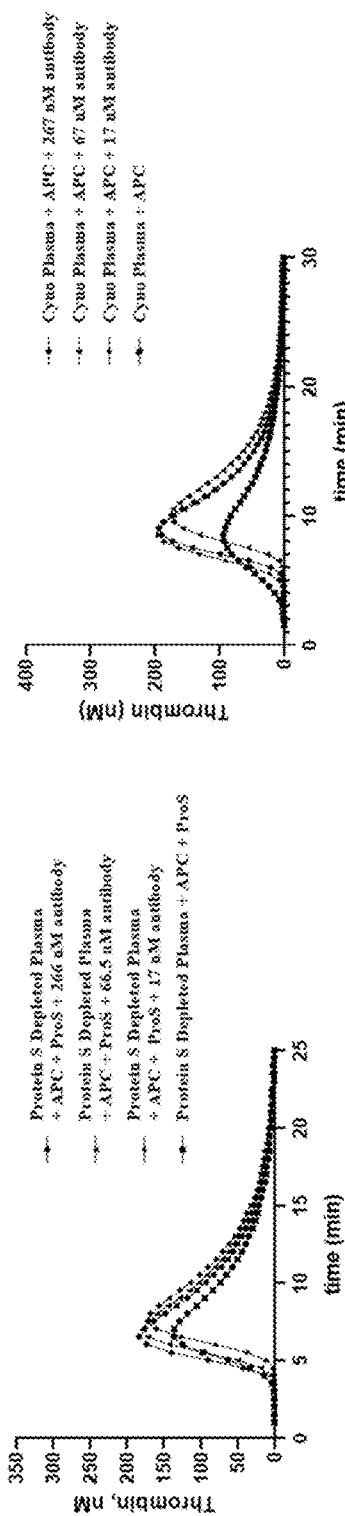
FIGS. 18A-18G depict the characterization of Antibody 23 and Antibody 11, antibodies sharing the same human variable region, and are characterized as TFPI cofactor inhibitors.
Figure 18B:
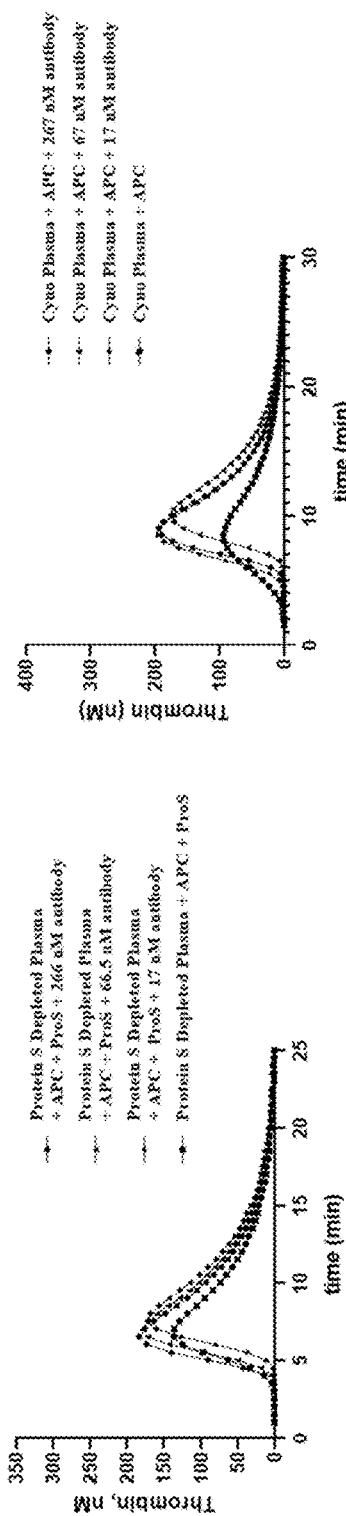
Figure 18C:
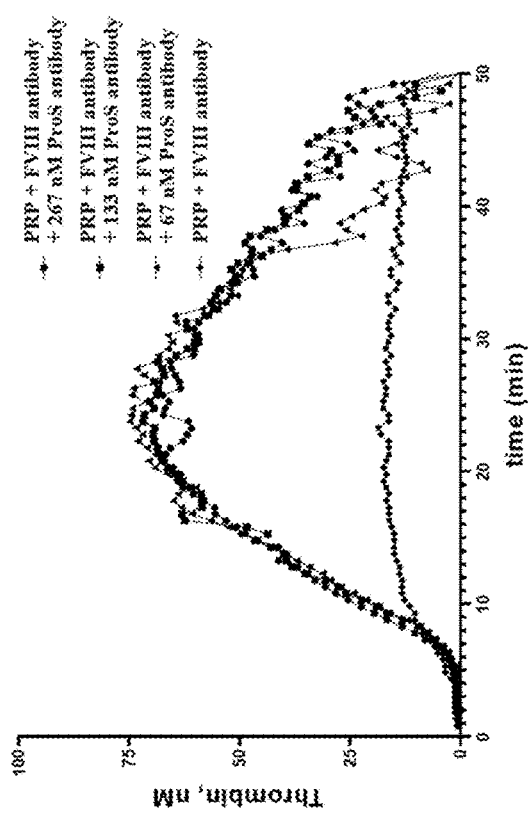

FIGS. 18A-18C depict the results of a APC cofactor assay for Antibody 23 using Protein S deficient human PPP, cynomolgus monkey PPP, and a TFPI cofactor assay using human PRP, respectively.

Figure 18E:
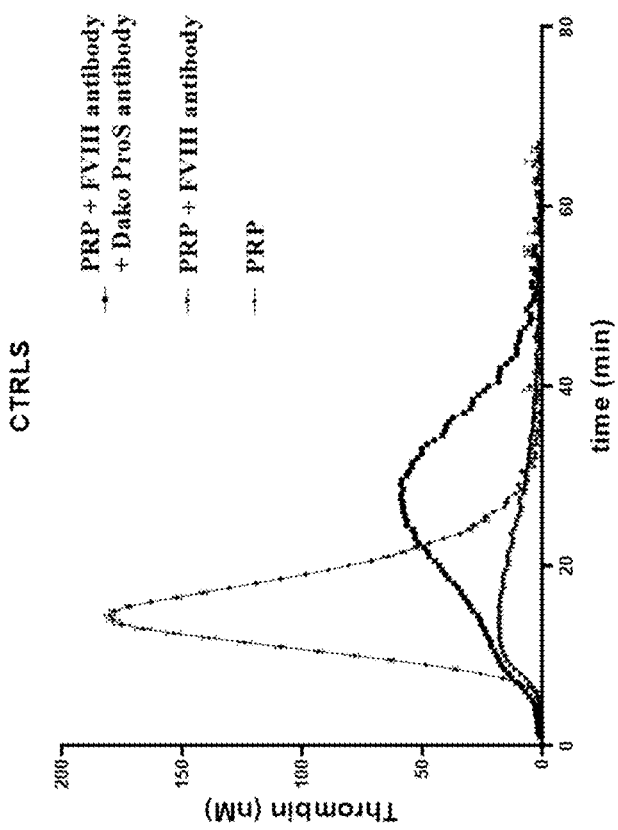
Figure 18D:
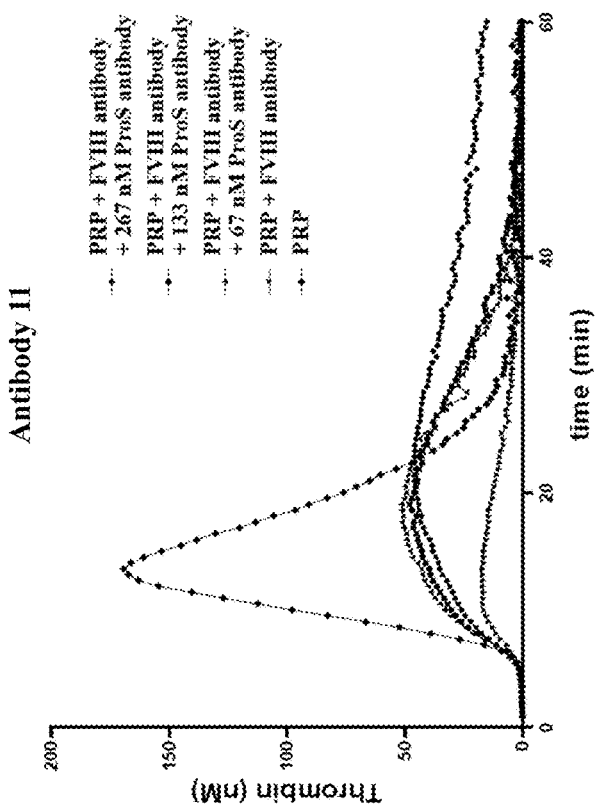

FIGS. 18D and 18E depict the results of a TFPI cofactor assay in human PRP using Antibody 11 and controls, respectively.

Figure 18F:
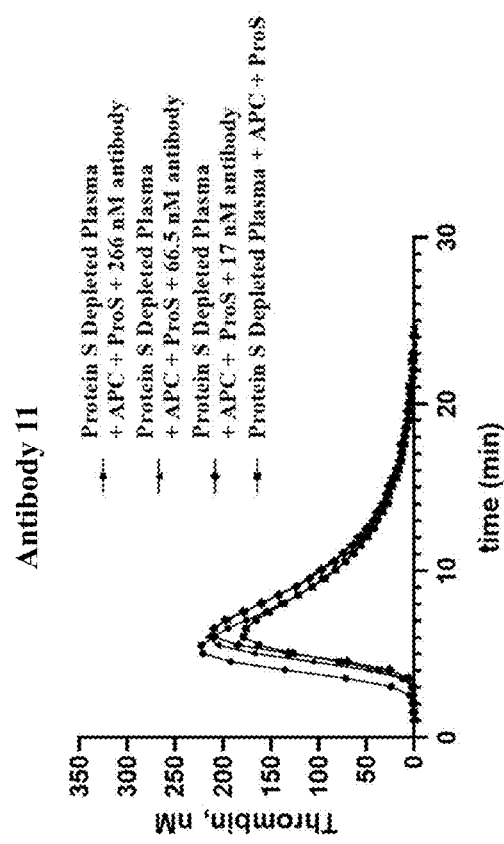
Figure 18G:
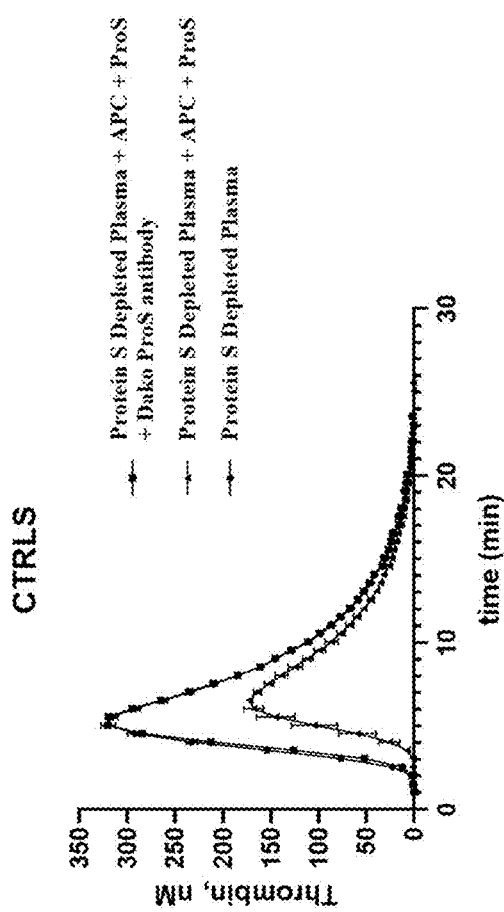

FIGS. 18F and 18G depict the results of a APC cofactor assay with Antibody 11 and controls, respectively.

These results indicate that Antibody 23 and Antibody 11 are TFPI cofactor inhibitors.

Antibody 24 and Antibody 12

FIGS. 19A-19H depict the characterization of Antibody 24 and Antibody 12, antibodies sharing the same human variable region, and are characterized as dual inhibitors.

FIG. 19A depicts a Western blot showing that Antibody 24 binds Protein S in the TSR of Protein S. The Western blot was carried out as described for FIG. 11A. By Western blot, Antibody 24 bound the full Protein S but did not bind the thrombin-cleaved Protein S. Antibody 24 did not bind the reduced Protein S or the reduced thrombin-cleaved Protein S. These results indicate that Antibody 24 binds Protein S at the TSR, and the lack of signal observed with the reduced Protein S showed that the epitope for this antibody is not a linear epitope.

Binding to the heavy chain of Protein S was determined using an ELISA based method, as described herein. Antibody 24 was determined to bind to the heavy chain of Protein S. Calcium dependence was determined, also as described herein, and Antibody 24 showed binding that was calcium-dependent.

FIGS. 19B-19D depict the results of a APC cofactor assay for Antibody 24 using Protein S deficient human PPP, cynomolgus monkey PPP, and a TFPI cofactor assay using human PRP, respectively.

Figure 19F:
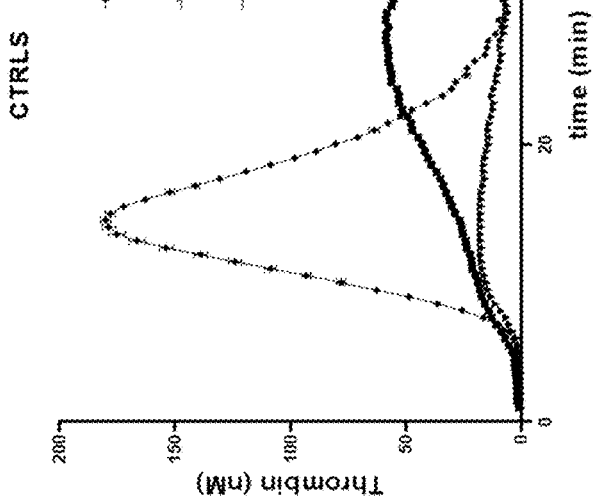
Figure 19E:
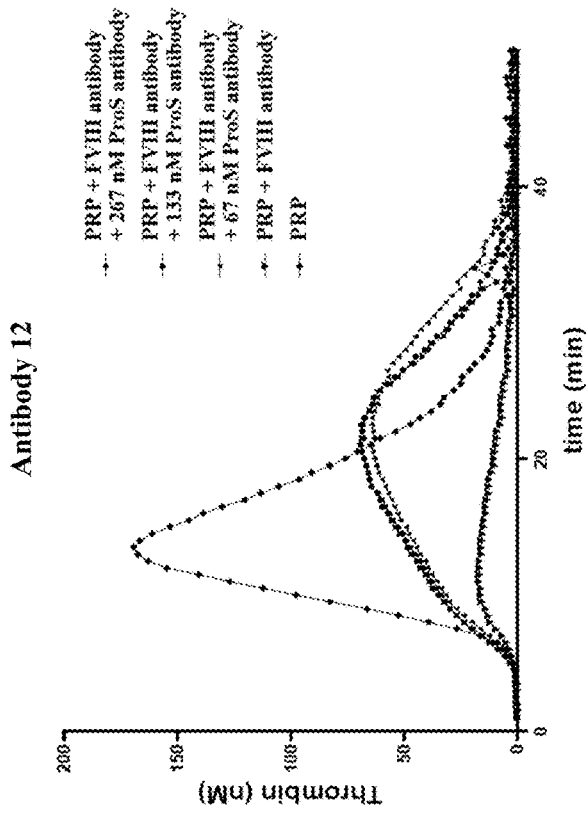

FIGS. 19E and 19F depict the results of a TFPI cofactor assay in human PRP using Antibody 12 and controls, respectively.

Figure 19H:
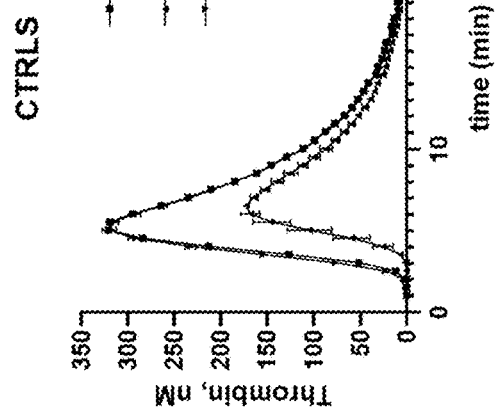
Figure 19G:
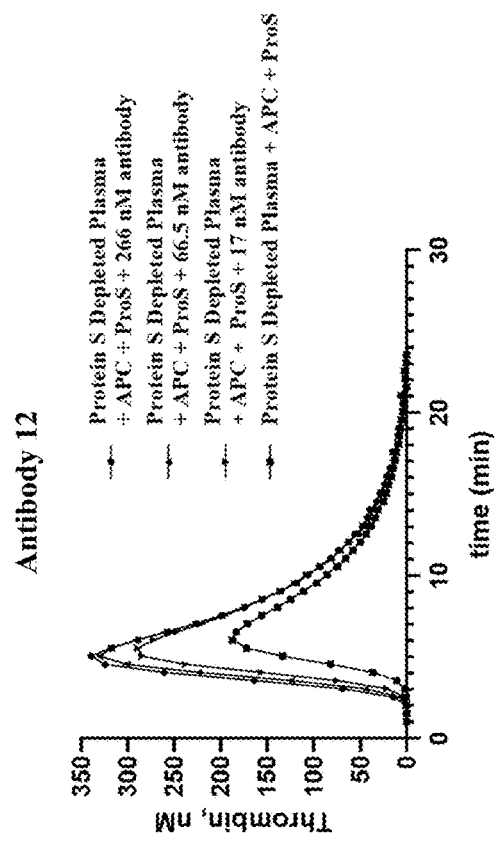

FIGS. 19G and 19H depict the results of a APC cofactor assay with Antibody 12 and controls, respectively.

These results indicate that Antibody 24 and Antibody 12 are dual inhibitors.

Antibody 18 and Antibody 6

FIGS. 20A-20H depict the characterization of Antibody 18 and Antibody 6, antibodies sharing the same human variable region, and are characterized as APC cofactor inhibitors.

Figure 20A:
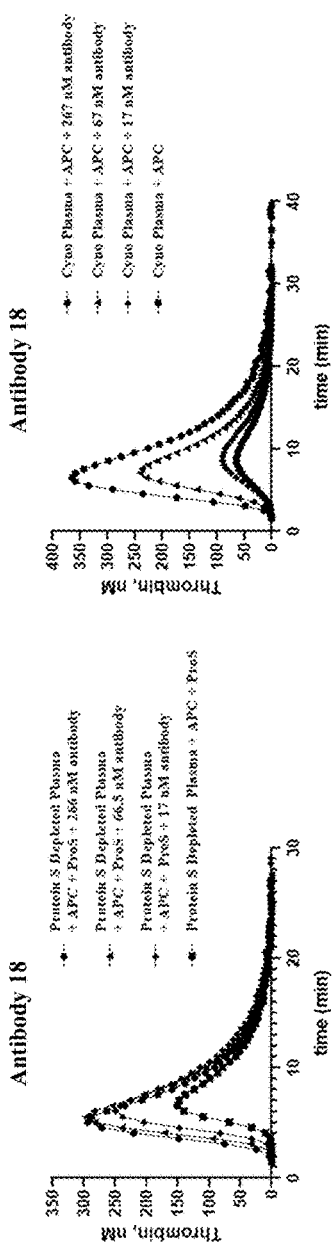
FIGS. 20A-20H depict the characterization of Antibody 18 and Antibody 6, antibodies sharing the same human variable region, and are characterized as APC cofactor inhibitors.

FIG. 20A depicts a Western blot showing that Antibody 18 does not bind Protein S in the TSR of Protein S. The Western blot was carried out as described for FIG. 20A. By Western blot, Antibody 18 bound the full Protein S and the thrombin-cleaved Protein S, but did not bind the reduced Protein S or the reduced thrombin-cleaved Protein S. These results indicate that Antibody 18 does not bind Protein S at the TSR, and the lack of signal observed with the reduced Protein S showed that the epitope for this antibody is not a linear epitope.

Binding to the heavy chain of Protein S was determined using an ELISA based method, as described herein. Antibody 18 was determined to bind to the heavy chain of Protein S. Calcium dependence was determined, also as described herein, and Antibody 18 showed binding that was calcium-dependent.

Figure 20B:
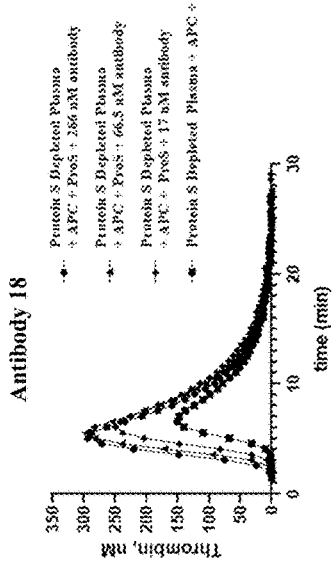
Figure 20C:
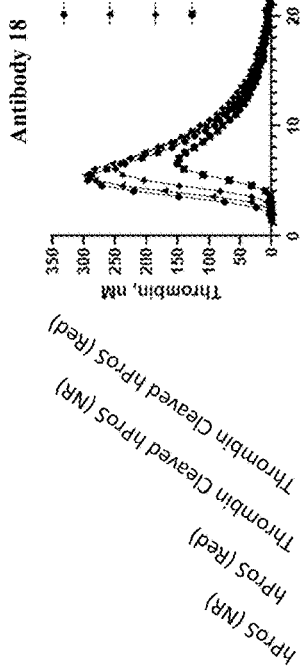
Figure 20D:
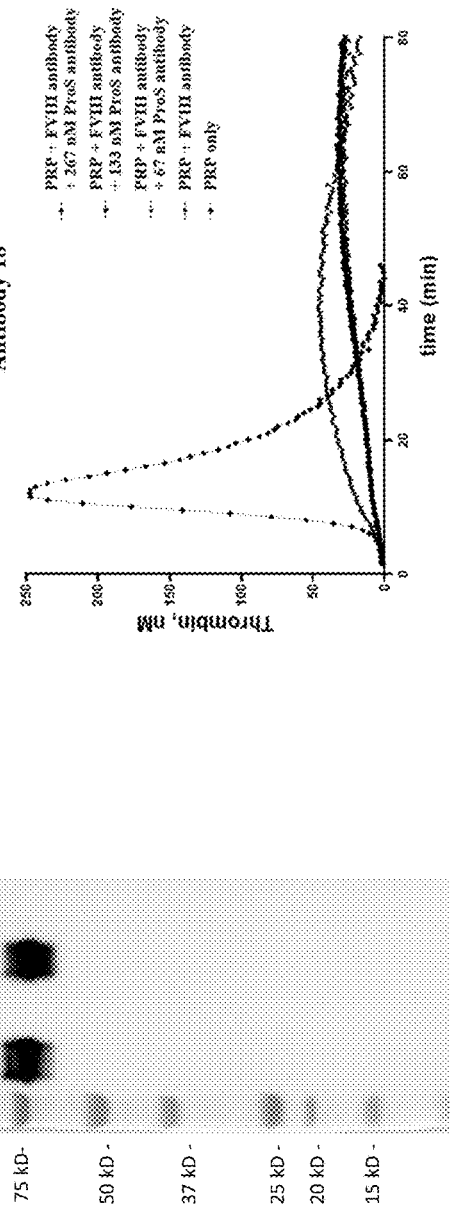

FIGS. 20B-20D depict the results of a APC cofactor assay for Antibody 18 using Protein S deficient human PPP, cynomolgus monkey PPP, and a TFPI cofactor assay using human PRP, respectively.

Figure 20E:
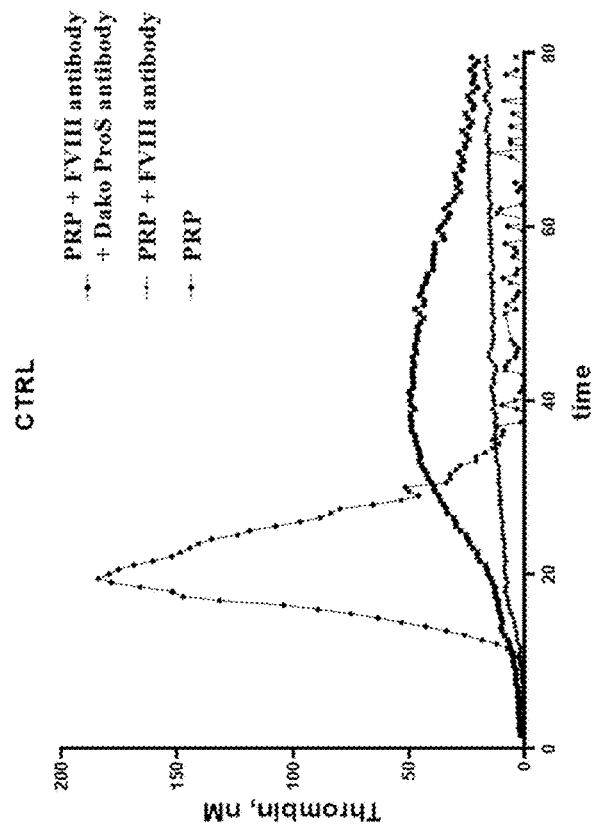
Figure 20F:
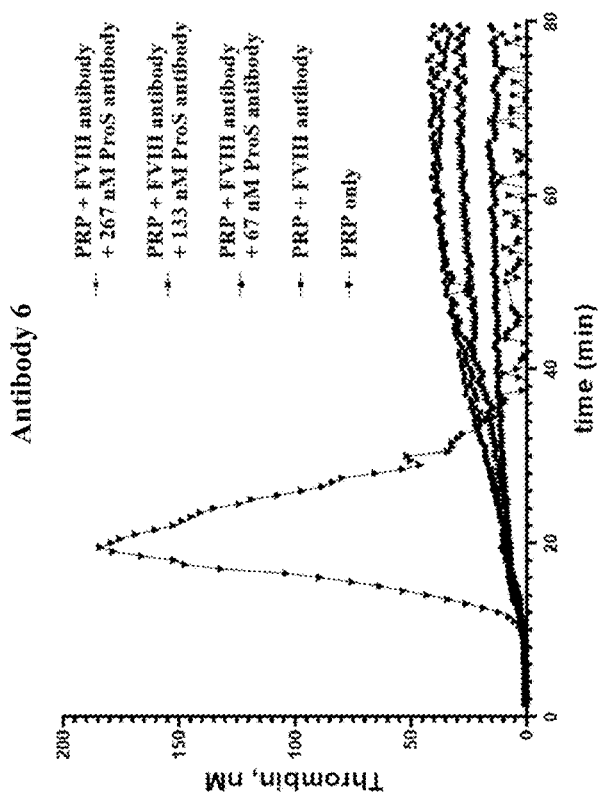

FIGS. 20E and 20F depict the results of a TFPI cofactor assay in human PRP using Antibody 6 and controls, respectively.

Figure 20H:
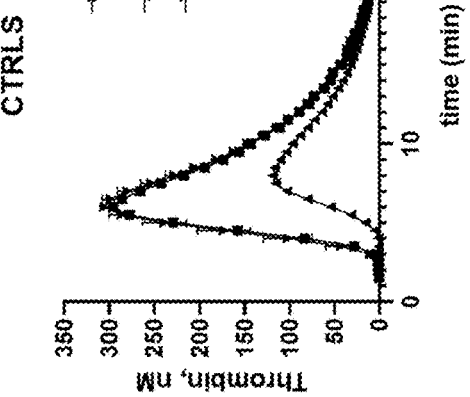
Figure 20G:
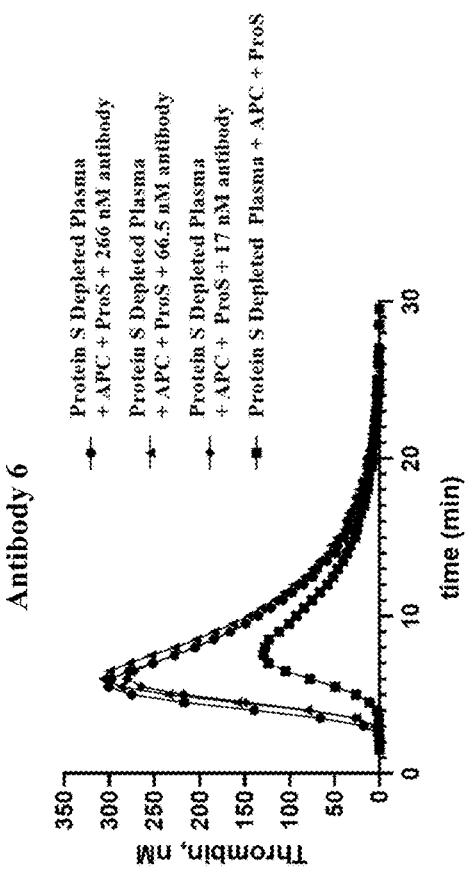

FIGS. 20G and 20H depict the results of a APC cofactor assay with Antibody 6 and controls, respectively.

These results indicate that Antibody 18 and Antibody 6 are APC cofactor inhibitors.

A summary of the characterizations exemplified above is presented in Table 13 below.

TABLE 13

| Human Antibody: Corresponding Protein S Antibody with Human Fc | Rat Antibody: Protein S Antibody with Rat Fc | Inhibitor Type |
|---|---|---|
| Antibody 1 | Antibody 13 | Dual |
| Antibody 2 | Antibody 14 | Dual |
| Antibody 3 | Antibody 15 | Dual |
| Antibody 4 | Antibody 16 | Dual |
| Antibody 6 | Antibody 18 | APC cofactor |
| Antibody 7 | Antibody 19 | Dual |
| Antibody 8 | Antibody 20 | Dual |
| Antibody 9 | Antibody 21 | APC cofactor |
| Antibody 11 | Antibody 23 | TFPI cofactor |
| Antibody 12 | Antibody 24 | Dual |

Example 4: Thrombin Generation Improvement in Plasma Samples from Patients with Various Factor Deficiencies and Von Willebrand Disease FIGS. 21A-21G depict enhanced thrombin generation when Antibody 15 is added to various samples of congenital factor deficient plasma containing soluble thrombomodulin, a cofactor of thrombin that is involved in conversion of thrombin to an anti-coagulant enzyme. Plasma samples were taken from patients having various factor deficiencies and conditions: Factor VII, Factor VIII, Factor IX, or Factor XI deficiencies, and von Willebrand disease (vWD) type 1, 2, or 3.

Figure 21A:
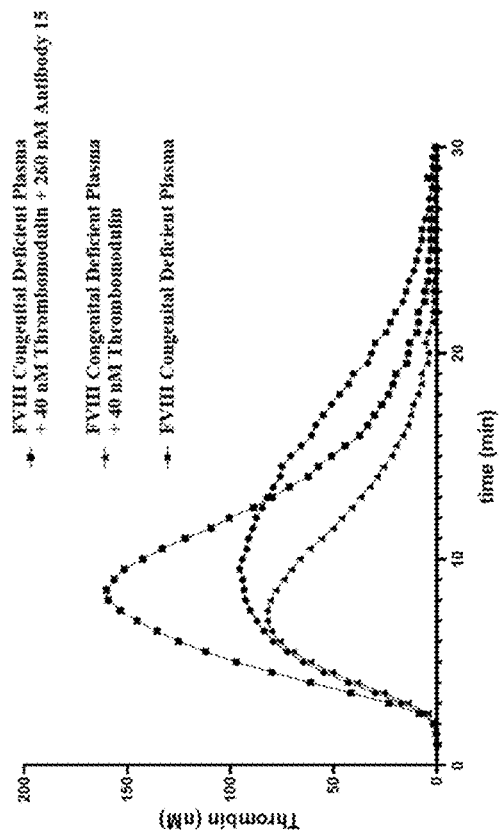
FIGS. 21A-21G depict enhanced thrombin generation when Antibody 15 is added to various samples of congenital factor deficient plasma containing soluble thrombomodulin.
Figure 21B:
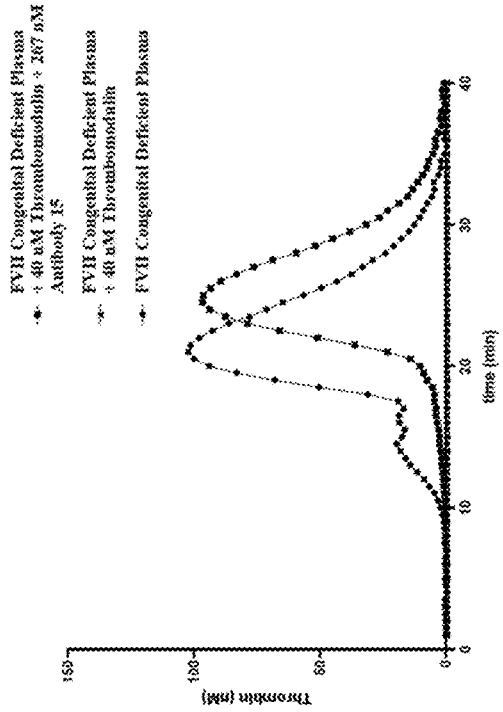
Figure 21C:
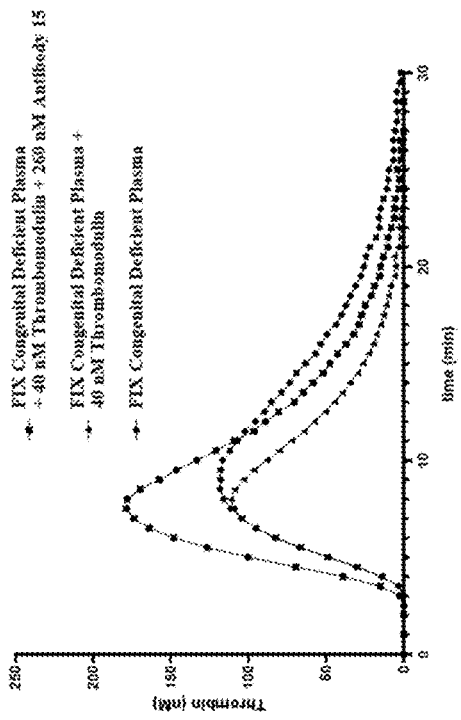
Figure 21E:
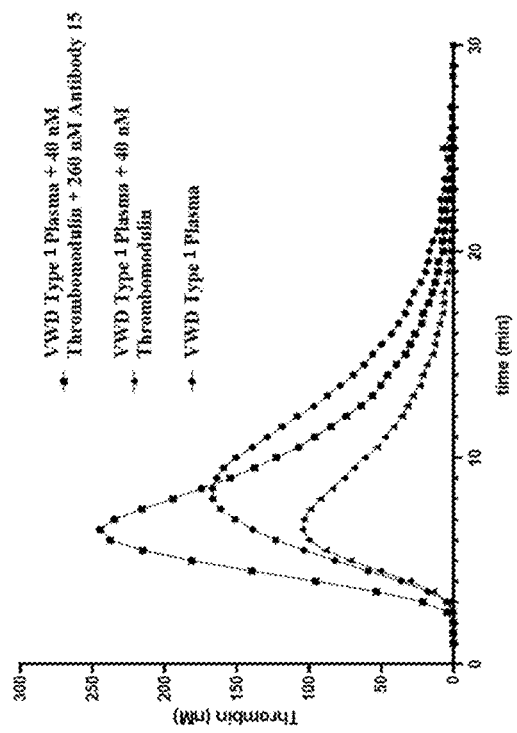
Figure 21D:
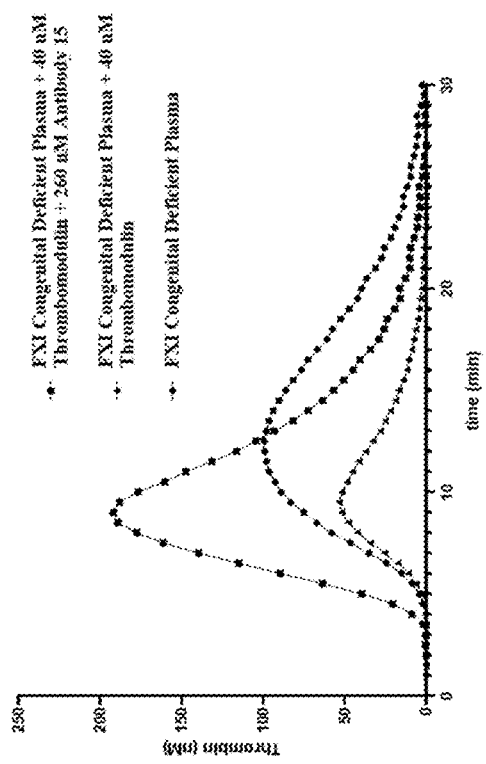
Figure 21F:
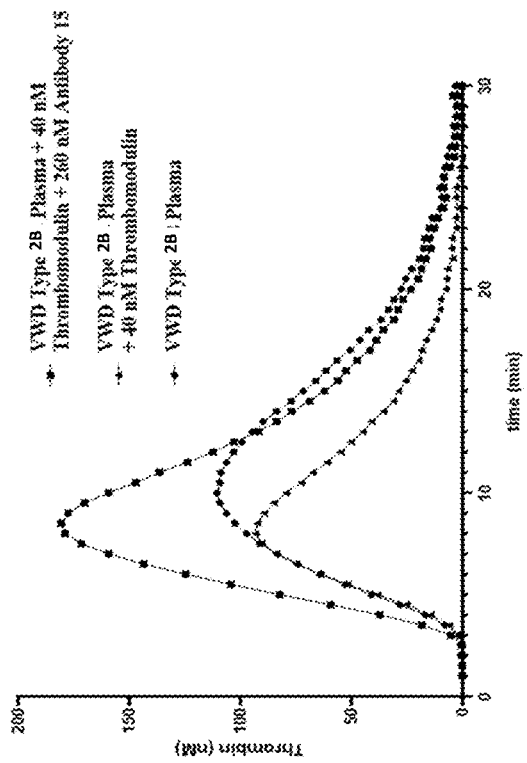
Figure 21G:
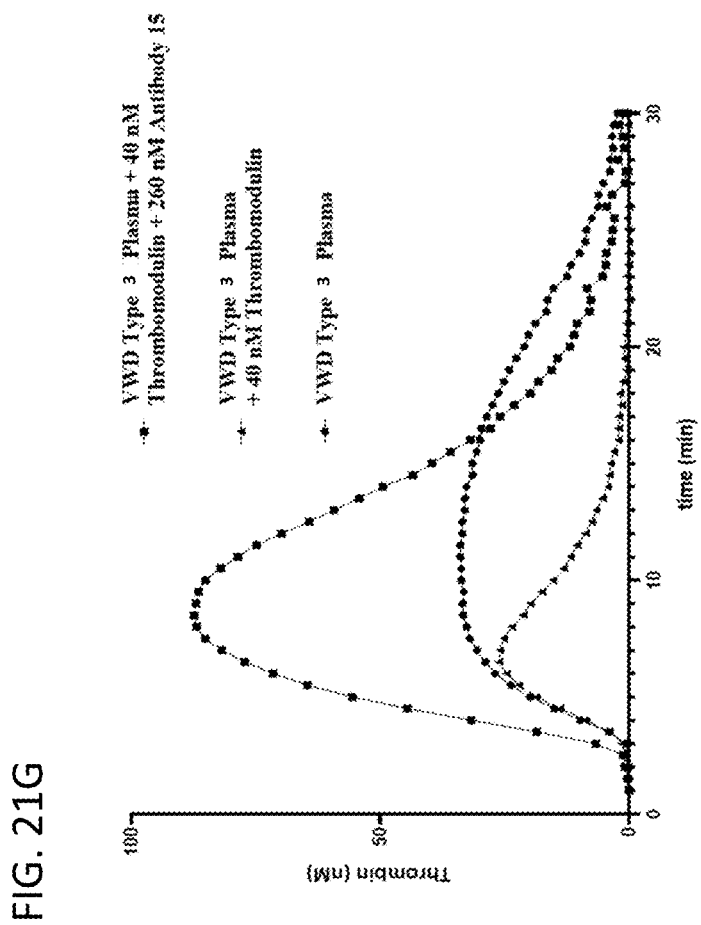

FIG. 21A depicts soluble tissue factor added to congenital Factor VII deficient plasma in the presence or absence of 40 nM soluble thrombomodulin. The level of thrombin generated is measured over time. When Antibody 15 is added to the deficient plasma containing thrombomodulin, increased thrombin was observed. FIGS. 21B-21G depict data generated from experiments performed in a similar manner, but using congenital Factor VIII deficient plasma, congenital Factor IX deficient plasma, congenital Factor XI deficient plasma, vWD type 1 plasma, vWD type 2B plasma or vWD type 3 plasma, respectively. These results show that the tested antibodies were able to promote thrombin generation in samples having a factor deficiency or vWD disease.

Figure 22A:
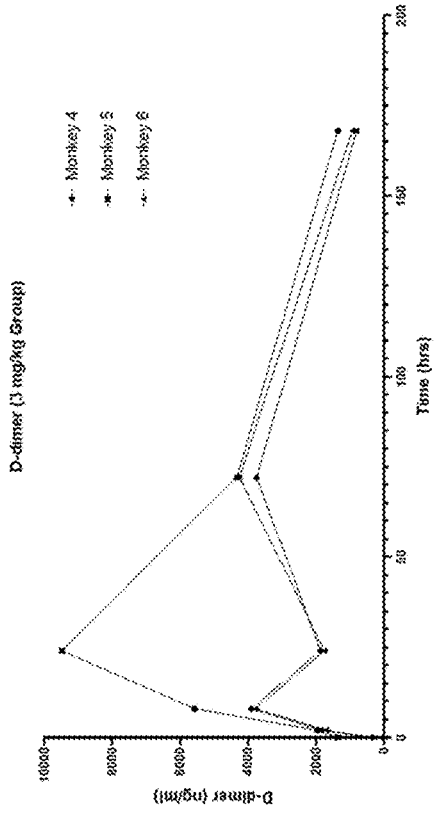
FIGS. 22A-22B depict the levels of D-dimer, as a marker of coagulation activity, observed over time in cynomolgus monkeys injected with either 1 mg/kg or 3 mg/kg of Antibody 1.
Figure 22B:
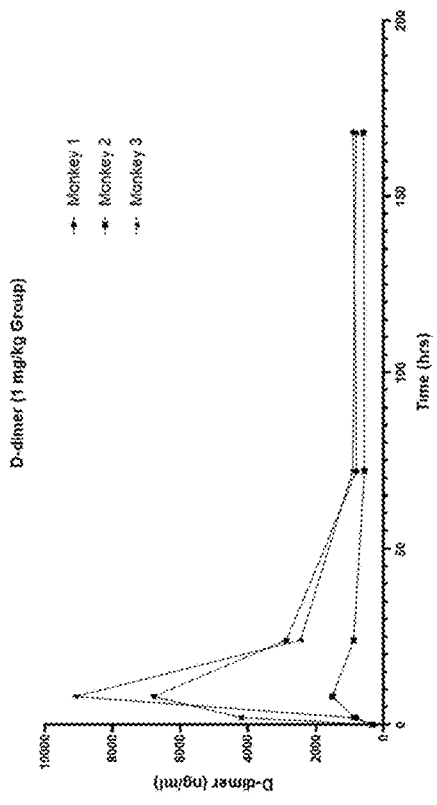

Example 5: Activity of Protein S Antibodies Post-Treatment in Cynomolgus Monkeys Using D-Dimer as a Marker FIGS. 22A and 22B depict D-dimer levels observed in cynomolgus monkeys treated with 1 mg/kg or 3 mg/kg, respectively, of Antibody 1. At varying times post-injection of the antibody, blood was collected in sodium citrate tubes. Plasma samples were analyzed for the presence of D-dimer, a fibrin degradation product which acts as a marker of coagulation. Increases in the levels of D-dimer indicated that the tested antibodies activate the coagulation cascade and remain active in vivo for a period of time after treatment. FIG. 22A shows that treatment with 1 mg/kg of Antibody 1 showed activity for approximately 70 hours after treatment, and FIG. 22B shows that treatment with 3 mg/kg of Antibody 1 showed activity for approximately 105-110 hours after treatment.

Example 6: Restoration of Fibrin Deposition by Protein S Antibodies

Figure 23C:
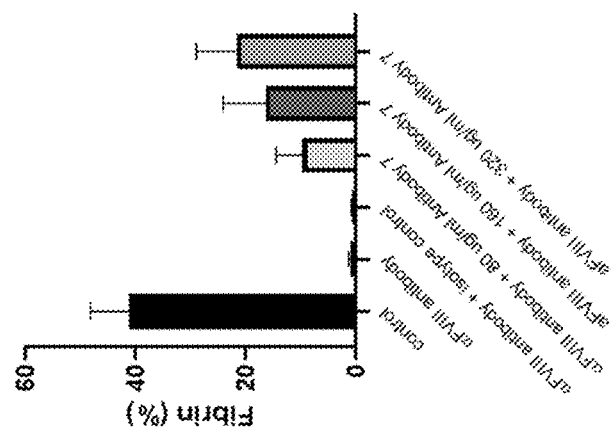
FIGS. 23A-23C depict the level of fibrin deposited onto collagen coated spots in Factor VIII (FVIII) neutralized blood treated with various Protein S antibodies, showing a restoration of fibrin deposition activity by the Protein S antibodies in monoclonal humanized antibodies. In some embodiments, the antibodies are monoclonal chimeric antibodies.
Figure 23B:
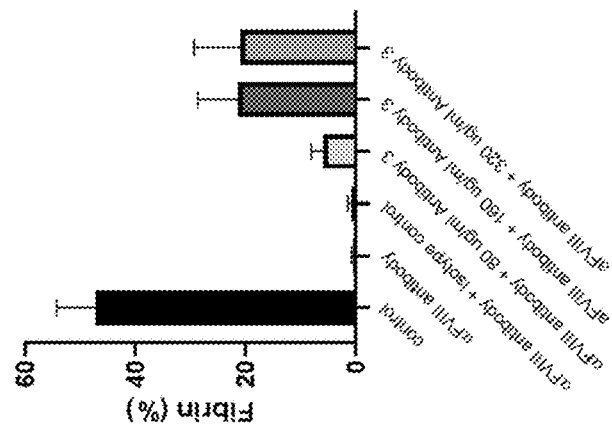
Figure 23A:
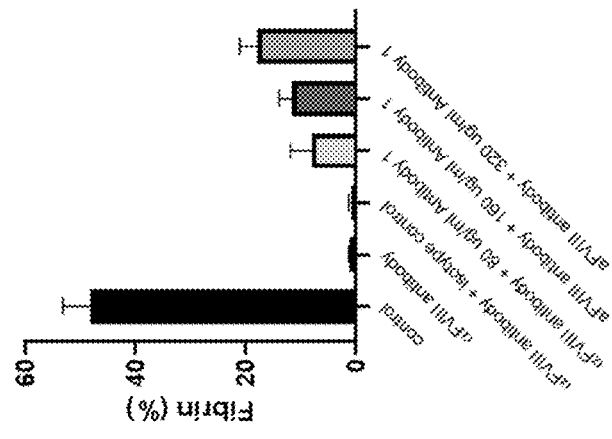

FIGS. 23A-23C depict the level of fibrin deposited onto collagen spots in a microfluidic system. Certain coagulation factor deficiencies can cause fibrin deposition to be at levels lower than that of subjects not having a factor deficiency. The microfluidic system can allow measurement of coagulation occurring during flow of blood.

Normal human blood, from a patient without any factor deficiencies, was untreated or treated with Factor VIII (FVIII) neutralizing antibody. This was then passed over collagen spots in a microfluidic system. Strong fibrin deposition was observed in untreated blood, but not in treated blood. When Antibodies 1, 3 and 7 were added to the treated blood, fibrin deposition was restored in a dose dependent manner. These results show that in blood neutralized with FVIII antibody, the Protein S antibodies disclosed herein may be used for restoration of fibrin formation or deposition, which may serve as a desired marker for coagulation activity.

Example 7: Binding of Protein S Antibodies to the Protein S-C4BP Complex

The Octet assay was used to determine the capability of the Protein S antibodies provided herein to bind to Protein S either alone, or when complexed to C4BP. A summary of the binding to Protein S or the Protein S-C4BP complex is provided in Table 14. Table 14 presents an X where a tested antibody was able to bind to either the Protein S-C4BP Complex, and/or the Protein S alone. A dash indicates that the binding did not occur.

Using the Octet System (Sartorius), the binding of each antibody to both Protein S and Protein S in complex with C4BP was determined. It had previously been determined that the C4BP preparation from Complement Technologies contains Protein S precomplexed to human C4BP. Therefore, this preparation represented the Protein S-C4BP complex and plasma purified Protein S from Haematologic Technologies was used as the source of free Protein S. The human Fc antibodies were immobilized onto anti-human Fc capture probes by placing the probes into 10 µg/ml antibody solution in 10 mg/ml bovine serum albumin, 20 mM Tris pH 7.0, 150 mM NaCl, and 4 mM calcium chloride. Then the bound antibodies were placed into solutions containing either 75 µg/ml Protein S or 100 µg/ml C4BP (C4BP-Protein S complex). With antibodies that do not bind Protein S in complex with C4BP, no binding is observed. With antibodies that bind Protein S in free form or in complex with C4BP, an association is observed under both conditions. All antibodies tested bound free Protein S, as depicted in Table 14.

TABLE 14

| Antibody with Human Fc | Binding to ProS-C4BP Complex | Binding to ProS |
|---|---|---|
| Antibody 1 | X | X |
| Antibody 2 | X | X |
| Antibody 3 | X | X |
| Antibody 4 | X | X |
| Antibody 6 | X | X |
| Antibody 7 | X | X |
| Antibody 8 | X | X |
| Antibody 9 | X | X |
| Antibody 11 | — | X |
| Antibody 12 | X | X |
| Antibody 25 | — | X |
| Antibody 27 | X | X |
| Antibody 28 | X | X |
| Antibody 29 | — | X |
| Antibody 30 | — | X |
| Antibody 37 | — | X |
| Antibody 39 | — | X |
| Antibody 41 | — | X |
| Antibody 43 | X | X |

Example 8: Effects of Protein S Antibodies on Fibrin Deposition

These experiments were carried out as follows. Bioflux 1000z 48-well high shear microfluidics plates (0-200 dynes/cm2) employed in the experiments were purchased from Bioflux. The device has the #1.5 borosilicate glass coverslip which forms the floor of the microfluidic channel engineer to facilitate the coated of collagen. Collagen type 1 was purchase from Chrono-Par collagen (chrono-Log Corp, Havertown, PA). Collagen was perfused from the wells at room temperature and incubated for 1 hour. Precoated plates with collagen type 1 were rinsed with PBS and channels were blocked with 0.5% (v/v) BSA for 10 min in PBS prior to the addition of the labeled blood to the wells. Sodium citrate anti-coagulated whole human blood (ALLCells, Oakland, CA) was used within 4-8 h of collection. Whole blood was incubated for 1 hour with 100 µg/mL Sheep anti-Human Factor VIII (Haematologic Technologies, Essex, VT). The antibodies were added and incubated with whole blood. Fibrinogen from human plasma, Alexa Fluor 546 (Invitrogen, Carlsbad, CA) was added at a final concentration of 50 µg/mL prior to biological experiments. Whole blood was added to the input wells and perfused at 30 dyn/cm2 using the BioFlux Controller and software. The samples were illuminated for no more than 30 ms for each capture. The BioFlux software imaging module was used to control the image acquisition settings and to process the fluorescence intensity measurements. Fluorescent micrographs were captured with the blood under flow using an inverted microscope (ZEISS Axio Observer 7) and sCMOS Camera. Images were timelapse recorded using the BioFlux 1000 imaging system (Fluxion Biosciences). Data was processed using BioFlux Montage Software.

Figure 25A:
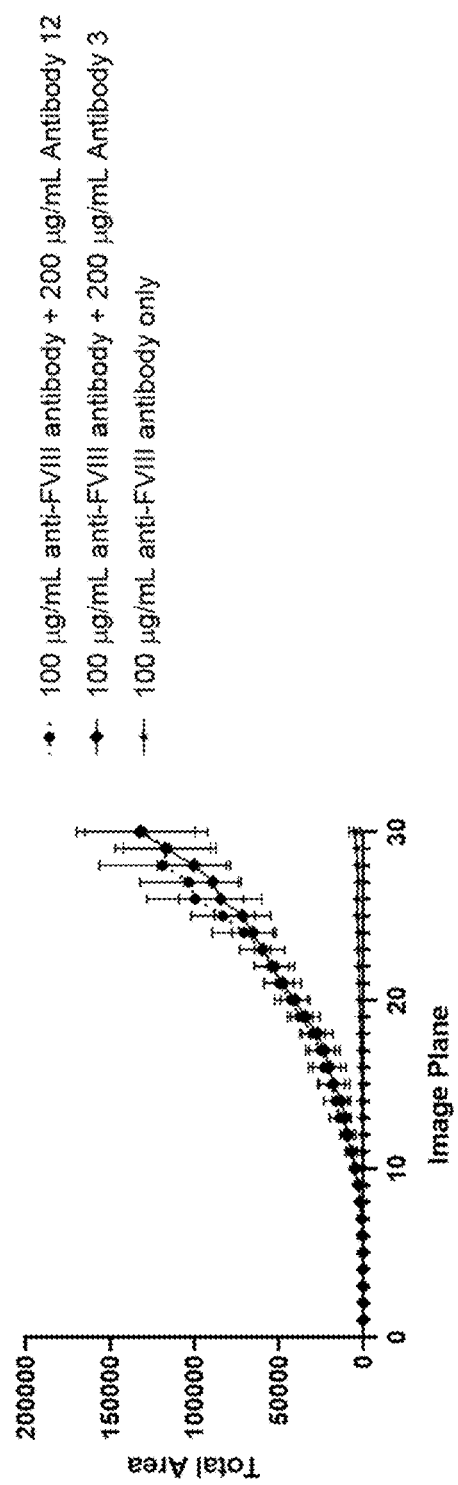
Figure 25B:
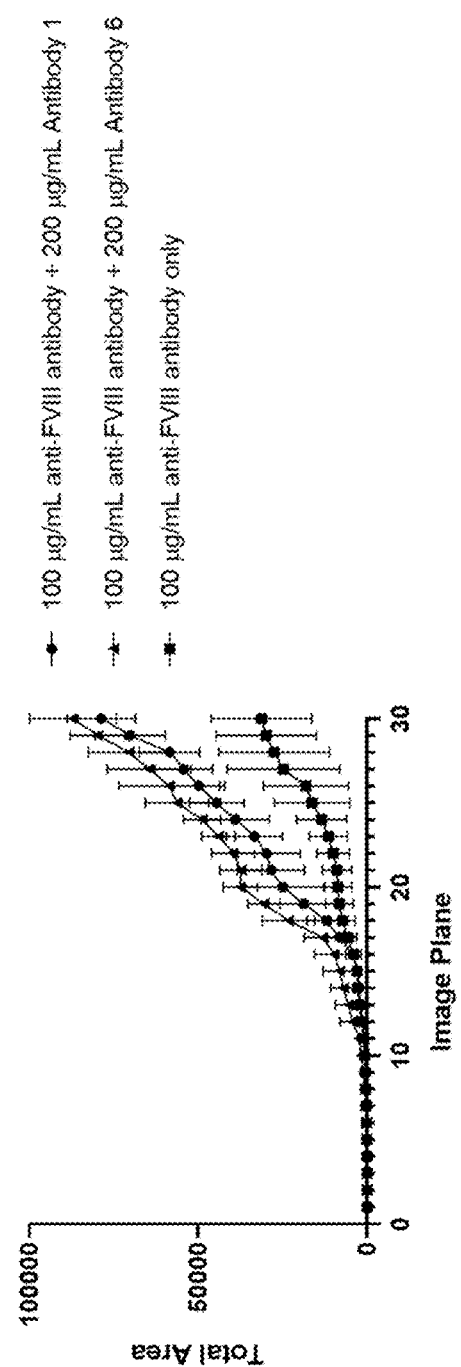

FIGS. 25A-25B depict the level of fibrin deposition resulting from the Protein S antibodies added to whole blood treated with Factor VIII neutralizing antibodies. This experiment tests the ability of the Protein S antibodies to restore or increase fibrin deposition in an in vitro microfluidic Hemophilia A model. Whole blood was treated with Factor VIII antibody to decrease fibrin deposition. FIG. 25A depicts the effects of Antibodies 12, and 3, and a control on fibrin deposition in anti-FVIII treated human plasma, and FIG. 25B depicts the effects of Antibodies 1 and 6 and a control on fibrin deposition in anti-FVIII treated human plasma. These results demonstrate that the Protein S antibodies 12, 3, 1 and 6 could restore or increase fibrin deposition in an in vitro microfluidic Hemophilia A model.

Example 9: Effect of Protein S Antibodies in an In Vitro Microfluidics Hemophilia A Bleeding Model These experiments were carried out using a fully endothelialized microfluidic system that was coupled to a microengineered pneumatic valve that mimics vascular damage (Sakurai, et al. Nature Communications 2018). Briefly, whole blood collected from healthy volunteers were treated with a sheep anti-human FVIII antibody to mimic whole blood from a hemophilia A patient. After treatment, the whole blood was perfused into the microfluidics system at which time an "injury" was introduced using the pneumatic valve. The localization of both platelets and fibrin at the site of "injury" was monitored and the time to cessation of "bleeding" was measured.

Figure 26A:
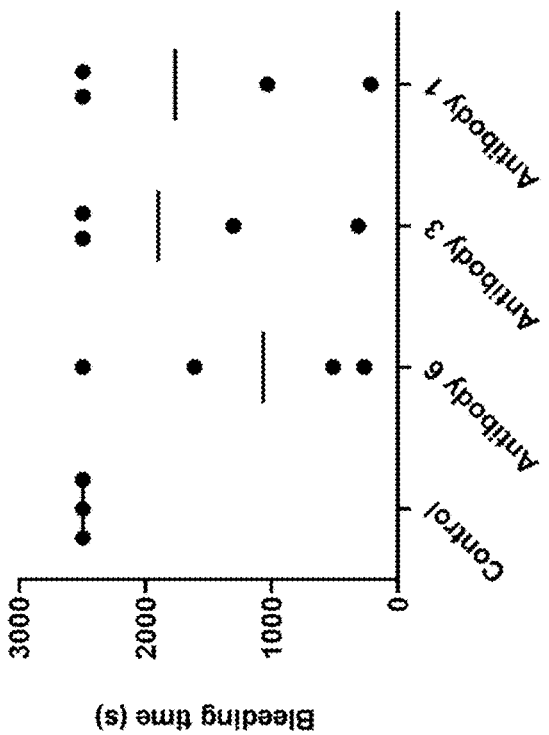
Figure 26B:
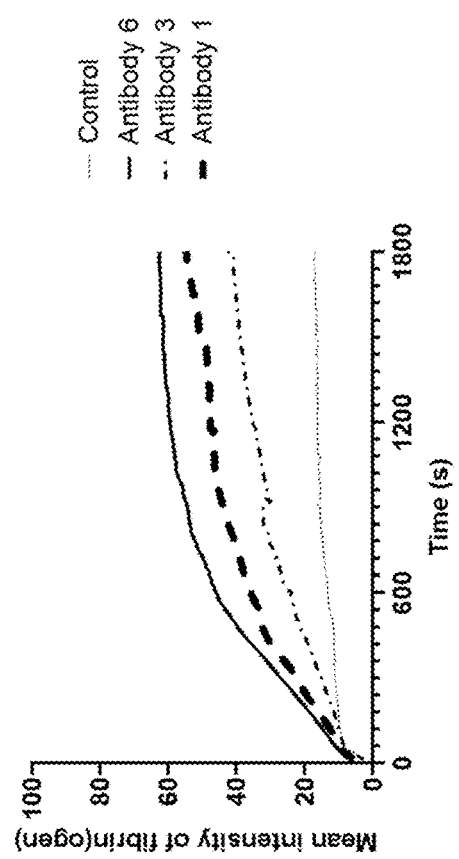

FIGS. 26A-26B depict the effects of Protein S antibodies in an in vitro microfluidics Hemophilia A bleeding model, measured by microfluidics experiments. These experiments were performed to measure the time of various Protein S antibodies to stop bleeding, and to determine the extent to which these antibodies induced fibrin deposition, respectively, in a microengineered, vascularized Hemophilia A bleeding model. The tested antibodies were Antibodies 6, 3, and 1. These results demonstrate that the antibodies were able to restore or increase fibrin deposition in a Hemophilia A bleeding model and therefore stop bleeding.

Example 10: Effect of Protein S Antibodies on Thrombin Generation

These experiments were carried out as follows. The Thrombin Generation Assay (TGA) was performed using a Thermo Fluoroskan Ascent Microplate Fluorometer and Thrombinoscope software. The PPP low reagent (Diagnostica Stago) was used in this experiment. Briefly, plasma from von Willebrand diseased patients was mixed with increasing levels of Protein S antibodies and incubated at room temperature. Then soluble human thrombomodulin was added prior to initiation of the reaction. To start the reaction, PPP low reagent was added along with calcium and the thrombin substrate. The levels of thrombin were then monitored.

FIGS. 27A-27F depict various results of enhanced dose-dependent thrombin generation when Protein S antibodies were added to plasma obtained from patients with various types of von Willebrand disease, with thrombomodulin added. These results demonstrate that the Protein S antibodies could effectively increase thrombin generation in a dose-dependent manner, and that different Protein S antibodies were more efficacious for different types of von Willebrand disease. Generally, the tested antibodies were more effective at increasing thrombin generation for Type 1 than Types 2A, 2B, and 3.

Figure 27B:
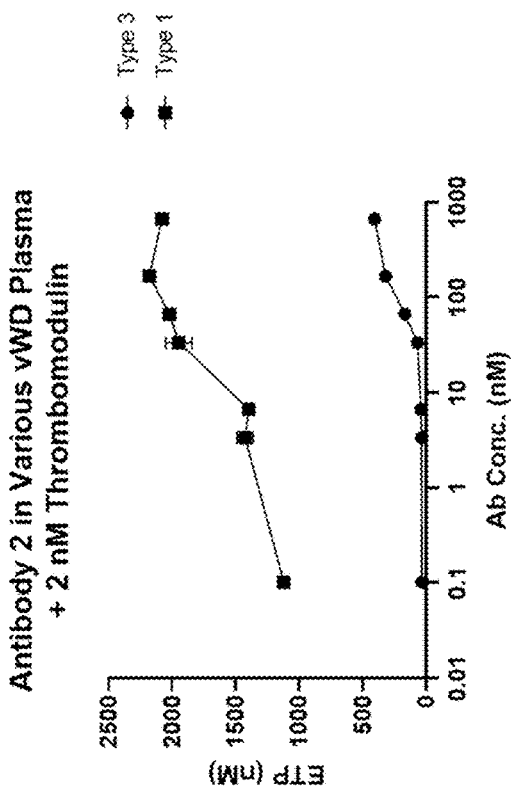
Figure 27A:
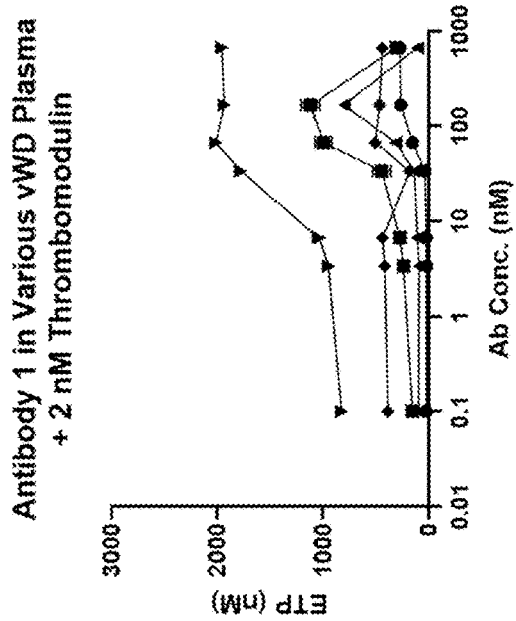
Figure 27D:
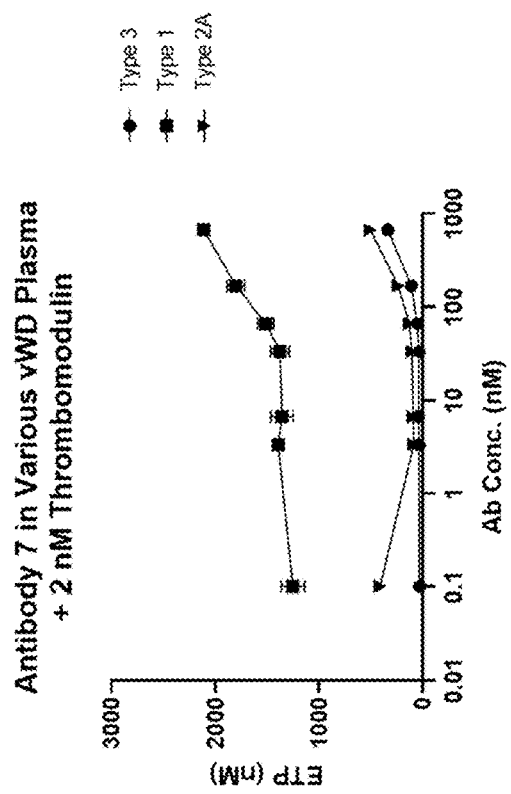
Figure 27C:
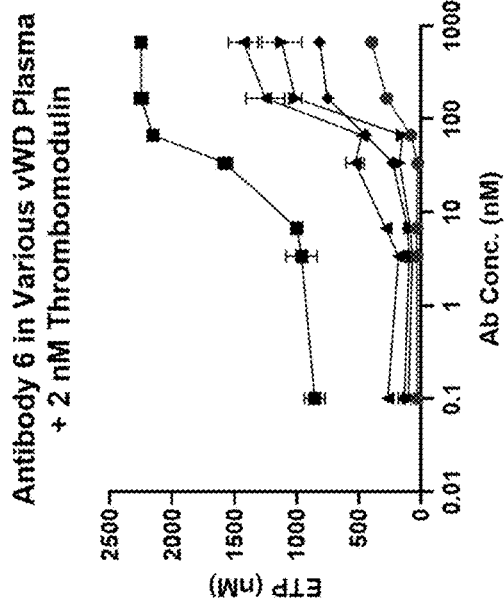
Figure 27F:
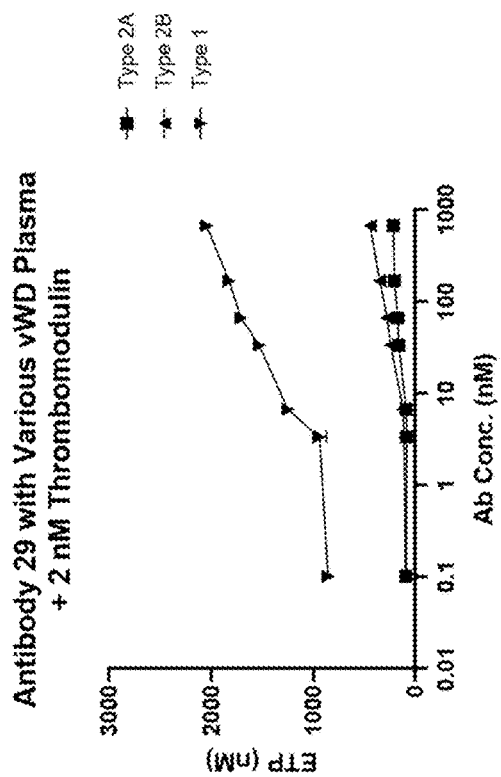
Figure 27E:
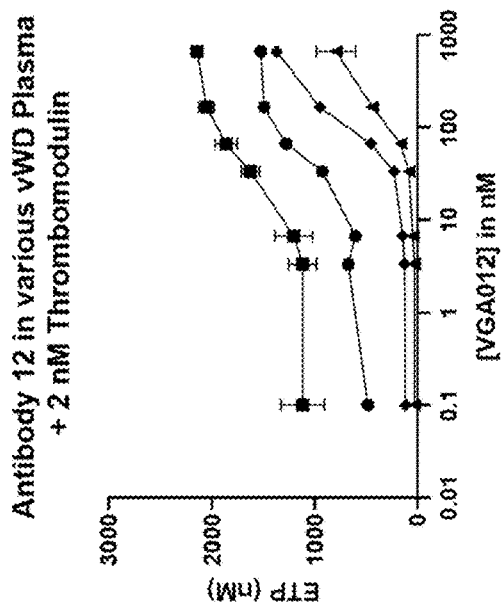

FIGS. 27A-27B depict enhanced dose-dependent thrombin generation when Antibodies 1 and 2 were added to plasma obtained from patients with various types of von Willebrand disease. FIGS. 27C-27D depict enhanced dose-dependent thrombin generation when Antibodies 6 and 7 were added to plasma obtained from patients with various types of von Willebrand disease, with thrombomodulin added. FIGS. 27E-27F depict enhanced dose-dependent thrombin generation when Antibodies 12 and 29 were added to plasma obtained from patients with various types of von Willebrand disease, with thrombomodulin added.

Example 11: APC Cofactor Assay in Cynomolgus Monkeys with Subcutaneous and Intravenous Injection The APC cofactor assay was performed using a Thermo Fluoroskan Ascent Microplate Fluorometer and Thrombinoscope software. The PPP reagent (Diagnostica Stago) was used in this experiment. Briefly, cynomolgus monkey plasma was mixed with PPP reagent and 5 µg/ml of activated Protein C along with calcium and substrate and the levels of thrombin generation was monitored over 1 hour. The PK assay was performed by incubating diluted cynomolgus monkey plasma onto plates immobilized with human Protein S. The plates used were MSD 96-well plates. 30 µl of 2 µg/ml plasma purified Protein S in Tris buffer containing calcium was used to coat the plate overnight. After blocking, the wells were incubated with samples, standards and QCs. 25 µl per well of 2 µg/ml sulfo-tagged goat anti-human IgG, monkey ads and incubated at room temperature for 1 hr. After washing, 150 µl of 1×MSD Read Buffer T in water was added to each well and the plate was read on a MSD plate reader. The levels of D-dimer were measured using the D-dimer assay kit from Diagnostica Stago following manufacturer's recommended protocol.

Figure 28B:
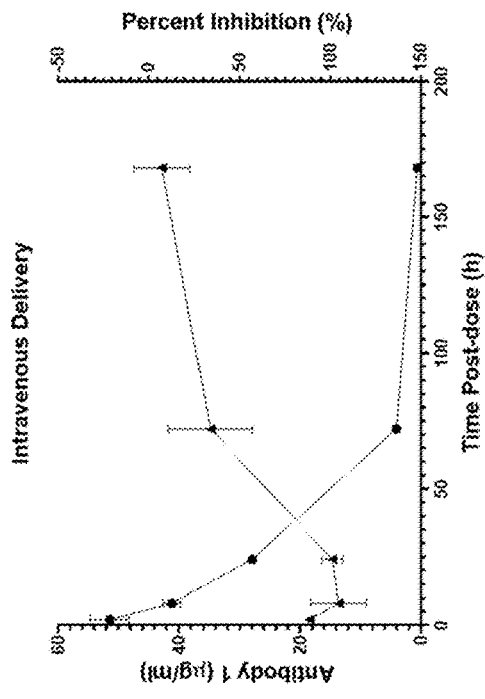
Figure 28A:
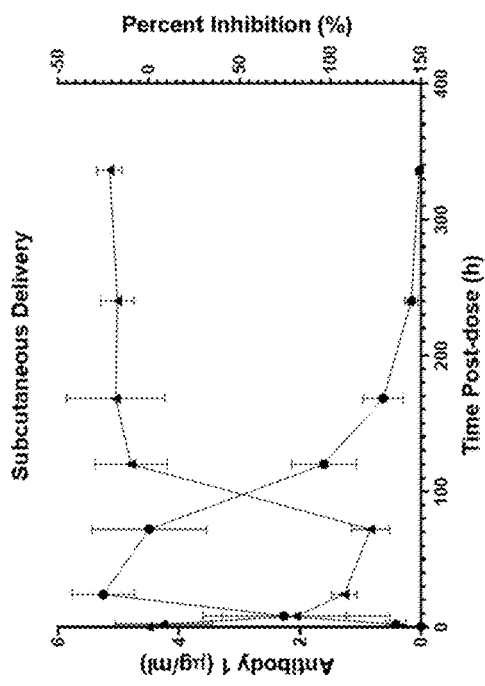
Figure 28C:
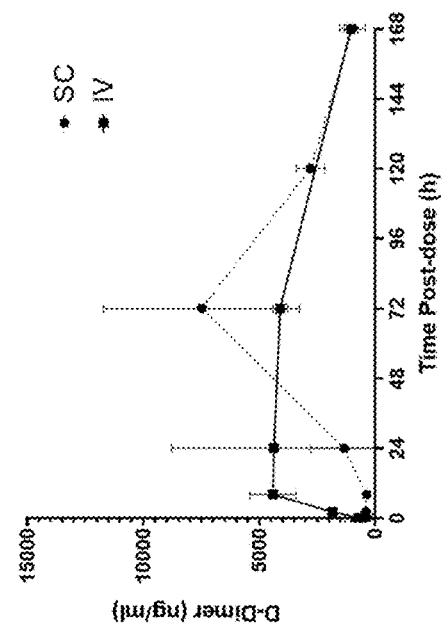
Figure 28E:
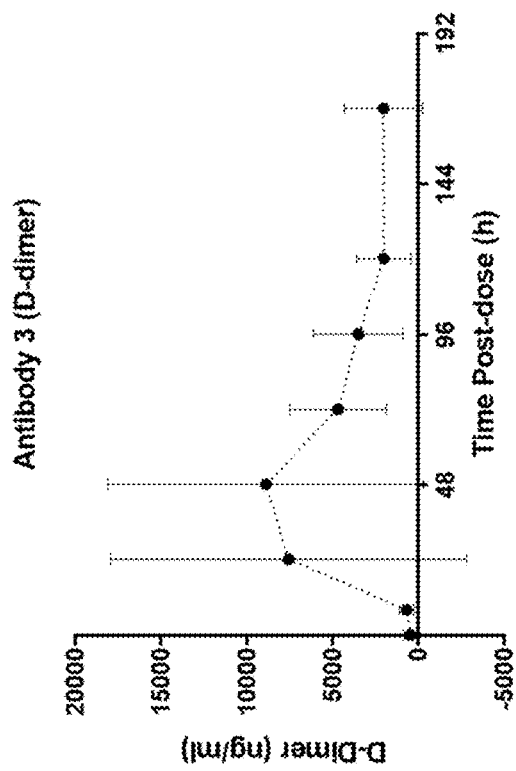
Figure 28D:
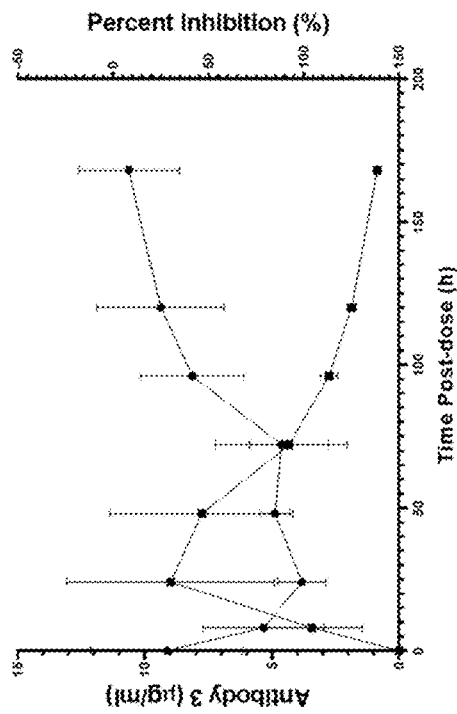
Figure 28J:
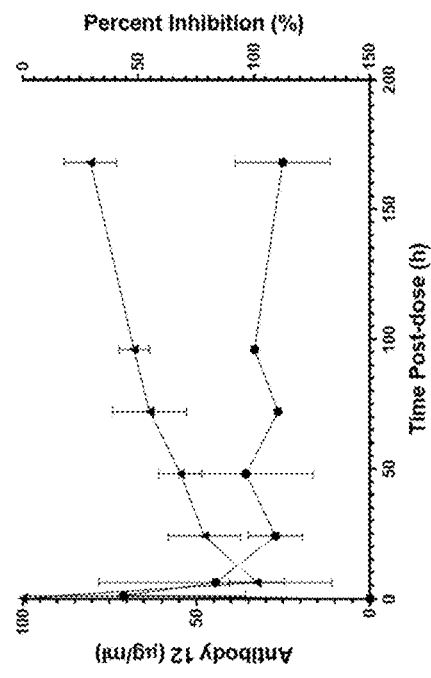
Figure 28I:
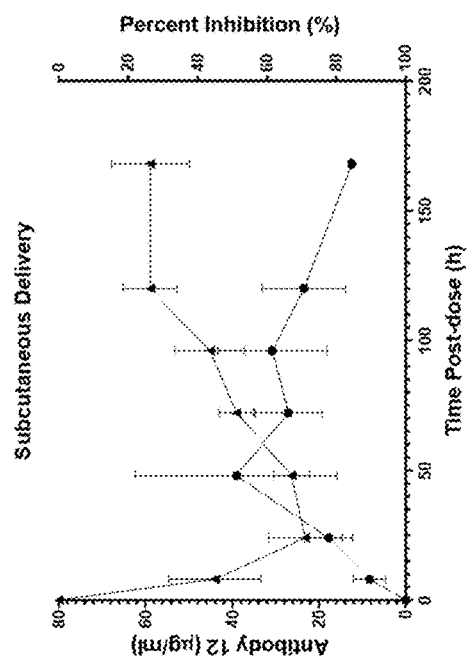
Figure 28K:
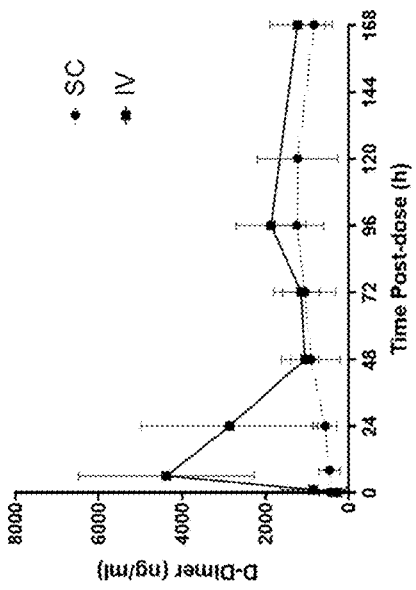
Figure 28M:
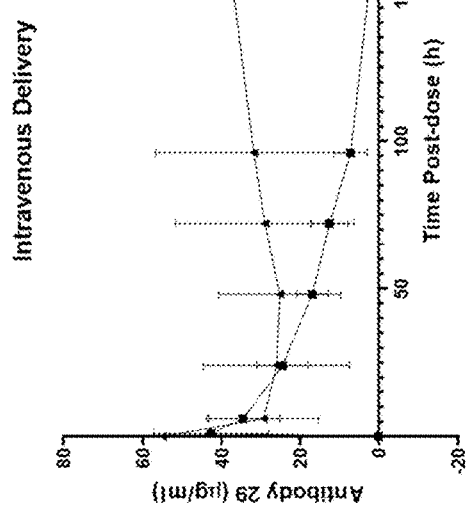
Figure 28L:
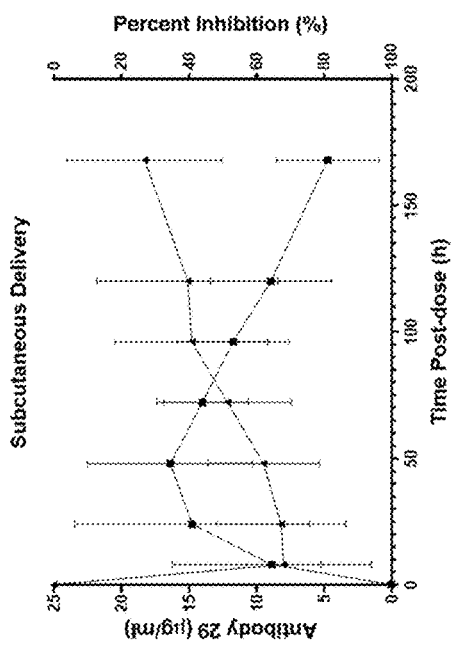
Figure 28N:
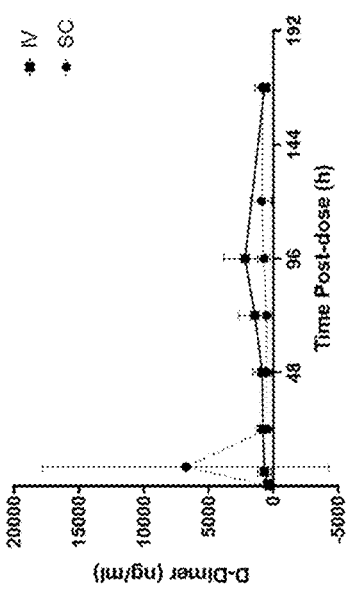

FIGS. 28A-28N depict the results of APC cofactor assays, PK assays, and D-dimer assays for plasma samples collected after administration of Protein S antibodies into cynomolgus monkeys at 3 mg/kg subcutaneously and intravenously. The APC cofactor assay was used to measure the pharmacodynamic activity of the administered Protein S antibodies at the various times. In addition, FIGS. 28A-28N also show the levels of free antibody which was measured using an ELISA assay. And finally, elevated D-dimer, which was used as a biomarker of Protein S antibody induced coagulation activity, was observed in the monkeys and the data shown.

Specifically, FIGS. 28A-28B depict the levels of free antibody (left axis, filled circles) and percent inhibition in an APC cofactor assay (right axis, filled triangles) when Antibody 1 was administered to cynomolgus monkeys at 3 mg/kg subcutaneously and intravenously, respectively.

FIG. 28C depicts levels of D-dimer, as a marker of coagulation activity, measured over time in cynomolgus monkeys injected with Antibody 1, subcutaneously (SC) and intravenously (IV).

FIG. 28D depicts the levels of free antibody (left axis, filled squares) and percent inhibition in an APC cofactor assay (right axis, filled circles) when Antibody 3 was administered to cynomolgus monkeys at 3 mg/kg subcutaneously.

FIG. 28E depicts levels of D-dimer, as a marker of coagulation activity, measured over time in cynomolgus monkeys injected with Antibody 3.

FIGS. 28F-28G depict the levels of free antibody (left axis, filled squares) and percent inhibition in an APC cofactor assay (right axis, filled triangles) when Antibody 6 was administered to cynomolgus monkeys at 3 mg/kg subcutaneously and intravenously, respectively.

FIG. 28H depicts levels of D-dimer, as a marker of coagulation activity, measured over time in cynomolgus monkeys injected with Antibody 6.

FIGS. 28I-28J depict the levels of free antibody (left axis, filled circles) and percent inhibition in an APC cofactor assay (right axis, filled triangles) when Antibody 12 was administered to cynomolgus monkeys at 3 mg/kg subcutaneously and intravenously, respectively.

FIG. 28K depicts levels of D-dimer, as a marker of coagulation activity, measured over time in cynomolgus monkeys injected with Antibody 12.

FIGS. 28L-28M depict the levels of free antibody (left axis, filled squares) and percent inhibition in an APC cofactor assay (right axis, filled triangles) when Antibody 29 was administered to cynomolgus monkeys at 3 mg/kg subcutaneously and intravenously, respectively.

FIG. 28N depicts levels of D-dimer, as a marker of coagulation activity, measured over time in cynomolgus monkeys injected with Antibody 29.

Example 12: Effects of Protein S Antibodies on the Binding of Protein S to TFPI

The effect of the antibodies of the disclosure on the binding of Protein S to TFPI was measured.

Using the Octet System (Sartorius), an assay to measure the binding of TFPI to Protein S was developed. Briefly, the human Fc antibodies were immobilized onto anti-human Fc capture probes by placing the probes into 10 µg/ml antibody solution in 10 mg/ml bovine serum albumin, 20 mM Tris pH 7.0, 150 mM NaCl, and 4 mM calcium chloride. Then the bound antibodies were placed into a solution containing 10 µg/ml human Protein S followed by a 10 µg/ml solution containing human TFPI. Finally, the probe was placed into a buffer solution (wash) to observe the dissociation of TFPI from Protein S. The kinetics of association and dissociation of TFPI to Protein S were measured.

Figure 29:
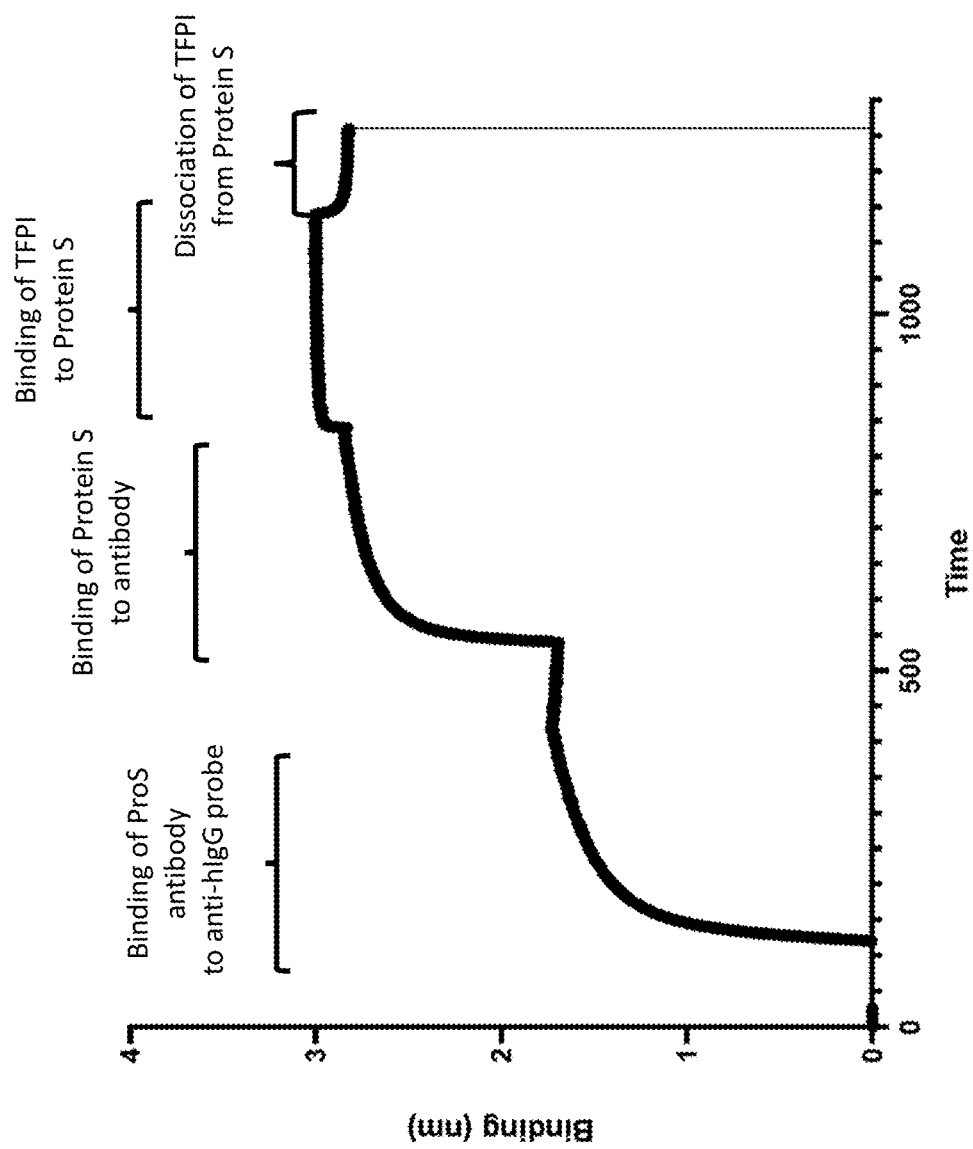

FIG. 29 depicts the binding of human TFPI to Protein S after the binding of Protein S to Antibody 2. These results demonstrate that Antibody 2 does not block the binding of TFPI to Protein S.

Figure 30B:
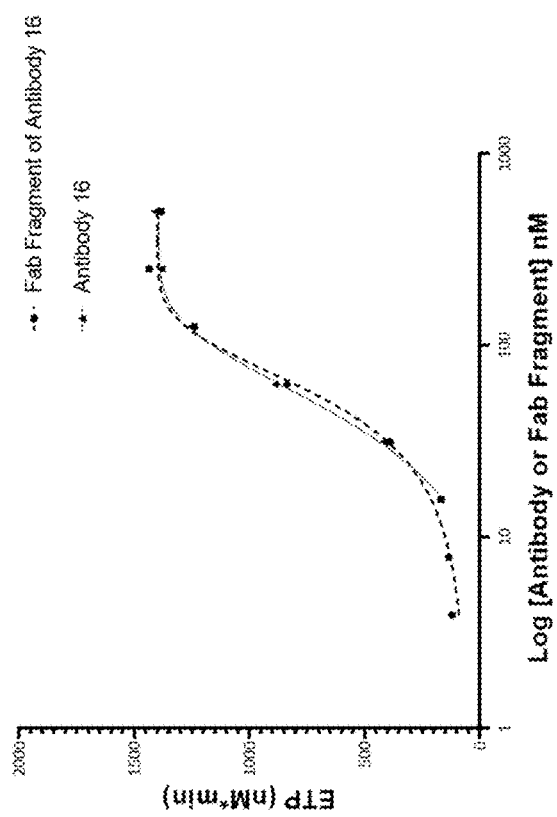
Figure 30A:
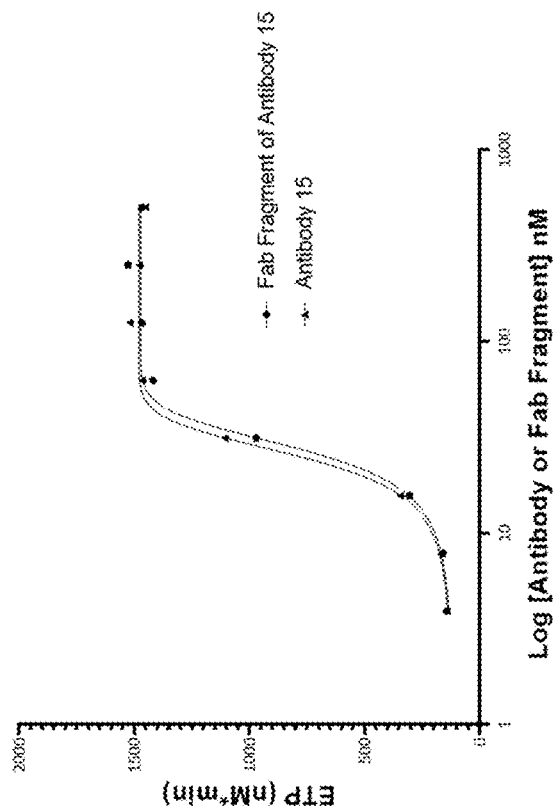

Example 13: Full-Length and Fab Fragments of Protein S Antibodies in APC Cofactor Assays FIGS. 30A-30B depict similar dose-titration curves resulting from a full-length antibody or a Fab fragment of the same antibody in an APC cofactor assay. FIG. 30A shows the results using the full-length and Fab fragment of Antibody 15, and FIG. 30B shows the results using the full-length and Fab fragment of Antibody 16. These results demonstrate that both the full-length and the Fab fragments of the antibodies tested gave similar results in the APC cofactor assay.

The invention claimed is:

1. An antibody that binds Protein S, wherein the antibody comprises a heavy chain variable region (VH) and a light chain variable region (VL), wherein the VH and VL comprise a combination of six complementarity determining regions (CDRs), whose amino acid sequences are selected from the group consisting of:
   a. SEQ ID NO: 1, an amino acid sequence of QNS, SEQ ID NO: 24, SEQ ID NO: 36, SEQ ID NO: 48, and SEQ ID NO: 60; and
   b. SEQ ID NO: 10, an amino acid sequence of DAS, SEQ ID NO: 31, SEQ ID NO: 43, SEQ ID NO: 55, and SEQ ID NO: 67.

2. The antibody of claim 1, wherein the antibody is:
   a. a monoclonal antibody;
   b. a full-length antibody;
   c. an antibody fragment; or
   d. a humanized antibody.

3. The antibody of claim 1, wherein the antibody comprises an Fc domain selected from the group consisting of: human IgG1, human IgG2, human IgG3, or human IgG4.

4. The antibody of claim 3, wherein the antibody comprises an Fc domain further comprising an amino acid sequence of SEQ ID NO: 218, and wherein the amino acid sequence comprises at least one amino acid substitution at a position selected from the group consisting of: 215, 221, 222, 228, 234, 235, 236, 239, 240, 241, 243, 244, 245, 247, 250, 252, 254, 256, 262, 263, 264, 265, 266, 267, 268, 269, 270, 292, 296, 297, 298, 299, 300, 305, 313, 324, 325, 326, 327, 328, 329, 330, 332, 333, 334, 345, 396, 428, 430, 433, 434, and 440.

5. The antibody of claim 3, wherein the Fc domain comprises one or more of the substitutions selected from the group consisting of T250Q/M428L, M252Y/S254T/T256E, M428L/N434S, S267E/L328F, N325S/L328F, and H433K/N434F, wherein the position numbers of the amino acid residues are of the EU numbering scheme.

6. An antibody that binds Protein S, wherein the antibody comprises a heavy chain variable region (VH) and a light chain variable region (VL), selected from the group consisting of:
   a. a VH comprising the amino acid sequence of SEQ ID NO: 76; and a VL comprising the amino acid sequence of SEQ ID NO: 75; and
   b. a VH comprising the amino acid sequence of SEQ ID NO: 90; and a VL comprising the amino acid sequence of SEQ ID NO: 89.

7. The antibody of claim 6, wherein the VH and VL comprise a combination of six complementarity determining regions (CDRs), whose amino acid sequences comprise:
   SEQ ID NO: 1, an amino acid sequence of QNS, SEQ ID NO: 24, SEQ ID NO: 36, SEQ ID NO: 48, and SEQ ID NO: 60.

8. The antibody of claim 6, wherein the VH and VL comprise a combination of six complementarity determining regions (CDRs), whose amino acid sequences comprise SEQ ID NO: 10, an amino acid sequence of DAS, SEQ ID NO: 31, SEQ ID NO: 43, SEQ ID NO: 55, and SEQ ID NO: 67.

9. The antibody of claim 6, wherein the antibody binds to a thrombin-sensitive region of the Protein S.

10. The antibody of claim 6, wherein the antibody is:
    a. a monoclonal antibody;
    b. a full-length antibody;
    c. an antibody fragment; or
    d. a humanized antibody.

11. The antibody of claim 6, wherein the antibody comprises an Fc domain selected from the group consisting of: human IgG1, human IgG2, human IgG3, or human IgG4.

12. The antibody of claim 11, wherein the Fc domain of the antibody is human IgG4, optionally wherein the Fc domain comprises an amino acid sequence of SEQ ID NO: 218, and comprises at least one amino acid substitution at a position selected from the group consisting of: 215, 221, 222, 228, 234, 235, 236, 239, 240, 241, 243, 244, 245, 247, 250, 252, 254, 256, 262, 263, 264, 265, 266, 267, 268, 269, 270, 292, 296, 297, 298, 299, 300, 305, 313, 324, 325, 326, 327, 328, 329, 330, 332, 333, 334, 345, 396, 428, 430, 433, 434, and 440.

13. The antibody of claim 11, wherein the Fc domain of the antibody comprises one or more of the substitutions selected from the group consisting of T250Q/M428L, M252Y/S254T/T256E, M428L/N434S, S267E/L328F, N325S/L328F, and H433K/N434F, wherein the position numbers of the amino acid residues are of the EU numbering scheme.

14. The antibody of claim 1, wherein the antibody is capable of promoting generation of a marker associated with coagulation activity.

15. The antibody of claim 1, wherein the antibody is capable of promoting thrombin generation.

16. The antibody of claim 1, wherein the antibody is capable of promoting D-dimer levels.

17. The antibody of claim 1, wherein the antibody is capable of promoting fibrin generation.

18. The antibody of claim 6, wherein the antibody is capable of promoting generation of a marker associated with coagulation activity.

19. The antibody of claim 6, wherein the antibody is capable of promoting thrombin generation.

20. The antibody of claim 6, wherein the antibody is capable of promoting D-dimer levels.

21. The antibody of claim 6, wherein the antibody is capable of promoting fibrin generation.

22. The antibody of claim 3, wherein the antibody comprises an Fc Domain of human IgG4.

23. The antibody of claim 5, wherein the Fc domain comprises the M428L/N434S substitutions.

24. The antibody of claim 11, wherein the antibody comprises an Fc domain of human IgG4.

25. The antibody of claim 13, wherein the Fc domain comprises the M428L/N434S substitutions.

* * * * *